United States Patent
Takenouchi et al.

(10) Patent No.: US 9,073,885 B2
(45) Date of Patent: Jul. 7, 2015

(54) VITAMIN $D_3$ LACTONE DERIVATIVES

(75) Inventors: Kazuya Takenouchi, Tokyo (JP); Miyuki Anzai, Tokyo (JP); Hiroshi Saito, Tokyo (JP); Kazuhisa Okada, Tokyo (JP); Seiichi Ishizuka, Tokyo (JP); Daishiro Miura, Tokyo (JP); Hiroaki Takayama, Tokyo (JP); Atsushi Kittaka, Kanagawa (JP); Nozomi Saito, Kanagawa (JP); Toshie Fujishima, Kanagawa (JP)

(73) Assignee: Teijin Pharma Limited, Tokyo (JP)

( * ) Notice: Subject to any disclaimer, the term of this patent is extended or adjusted under 35 U.S.C. 154(b) by 1889 days.

(21) Appl. No.: 10/543,881

(22) PCT Filed: Jan. 29, 2004

(86) PCT No.: PCT/JP2004/000815
§ 371 (c)(1),
(2), (4) Date: Jul. 29, 2005

(87) PCT Pub. No.: WO2004/067525
PCT Pub. Date: Aug. 12, 2004

(65) Prior Publication Data
US 2006/0148768 A1     Jul. 6, 2006

(30) Foreign Application Priority Data

Jan. 30, 2003 (JP) .................. 2003-021650
Sep. 30, 2003 (JP) .................. 2003-339658

(51) Int. Cl.
*A61K 31/593* (2006.01)
*C07D 307/58* (2006.01)

(52) U.S. Cl.
CPC ............ *C07D 307/58* (2013.01); *A61K 31/593* (2013.01)

(58) Field of Classification Search
USPC .................... 514/167; 549/502, 295; 552/653
See application file for complete search history.

(56) References Cited

U.S. PATENT DOCUMENTS

| | | | | |
|---|---|---|---|---|
| 4,666,634 | A * | 5/1987 | Miyamoto et al. | 552/653 |
| 6,124,276 | A * | 9/2000 | Miyamoto et al. | 514/167 |
| 6,127,559 | A * | 10/2000 | DeLuca et al. | 552/653 |
| 6,281,249 | B1 * | 8/2001 | DeLuca et al. | 514/675 |
| 6,531,460 | B1 * | 3/2003 | Takenouchi et al. | 514/167 |

FOREIGN PATENT DOCUMENTS

| | | |
|---|---|---|
| EP | 712843 A1 | 5/1996 |
| EP | 0712843 A1 | 5/1996 |
| EP | 123921 A1 | 8/2001 |
| EP | 1123921 A1 | 8/2001 |
| JP | 61-267549 A | 11/1986 |
| JP | 11-116551 A | 4/1999 |
| JP | 11-116551 A1 | 4/1999 |
| JP | 2006-041059 A | 2/2006 |
| JP | 2008-134052 A | 6/2008 |
| WO | WO 95/33716 A1 | 12/1995 |

(Continued)

OTHER PUBLICATIONS

A Kittaka et al. (Organic Letters, 2000, vol. 2, No. 17, 2619-2622).*
Rafal R. Sciniski, J. Med. Chem. 1988, 41, 4662-4672.*
Yoshitomo Suhara et al. (Bioorganic and Medicinal Chemistry Letters 10 (2000) 1129-1132.*
BPAI Decision—Appeal 2009-006921.*
Gul-Dong Zhu et al (Chem REv 1995, 95, 1877-1952).*
Nozomi Saito, et al; Dramatic Enhancement of Antagonistic Activity on Vitamin D Receptor: A Double Functionalization of 1α-Hydroxyvitamin $D_3$ 26,23-Lactones; 2003 American Chemical Society; Org. Lett., vol. 5, No. 25, 2003; pp. 4859-4862.

(Continued)

*Primary Examiner* — Sabiha N Qazi
(74) *Attorney, Agent, or Firm* — Sughrue Mion, PLLC

(57) ABSTRACT

A compound represented by the following Formula (1) that is effective for the treatment of Paget's disease of bone or hypercalcemia or a medically acceptable solvate thereof;

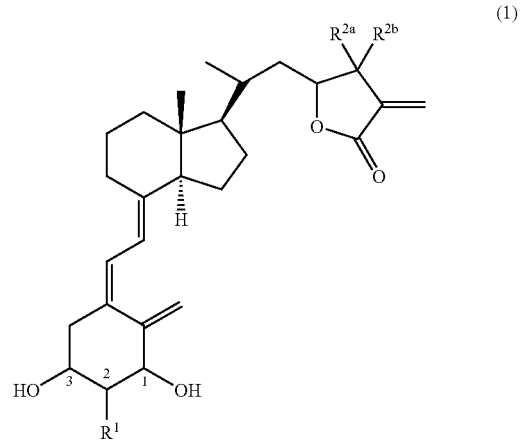

[wherein $R_1$ refers to hydrogen atom, $C_1$-$C_6$ alkyl group optionally substituted with hydrogen group or $C_1$-$C_6$ alkoxy group optionally substituted with hydroxyl group, $R^{2a}$ and $R^{2b}$ refer to hydrogen atom, $C_1$-$C_{10}$ alkyl group optionally substituted with hydroxyl group, $C_6$-$C_{10}$ aryl group optionally substituted with hydroxyl group or $C_7$-$C_{12}$ aralkyl group optionally substituted with a hydroxyl group, or are combined to represent ethylene group. However, a compound in which $R^1$ is a hydrogen atom or a methyl group and $R^{2a}$ and $R^{2b}$ are hydrogen atoms is excluded].

9 Claims, No Drawings

(56) References Cited

FOREIGN PATENT DOCUMENTS

| WO | WO 98/50353 A1 | 11/1998 |
|----|----------------|---------|
| WO | WO 00/24712 A1 | 5/2000 |
| WO | WO 02/15894 A3 | 2/2002 |
| WO | WO 03/070716 A1 | 8/2003 |

OTHER PUBLICATIONS

Cheikh Menaa, et al., "1,25-Dihydroxyvitamin $D_3$ Hypersensitivity of Osteoclast Precursors from Patients with Paget's Disease," *Journal of Bone and Mineral Research*, vol. 15, No. 2, pp. 228-236, 2000.

John S. Adams, et al., Vitamin D Metabolite-Mediated Hypercalcemia and Hypercalciuria Patients with AIDS- and Non-AIDS-Associated Lymphoma, *Blood*, vol. 73, No. I, pp. 235-239, Jan. 1989.

John F. Seymour, et al, "Calcitriol: The Major Humoral Mediator of Hypercalcemia in Hodgkin's Disease and Non-Hodgkin's Lymphomas," *Blood*, vol. 82, No. 5, pp. 1383-1394, Sep. 1, 1993.

Peter J. Gkonos, et al., "Hypercalcemia and Elevated 1,25-dihydroxyvitamin D Levels in a Patient with End-stage Renal Disease and Active Tuberculosis," *The New England Journal of Medicine*, vol. 311, No. 26, pp. 1683-1685, Dec. 27, 1984.

John S. Adams, et al., "Isolation and Structural Identification of 1,25-Dihydroxyvitamin $D_3$ Produced by Cultured Alveolar Macrophages in Sarcoidosis," Journal of Clinical Endocrinology and Metabolism, vol. 60, No. 5, pp. 960-966, 1985.

Hagop M. Kantarjian, et al., "Hypercalcemia in Disseminated Candidiasis," *The American Journal of Medicine*, vol. 74, pp. 721-724, Apr. 1983.

Gregory A. Kozeny, et al., "Hypercalcemia Associated with Silicone-Induced Granulomas," *The New England Journal of Medicine*, vol. 311, No. 17, pp. 1103-1105, Oct. 25, 1984.

Gary W. Edelson, et al., "Hypercalcemia Associated with Wegener's Granulomatosis and Hyperparathyroidism: Etiology and Management," *Am J. Nephrol*, vol. 13, pp. 275-277, 1993.

Steven J. Scheinman, et al., "Case Report: Hypercalcemia wth Excess Serum 1,25 Dihydroxyvitamin D in Lymphomatoid Granulomatosis/Angiocentric Lypmphoma," *The American Journal of Medical Sciences*, vol. 301, No. 3, pp. 178-181, Mar. 1991.

Vicki N. Hoffman, et al., "Leprosy, Hypercalcemia, and Elevated Serum Calcitriol Levels," *Annals of Internal Medicine*, vol. 105, No. 6, pp. 890-891, Dec. 1986'.

Daishiro Miura, et al., "Antagonistic Action of Novel $I\alpha,25$-Dihydroxyvitamin $D_3$-26,23-lactone Analogs on Differentiation of Human Leukemia Cells (HL-60) Induced by $l\alpha,25$-Dihydroxyvitamin $D\alpha$," *The Journal of Biological Chemistry*, vol. 274, No. 23, pp. 16392-16399, Jun. 4, 1999.

Keiichi Ozono, et al., "Analysis of the Molecular Mechanism for the Antagonistic Action of a Novel $1\alpha,25$-Dihydroxyvitamin $D_3$ Analogue toward Vitamin D Receptor Function," *The Journal of Biological Chemistry*, vol. 274, No. 45, pp. 32376-32381, Nov. 5, 1999.

\* cited by examiner

VITAMIN D₃ LACTONE DERIVATIVES

This is a U.S. national stage of Application No. PCT/JP2004/000815 filed Jan. 29, 2004.

TECHNICAL FIELD

The present invention relates to vitamin $D_3$ lactone derivatives useful as pharmaceutical products. More specifically, the present invention relates to 1α-hydroxyvitamin $D_3$ lactone derivatives or pharmaceutically acceptable solvates thereof, therapeutic agents containing these derivatives as active ingredients for hypercalcemia or Paget's disease of bone, pharmaceutical compositions containing these derivatives, processes for synthesizing intermediates thereof, and intermediates thereof.

BACKGROUND ART

Paget's disease of bone is a disorder of an unknown cause in which bone resorption is abnormally increased at pelvis, femur, skull and the like so that symptoms such as bone deformity and bone pain develop. Therapeutic agents of Paget's disease of bone that are currently in use are bisphosphonates formulations and calcitonin formulations, which are also used as a therapeutic agent of osteoporosis. However, both formulations have drawbacks in that the former have poor compliance because they require a dosage that is 4 to 5 times larger than that used against osteoporosis patients and the latter cannot exert a sufficient inhibitory action on bone resorption. Furthermore, these formulations cannot completely core the disease because they are symptomatic treatment agents based on an inhibitory action on bone resorption. Recently, it has been found that osteoclast precursor cells collected from patients with Paget's disease of bone have a 1α, 25-dihydroxy vitamin $D_3$ receptor and that the responsitivity of the cells to 1α, 25-dihydroxy vitamin $D_3$ has increased by a factor of 10 to 100 compared to osteoclast precursor cells collected from normal individuals (J. Bone Miner. Res., Vol. 15, 228-236, 2000). In addition, it has been assumed that increased bone resorption by endogenous 1α, 25-dihydroxy vitamin $D_3$ plays a key role in the development of Paget's disease of bone, as 1α, 25-dihydroxy vitamin $D_3$ in the blood of patients with Paget's disease of bone is present at the same concentration as in the blood of normal individuals. Consequently, a compound which suppresses the action of 1α, 25-dihydroxy vitamin $D_3$ on osteoclast precursor cells, that is, a compound like a vitamin D antagonist may more fundamentally suppress increased bone resorption of patients with Paget's disease of bone and can be expected to have a therapeutic effect superior to current bone resorption suppressors.

On the other hand, hypercalcemia is developed by increased vitamin D production associated with various diseases, for example, lymphoma (Blood, Vol. 73, 235-239, 1989; Blood, Vol. 82, 1383-1394, 1993), tuberculosis (N. Engl. J. Med., Vol. 311, 1683-1685, 1984), sarcoidosis (J. Clin. Endocrinol. Metab., Vol. 60, 960-966, 1985), candida (Am. J. Med., Vol. 74, 721-724, 1983), granuloma (N. Engl. J. Med., Vol. 311, 1103-1105, 1984; Am. J. Nephrol., Vol. 13, 275-277, 1993; Am. J. Med. Sci., Vol. 301, 178-181, 1991), leprosy (Ann. Intern Med., Vol. 105, 890-891, 1986), primary hyperparathyroidism, malignant tumors and the like. As the level of calcium in the blood is known to be increased by the action of active form of vitamin $D_3$, a compound antagonistic to active form of vitamin $D_3$, that is, a vitamin $D_3$ antagonist is believed to be effective for the treatment of hypercalcemia.

The prior art relating to compounds of the present invention is the following. The specification of International Publication WO 95/33716 describes compounds having an α-methylene lactone structure as a D-ring side-chain of vitamin $D_3$. However, none of these compounds are included in the compounds of the present invention, and no descriptions or suggestions have been made in the specification whether the compounds described have a vitamin $D_3$ antagonist action or not. Furthermore, there is a description in J. Biol. Chem. Vol. 274, 16392-16399, 1999 and J. Biol. Chem. Vol. 274, 32376-32381, 1999 indicating that the compounds described in the above specification of International Publication WO 95/33716 have a vitamin $D_3$ antagonist action. These compounds are, however, not included in the compounds of the present invention. Also, in the specification of WO 00/24712, there is disclosed compounds that have an α-methylene-cycloalkanone structure as a side chain of the D-ring of vitamin $D_3$. Additionally, the publication of Japanese Unexamined Patent Application No. 11-116551 and the specification of International Publication WO 98/50353 disclose compounds having a methyl group as a substituent at 2-position of vitamin $D_3$. However, the compounds described in these application specifications have a 1α, 25-dihydroxy vitamin $D_3$ structure (6-hydroxy-6-methylheptan-2-yl) as the D-ring side-chain of vitamin $D_3$, which are different from the compounds having an α-methylene-lactone structure disclosed in the present invention. Moreover, there are neither descriptions nor suggestions in the specifications whether the described compounds have a vitamin $D_3$ antagonist action or not.

DISCLOSURE OF THE INVENTION

An object of the present invention is to provide a novel vitamin $D_3$ derivative or a pharmaceutically acceptable solvate thereof that is effective as a therapeutic agent for Paget's disease of bone or hypercalcemia. Also, another object of the present invention is to provide a therapeutic agent for Paget's disease of bone or hypercalcemia containing the vitamin $D_3$ derivative or the pharmaceutically acceptable solvate thereof as an active ingredient.

Further, another object of the present invention is to provide a pharmaceutical composition containing the vitamin $D_3$ derivative or the pharmaceutically acceptable solvate thereof as an active ingredient.

Furthermore, another object of the present invention is to provide a process for synthesizing a lactone compound which is a useful intermediate for producing the vitamin $D_3$ derivative or the pharmaceutically acceptable solvate thereof.

Further, another object of the present invention is to provide a lactone compound which is a useful intermediate for producing the vitamin $D_3$ derivative or the pharmaceutically acceptable solvate thereof.

The present invention is a vitamin $D_3$ derivative represented by the following Formula (1) or a pharmaceutically acceptable solvate thereof:

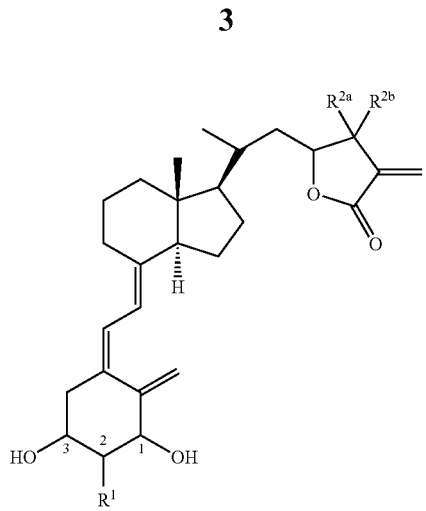

(1)

[wherein $R_1$ refers to hydrogen atom, $C_1$-$C_6$ alkyl group optionally substituted with hydroxyl group or $C_1$-$C_6$ alkoxy group optionally substituted with hydroxyl group; $R^{2a}$ and $R^{2b}$ are identical or different and refer to hydrogen atom, $C_1$-$C_{10}$ alkyl group optionally substituted with hydroxyl group, $C_6$-$C_{10}$ aryl group optionally substituted with hydroxyl group, or $C_7$-$C_{12}$ aralkyl group optionally substituted with hydroxyl group; alternatively, $R^{2a}$ and $R^{2b}$ may be combined together to form a cyclopropane ring together with the carbon atom to which they are bonded; however, a compound in which $R^1$, $R^{2a}$ and $R^{2b}$ are all hydrogen atoms and a compound in which $R^1$ is methyl group and $R^{2a}$ and $R^{2b}$ are hydrogen atoms are excluded.]

Further, the present invention is a therapeutic agent for Paget's disease of bone or hypercalcemia containing a vitamin $D_3$ derivative represented by the above-described Formula (1) or a pharmaceutically acceptable solvate thereof in a therapeutically effective amount as an active ingredient.

In addition, the present invention is a pharmaceutical composition comprising a vitamin $D_3$ derivative represented by the above-described Formula (1) or a pharmaceutically acceptable solvate thereof and a pharmaceutically acceptable carrier.

Furthermore, the present invention is a process characterized by reacting, in the presence of divalent chromium, an aldehyde compound represented by the following Formula (2):

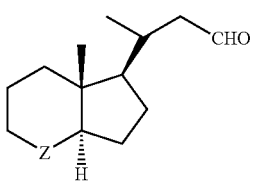

(2)

[wherein Z refers to any one of Formulas (2-1), (2-2), (2-3), (2-4) and (2-5):

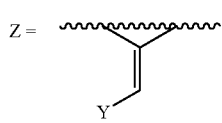

(2-1)

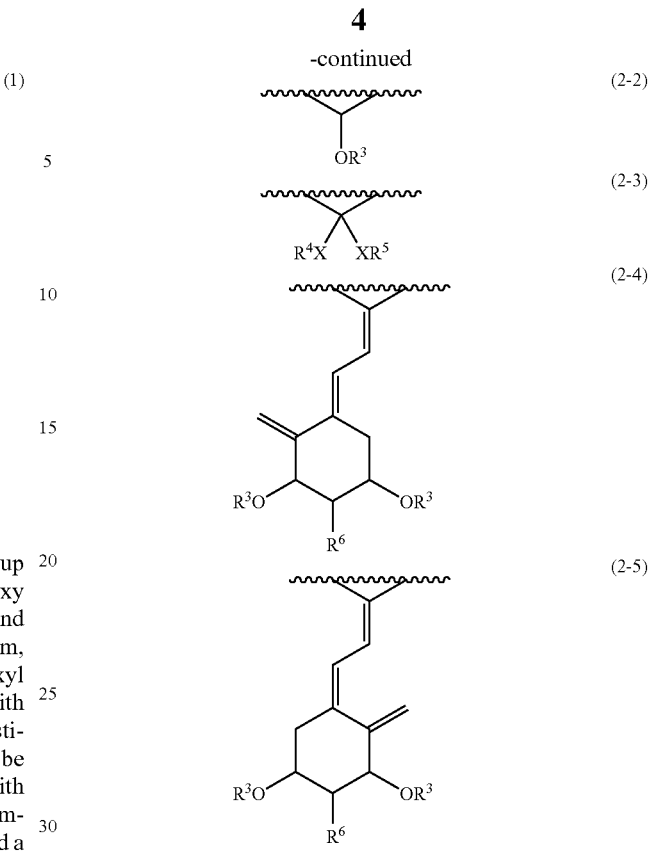

among Formulas (2-1) to (2-5), Y refers to bromine atom or iodine atom; $R^3$ refers to trimethylsilyl group, triethylsilyl group, triisopropylsilyl group, t-butyldimethylsilyl group, t-butyldiphenylsilyl group, acetyl group, methoxymethyl group or tetrahydro-4H-pyran-2-yl group; $R^4$ or $R^5$ independently refers to methyl group, ethyl group, propyl group, trichloroethyl group, or $R^4$ and $R^5$ are combined to form ethylene group or propylene group, X refers to oxygen atom or sulfur atom; $R^6$ refers to hydrogen atom, $C_1$-$C_6$ alkyl group optionally substituted with hydroxyl group protected by a group defined by $R^3$, or $C_1$-$C_6$ alkoxy group which may be optionally substituted by hydroxyl group protected by a group defined by $R^3$], with an acrylic acid derivative represented by the following Formula (3),

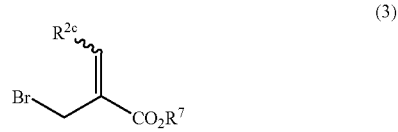

(3)

[wherein $R^{2c}$ refers to $C_1$-$C_{10}$ alkyl group which may be substituted with hydroxyl group protected by a group defined by $R^3$, $C_6$-$C_{10}$ aryl group which may be substituted with hydroxyl group protected by a group defined by $R^3$, or $C_7$-$C_{12}$ aralkyl group which may be substituted with hydroxyl group protected by a group defined by $R^3$, and $R^7$ refers to $C_1$-$C_6$ alkyl group], for synthesizing a lactone compound useful as an intermediate of a vitamin $D_3$ derivative represented by the following Formula (4syn),

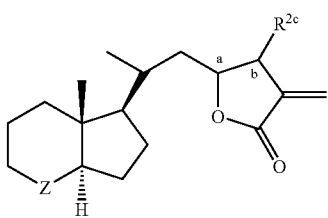

(4syn)

[wherein $R^{2c}$ has the same definition as in the above Formula (3), Z has the same definition as in the above Formula (2), and the relative configuration of carbon a and carbon b is syn.]

Further, the present invention is a process which comprises, in the following order, the steps of:

reducing a lactone ring of a lactone compound represented by the following Formula (4syn),

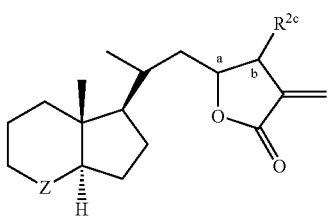

(4syn)

[wherein $R^2$ has the same definition as in the above Formula (3), Z has the same definition as in the above Formula (2) and the relative configuration of carbon a and carbon b is syn];

protecting the resultant primary hydroxyl group to yield an alcohol compound represented by the following Formula (5syn),

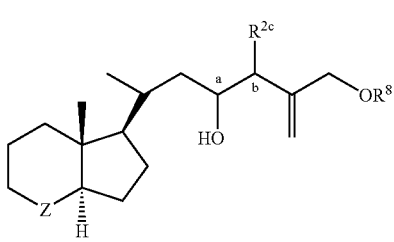

(5syn)

[wherein $R^{2c}$ has the same definition as in the above Formula (3), Z has the same definition as in the above Formula (2), $R^8$ refers to acetyl group, 4-oxopentanoyl group, pivaroyl group, benzoyl group, triisopropylsilyl group, t-butylmethylsilyl group or t-butyldiphenylsilyl group, and the relative configuration of carbon a and carbon b is syn];

oxidizing the secondary hydroxyl group of the alcohol compound to yield a ketonic compound represented by the following Formula (6),

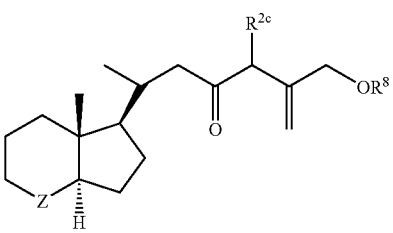

(6)

[wherein $R^{2c}$ has the same definition as in the above Formula (3), Z has the same definition as in the above Formula (2), and $R^8$ has the same definition as in the above Formula (5syn)];

reducing the ketone group of the ketonic compound to yield an alcohol compound represented by the following Formula (5anti),

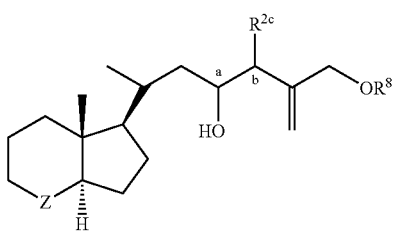

(5anti)

[wherein $R^{2c}$ has the same definition as in the above Formula (3), Z has the same definition as in the above Formula (2), $R^8$ has the same definition as in the above Formula (5syn), and the relative configuration of carbon a and carbon b is anti]; and deprotecting $R^8$ of the alcohol compound and then oxidizing the resultant primary hydroxyl group to form a lactone ring, for synthesizing a lactone compound useful as an intermediate of vitamin $D_3$ derivatives represented by the following Formula (4anti),

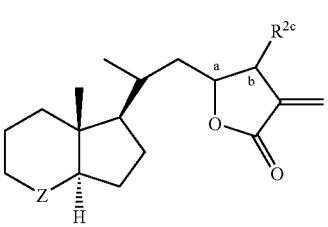

(4anti)

[wherein, $R^{2c}$ has the same definition as in the above Formula (3), Z has the same definition as in the above Formula (2) and the relative configuration of carbon a and carbon b is anti].

Further, the present invention is a vitamin $D_3$ derivative intermediate represented by the following Formula (4),

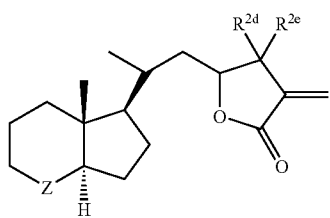

(4)

[wherein $R^{2d}$ and $R^{2e}$ refer to $C_1$-$C_{10}$ alkyl group optionally substituted with hydroxyl group protected by the group defined by $R^3$ of the above Formula (2), $C_6$-$C_{10}$ aryl group optionally substituted with hydroxyl group protected by the group defined by $R^3$ of the above Formula (2), or $C_7$-$C_{12}$ aralkyl group optionally substituted with hydroxyl group protected by the group defined by $R^3$ of the above Formula (2); alternatively, $R^{2d}$ and $R^{2e}$ may be combined together to form a cyclopropane ring together with the carbon atom to which $R^{2d}$ and $R^{2e}$ are bonded; and Z has the same definition as in the above Formula (2)].

Among Formulas (1), (2), (4syn), (4anti), (5syn), (5anti), (6) and (4), when an asymmetric carbon is present in the compound structure, unless otherwise specified, the steric configuration may be either (S) configuration, (R) configuration, α configuration, or β configuration.

According to the present invention, there is provided a novel vitamin $D_3$ derivative useful for the treatment of Paget's disease of bone or a pharmaceutically acceptable solvate thereof. Further, according to the present invention, there is provided a novel vitamin D3 derivative useful for the treatment of hypercalcemia or a pharmaceutically acceptable solvate thereof.

Still further, according to the present invention, a lactone compound which is a production intermediate of these vitamin $D_3$ derivatives and the like can be readily synthesized.

BEST MODE OF CARRYING OUT THE INVENTION

The terms herein are defined as follows.

$C_1$-$C_6$ alkyl group refers to a straight-chain, branched-chain or cyclic aliphatic hydrocarbon group of 1 to 6 carbon atoms. Specifically, it refers to methyl group, ethyl group, propyl group, isopropyl group, butyl group, isobutyl group, pentyl group, isopentyl group, hexyl group, cyclopropyl group, cyclopropylmethyl group, cyclohexyl group and the like.

$C_1$-$C_{10}$ alkyl group refers to a straight-chain, branched-chain or cyclic aliphatic hydrocarbon group of 1 to 10 carbon atoms. Specifically, it refers to methyl group, ethyl group, propyl group, isopropyl group, butyl group, isobutyl group, pentyl group, isopentyl group, hexyl group, octyl group, decyl group, cyclopropyl group, cyclopropylmethyl group, cyclohexyl group and the like.

$C_1$-$C_6$ alkoxy group refers to a straight-chain, branched-chain or cyclic aliphatic hydrocarbon oxy group of 1 to 6 carbon atoms. Specifically, it refers to methoxy group, ethoxy group, propoxy group, isopropoxy group, butoxy group, isobutoxy group, pentyloxy group, isopentyloxy group, hexyloxy group, cyclopropoxy group, cyclopropylmethoxy group, cyclohexyloxy group and the like.

$C_6$-$C_{10}$ aryl group refers to an aromatic hydrocarbon group of 6 to 10 carbon atoms. Specifically, it refers to phenyl group or naphthyl group. Specific examples of aryl group include phenyl group, 1-naphthyl group, 2-naphthyl group and the like.

$C_7$-$C_{12}$ aralkyl group refers to a straight-chain, branched chain or cyclic aliphatic hydrocarbon group which is substituted with an aromatic hydrocarbon group and has 7 to 12 carbon atoms. Specifically, it refers to a phenylalkyl group or a naphthylalkyl group with a total number of carbon atoms of 7 to 12. Specifically, aralkyl group is exemplified by benzyl group, phenethyl group, 3-phenylpropyl group, naphthylmethyl group, 2-naphthylethyl group and the like.

In the above Formula (1), $R^1$ refers to hydrogen atom, $C_1$-$C_6$ alkyl group optionally substituted with hydroxyl group, or $C_1$-$C_6$ alkoxy group optionally substituted with hydroxyl group. Among them, it is preferably hydrogen atom, methyl group, ethyl group, propyl group, butyl group, hydroxymethyl group, 2-hydroxyethyl group, 3-hydroxypropyl group, 4-hydroxybutyl group, 2-hydroxyethoxy group, 3-hydroxypropoxy group or 4-hydroxybutoxy group, and particularly more preferably methyl group, 3-hydroxypropyl group or 3-hydroxypropoxy group.

In the above Formula (1), $R^{2a}$ and $R^{2b}$ are identical or different and refer to hydrogen atom, $C_1$-$C_{10}$ alkyl group optionally substituted with hydroxyl group, $C_6$-$C_{10}$ aryl group optionally substituted with hydroxyl group, or $C_7$-$C_{12}$ aralkyl group optionally substituted with hydroxyl group. Alternatively, $R^{2a}$ and $R^{2b}$ may be combined together to form a cyclopropane ring together with the carbon atom to which they are bonded. Preferably, a combination of $R^{2a}$ and $R^{2b}$ is hydrogen atom and methyl group, hydrogen atom and ethyl group, hydrogen atom and propyl group, hydrogen atom and isopropyl group, hydrogen atom and butyl group, hydrogen atom and isobutyl group, hydrogen atom and hexyl group, hydrogen atom and octyl group, hydrogen atom and phenyl group, hydrogen atom and phenethyl group, hydrogen atom and 2-hydroxyethyl group, two hydrogen atoms, and two methyl group. Alternatively, it is preferable that $R^{2a}$ and $R^{2b}$ may be combined together to form a cyclopropane ring together with the carbon atom to which they are bonded. Specifically, a more preferable combination of $R^{2a}$ and $R^{2b}$ is hydrogen atom and methyl group, hydrogen atom and ethyl group, hydrogen atom and butyl group, hydrogen atom and isobutyl group, hydrogen atom and hexyl group, or two methyl groups.

In the above Formula (1), when an asymmetric carbon is present in the compound structure, unless otherwise specified, the steric configuration may be either (S) configuration, (R) configuration, α configuration, or β configuration. Preferably the position 1 is α configuration and the position 3 is β configuration or the position 1 is α configuration and the position 3 is α configuration. Specifically, most preferably the position 1 is α configuration and the position 3 is β configuration. Further, when the position 2 is $C_1$-$C_6$ alkyl group optionally substituted with a hydroxyl group, or is $C_1$-$C_6$ alkoxy group optionally substituted with a hydroxyl group, the steric configuration of the position 2 is preferably α configuration. In addition, the α or β configuration used here refers to the steric configuration on the carbon atoms composing the A-ring in a vitamin $D_3$ derivative or a synthetic precursor thereof. The steric configuration which is upward against the paper surface refers to the α configuration and the steric configuration which is downward against the paper surface refers to the β configuration.

As specific examples suitable as vitamin $D_3$ derivatives represented by Formula (1) of the present invention, the compounds shown in the following Table are included. Moreover, when a compound in the Table has an asymmetric carbon, unless otherwise specified, the steric configuration may be either (S) configuration, (R) configuration, α configuration, or β configuration.

(1)

| Compound No. | R¹ | R²ᵃ/R²ᵇ |
|---|---|---|
| 101 | Hydrogen atom | Methyl group/Hydrogen atom |
| 102 | Hydrogen atom | Ethyl group/Hydrogen atom |
| 103 | Hydrogen atom | Propyl group/Hydrogen atom |
| 104 | Hydrogen atom | Isopropyl group/Hydrogen atom |
| 105 | Hydrogen atom | Butyl group/Hydrogen atom |
| 106 | Hydrogen atom | Isobutyl group/Hydrogen atom |
| 107 | Hydrogen atom | Hexyl group/Hydrogen atom |
| 108 | Hydrogen atom | Octyl group/Hydrogen atom |
| 109 | Hydrogen atom | Phenyl group/Hydrogen atom |
| 110 | Hydrogen atom | Phenethyl group/Hydrogen atom |
| 111 | Hydrogen atom | Methyl group/Methyl group |
| 112 | Hydrogen atom | Ethyl group/Ethyl group |
| 113 | Hydrogen atom | Cyclopropyl group |
| 114 | Hydrogen atom | 2-Hydroxyethyl group/Hydrogen atom |
| 201 | Methyl group | Methyl group/Hydrogen atom |
| 202 | Methyl group | Ethyl group/Hydrogen atom |
| 203 | Methyl group | Propyl group/Hydrogen atom |
| 204 | Methyl group | Isopropyl group/Hydrogen atom |
| 205 | Methyl group | Butyl group/Hydrogen atom |
| 206 | Methyl group | Isobutyl group/Hydrogen atom |
| 207 | Methyl group | Hexyl group/Hydrogen atom |
| 208 | Methyl group | Octyl group/Hydrogen atom |
| 209 | Methyl group | Phenyl group/Hydrogen atom |
| 210 | Methyl group | Phenethyl group/Hydrogen atom |
| 211 | Methyl group | Methyl group/Methyl group |
| 212 | Methyl group | Ethyl group/Ethyl group |
| 213 | Methyl group | Cyclopropyl group |
| 214 | Methyl group | 2-Hydroxyethyl group/Hydrogen atom |
| 301 | Ethyl group | Hydrogen atom/Hydrogen atom |
| 302 | Ethyl group | Methyl group/Hydrogen atom |
| 303 | Ethyl group | Ethyl group/Hydrogen atom |
| 304 | Ethyl group | Propyl group/Hydrogen atom |
| 305 | Ethyl group | Butyl group/Hydrogen atom |
| 306 | Ethyl group | Isobutyl group/Hydrogen atom |
| 307 | Ethyl group | Hexyl group/Hydrogen atom |
| 308 | Ethyl group | Octyl group/Hydrogen atom |
| 309 | Ethyl group | Phenethyl group/Hydrogen atom |
| 310 | Ethyl group | Methyl group/Methyl group |
| 311 | Ethyl group | Ethyl group/Ethyl group |
| 312 | Ethyl group | Cyclopropyl group |
| 313 | Ethyl group | 2-Hydroxyethyl group/Hydrogen atom |
| 401 | Propyl group | Hydrogen atom/Hydrogen atom |
| 402 | Propyl group | Methyl group/Hydrogen atom |
| 403 | Propyl group | Ethyl group/Hydrogen atom |
| 404 | Propyl group | Propyl group/Hydrogen atom |
| 405 | Propyl group | Butyl group/Hydrogen atom |
| 406 | Propyl group | Isobutyl group/Hydrogen atom |
| 407 | Propyl group | Hexyl group/Hydrogen atom |
| 408 | Propyl group | Octyl group/Hydrogen atom |
| 409 | Propyl group | Phenethyl group/Hydrogen atom |
| 410 | Propyl group | Methyl group/Methyl group |
| 411 | Propyl group | Ethyl group/Ethyl group |
| 412 | Propyl group | Cyclopropyl group |
| 413 | Propyl group | 2-Hydroxyethyl group/Hydrogen atom |
| 501 | Butyl group | Hydrogen atom/Hydrogen atom |
| 502 | Butyl group | Methyl group/Hydrogen atom |
| 503 | Butyl group | Ethyl group/Hydrogen atom |
| 504 | Butyl group | Propyl group/Hydrogen atom |
| 505 | Butyl group | Butyl group/Hydrogen atom |
| 506 | Butyl group | Isobutyl group/Hydrogen atom |
| 507 | Butyl group | Hexyl group/Hydrogen atom |
| 508 | Butyl group | Octyl group/Hydrogen atom |
| 509 | Butyl group | Phenethyl group/Hydrogen atom |
| 510 | Butyl group | Methyl group/Methyl group |
| 511 | Butyl group | Ethyl group/Ethyl group |
| 512 | Butyl group | Cyclopropyl group |
| 513 | Butyl group | 2-Hydroxyethyl group/Hydrogen atom |
| 601 | Hydroxymethyl group | Hydrogen atom/Hydrogen atom |
| 602 | Hydroxymethyl group | Methyl group/Hydrogen atom |
| 603 | Hydroxymethyl group | Ethyl group/Hydrogen atom |
| 604 | Hydroxymethyl group | Propyl group/Hydrogen atom |
| 605 | Hydroxymethyl group | Butyl group/Hydrogen atom |
| 606 | Hydroxymethyl group | Isobutyl group/Hydrogen atom |
| 607 | Hydroxymethyl group | Hexyl group/Hydrogen atom |
| 608 | Hydroxymethyl group | Octyl group/Hydrogen atom |
| 609 | Hydroxymethyl group | Phenethyl group/Hydrogen atom |
| 610 | Hydroxymethyl group | Methyl group/Methyl group |
| 611 | Hydroxymethyl group | Ethyl group/Ethyl group |
| 612 | Hydroxymethyl group | Cyclopropyl group |
| 613 | Hydroxymethyl group | 2-Hydroxyethyl group/Hydrogen atom |
| 701 | 2-Hydroxyethyl group | Hydrogen atom/Hydrogen atom |
| 702 | 2-Hydroxyethyl group | Methyl group/Hydrogen atom |
| 703 | 2-Hydroxyethyl group | Ethyl group/Hydrogen atom |
| 704 | 2-Hydroxyethyl group | Propyl group/Hydrogen atom |
| 705 | 2-Hydroxyethyl group | Butyl group/Hydrogen atom |
| 706 | 2-Hydroxyethyl group | Isobutyl group/Hydrogen atom |
| 707 | 2-Hydroxyethyl group | Hexyl group/Hydrogen atom |
| 708 | 2-Hydroxyethyl group | Octyl group/Hydrogen atom |
| 709 | 2-Hydroxyethyl group | Phenethyl group/Hydrogen atom |
| 710 | 2-Hydroxyethyl group | Methyl group/Methyl group |
| 711 | 2-Hydroxyethyl group | Ethyl group/Ethyl group |
| 712 | 2-Hydroxyethyl group | Cyclopropyl group |
| 713 | 2-Hydroxyethyl group | 2-Hydroxyethyl group/Hydrogen atom |
| 801 | 3-Hydroxypropyl group | Hydrogen atom/Hydrogen atom |
| 802 | 3-Hydroxypropyl group | Methyl group/Hydrogen atom |
| 803 | 3-Hydroxypropyl group | Ethyl group/Hydrogen atom |
| 804 | 3-Hydroxypropyl group | Propyl group/Hydrogen atom |
| 805 | 3-Hydroxypropyl group | Isopropyl group/Hydrogen atom |
| 806 | 3-Hydroxypropyl group | Butyl group/Hydrogen atom |

-continued

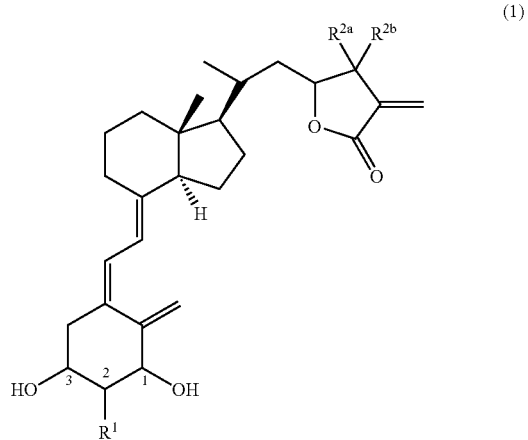
(1)

| Compound No. | $R^1$ | $R^{2a}/R^{2b}$ |
|---|---|---|
| 807 | 3-Hydroxypropyl group | Isobutyl group/Hydrogen atom |
| 808 | 3-Hydroxypropyl group | Hexyl group/Hydrogen atom |
| 809 | 3-Hydroxypropyl group | Octyl group/Hydrogen atom |
| 810 | 3-Hydroxypropyl group | Phenyl group/Hydrogen atom |
| 811 | 3-Hydroxypropyl group | Phenethyl group/Hydrogen atom |
| 812 | 3-Hydroxypropyl group | Methyl group/Methyl group |
| 813 | 3-Hydroxypropyl group | Ethyl group/Ethyl group |
| 814 | 3-Hydroxypropyl group | Cyclopropyl group |
| 815 | 3-Hydroxypropyl group | 2-Hydroxyethyl group/Hydrogen atom |
| 901 | 4-Hydroxybutyl group | Hydrogen atom/Hydrogen atom |
| 902 | 4-Hydroxybutyl group | Methyl group/Hydrogen atom |
| 903 | 4-Hydroxybutyl group | Ethyl group/Hydrogen atom |
| 904 | 4-Hydroxybutyl group | Propyl group/Hydrogen atom |
| 905 | 4-Hydroxybutyl group | Butyl group/Hydrogen atom |
| 906 | 4-Hydroxybutyl group | Isobutyl group/Hydrogen atom |
| 907 | 4-Hydroxybutyl group | Hexyl group/Hydrogen atom |
| 908 | 4-Hydroxybutyl group | Octyl group/Hydrogen atom |
| 909 | 4-Hydroxybutyl group | Phenethyl group/Hydrogen atom |
| 910 | 4-Hydroxybutyl group | Methyl group/Methyl group |
| 911 | 4-Hydroxybutyl group | Ethyl group/Ethyl group |
| 912 | 4-Hydroxybutyl group | Cyclopropyl group |
| 913 | 4-Hydroxybutyl group | 2-Hydroxyethyl group/Hydrogen atom |
| 1001 | 2-Hydroxyethoxy group | Hydrogen atom/Hydrogen atom |
| 1002 | 2-Hydroxyethoxy group | Methyl group/Hydrogen atom |
| 1003 | 2-Hydroxyethoxy group | Ethyl group/Hydrogen atom |
| 1004 | 2-Hydroxyethoxy group | Propyl group/Hydrogen atom |
| 1005 | 2-Hydroxyethoxy group | Butyl group/Hydrogen atom |
| 1006 | 2-Hydroxyethoxy group | Isobutyl group/Hydrogen atom |
| 1007 | 2-Hydroxyethoxy group | Hexyl group/Hydrogen atom |
| 1008 | 2-Hydroxyethoxy group | Octyl group/Hydrogen atom |
| 1009 | 2-Hydroxyethoxy group | Phenethyl group/Hydrogen atom |
| 1010 | 2-Hydroxyethoxy group | Methyl group/Methyl group |
| 1011 | 2-Hydroxyethoxy group | Ethyl group/Ethyl group |
| 1012 | 2-Hydroxyethoxy group | Cyclopropyl group |
| 1013 | 2-Hydroxyethoxy group | 2-Hydroxyethyl group/Hydrogen atom |
| 1101 | 3-Hydroxypropoxy group | Hydrogen atom/Hydrogen atom |
| 1102 | 3-Hydroxypropoxy group | Methyl group/Hydrogen atom |
| 1003 | 3-Hydroxypropoxy group | Ethyl group/Hydrogen atom |
| 1104 | 3-Hydroxypropoxy group | Propyl group/Hydrogen atom |
| 1105 | 3-Hydroxypropoxy group | Isopropyl group/Hydrogen atom |
| 1106 | 3-Hydroxypropoxy group | Butyl group/Hydrogen atom |
| 1107 | 3-Hydroxypropoxy group | Isobutyl group/Hydrogen atom |
| 1108 | 3-Hydroxypropoxy group | Hexyl group/Hydrogen atom |
| 1109 | 3-Hydroxypropoxy group | Octyl group/Hydrogen atom |
| 1110 | 3-Hydroxypropoxy group | Phenyl group/Hydrogen atom |
| 1111 | 3-Hydroxypropoxy group | Phenethyl group/Hydrogen atom |
| 1112 | 3-Hydroxypropoxy group | Methyl group/Methyl group |
| 1113 | 3-Hydroxypropoxy group | Ethyl group/Ethyl group |
| 1114 | 3-Hydroxypropoxy group | Cyclopropyl group |
| 1115 | 3-Hydroxypropoxy group | 2-Hydroxyethyl group/Hydrogen atom |
| 1201 | 4-Hydroxybutoxy group | Hydrogen atom/Hydrogen atom |

-continued

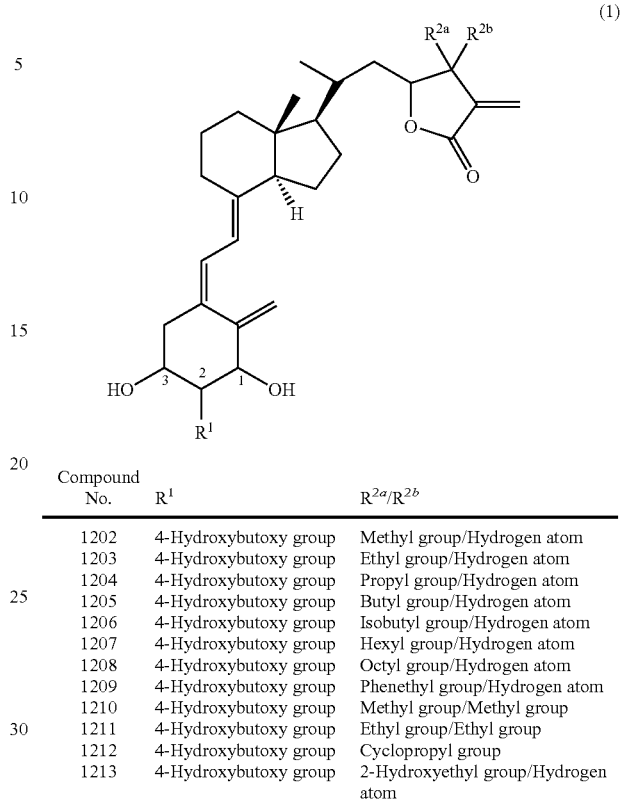
(1)

| Compound No. | $R^1$ | $R^{2a}/R^{2b}$ |
|---|---|---|
| 1202 | 4-Hydroxybutoxy group | Methyl group/Hydrogen atom |
| 1203 | 4-Hydroxybutoxy group | Ethyl group/Hydrogen atom |
| 1204 | 4-Hydroxybutoxy group | Propyl group/Hydrogen atom |
| 1205 | 4-Hydroxybutoxy group | Butyl group/Hydrogen atom |
| 1206 | 4-Hydroxybutoxy group | Isobutyl group/Hydrogen atom |
| 1207 | 4-Hydroxybutoxy group | Hexyl group/Hydrogen atom |
| 1208 | 4-Hydroxybutoxy group | Octyl group/Hydrogen atom |
| 1209 | 4-Hydroxybutoxy group | Phenethyl group/Hydrogen atom |
| 1210 | 4-Hydroxybutoxy group | Methyl group/Methyl group |
| 1211 | 4-Hydroxybutoxy group | Ethyl group/Ethyl group |
| 1212 | 4-Hydroxybutoxy group | Cyclopropyl group |
| 1213 | 4-Hydroxybutoxy group | 2-Hydroxyethyl group/Hydrogen atom |

Among the compounds listed in the table, specifically preferable compounds are Compound No. 101 (wherein the configuration of the 1-position is α configuration and the configuration of the 3-position is β configuration (hereinafter referred to as (1α, 3β)), 102 (1α, 3β), 103 (1α, 3β), 104 (1α, 3β), 105 (1α, 3β), 106 (1α, 3β), 107 (1α, 3β), 108 (1α, 3β), 109 (1α, 3β), 110 (1α, 3β), 111 (1α, 3β), 113 (1α, 3β), 114 (1α, 3β), 201 (1α, 2α, 3β), 202 (1α, 2α, 3β), 205 (1α, 2α, 3β), 206 (1α, 2α, 3β), 207 (1α, 2α, 3β), 209 (1α, 2α, 3β), 211 (1α, 2α, 3β), 810 (1α, 2α, 3β), 802 (1α, 2α, 3β), 803 (1α, 2α, 3β), 806 (1α, 2α, 3β), 808 (1α, 2α, 3β), 810 (1α, 2α, 3β), 812 (1α, 2α, 3β), 1101 (1α, 2α, 3β), 1102 (1α, 2α, 3β), 1103 (1α, 2α, 3β), 1106 (1α, 2α, 3β), 1108 (1α, 2α, 3β), 1110 (1α, 2α, 3β) and 1112 (1α, 2α, 3β).

Furthermore, a vitamin $D_3$ derivative of the present invention can be converted to a pharmaceutically acceptable solvate thereof when necessary. Examples of such solvents include water, methanol, ethanol, propyl alcohol, isopropyl alcohol, butanol, t-butanol, acetonitrile, acetone, methylethyl ketone, chloroform, ethyl acetate, diethyl ether, t-butylmethyl ether, benzene, toluene, DMF, DMSO and the like. Specifically preferable solvents are exemplified by water, methanol, ethanol, propyl alcohol, isopropyl alcohol, acetolnitrile, acetone, methylethyl ketone and ethyl acetate.

A Vitamin $D_3$ derivative represented by the above Formula (1) can be synthesized as follows. That is, an aldehyde compound represented by the following Formula (2) (Z=(2-1)) is reacted with an acrylic acid derivative represented by the following Formula (3a) to be converted to a lactone compound represented by the following Formula (4) (Z=(2-1)), and the resultant lactone compound is coupled with an enyne compound represented by the following Formula (7) in the presence of a palladium catalyst, followed by deprotection of protective groups of hydroxyl groups, forming a vitamin D$_3$ derivative (Scheme 1).

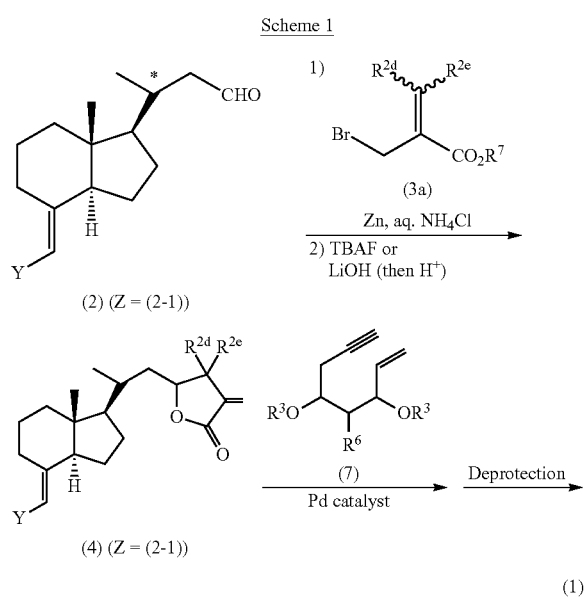

[In the scheme described above, Y, R$^3$ and R$^6$ have the same definition as in the above Formula (2). R$^7$ has the same definition as in Formula (3) described above. R$^{2d}$ and R$^{2e}$ have the same definition as in Formula (4) described above.]

An aldehyde compound (2) (Z=(2-1)) used herein in which the configuration of a carbon with an asterisk (*) has an (R) structure can be produced, for example, by a combination of a well-known method which is illustrated by Scheme 2 described below.

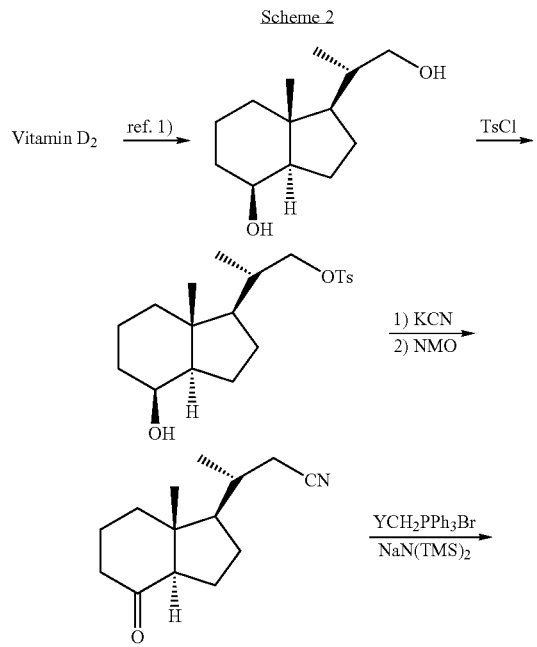

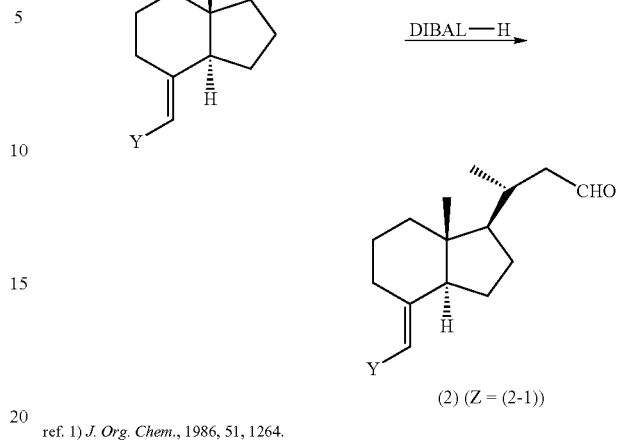

ref. 1) *J. Org. Chem.*, 1986, 51, 1264.

[In Scheme 2 described above, Y has the same definition as in Formula (2) described above.]

In addition, these compounds (2) (Z=(2-1)) in which the steric configuration of a carbon with an asterisk (*) has an (S) structure can be produced, for example, using the intermediate diol produced in Scheme 2 by a method which is illustrated in Scheme 3 described below.

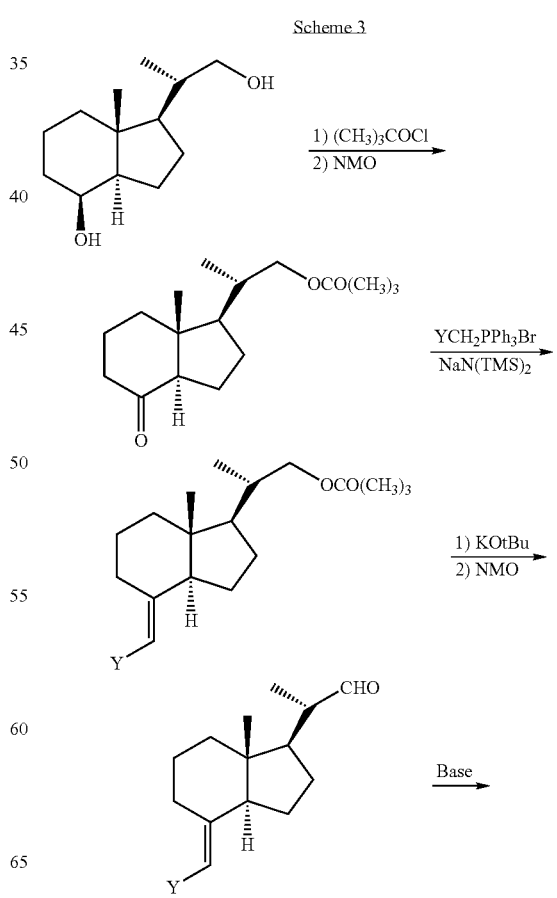

-continued

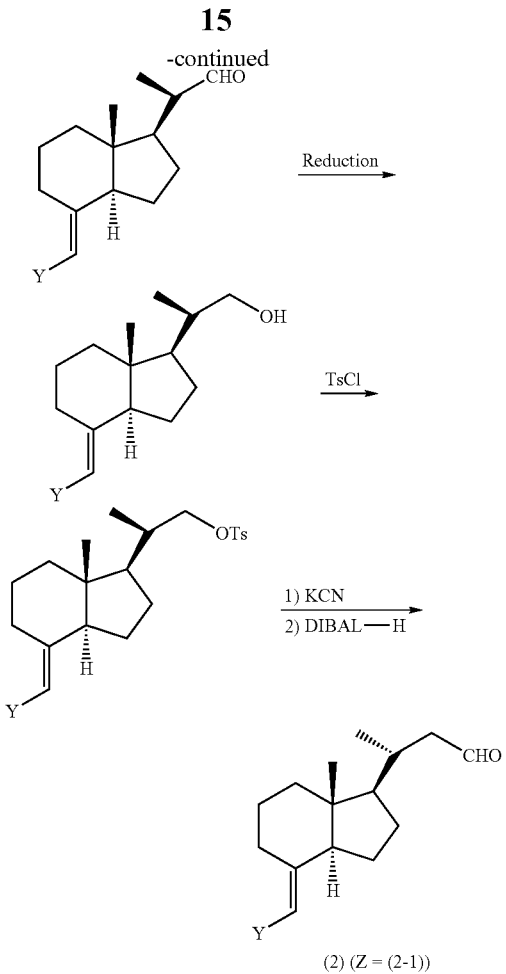

(2) (Z = (2-1))

[In the scheme described above, Y has the same definition as in Formula (2) described above.]

An acrylic acid derivative (3a) used in Scheme 1 can be produced as follows.

An acrylic acid derivative in which both $R^{2d}$ and $R^{2e}$ are hydrogen atoms is commercially available.

An acrylic acid derivative in which one of $R^{2d}$ and $R^{2e}$ is a hydrogen atom and the other is not a hydrogen atom can be obtained by a method described in the literature (for example, Helv. Chem. Acta, Vol. 67, 413-415, 1984). An acrylic acid derivative in which neither $R^{2d}$ nor $R^{2e}$ are hydrogen atoms can be obtained, for example, by a method illustrated in Scheme 4 described below.

Scheme 4

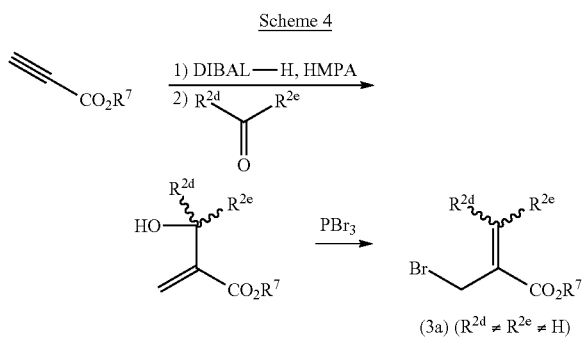

(3a) ($R^{2d} \neq R^{2e} \neq H$)

[In the scheme described above, $R^7$ has the same definition as in Formula (3) described above. $R^{2d}$ and $R^{2e}$ have the same definition as in Formula (4) described above.]

The conversion to a lactone compound represented by (4) (Z=(2-1)) by reacting a compound represented by (2) (Z=(2-1)) with a compound represented by (3a), for example, as illustrated in Scheme 1, can be carried out by reacting the compound represented by (2) (Z=(2-1)) with the compound represented by (3a) in the presence of zinc and an aqueous ammonium chloride solution, followed by treating the resultant hydroxyl ester compound with tetra-n-butylammonium fluoride (TBAF), or by hydrolyzing the resultant ester then treating with dilute hydrochloric acid when needed.

Furthermore, the enyne compound (7) used in Scheme 1 can be obtained by a method described in the literature. For example, the method is described in: Trost et al., J. Am. Chem. Soc., Vol. 114, 9836-9845, 1992, Tetrahedron Lett., Vol. 35, 8119-8122, 1994, etc. in the case where $R^3$ is t-butylmethylsilyl (TBS) group and $R^6$ is a hydrogen atom; in Konno et al. J. Med. Chem., Vol. 43, 4247-4265, 2000 etc. in the case where $R^3$ is TBS group and $R^6$ is methyl group; Suhara et al., J. Org. Chem., Vol. 66, 8760-8771, 2001 etc. in the case where $R^3$ is t-butyldimethylsilyl group and $R^6$ is ethyl group, propyl group, butyl group, t-butyldimethylsilyloxymethyl group, 2-t-butyldimethylsilyloxyethyl group, 3-t-butyldimethylsilyloxypropyl group and 4-t-butyldimethylsilyloxybutyl group; and in Kittaka et al., Org. Lett. Vol. 2, 2619-2622, 2000 etc. in the case where $R^3$ is t-butyldimethylsilyl (TBS) group and $R^6$ is 2-t-butyldimethylsilyloxyethoxy group, 3-t-butyldimethylsilyloxypropoxy group and 4-t-butyldimethylsilyloxybutoxy group.

The coupling reaction of the compound represented by (4) (Z=(2-1)) with the compound represented by (7) can be conducted by the method of Trost et al. (J. Am. Chem. Soc., Vol. 114, 9836-9845, 1992).

The deprotection reaction of the protective group of the hydroxyl group of the resultant coupling product can be performed according to a well-known method (for example, refer to Green et al., Protective Groups in Organic Synthesis, 3rd edition, John Wiley & Sons, Inc., 1999).

More specifically, when the protective group is an acetyl group or a benzoyl group, usual alkaline hydrolysis, potassium cyanide, ammonia-methanol and the like can be used for the deprotection reaction. When the protective group is a methoxymethyl group or a tetrahydro-4H-pyran-2-yl group, for example, hydrochloric acid, acetic acid, trifluoroacetic acid and the like under acidic conditions, or pyridinium p-toluene sulfonate (PPTS) and the like can be used for the deprotection reaction. When the protective group is a tri (alkyl/aryl)silyl group such as trimethylsilyl group, triethylsilyl group, triisopropylsilyl group, t-butyldimethylsilyl group, t-butyldiphenylsilyl group, etc., the deprotection reaction can be carried out according to a method known in the art. For example, TBAF, PPTS (pyridinium p-toluene sulfonate), p-toluene sulfonic acid, hydrogen fluoride, camphor sulfonic acid, hydrochloric acid, sulfuric acid, a reagent composed of a combination of a tetrafluoroborate alkali metal salt and sulfuric acid and the like can be used in the deprotection reaction.

Moreover, a vitamin $D_3$ derivative represented by the above Formula (1) in which $R^{2a}$ and $R^{2b}$ are combined together to represent a cyclopropyl group together with the carbon atom to which they are bonded, can be obtained by carrying out the reaction according to Scheme 1 described above by using the compound (4) (Z=(2-1), $R^{2d}$—$R^{2e}$=$CH_2$—$CH_2$). The compound (4) (Z=(2-1), $R^{2d}$—$R^{2e}$=$CH_2$—$CH_2$), can be produced, for example, according to Scheme 5 described below.

That is, an acetylene compound represented by Formula (9) described below is obtained by reacting an aldehyde compound represented by Formula (2) (Z=(2-1)) described below with an acetylene compound represented by Formula (8) described below, followed by protecting the resultant hydroxyl group. Ethylene is added to the acetylene compound using the Grubbs complex to obtain a diene compound represented by Formula (10) described below. Next, after selectively deprotecting the protective group ($R^{10}$) of the hydroxyl group, the diene compound is subjected to cyclopropanization to obtain a cyclopropane compound represented by Formula (11) described below. After deprotecting of the protective group ($R^9$) of the hydroxyl group, the resultant primary hydroxyl group is oxidized to form a lactone ring, yielding the compound (4) (Z=(2-1), $R^{2d}$—$R^{2e}$=$CH_2$—$CH_2$).

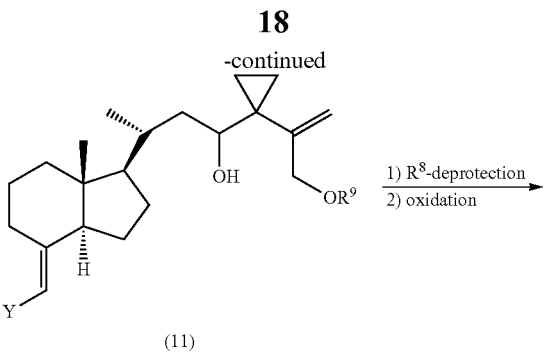

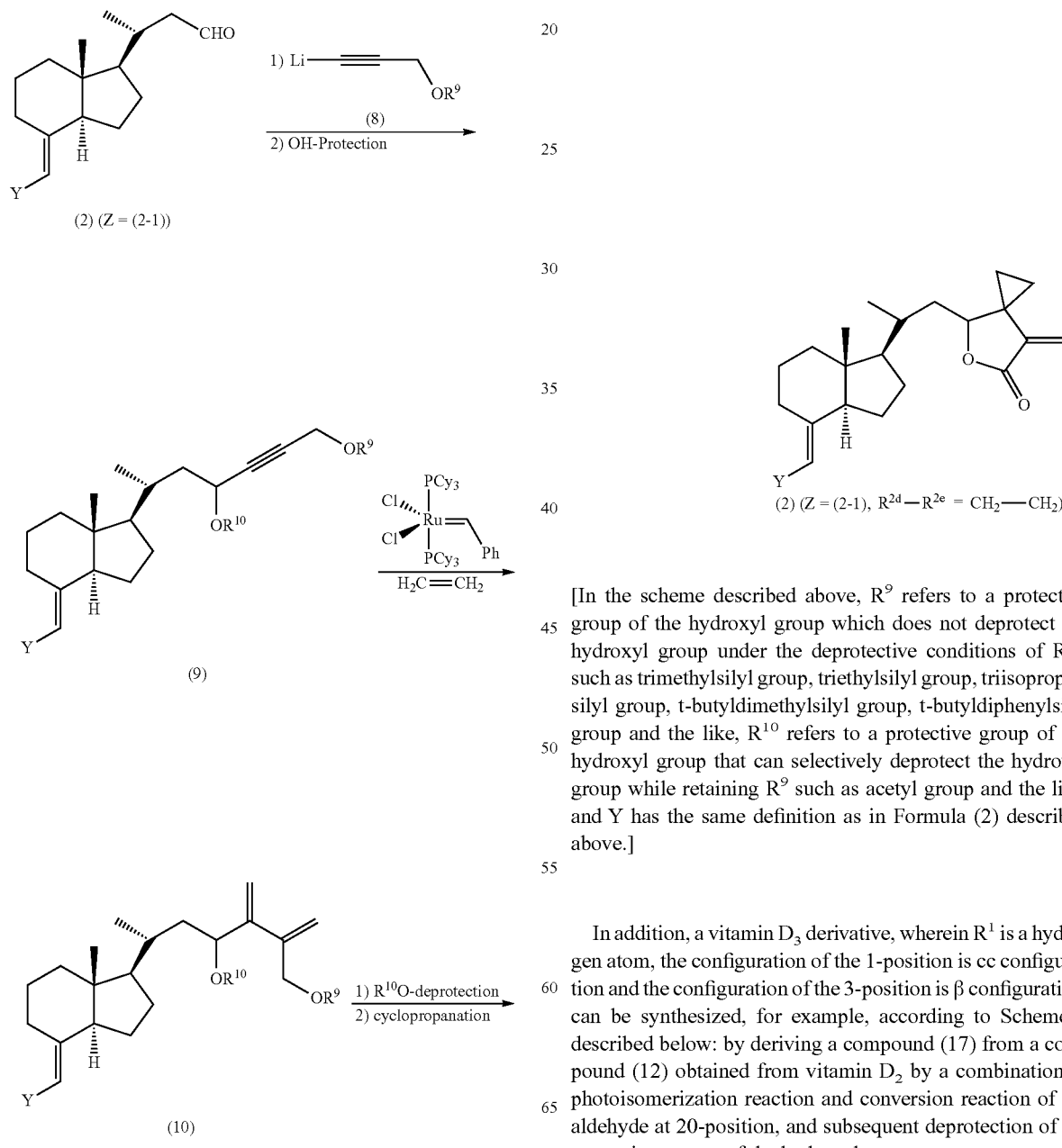

[In the scheme described above, $R^9$ refers to a protective group of the hydroxyl group which does not deprotect the hydroxyl group under the deprotective conditions of $R^{10}$, such as trimethylsilyl group, triethylsilyl group, triisopropylsilyl group, t-butyldimethylsilyl group, t-butyldiphenylsilyl group and the like, $R^{10}$ refers to a protective group of the hydroxyl group that can selectively deprotect the hydroxyl group while retaining $R^9$ such as acetyl group and the like, and Y has the same definition as in Formula (2) described above.]

In addition, a vitamin $D_3$ derivative, wherein $R^1$ is a hydrogen atom, the configuration of the 1-position is α configuration and the configuration of the 3-position is β configuration, can be synthesized, for example, according to Scheme 6 described below: by deriving a compound (17) from a compound (12) obtained from vitamin $D_2$ by a combination of photoisomerization reaction and conversion reaction of the aldehyde at 20-position, and subsequent deprotection of the protective groups of the hydroxyl group.

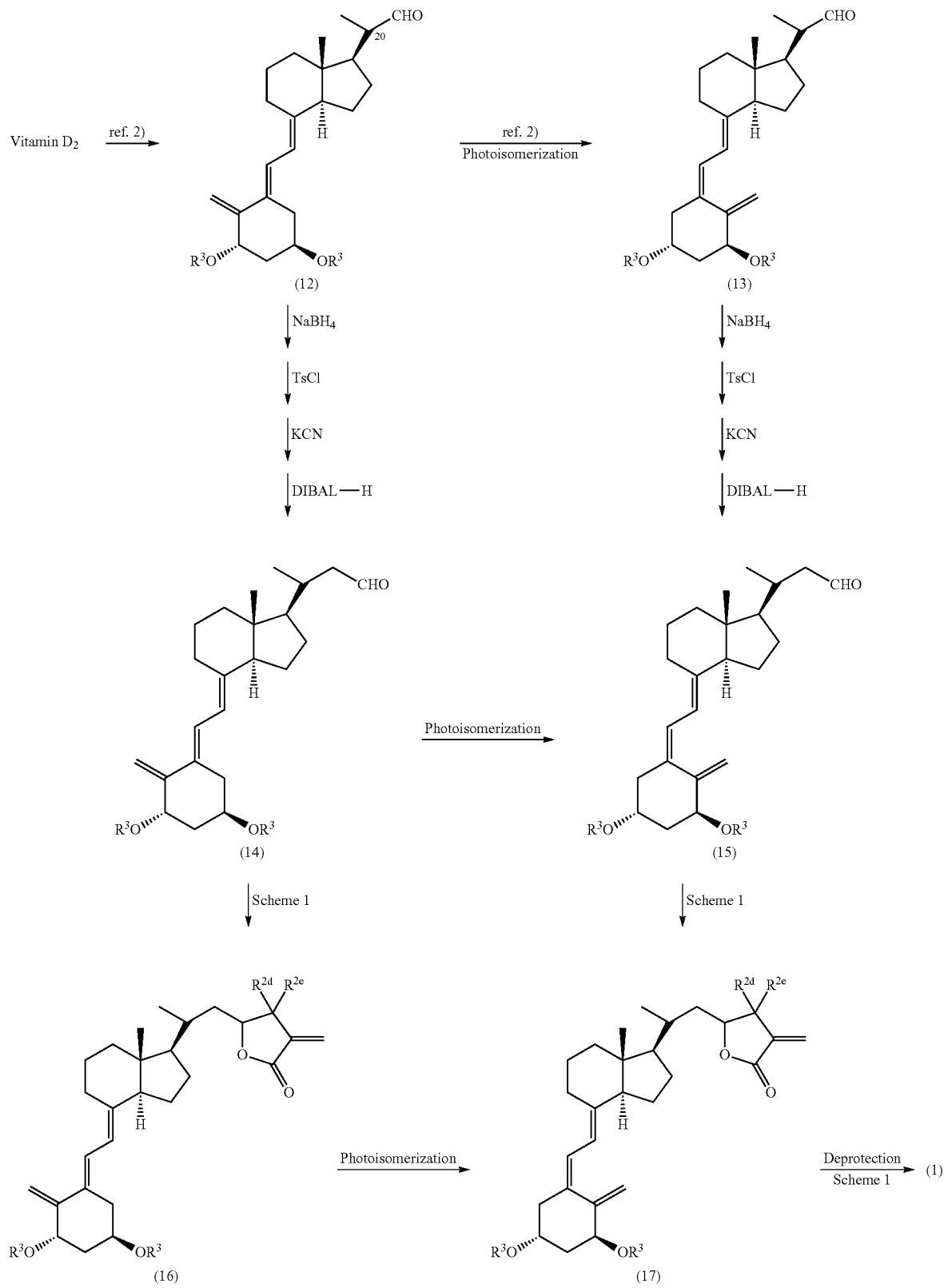
ref. 2) *Tetrahedron*, 1987, 20, 4609.

[In the scheme described above, $R^3$ has the same definition as in Formula (2) described above. $R^{2d}$ and $R^{2e}$ have the same definition as in Formula (4) described above.]

The compound represented by Formula (12) described above and Formula (13) described above used here can be obtained from vitamin $D_2$ by a method described in the literature (Tetrahedron, Vol. 43 (原原の間違い), 4609-4619, 1987).

The conversion of the compound represented by Formula (14) described above into the compound represented by Formula (15) described above and the compound represented by Formula (16) described above into the compound represented by Formula (17) described above can be accomplished by photoisomerization using the method similar to the conversion of the compound represented by Formula (12) described above into the compound represented by Formula (13) described above.

The conversion of the compound represented by the Formula (14) described above into the compound represented by the Formula (16) described above, the compound represented by the Formula (15) described above into the compound represented by the above Formula (17) and the compound represented by the Formula (17) described above into the compound represented by the Formula (1) described above can be carried out by the method similar to that described in Scheme 1.

Furthermore, among the above-mentioned lactone compounds (4), for compounds in which one of $R^{2d}$ and $R^{2e}$ is a hydrogen atom and the other is not a hydrogen atom, a compound (syn) in which the relative configuration between carbon a to which an oxygen atom is bonded on the lactone ring and the adjacent carbon b to which $R^2$ is bonded is syn and a compound (anti) in which that configuration is anti can be obtained selectively by a method described in the following Scheme 7. That is, an aldehyde compound represented by Formula (2) can be reacted with an acrylic acid ester compound represented by Formula (3) in the presence of bivalent chromium to selectively obtain a syn compound (4syn) (refer to Okuda et al., Chemistry Letters, 481-484, 1985). A compound (4anti) in which the relative configuration between carbon a to which an oxygen atom is bonded on the lactone ring and the adjacent carbon b to which R is bonded is anti can be obtained in the following manner. That is, the lactone ring of the (4syn) compound obtained is reduced, and an alcohol compound represented by (5syn) is obtained by protecting the primary hydroxyl group formed in the above reduction step. The secondary hydroxyl group of this compound is oxidized to obtain a ketone compound represented by (6), whose ketone group is reduced to obtain an alcohol compound represented by (5anti). Lastly, $R^8$ of this compound is deprotected, and the resultant primary hydroxyl group is oxidized to form a lactone ring, yielding the desired compound. By carrying out the reactions of Schemes 1 and 5 using these stereoselectively obtained (4syn) and (4anti) compounds, the compound (1) in which the configuration of the asymmetric carbon to which an oxygen atom is bonded on the lactone ring and the adjacent asymmetric carbon to which $R^2$ is bonded can be stereoselectively obtained.

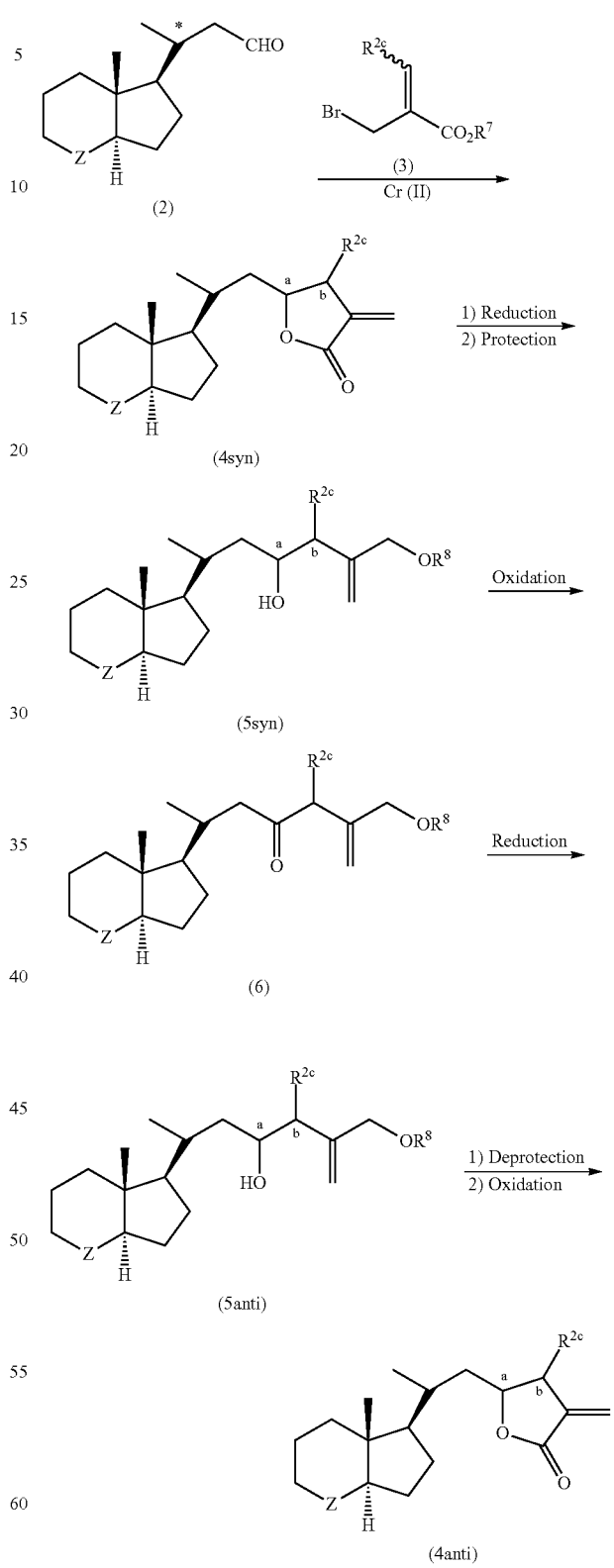

In the above Formulas (2), (4syn), (5syn), (6), (5anti) and (4anti), Z refers to any one of the following Formulas (2-1), (2-2), (2-3), (2-4) and (2-5).

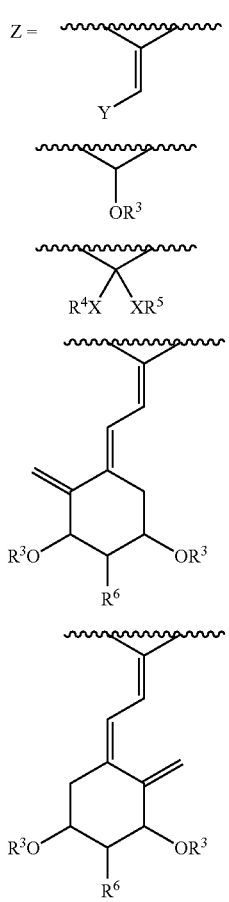

(2-1)
(2-2)
(2-3)
(2-4)
(2-5)

In the above Formula (2-1), Y refers to a bromine atom or an iodine atom. Among these, bromine atom is preferable.

In the above Formulas (2-2), (2-4) and (2-5), $R^3$ refers to trimethylsilyl group, triethylsilyl group, triisopropylsilyl group, t-butyldimethylsilyl group, t-butyldiphenylsilyl group, acetyl group, benzoyl group, methoxymethyl group or tetrahydro-4H-pyran-2-yl group. Among them, it is preferably trimethylsilyl group, t-butyldimethylsilyl group, t-butyldiphenyl group and methoxymethyl group.

In the above Formula (2-3), $R^4$ and $R^5$ each independently refer to methyl group, ethyl group, propyl group, or trichloroethyl group; or to ethylene group or propylene group when $R^4$ and $R^5$ are combined. Among these, it is preferably methyl group, ethylene group when $R^4$ and $R^5$ are combined or propylene group when $R^4$ and $R^5$ are combined.

In the above Formula (2-3), X refers to oxygen atom or sulfur atom. Among them, oxygen atom is preferable.

In the above Formula (2-4) and (2-5), $R^6$ refers to hydrogen atom, $C_1$-$C_6$ alkyl group optionally substituted with hydroxyl group protected by a group defined by $R^3$ or $C_1$-$C_6$ alkoxy group optionally substituted with hydroxyl group protected by a group defined by $R^3$. Among them, it is preferably hydrogen atom, methyl group, ethyl group, propyl group, butyl group, trimethylsilyloxymethyl group, t-butyldimethylsilyloxymethyl group, 2-trimethylsilyloxyethyl group, 2-t-butyldimethylsilyloxyethyl group, 3-trimethylsilyloxypropyl group, 3-t-butyldimethylsilyloxypropyl group, 4-trimethylsilyloxybutyl group, 4-t-butyldimethylsilyloxybutyl group, 2-trimethylsilyloxyethoxy group, 2-t-butyldimethylsilyloxyethoxy group, 3-trimethylsilyloxypropoxy group, 3-t-butyldimethylsilyloxypropoxy group, 4-trimethylsilyloxybutoxy group or 4-t-butyldimethylsilyloxybutoxy group, and particularly it is more preferably methyl group, 3-t-butyldimethylsilyloxypropyl group or 3-t-butyldimethylsilyloxypropoxy group.

In the above Formulas (3), (4syn), (5syn), (6), (5anti) and (4anti), $R^{2c}$ refers to $C_1$-$C_{10}$ alkyl group optionally substituted with hydroxyl group protected by a group defined by $R^3$, $C_6$-$C_{10}$ aryl group optionally substituted with hydroxyl group protected by a group defined by $R^3$ or $C_7$-$C_{12}$ aralkyl group optionally substituted with hydroxyl group protected by a group defined by $R^3$. Among them, it is preferably methyl group, ethyl group, propyl group, isopropyl group, butyl group, isobutyl group, hexyl group, octyl group, phenyl group, phenethyl group or 2-hydroxyethyl group, and particularly more preferably methyl group, ethyl group, butyl group, isobutyl group or hexyl group.

In the above formula (3), $R^7$ refers to $C_1$-$C_6$ alkyl group. Among others, it is preferably methyl group or ethyl group.

In the above Formulas (5syn), (5anti) and (6), $R^8$ refers to acetyl group, 4-oxopentanoyl group, pivaroyl group, benzoyl group, triisopropylsilyl group, t-butyldimethylsilyl group or t-butyldiphenylsilyl group. Among others, it is preferably pivaroyl group or benzoyl group.

In the reaction in which the aldehyde compound represented by Formula (2) is reacted with the acrylic acid derivative represented by Formula (3) in the presence of divalent chromium to obtain (4syn), divalent chromium can be generated by mixing chromium chloride (III) with lithium aluminum hydride (LAH) in the reaction system or chromium chloride (II) can be used. Examples of organic solvents used for the reaction include a halogen-based solvent such as methylene chloride, chloroform, carbon tetrachloride and the like; a hydrocarbon-based solvent such as hexane, toluene and the like; an ether-based solvent such as tetrahydrofuran (THF), dioxane and the like; a water-soluble solvent such as N,N-dimethylformamide, acetonitrile and the like; and a mixed solvent thereof, which can be selected in view of the solubility and reactivity of the compound. Particularly THF is preferable. Typically a reaction temperature between −20° C. and the boiling point of a solvent is employed, and specifically the range from 0° C. to room temperature is preferable. The reaction time varies depending on reaction raw materials, reaction solvents and reaction temperatures, and usually it is desirable to continue the reaction until starting materials disappear by using analytical tools such as thin-layer chromatography.

The reaction in which the lactone ring of the lactone compound represented by (4syn) is reduced, and subsequently the resultant primary hydroxyl group is protected to yield the alcohol compound represented by (5syn) can be carried out as follows. The reduction reaction can be carried out with diisobutylaluminum hydride (DIBAL-H), LAH or sodium borohydride. Specifically DABAL-H is preferable. Examples of organic solvents used in the reaction include a halogen-based solvent such as methylene chloride, chloroform, carbon tetrachloride and the like; a hydrocarbon-based solvent such as hexane, toluene and the like; an ether-based solvent such as tetrahydrofuran (THF), dioxane and the like; a water-soluble solvent such as N,N-dimethylformamide, acetonitrile and the like; and a mixed solvent thereof, which can be selected in view of the solubility and reactivity of the compound. Specifically, toluene, THF and methanol are preferable. Typically a reaction temperature between −78° C. and the boiling point of a solvent is employed, and specifically the range from 0° C. to room temperature is preferable. The reaction time varies depending on reaction raw materials, reaction solvents and reaction temperatures, and usually it is desirable to continue the reaction until starting materials disappear by using analytical tools such as thin-layer chromatography. The reaction for protecting a primary hydroxyl group, of which reaction conditions vary by a protective group, can be performed according to a method described in the literature (Protective Groups in Organic Synthesis, 3rd edition, John Wiley & Sons, Inc, 1999).

The reaction in which the secondary hydroxyl group of the alcohol compound represented by (5syn) is oxidized to obtain the ketone compound represented by (6) can be carried out using a combination of tetrapropylammonium perruthenate ($Pr_4NRuO_4$) and N-methylmorphorine N-oxide (NMO), a combination of dichlorotris(triphenylphosphine) ruthenium (II) and NMO, pyridinium chlorocromate (PCC) or pyridinium dicromate (PDC) and the like. Examples of organic solvents used in the reaction include a halogen-based solvent such as methylene chloride, chloroform, carbon tetrachloride and the like; a hydrocarbon-based solvent such as hexane, toluene and the like; an ether-based solvent such as tetrahydrofuran (THF), dioxane and the like; a water-soluble solvent such as N,N-dimethylformamide, acetonitrile, acetone and the like; and a mixed solvent thereof, which can be selected in view of the solubility and reactivity of the compound. Specifically toluene, THF and methanol are preferable. Typically a reaction temperature between −78° C. and the boiling point of a solvent is employed, and specifically the range from −20° C. to room temperature is preferable. The reaction time varies depending on reaction raw materials, reaction solvents and reaction temperatures, and usually it is desirable to continue the reaction until starting materials disappear by using analytical tools such as thin-layer chromatography.

The reaction in which the ketone group of the ketone compound represented by (6) is reduced to obtain the alcohol compound represented by (5anti) can be carried out by using lithium aluminum hydride triisopropoxide, lithium aluminum hydride, sodium borohydride or K-Selectride. Specifically lithium aluminum hydride triisopropoxide and lithium aluminum hydride are preferable. Examples of organic solvents used in the reaction include a halogen-based solvent such as methylene chloride, chloroform, carbon tetrachloride and the like; a hydrocarbon-based solvent such as hexane, toluene and the like; an ether-based solvent such as tetrahydrofuran (THF), dioxane and the like; a water-soluble solvent such as N,N-dimethylformamide, acetonitrile, acetone and the like; and a mixed solvent thereof, which can be selected in view of solubility and reactivity of the compound. Specifically THF and methanol are preferable. Typically a reaction temperature between −78° C. to the boiling point of a solvent is employed. Specifically the range from −20° C. to room temperature is preferable. The reaction time varies depending on reaction raw materials, reaction solvents and the reaction temperature, and usually it is desirable to continue the reaction until starting materials disappear by using analytical tools of analysis thin-layer chromatography.

The reaction, in which the $R^8$ portion of the alcohol compound represented by (5anti) is deprotected and the resultant primary hydroxyl group is oxidized to form a lactone ring, to yield the lactone compound represented by (4anti), can be carried out as follows. The reaction for protecting the primary hydroxyl group, of which reaction conditions vary by the protective group, can be performed according to a method described in the literature (Green et al., Protective Groups in Organic Synthesis, 3rd edition, John Wiley & Sons, Inc, 1999). The oxidization reaction can be conducted by manganese dioxide, $AgCO_3$-Celite or platinum dioxide. Examples of organic solvents used in the reaction include a halogen-based solvent such as methylene chloride, chloroform, carbon tetrachloride and the like; a hydrocarbon-based solvent such as hexane, benzene, toluene and the like; an ether-based solvent such as tetrahydrofuran (THF), dioxane and the like; a water-soluble solvent such as N,N-dimethylformamide, acetonitrile and the like; and a mixed solvent thereof, which can be selected in view of the solubility and reactivity of the compound. Specifically methylene chloride, toluene, THF and methanol are preferable. Typically a reaction temperature between −78° C. and the boiling point of a solvent is employed. Specifically the range from −20° C. to room temperature is preferable. The reaction time varies depending on reaction raw materials, reaction solvents and the reaction temperature, and usually it is desirable to continue the reaction until starting materials disappear by using analytical tools such as thin-layer chromatography.

These resultant compounds represented by the above Formula (4syn) or (4anti) can be converted to a vitamin $D_3$ lactone derivative represented by Formula (1) as follows. That is, in the case of Z=(2-1), the compounds can be reacted according to Scheme 1 to be converted to a vitamin $D_3$ lactone derivative (1). In the case of Z=(2-2) and Z=(2-3), the compounds can be reacted according to Scheme 8 described below to be converted to a vitamin $D_3$ lactone derivative (1). More specifically, the compound (18) can be obtained by oxidizing an alcohol, which is obtained by deprotecting the protective group, $R^3$ of the hydroxy group, to a ketone group in the case of Z=(2-2), and deprotecting the protective group, $R^4X/R^5X$ of the ketone group in the case of Z=(2-3). The compound (18) can be bromomethylenated or iodomethylenated to yield the compound (4syn) (Z=(2-1)) or the compound (4anti) (Z=(2-1)). The resultant compound can be converted to the vitamin $D_3$ lactone derivative (1) by carrying out the reaction according to Scheme 1. Moreover, the compound (18) can also be converted to the vitamin $D_3$ lactone derivative (1) by carrying out the Wittig reaction with a compound (19) obtained by a method described in the literature (for example, J. Org. Chem., Vol. 67, 1580, 2002), and then by deprotecting the protective group of the hydroxyl group of the resultant triene derivative.

Scheme 8

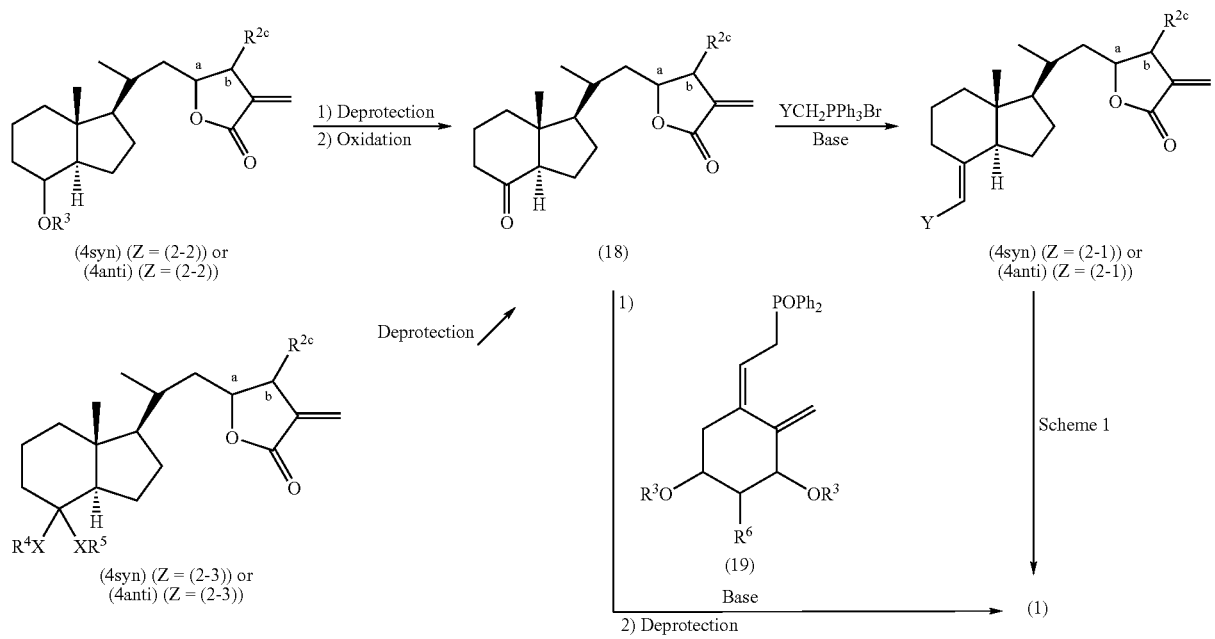

In the case of Z=(2-4) or Z=(2-5), the compounds can be reacted according to Scheme 6 to be converted to a vitamin $D_3$ lactone derivative (1).

The vitamine $D_3$ lactone derivative obtained by the above methods can be converted to the previously described pharmaceutically acceptable solvate when needed.

In addition, the present invention is a therapeutic agent which contains a therapeutic effective amount of the vitamin $D_3$ derivative represented by the above Formula (1) or a pharmaceutically acceptable solvate thereof for Paget's disease of bone or hypercalcemia.

The therapeutic agent of the present invention can be administered orally or parenterally including intravenous, subcutaneous, intramuscular, transdermal, transnasal, intrarectal and the like or by inhalation.

Dosage forms for oral administration include tablets, pills, powders, granules, solutions, suspensions, syrups, capsules and the like.

In accordance with conventional methods in preparing tablets, additives are used to formulate tablets, examples of which include an excipient such as lactose, starch, calcium carbonate, crystalline cellulose, hydrated silica or the like; a binding agent such as carboxymethylcellulose, methylcellulose, calcium phosphate, polyvinyl pyrrolidone or the like; a disintegrating agent such as sodium alginate, sodium bicarbonate, sodium lauryl sulfate, monoglyceride stearate or the like; a lubricating agent such as glycerine or the like; an absorbent such as kaolin, colloidal silica or the like; and a lubricating agent such as talc, granular boric acid or the like.

Pills, powders or granules are also formulated with the above additives in accordance with conventional methods.

Liquid formulations such as solutions, suspensions, syrups and the like are formulated in accordance with conventional methods. A carrier is exemplified by glycerol esters such as tricaprilin, triacetin, fatty acid esters of iodized poppy seed oil and the like; water; alcohols such as ethanol and the like; and oily bases such as liquid paraffin, coconut oil, soybean oil, sesame oil, corn oil and the like.

A capsule formulation is prepared by filling powders, granules, solutions and the like into a capsule.

A parenteral injection in the form of a sterile, aqueous or nonaqueous solution includes dosage forms for intravenous, subcutaneous and intramuscular administration. As an aqueous solution, for example, physiological saline is used. As a nonaqueous solution, for example, polypropylene glycol, polyethylene glycol, a vegetable oil such as olive oil or injectable organic esters such as ethyl oleate, fatty-acid ester of iodized poppy seed oil and the like are used. To these formulations are added an isotonic agent, a preservative, a wetting agent, an emulsifying agent, a dispersant, a stabilizer and the like when needed. In addition, the formulations can be sterilized by conducting filtration of passing through a bacteria-holding filter, addition of a pesticide, treatment with irradiation and the like where necessary. Also, an aseptic solid preparation can be synthesized to be used by dissolving in sterile water or a sterile solvent for injection immediately before use. Further, the compound of the present invention can be used by forming a clathrate compound with α-, β-, or γ-cyclodextrin, methylated cyclodextrin etc., or may be used as an injection in lipo-injection.

Dosage forms of medicaments for dermal administration include ointments, creams, lotions, solutions and the like. Ointment bases include, for example, fatty oils such as castor oil, olive oil, sesame oil, safflower oil and the like; lanolin; white, yellow or hydrophilic vaseline; wax; higher alcohols such as oleyl alcohol, isostearyl alcohol, octyldecanol, hexyldecanol and the like; glycols such as glycerine, diglycerine, ethyleneglycol, propyleneglycol, sorbitol, 1,3-butanediol and the like. Ethanol, dimethylsufoxide, polyethyleneglycol etc. may also be used as a solubilizing agent of the compound of the present invention. Moreover, preservatives such as p-oxybenzoate ester, sodium benzoate, salicylic acid, sorbic acid, boric acid and the like; and antioxidants such as butylhydroxyanisole, dibutylhydroxytoluene and the like may be used when necessary. Further, absorption promoters such as diisopropyl adipate, diethyl sebacate, ethyl caproate, ethyl laurate and the like may be added to enhance percutaneous absorption. Also, in order to provide stability, the compound of the present invention can also be used by forming a clathrate compound with α-, β-, or γ-cyclodextrin, methylated cyclodextrin and the like.

Ointments can be synthesized by conventional methods. A dosage form of an oil-in-water type cream formulation is preferable as the cream formulation in improving the stability of the compound of the present invention. In addition, as mentioned above, fatty oil, higher alcohols and glycols are used as the bases of the cream formulation, and emulsifiers such as diethyleneglycol, propyleneglycol, sorbitan monofatty acid ester, Polysorbate 80, sodium lauryl sulfate and the like are used. Further, the above-mentioned preservatives and antioxidants may be used when needed. Furthermore, as with ointments, the compound of the present invention may be used as a clathrate compound of cyclodextrin or methylated cyclodextrin. Cream formulations can be synthesized by conventional methods.

Lotion formulations include suspended-type, emulsified-type and solution-type lotion formulations. Suspended-type formulations are obtained by using a suspending agent such as sodium alginate, gum tragacanth, sodium carboxymethylcellulose and the like, and by adding an antioxidant and a preservative when needed. Emulsified-type lotion formulations are obtained by using an emulsifier such as sorbitan monofatty acid ester, Polysorbate 80, sodium lauryl sulfate and the like with conventional methods. Solution-type lotion formulations are obtained by dissolving a compound of the present invention in an alcohol solution such as ethanol and the like, and by adding an antioxidant and a preservative when needed.

Dosage forms other than those of the above formulations include pastas, cataplasms, aerosols and the like, which can be synthesized by conventional methods.

Formulations for transnasal administration are provided as a liquid or powdery composition. As a base of liquid formulations, water, saline, phosphate buffer solution, acetic acid buffer solution and the like are used, and additionally surfactant, antioxidant, stabilizer, preservative, tackifier and the like may be contained. As a base of the powdery formulation, water absorbent materials are preferable, which include, for example, readily water-soluble polyacrylates such as sodium polyacrylate, potassium polyacrylate, ammonium polyacrylate and the like, cellulose lower alkyl ethers such as methylcellulose, hydroxyethylcellulose, hydroxypropylcellulose, sodium carboxymethylcellulose and the like, polyethylene glycol, polyvinylpyrrolidone, amylose, pullulan, and the like. In addition, the base of the powdery formulation includes celluloses such as practically water-insoluble crystalline cellulose, α-cellulose, cross-linked sodium carboxymethylcellulose and the like, starches such as hydroxypropyl starch, carboxymethyl starch, cross-linked starch, amylose, amylopectin, pectin and the like, proteins such as gelatin, casein, sodium caseinate and the like, gums such as gum arabic, gum tragacanth, glucomannan and the like, polyvinylpyrrolidone, crosslinked polyacrylic acid and salts thereof, cross-linked polyvinyl alcohol and the like, which may be mixed to be used. Moreover, antioxidant, coloring agent, preservative, anticeptic etc. may be added to the powdery formulation. These liquid formulations and powdery formulations can be administered by use of, for example, spraying tools.

For intrarectal administration, a conventional suppository like gelatin soft capsule and the like is used.

In addition, for inhalation, the vitamin $D_3$ derivative, an active ingredient, of the present invention alone or a powdery or liquid composition which is prepared by a combination of the derivative with a suitable biocompatible excipient can also be administered to the site of the disease using an administration device such as sprayer, nebulizer, atomizer and the like. Alternatively, the vitamin $D_3$ derivative can be suspended in a propellant for an aerosol such as chlorofluorocarbon etc. to be administered to the site of the disease.

Although a therapeutically effective amount of the active ingredient of the present invention varies according to age, sex and the extent of disease, it is usually in the order of 0.001 to 10,000 μg daily, the dosage frequency is usually 1 to 3 times daily or 1 to 3 times weekly, and thus it is preferable to prepare formulations which satisfy these conditions.

In addition, the therapeutic agent of the present invention can be used in combination with existing medicaments.

The efficacy of the vitamin $D_3$ derivative represented by the above-described Formula (1) of the present invention as a therapeutic agent of Paget's disease of bone and hypercalcemia is shown by, as an indicator, the binding ability of the compound of the present invention to the 1α,25-dihydroxyvitamin $D_3$ receptor (VDR) and the differentiation-inducing action using HL-60 cells, as will be specifically shown in the examples described below. That is, it has been found that the compound of the present invention binds to VDR with extremely high affinity and specifically suppresses the differentiation of HL-60 cells induced by 1α,25-dihydroxyvitamin $D_3$. These results have demonstrated that the compound of the present invention acts as a vitamin $D_3$ antagonist. As Paget's disease of bone and hypercalcemia are induced as a result of increased action of an activated vitamin $D_3$, vitamin $D_3$ antagonists are useful as a therapeutic agent of these diseases. And the activity of the compound of the present invention as one of these antagonists is higher than that of vitamin $D_3$ antagonists of the prior art (J. Biol. Chem., Vol. 274, 16392-16399, 1999; J. Biol. Chem., Vol. 274, 32376-32381, 1999; International Publication WO 00/24712, Specification). Moreover, the compound of the present invention is superior as an active ingredient of pharmaceutical products in that it has higher stability in the blood than vitamin $D_3$ antagonists of the prior art.

EXAMPLES

Hereinafter, the present invention is illustrated in detail by the following examples. It is to be understood, however, that the invention is not limited to the specific details of these examples. Compound No. in each example refers to the compound No. shown in the Table described above. Moreover, a compound with an alphabet letter attached to Compound No. refers to an isomer thereof.

Reference Example 1

Synthesis of ethyl 2-bromomethyl-2-butenoate (Compound (3a) ($R^{2d}/R^{2e}$=Me/Hydrogen atom, $R^7$=Et)

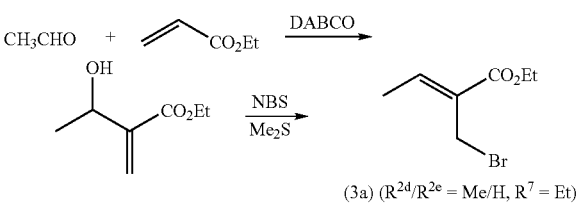

(3a) ($R^{2d}/R^{2e}$ = Me/H, $R^7$ = Et)

The above reaction was carried out according to the literature (Helv. Chem. Acta, Vol. 67, 413-415, 1984).

(1) A reaction solution prepared by mixing 1 g (9.99 mmol) of ethyl acrylate, approximately 0.6 ml of acetaldehyde and 168 mg (1.50 mmol) of DABCO (1,4-diazabicyclo[2.2.2] octane) was stirred at room temperature for 9 days. The reaction solution was extracted with diethyl ether and the organic layer was washed with water. The organic layer was dried with anhydrous magnesium sulfate and concentrated to obtain 1.7 g of allyl alcohol. Yield: 100%.

(2) A reaction solution prepared by adding dropwise 431 μl (5.9 mmol) of dimethylsulfide to a dichloromethane (4 ml) suspension solution of 950 mg (5.3 mmol) of NBS (N-bromosuccinimide) at 0° C. was stirred at 0° C. for 10 minutes. To the reaction solution was added dropwise a dichloromethane solution (6 ml) of 700 mg (4.86 mmol) of the allyl alcohol obtained by the above method at 0° C. and the resultant solution was stirred at room temperature for 22 hours. The reaction solution was poured into a mixture of saturated brine and ice, and the dichloromethane layer was separated. The aqueous layer was washed with diethyl ether and combined with the above dichloromethane layer, and then the mixed layer was dried with anhydrous magnesium sulfate and concentrated. The residue was purified by silica gel chromatography (diethyl ether:dichloromethane=1:1) to obtain 730 mg of ethyl-2-bromomethyl-1-butenoate. Yield: 73%.

$^1$H-NMR (CDCl$_3$) δ: 1.32 (t, J=7.1 Hz, 3 H), 1.92 (d, J=7.3 Hz, 3 H), 4.25 (s, 2 H), 4.27 (q, J=7.1 Hz, 2 H), 7.07 (q, J=7.3 Hz, 1 H).

Reference Example 2

Synthesis of ethyl 2-bromomethyl-2-pentenoate (Compound (3a) ($R^{2d}/R^{2e}$=Et/Hydrogen atom, $R^7$=Et))

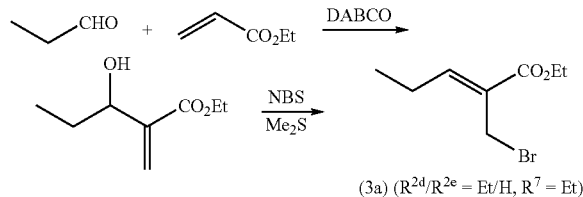

As in Reference Example 1, the reaction was carried out by replacing acetaldehyde with propionaldehyde. Yield: 42% (based on propionaldehyde).

$^1$H-NMR (CDCl$_3$) δ: 1.13 (t, J=7.6 Hz, 3 H), 1.33 (t, J=7.1 Hz, 3 H), 2.32 (dt, J=7.6, 15.2 Hz, 2 H), 4.23 (s, 2 H), 4.26 (q, J=7.1 Hz, 2 H), 6.96 (t, J=7.6 Hz, 1 H).

Reference Example 3

Synthesis of ethyl 2-bromomethyl-2-hexenoate (Compound (3a) ($R^{2d}/R^{2e}$=Pr/Hydrogen atom, $R^7$=Et))

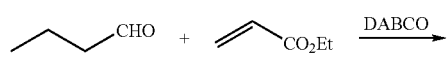

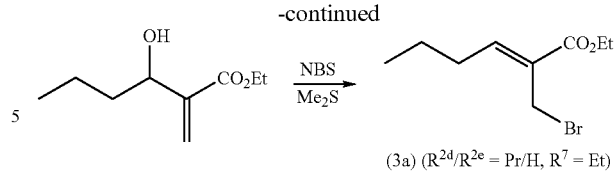

As in Reference Example 1, the reaction was carried out by replacing acetaldehyde with butylaldehyde. Yield: 29% (based on butylaldehyde).

$^1$H-NMR (CDCl$_3$) δ: 0.99 (t, J=7.4 Hz, 3 H), 1.33 (t, J=7.1 Hz, 3 H), 1.49-1.62 (m, 2 H), 2.28 (q, J=7.4 Hz, 2 H), 4.24 (s, 2 H), 4.26 (q, J=7.1 Hz, 2 H), 6.97 (t, J=7.6 Hz, 1 H).

Reference Example 4

Synthesis of ethyl 2-bromomethyl-4-methyl-2-pentenoate (Compound (3a) ($R^{2d}/R^{2e}$=i-Pr/Hydrogen atom, $R^7$=Et))

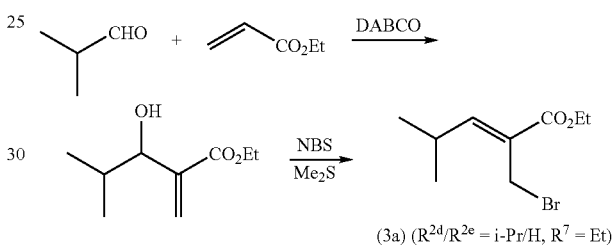

As in Reference Example 1, the reaction was carried out by replacing acetaldehyde with isobutylaldehyde. Yield: 27% (first stage reaction), Yield: 29% (second stage reaction).

$^1$H-NMR (CDCl$_3$) δ: 1.10 (d, J=6.6 Hz, 5 H), 1.33 (t, J=7.1 Hz, 3 H), 2.72-2.82 (m, 1 H), 4.24 (s, 2 H), 4.26 (q, J=7.1 Hz, 1 H), 6.76 (d, J=10.5 Hz, 1 H).

Reference Example 5

Synthesis of ethyl 2-bromomethyl-2-heptenoate (Compound (3a) ($R^{2d}/R^{2e}$=Bu/Hydrogen atom, $R^7$=Et))

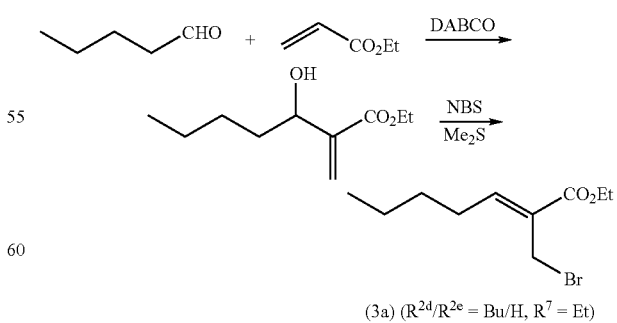

As in Reference Example 1, the reaction was carried out by replacing acetaldehyde with valeraldehyde. Yield: 25% (from valeraldehyde).

$^1$H-NMR (CDCl$_3$) δ: 0.94 (t, J=7.3 Hz, 3 H), 1.32 (t, J=7.1 Hz, 3 H), 1.34-1.59 (m, 4 H), 2.30 (q, J=7.3 Hz, 2 H), 4.24 (s, 2 H), 4.25 (q, J=7.1 Hz, 2 H), 6.97 (t, J=7.6 Hz, 1 H).

Reference Example 6

Synthesis of ethyl 2-bromo-5-methyl-2-hexenoate (Compound (3a) (R$^{2d}$/R$^{2e}$=i-Bu/Hydrogen atom, R$^7$=Et))

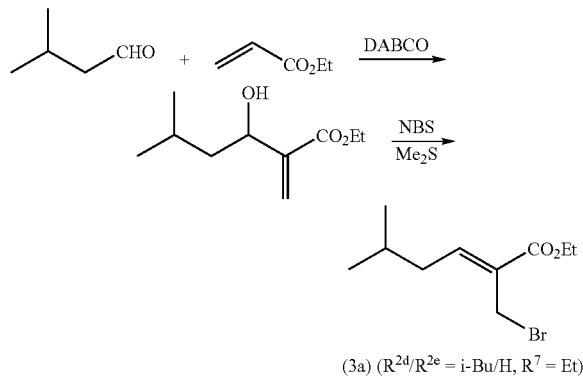

(3a) (R$^{2d}$/R$^{2e}$ = i-Bu/H, R$^7$ = Et)

As in Reference Example 1, the reaction was carried out by replacing acetaldehyde with isovaleraldehyde. Yield: 22% (first stage reaction), Yield: 83% (second stage reaction).

$^1$H-NMR (CDCl$_3$) δ: 0.97 (d, J=6.8 Hz, 6 H), 1.33 (t, J=7.1 Hz, 3 H), 1.78-1.92 (m, 1 H), 2.16-2.22 (m, 2 H), 4.23 (s, 2 H), 4.26 (q, J=7.1 Hz, 2 H), 7.00 (t, J=7.8 Hz, 1 H).

Reference Example 7

Synthesis of ethyl 2-bromomethyl-2-nonenoate (Compound (3a) (R$^{2d}$/R$^{2c}$=Hex/Hydrogen atom, R$^7$=Et))

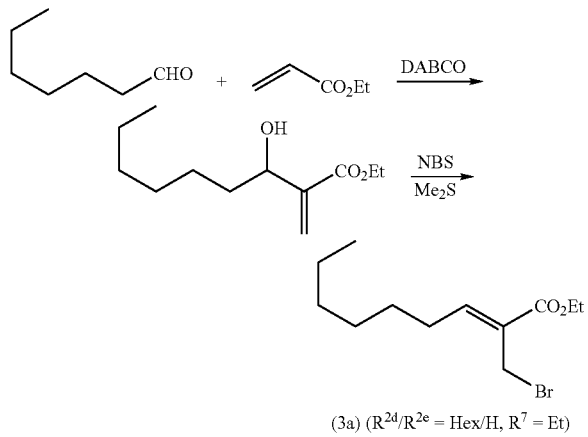

(3a) (R$^{2d}$/R$^{2e}$ = Hex/H, R$^7$ = Et)

As in Reference Example 1, the reaction was carried out by replacing acetaldehyde with heptanal. Yield: 44% (based on heptanal).

$^1$H-NMR (CDCl$_3$) δ: 0.89 (t, J=7.1 Hz, 3 H), 1.29-1.53 (m, 11 H), 2.26-2.33 (m, 4 H), 4.19-4.28 (m, 4 H), 6.97 (t, J=7.6 Hz, 1 H).

Reference Example 8

Synthesis of ethyl 2-bromomethyl-2-undecenoate (Compound (3a) (R$^{2d}$/R$^{2e}$=Octyl/Hydrogen atom, R$^7$=Et))

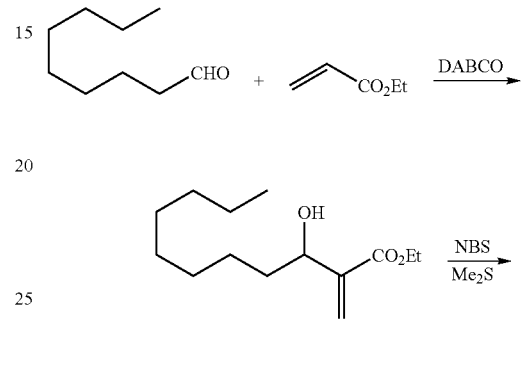

(3a) (R$^{2d}$/R$^{2e}$ = Octyl/H, R$^7$ = Et)

As in Reference Example 1, the reaction was carried out by replacing acetaldehyde with nonylaldehyde. Yield: 62% (based on nonylaldehyde).

$^1$H-NMR (CDCl$_3$) δ: 0.88 (t, J=7.1 Hz, 3 H), 1.24-1.65 (m, 15 H), 2.29 (q, J=7.6 Hz, 2 H), 4.19-4.34 (m, 4 H), 6.97 (t, J=7.6 Hz, 1 H).

Reference Example 9

Synthesis of ethyl 2-bromomethyl-3-phenyl-2-propenoate (Compound (3a) (R$^{2d}$/R$^{2e}$=Ph/Hydrogen atom, R$^7$=Et))

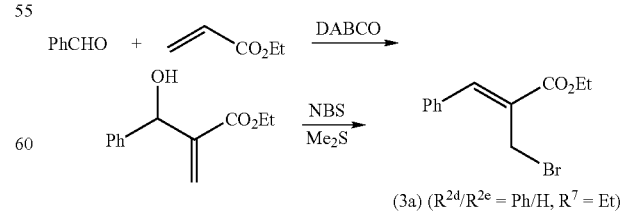

(3a) (R$^{2d}$/R$^{2e}$ = Ph/H, R$^7$ = Et)

As in Reference Example 1, the reaction was carried out by replacing acetaldehyde with benzaldehyde. Yield: 84% (first stage reaction), Yield: 82% (second stage reaction).

¹H-NMR (CDCl₃) δ: 1.39 (t, J=7.1 Hz, 1 H), 4.34 (q, J=7.1 Hz, 2 H), 4.41 (s, 2 H), 7.38-7.50 (m, 3 H), 7.55-7.60 (m, 2 H), 7.83 (s, 1 H).

Reference Example 10

Synthesis of ethyl 2-bromomethyl-5-phenyl-2-pentenoate (Compound (3a) ($R^{2d}/R^{2e}$=Phenethyl/Hydrogen atom, $R^7$=Et))

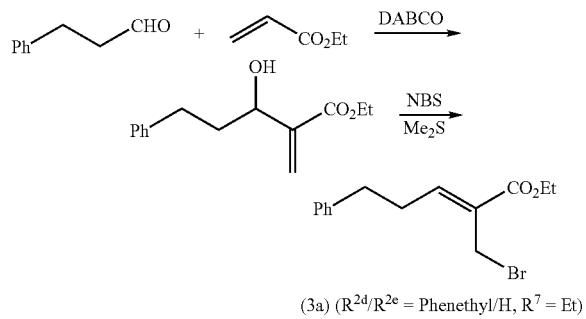

As in Reference Example 1, the reaction was carried out by replacing acetaldehyde with 3-phenylpropionaldehyde. Yield: 46% (based on 3-phenylpropionaldehyde).
¹H-NMR (CDCl₃) δ: 1.31 (t, J=7.1 Hz, 3 H), 2.62 (t, J=7.6 Hz, 2 H), 2.83 (t, J=7.6 Hz, 2H), 4.15 (s, 2 H), 4.25 (q, J=7.1 Hz, 2 H), 7.00 (t, J=7.6 Hz, 1 H), 7.19-7.30 (m, 5 H).

Reference Example 11

Synthesis of methyl 2-bromomethyl-3-methyl-2-butenoate (Compound (3a) ($R^{2d}=R^{2e}=R^7$=Me))

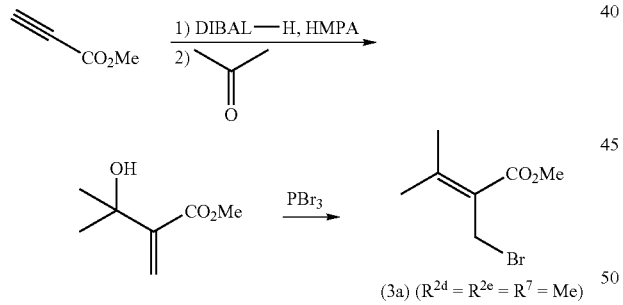

(1) Allyl alcohol was obtained according to the literature (Helv. Chem. Acta Vol. 77, 1480-1484, 1994). Yield: 50%.
(2) A reaction solution prepared by dissolving 200 mg (1.4 mmol) of the allyl alcohol obtained by the method described above in diethyl ether (4.6 ml) and adding 0.08 ml (0.83 mmol) of PBr₃ at 0° C. was stirred at room temperature for one hour. Water was added to the reaction solution at 0° C. and the aqueous layer was extracted with diethyl ether. The organic layer was washed with a saturated aqueous sodium hydrogen carbonate solution and saturated brine and dried with anhydrous sodium sulfate. The solvent was distilled off under reduced pressure and the resultant residue was purified by silica gel chromatography (hexane:ethyl acetate=20:1) to obtain 240 mg of Compound (3) ($R^{2a}=R^{2e}=R^7$=Me)). Yield: 83%, a colorless oily substance.

¹H-NMR (CDCl₃) δ: 1.99 (s, 3 H), 2.16 (s, 3 H), 3.79 (s, 3 H), 4.31 (s, 2 H).
³C-NMR (CDCl₃) δ: 23.0, 24.0, 29.4, 51.7, 124.6, 153.8, 166.9.
LRMS m/z 205 (M⁺), 191, 175
HRMS calcd for $C_7H_{11}O_2{}^{79}Br$ 205.9942, found 205.9951.

Reference Example 12

Synthesis of ethyl 2-bromomethyl-5-(t-butyldimethylsilyloxy)-2-pentenoate (Compound (3a) ($R^{2d}/R^{2e}$=TBSOEt/Hydrogen atom, $R^7$=Et))

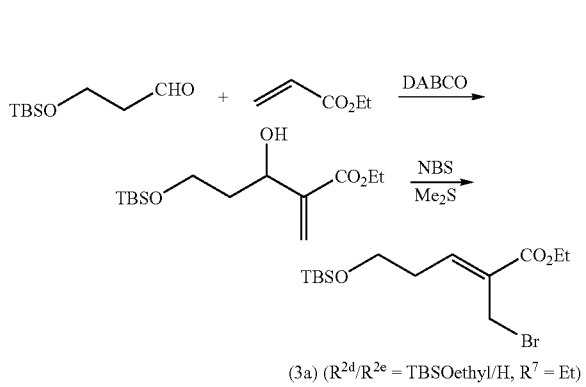

As in Reference Example 1, the reaction was carried out by replacing acetaldehyde with 3-(t-butyldimethylsilyloxy)propionaldehyde. Yield: 20% (based on 3-(t-butyldimethylsilyloxy)propionaldehyde). In addition, 3-(t-butyldimethylsilyloxy)propionaldehyde was obtained by converting the propanediol to a mono(t-butyldimethylsilyloxy) structure, followed by oxidation of the resultant monoalcohol.

¹H-NMR (CDCl₃) δ: 1.05 (s, 9 H), 1.32 (t, J=7.1 Hz, 3 H), 2.50-2.57 (m, 2 H), 3.80 (t, J=6.4 Hz, 2 H), 4.19 (s, 2H), 4.26 (q, J=7.1 Hz, 2 H), 7.05 (t, J=7.6 Hz, 1 H), 7.35-7.47 (m, 6 H), 7.63-7.67 (m, 4 H)

Reference Example 13

Synthesis of 1α,3β-bis-(t-butyldimethylsilyloxy)-20 (R)-formylmethyl-9,10-secopregna-5(Z),7(E),10 (19)-triene (Compound (15))

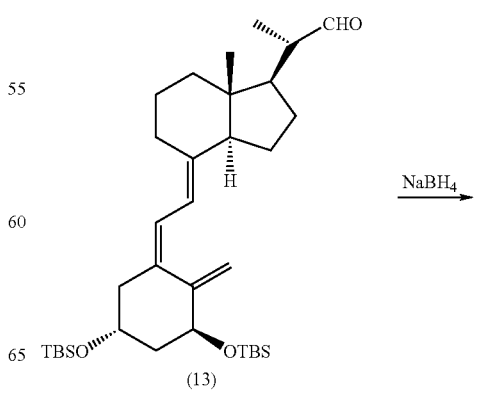

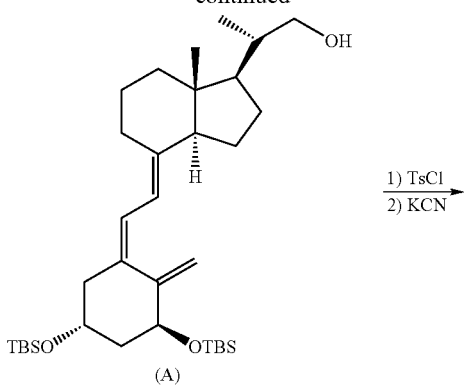

(A)

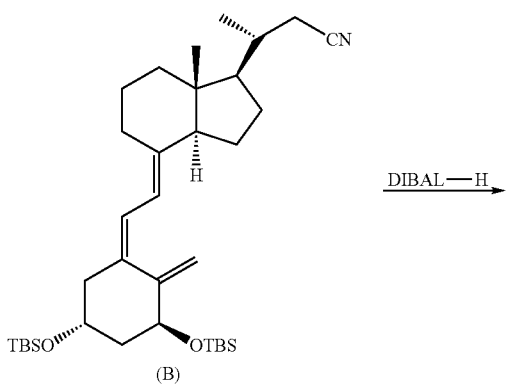

(B)

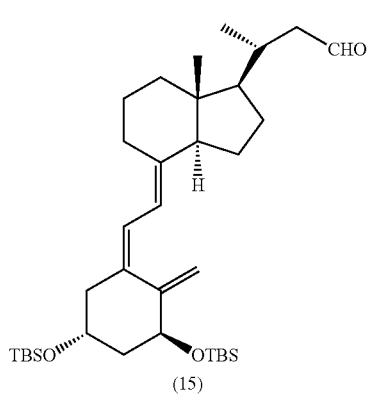

(15)

(1) A solution prepared by dissolving 1.15 g (2.0 mmol) of a compound (13) (PG=TBS, the configuration at position 20=(S) configuration) obtained by a method described in the literature (Tetrahedron, Vol. 20, 4609-4619, 1987) in a mixed solvent of THF (10 ml) and MeOH (10 ml) was chilled with ice. A reaction solution prepared by adding 38 mg (2.0 mmol) of sodium borohydride to the above solution was stirred for 1.5 hours as it was. A saturated aqueous ammonium chloride solution was added to the reaction solution and then the reaction solution was concentrated approximately to a half volume. The concentrated solution was subjected to extraction with ethyl acetate, and the organic layer was washed with saturated brine, dried, and concentrated. The residue was purified by silica gel chromatography (hexane:ethyl acetate=20:1 to 15:1) to obtain 200 mg of compound (A). Yield: 17%.

(2) A reaction solution prepared by dissolving 200 mg (0.348 mmol) of the compound (A) obtained by the above method in 1.5 ml of pyridine and then adding 133 mg (0.696 mmol) of tosylchloride was stirred at room temperature for 7.5 hours. After 1 M hydrochloric acid was added to the reaction solution, the reaction solution was subjected to extraction with ethyl acetate, and the organic layer was washed with saturated brine, dried, and concentrated to obtain a crude product (275 mg) of a tosyl structure. A reaction solution prepared by dissolving the crude product in 3 ml of anhydrous N,N-dimethylformamide and then adding 45 mg (0.696 mmol) of potassium cyanide and 9 mg (0.035 mmol) of 18-crown-6 was stirred at 100° C. for 3.5 hours. After water was added to the reaction solution, the reaction solution was subjected to extraction with ethyl acetate, and the organic layer was washed with saturated brine, dried and concentrated. The residue was purified by silica gel chromatography (hexane:ethyl acetate=40:1) to obtain 121 mg of Compound (B). Yield: 60%.

(3) A reaction solution prepared by dissolving 121 mg (0.207 mmol) of Compound (B) obtained by the above method in 3 ml of anhydrous methylene chloride was chilled to −75° C. After adding 0.41 ml (1.01 M, 0.41 mmol) of a toluene solution of DIBAL-H to this solution, the resultant solution was stirred for 3 hours as it was. Further, to the reaction solution was added 0.41 ml (1.01 M, 0.41 mmol) of a toluene solution of DIBAL-H and the resultant solution was stirred for 3 hours while increasing the temperature gradually (from −75° C. to −10° C.). After water and 6 M hydrochloric acid were added to the reaction solution, the reaction solution was subjected to extraction with methylene chloride, and the organic layer was washed with a saturated aqueous sodium hydrogen carbonate solution and saturated brine, dried and concentrated. The residue was purified by silica gel chromatography (hexane:ethyl acetate=40:1) to obtain 70 mg of Compound (15). Yield: 58%.

Example 1
Synthesis of 20(R)-(tetrahydro-3-methylene-2-furanone-4-methyl-5-yl)methyl-9,10-secopregna-5(Z),7(E),10(19)-triene-1α,3β-diol (Compound No. 101a, Compound No. 101b, Compound No. 101c, and Compound No. 101d)
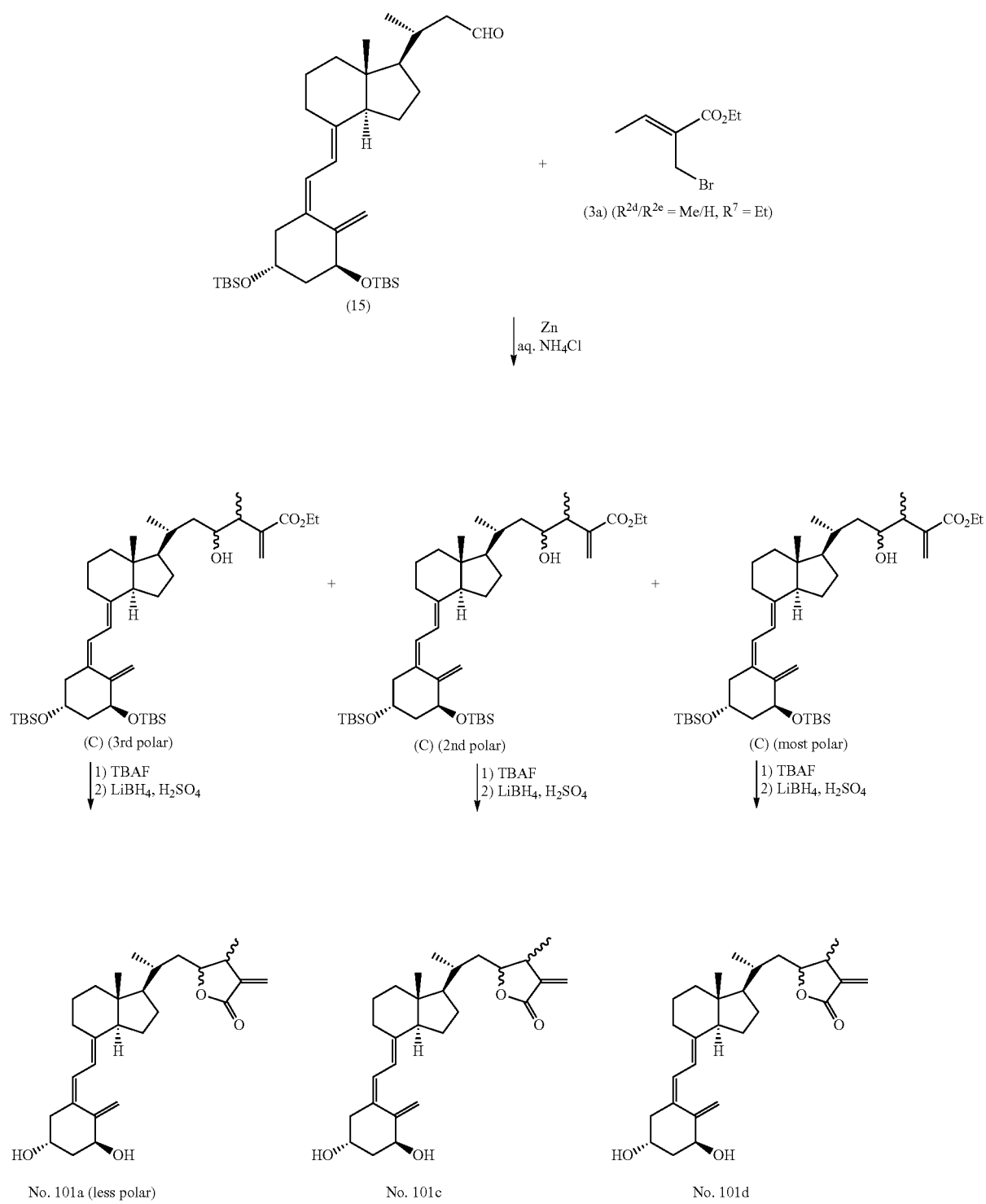

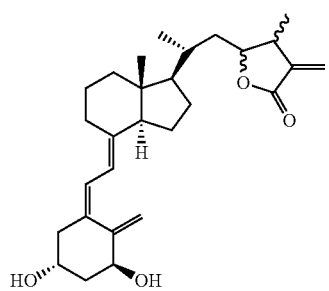

No. 101b (more polar)

(1) A reaction solution was prepared by adding 80 mg (0.386 mmol) of Compound (3a) ($R^{2d}/R^{2e}$=Me/Hydrogen atom, $R^7$=Et) obtained in Reference Example 1, 26 mg (0.397 mmol) of zinc and a saturated aqueous ammonium chloride solution (1.7 ml) to an anhydrous THF solution (3 ml) containing 113 mg (0.192 mmol) of Compound (15) obtained in Reference Example 13, and was stirred at room temperature for 3 hours. Water was added to the reaction solution, and the resultant solution was subjected to extraction with ethyl acetate. The organic layer was washed with water and then with saturated brine, dried with anhydrous magnesium sulfate, and concentrated. The resultant residue was purified by preparative TLC (hexane:ethyl acetate=4:1) to obtain 3 components of Compound (C). They are in the order of increasing polarity: 66 mg (yield: 48%) of Compound (C) (3rd polar), 22 mg (yield: 16%) of Compound (C) (2nd polar) and 39 mg (yield: 28%) of Compound (C) (most polar). These compounds are isomers due to the steric configuration of the asymmetric carbon to which a hydroxyl group is bonded and the adjacent asymmetric carbon to which a methyl group is bonded. Compound (C) (3rd polar) is a mixture of two isomers, and Compound (C) (2nd polar) and Compound (C) (most polar) each are a single isomer. Compound (C) (3rd Polar):

$^1$H-NMR (CDCl$_3$) δ: 0.04-0.07 (m, 12 H), 0.55 (s, 3 H), 0.87 (s, 9 H), 0.88 (s, 9 H), 0.94 (d, J=6.3 Hz, 2.4 H), 0.95 (d, J=6.3 Hz, 0.6 H), 1.10 (d, J=7.0 Hz, 2.4 H), 1.12 (d, J=6.8 Hz, 0.6 H), 1.15-2.05 (m, 20 H), 2.21 (dd, J=12.9, 7.7 Hz, 1 H), 2.42-2.47 (m, 1 H), 2.68-2.86 (m, 2 H), 3.62-3.70 (m, 0.2 H), 3.73-3.80 (m, 0.8 H), 4.15-4.30 (m, 3 H), 4.36 (dd, J=6.3, 3.4 Hz, 1 H), 4.86 (d, J=2.4 Hz, 1 H), 5.16 (d, J=1.7 Hz, 1 H), 5.58 (s, 0.8 H), 5.61 (s, 0.2 H), 6.01 (d, J=11.2 Hz, 1 H), 6.23 (d, J=10.0 Hz, 1 H), 6.26 (d, J=1.2 Hz, 1 H).

MS m/z 715 (M$^+$), 697 ((M–H$_2$O)$^+$), 583, 451, 249

Compound (C) (2nd Polar):

$^1$H-NMR(CDCl$_3$) δ: 0.06 (s, 9 H), 0.07 (s, 3 H), 0.53 (s, 3 H), 0.87 (s, 9 H), 0.88 (s, 9 H), 1.01 (d, J=6.3 Hz, 3 H), 1.16 (d, J=7.1 Hz, 3 H), 1.00-2.05 (m, 20 H), 2.18-2.25 (m, 1 H), 2.42-2.47 (m, 1 H), 2.70-2.85 (m, 2 H), 3.66-3.74 (m, 1 H), 4.15-4.30 (m, 3 H), 4.37 (dd, J=6.6, 3.9 Hz, 1 H), 4.86 (d, J=2.4 Hz, 1 H), 5.18 (d, J=1.5 Hz, 1 H), 5.66 (s, 1 H), 6.01 (d, J=11.7 Hz, 1 H), 6.20-6.30 (m, 2 H).

MS m/z 715 (M$^+$), 697 ((M–H$_2$O)$^+$), 583, 451, 249

Compound (C) (Most Polar):

$^1$H-NMR(CDCl$_3$) δ: 0.06 (s, 9 H), 0.07 (s, 3 H), 0.56 (s, 3 H), 0.87 (s, 9 H), 0.88 (s, 9 H), 1.03 (d, J=5.6 Hz, 3 H), 1.16 (d, J=6.8 Hz, 3 H), 1.15-2.05 (m, 20 H), 2.21 (dd, J=13.2, 7.3 Hz, 1 H), 2.41-2.48 (m, 1 H), 2.75-2.95 (m, 2 H), 3.78-3.83 (m, 1 H), 4.15-4.30 (m, 3 H), 4.35-4.40 (m, 1 H), 4.86 (d, J=3.9 Hz, 1 H), 5.17-5.20 (m, 1 H), 5.63 (s, 1 H), 6.02 (d, J=11.5 Hz, 1 H), 6.23 (d, J=11.0 Hz, 1 H), 6.32 (s, 1 H).

MS m/z 715 (M$^+$), 697 ((M–H$_2$O)$^+$), 583, 451, 249

(2-a) A reaction solution prepared by adding 92 µl (1.0 M, 92 µmol) of a THF solution of TBAF to an anhydrous THF solution (1.5 ml) containing 66 mg (92 µmol) of Compound (C) (3rd polar) obtained by the above method at 0° C. was stirred at 0° C. for 1.5 hours. Further 92 µl (1.0 M, 92 µmol) of a THF solution of TBAF was added to the reaction solution, and the resultant solution was stirred at 0° C. for 0.5 hours. Saturated brine was added to the reaction solution and the resultant solution was subjected to extraction with ethyl acetate. The organic layer was washed with water and saturated brine, dried with anhydrous magnesium sulfate and then concentrated. The residue was dissolved in a mixed solution of toluene and acetonitrile (1:1, 2 ml). To the solution was added 35 mg (0.373 mmol) of LiBF$_4$ and 3.7 ml of an acetonitrile solution containing sulfuric acid (0.1 M, 0.373 mmol) at 0° C., and the resultant solution was stirred at 0° C. for 15 minutes. After water was added to the reaction solution, extraction was performed with ethyl acetate. The organic layer was washed with a saturated aqueous sodium hydrogen carbonate solution and saturated brine, dried with magnesium sulfate and concentrated. The residue was purified by HPLC (reversed phase, A=95% H$_2$O/CH$_3$CN; B=95% CH$_3$OH/H$_2$O; B=80%) to obtain 3.0 mg (yield: 7%, purity: 99%) of Compound No. 101a (less polar) and 8.2 mg (yield: 20%, purity: 99%) of Compound No. 101b (more polarity). These compounds are isomers due to the steric configuration of the asymmetric carbon to which the methyl group is bonded on the lactone ring.

Compound No. 101a (Less Polar)

$^1$H-NMR (CDCl$_3$) δ: 0.57 (s, 3 H), 1.01 (d, J=6.3 Hz, 3 H), 1.23 (d, J=6.8 Hz, 3 H), 1.20-2.15 (m, 18 H), 2.31 (dd, J=13.4, 6.6 Hz, 1 H), 2.54-2.70 (m, 2 H), 2.83 (dd, J=12.2, 4.1 Hz, 1 H), 4.02-4.12 (m, 1 H), 4.18-4.28 (m, 1 H), 4.38-4.48 (m, 1 H), 5.01 (s, 1 H), 5.34 (s, 1 H), 5.53 (d, J=2.9 Hz, 1 H), 6.02 (d, J=11.2 Hz, 1 H), 6.22 (d, J=3.2 Hz, 1 H), 6.38 (d, J=11.2 Hz, 1 H).

MS m/z 458 ((M+23)$^+$), 441 ((M+1)$^+$), 423 ((M+1−H$_2$O)$^+$), 405

Compound No. 101b (More Polar)

$^1$H-NMR (CDCl$_3$) δ: 0.56 (s, 3 H), 1.00 (d, J=6.3 Hz, 3 H), 1.13 (d, J=7.1 Hz, 3 H), 1.00-2.10 (m, 18 H), 2.31 (dd, J=13.7, 6.6 Hz, 1 H), 2.53-2.63 (m, 1 H), 2.82 (dd, J=11.7, 3.2 Hz, 1 H), 3.10-3.20 (m, 1 H), 4.18-4.28 (m, 1 H), 4.38-4.48 (m, 1 H), 4.62-4.72 (m, 1 H), 5.00 (s, 1 H), 5.33 (d, J=1.5 Hz, 1 H), 5.53 (d, J=2.4 Hz, 1 H), 6.01 (d, J=11.2 Hz, 1 H), 6.22 (d, J=2.9 Hz, 1 H), 6.37 (d, J=11.2 Hz, 1 H)

MS m/z 458 ((M+23)$^+$), 441 ((M+1)$^+$), 423 ((M+1−H$_2$O)$^+$), 405

(2-b) A reaction solution prepared by adding 31 µl (1.0 M, 31 µmol) of a THF solution of TBAF to an anhydrous THF solution (1.0 ml) containing 22 mg (31 μmol) of Compound (C) (2nd polar) obtained by the above method at 0° C. was stirred at 0° C. for 2 hours. Saturated brine was added to the reaction solution and the resultant solution was subjected to extraction with ethyl acetate. The organic layer was washed with water and saturated brine, dried with anhydrous magnesium sulfate and then concentrated. The residue was dissolved in a mixed solution of toluene and acetonitrile (1:1, 2 ml). To the solution was added 12 mg (0.128 mmol) of LiBF$_4$ and 1.3 ml of an acetonitrile solution containing sulfuric acid (0.1 M, 0.128 mmol) at 0° C., and the resultant solution was stirred at 0° C. for 25 minutes. After water was added to the reaction solution, extraction was performed with ethyl acetate. The organic layer was washed with a saturated aqueous sodium hydrogen carbonate solution and saturated brine, dried with magnesium sulfate and concentrated. The residue was purified by HPLC (reversed phase, A=95% H$_2$O/CH$_3$CN; B=95% CH$_3$OH/H$_2$O; B=80%) to obtain 2.1 mg (yield: 16%, purity: 96%) of Compound No. 101c.

Compound No. 101c:
$^1$H-NMR (CDCl$_3$) δ: 0.57 (s, 3 H), 1.06 (d, J=6.1 Hz, 3 H), 1.25 (d, J=6.8 Hz, 3 H), 1.20-2.15 (m, 18 H), 2.32 (dd, J=13.7, 6.8 Hz, 1 H), 2.55-2.70 (m, 2 H), 2.78-2.87 (m, 1 H), 4.08 (dt, J=6.6, 5.4 Hz, 1 H), 4.18-4.28 (m, 1 H), 4.40-4.47 (m, 1 H), 4.99-5.01 (m, 1 H), 5.32-5.34 (m, 1 H), 5.54 (d, J=2.9 Hz 1 H), 6.02 (d, J=11.2 Hz, 1 H), 6.23 (d, J=3.2 Hz, 1H), 6.38 (d, J=11.2 Hz, 1 H).
MS m/z 458 ((M+23)$^+$), 441 ((M+1)$^+$), 423 ((M+1−H$_2$O)$^+$), 405

(2-c) A reaction solution prepared by adding 55 μl (1.0 M, 55 μmol) of a THF solution of TBAF to an anhydrous THF solution (1.5 ml) containing 39 mg (55 μmol) of Compound (C) (2nd polar) obtained by the above method was stirred at 0° C. for 2 hours. Saturated brine was added to the reaction solution and the resultant solution was subjected to extraction with ethyl acetate. The organic layer was washed with water and saturated brine, dried with anhydrous magnesium sulfate and then concentrated. The residue was dissolved in a mixed solution of toluene and acetonitrile (1:1, 2 ml). To the solution was added 20 mg (0.213 mmol) of LiBF$_4$ and 2.1 ml of an acetonitrile solution containing sulfuric acid (0.1M, 0.213 mmol) at 0° C., and the resultant solution was stirred at 0° C. for 25 minutes. After water was added to the reaction solution, extraction was performed with ethyl acetate. The organic layer was washed with a saturated aqueous sodium hydrogen carbonate solution and saturated brine, dried with magnesium sulfate and concentrated. The residue was purified by HPLC (reverse phase, A=95% H$_2$O/CH$_3$CN; B=95% CH$_3$OH/H$_2$O; B=80%) to yield 7.2 mg (yield: 30%, purity: 99%) of Compound No. 101d.

Compound No. 101d:
$^1$H-NMR (CDCl$_3$) δ: 0.56 (s, 3 H), 1.05 (d, J=6.3 Hz, 3 H), 1.13 (d, J=7.1 Hz, 3 H), 1.20-2.10 (m, 18 H), 2.32 (dd, J=13.7, 6.6 Hz, 1 H), 2.59 (d, J=13.4, 3.7 Hz, 1 H), 2.83 (dd, J=12.4, 4.4 Hz, 1 H), 3.05-3.15 (m, 1 H), 4.10-4.20 (m, 1 H), 4.40-4.48 (m, 1 H), 4.55-4.63 (m, 1 H), 4.99-5.01 (m, 1 H), 5.33-5.35 (m, 1 H), 5.54 (d, J=2.2 Hz, 1 H), 6.02 (d, J=11.2 Hz, 1 H), 6.19 (d, J=2.4 Hz, 1 H), 6.38 (d, J=11.2 Hz, 1 H).

MS m/z 458 ((M+23)$^+$), 441 ((M+1)$^+$), 423 ((M+1−H$_2$O)$^+$), 405

Example 2

Synthesis of 20(R)-(tetrahydro-3-methylene-2-furanone-4-ethyl-5-yl)methyl-9,10-secopregna-5(Z),7(E),10(19)-triene-1α,3β-diol (Compound No. 102a, Compound No. 102b, Compound No. 102c, and Compound No. 102d)

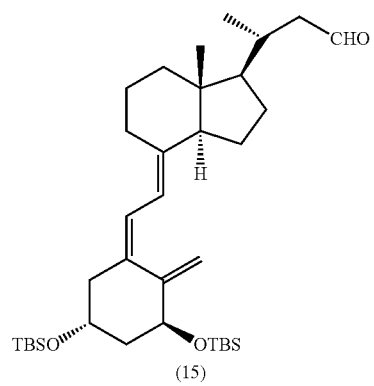 + 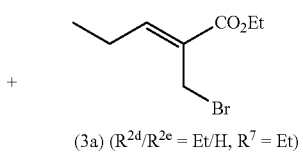

Zn
aq. NH$_4$Cl

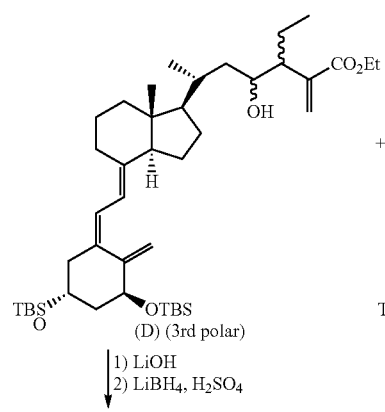
(D) (3rd polar)

1) LiOH
2) LiBH$_4$, H$_2$SO$_4$

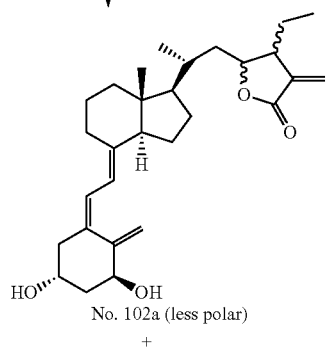
No. 102a (less polar)
+

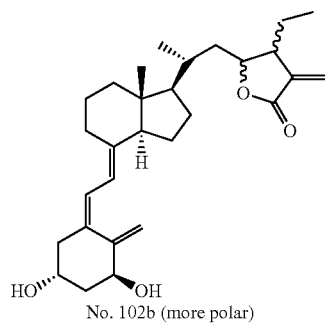
No. 102b (more polar)

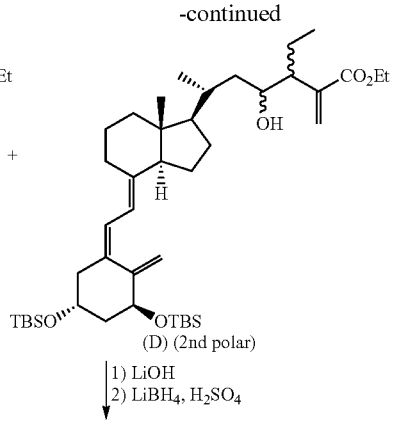
(D) (2nd polar)

1) LiOH
2) LiBH$_4$, H$_2$SO$_4$

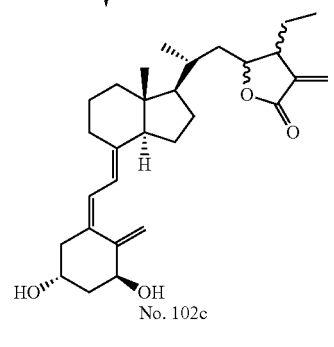
No. 102c

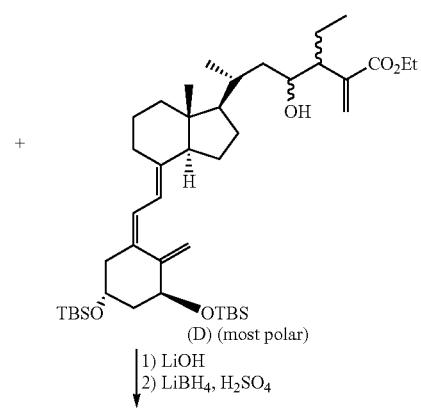
(D) (most polar)

1) LiOH
2) LiBH$_4$, H$_2$SO$_4$

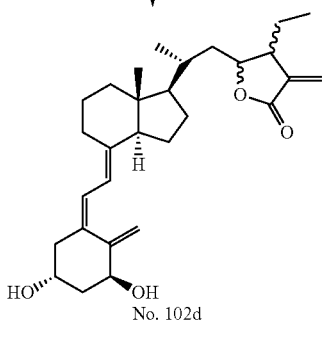
No. 102d (1) A reaction solution was prepared by adding an anhydrous THF solution (1.5 ml) containing 114 mg (0.516 mmol) of Compound (3c) ($R^{2d}/R^{2e}$=Et/Hydrogen atom, $R^7$=Et) obtained in Reference Example 2, 34 mg (0.516 mmol) of zinc and a saturated aqueous ammonium chloride solution (3 ml) to an anhydrous THF solution (1.5 ml) containing 202 mg (0.344 mmol) of Compound (15) obtained in Reference Example 13, and was stirred at room temperature for 3.5 hours. Water was added to the reaction solution, and the resultant solution was subjected to extraction with ethyl acetate. The organic layer was washed with water and then with saturated brine, dried with anhydrous magnesium sulfate and concentrated. The resultant residue was purified by preparative TLC (hexane:ethyl acetate=5:1) to give 3 components of Compound (D). They are in the order of increasing polarity: 101 mg (yield: 40%) of Compound (D) (3rd polar), 50 mg (yield: 20%) of Compound (D) (2nd polar) and 34 mg (yield: 14%) of Compound (D) (most polar). These compounds are isomers due to the steric configuration of the asymmetric carbon to which a hydroxyl group is bonded and the adjacent asymmetric carbon to which an ethyl group is bonded. Compound (D) (3rd polar) is a mixture of two isomers, and Compound (D) (2nd polar) and Compound (D) (most polar) each are a single isomer.

Compound (D) (3rd Polar)
$^1$H-NMR (CDCl$_3$) δ: 0.05 (s, 6 H), 0.06 (s, 6 H), 0.55 (s, 3 H), 0.87 (s, 9 H), 0.88 (s, 9 H), 0.90-0.96 (m, 3 H), 1.23-2.05 (m, 23 H), 2.17-2.25 (m, 2 H), 2.43-2.47 (m, 2 H), 2.80-2.84 (m, 1 H), 3.76 (br, 1 H), 4.08-4.24 (m, 3 H), 4.34-4.36 (m, 1 H), 4.86 (d, J=2.1 Hz, 1 H), 5.17 (d, J=1.8 Hz, 1 H), 5.47 & 5.52 (s, 1 H), 6.01 (d, J=11.2 Hz, 1 H), 6.23-6.29 (m, 2 H).
MS m/z 729.5 ((M+1)$^+$)

Compound (D) (2nd Polar)
$^1$H-NMR(CDCl$_3$) δ: 0.06 (s, 12 H), 0.53 (s, 3 H), 0.87 (s, 9 H), 0.88 (s, 9 H), 1.00 (d, J=6.3 Hz, 3 H), 1.23-2.04 (m, 24 H), 2.18-2.25 (m, 1 H), 2.43-2.48 (m, 2 H), 2.79-2.83 (m, 1 H), 3.79 (br, 1 H), 4.08-4.26 (m, 3 H), 4.38 (br, 1 H), 4.86 (d, J=2.1 Hz, 1 H), 5.18 (s, 1 H), 5.65 (s, 1 H), 6.01 (d, J=10.9 Hz, 1 H), 6.23 (d, J=11.2 Hz, 1 H), 6.29 (s, 1 H).
MS m/z 729.5 ((M+1)$^+$)

Compound (D) (Most Polar)
$^1$H-NMR(CDCl$_3$) δ: 0.06 (s, 12 H), 0.55 (s, 3 H), 0.87 (s, 9 H), 0.88 (s, 9 H), 1.02 (d, J=6.1 Hz, 3 H), 1.14-2.05 (m, 24 H), 2.18-2.25 (m, 1 H), 2.41-2.58 (m, 2 H), 2.80-2.84 (m, 1 H), 3.75-3.76 (m, 1 H), 4.08-4.26 (m, 3 H), 4.36-4.38 (m, 1 H), 4.87 (d, J=2.1 Hz, 1 H), 5.19 (s, 1 H), 5.59 (s, 1 H), 6.02 (d, J=11.2 Hz, 1 H), 6.23 (d, J=11.1 Hz, 1 H), 6.34 (s, 1 H).
MS m/z 729.5 ((M+1)$^+$)

(2-a) A reaction solution prepared by adding 1.0 ml (4.0 M, 4.0 mmol) of an aqueous lithium hydroxide solution to an anhydrous THF solution (2 ml) containing 101 mg (139 µmol) of the compound (D) (3rd polar) obtained by the above method was stirred at room temperature for one hour. Water was added to the reaction solution and the resultant solution was subjected to extraction with ethyl acetate. The organic layer was washed with water and saturated brine, dried with anhydrous sodium sulfate and then concentrated. The residue was dissolved in a mixed solution of toluene and acetonitrile (1:1, 2 ml). To the solution was added 39 mg (0.42 mmol) of $LiBF_4$ and then the resultant solution was chilled with ice. After 0.25 ml (1.0 M, 0.25 mmol) of an acetonitrile solution of sulfuric acid was added to the reaction solution, the resultant solution was stirred at 0° C. for one hour. To the reaction solution was added a saturated aqueous sodium hydrogen carbonate solution, and the resultant solution was subjected to extraction with ethyl acetate. The organic layer was washed with saturated brine, dried with anhydrous sodium sulfate and concentrated. The residue was purified by a Sep-Pack silica Plus cartridge (Waters, hexane:ethyl acetate=1:1→hexane: ethyl acetate:methanol=3:6:1) and HPLC (reversed phase, A=95% $H_2O/CH_3CN$; B=95% $CH_3OH/H_2O$; B=85%) to obtain 6.5 mg (yield: 10%, purity: 97%) of Compound No. 102a (less polar) and 15.3 mg (yield: 24%, purity: 97%) of Compound No. 102b (more polar). These compounds are isomers due to the steric configuration of the asymmetric carbon to which an ethyl group is bonded on the lactone ring.

Compound No. 102a (Less Polar):

$^1$H-NMR ($CDCl_3$) δ: 0.57 (s, 3 H), 0.98 (t, J=7.4 Hz, 3 H), 1.03 (d, J=6.6 Hz, 3 H), 1.26-1.73 (m, 5 H), 1.83-2.05 (m, 13 H), 2.31 (dd, J=13.4, 6.3 Hz, 1 H), 2.51-2.62 (m, 2 H), 2.80-2.85 (m, 1 H), 4.22-4.32 (m, 2 H), 4.41-4.46 (m, 1 H), 5.00 (s, 1 H), 5.33 (s, 1 H), 5.58 (d, J=2.3 Hz, 1 H), 6.01 (d, J=11.1 Hz, 1 H), 6.27 (d, J=2.8 Hz, 1 H), 6.37 (d, J=11.4 Hz, 1 H)

MS m/z 455.3 (($M+1$)$^+$)

Compound No. 102b (More Polar):

$^1$ H-NMR ($CDCl_3$) δ: 0.57 (s, 3 H), 0.98 (t, J=7.4 Hz, 3 H), 1.01 (d, J=6.4 Hz, 3 H), 0.72-2.05 (m, 18 H), 2.31 (dd, J=13.4, 6.3 Hz, 1 H), 2.57-2.62 (m, 1 H), 2.80-2.92 (m, 2 H), 4.22-4.25 (m, 1 H), 4.41-4.45 (m, 1 H), 4.64-6.70 (m, 1 H), 5.00 (s, 1 H), 5.33 (s, 1 H), 5.52 (d, J=2.3 Hz, 1 H), 6.01 (d, J=11.2 Hz, 1 H), 6.22 (d, J=2.5 Hz, 1 H), 6.37 (d, J=11.2 Hz, 1 H).

MS m/z 455.3 (($M+1$)$^+$)

(2-b) A reaction solution prepared by adding 0.5 ml (4.0 M, 2.0 mmol) of an aqueous lithium hydroxide solution to an anhydrous THF solution (2.0 ml) containing 50 mg (69 µmol) of Compound (D) (2nd polar) obtained by the above method was stirred at room temperature for 45 minutes. Water was added to the reaction solution and the resultant solution was subjected to extraction with ethyl acetate. The organic layer was washed with water and saturated brine, dried with anhydrous sodium sulfate and then concentrated. The residue was dissolved in a mixed solution of toluene and acetonitrile (1:1, 2 ml). To the resultant solution was added 19 mg (0.21 mmol) of $LiBF_4$, and the resultant solution was chilled with ice. A reaction solution prepared by adding 0.123 ml (1.0 M, 0.123 mmol) of an acetonitrile solution of sulfuric acid to this solution was stirred at 0° C. for one hour. To the reaction solution was added a saturated aqueous sodium bicarbonate solution, and the resultant solution was subjected to extraction with ethyl acetate. The organic layer was washed with saturated brine, dried with anhydrous sodium sulfate and concentrated. The residue was purified by a Sep-Pack silica Plus cartridge (Waters, hexane:ethyl acetate=1:1→hexane:ethyl acetate: methanol=3:6:1) and HPLC (reversed phase, A=95% $H_2O/CH_3CN$; B=95% $CH_3OH/H_2O$; B=85%) to obtain 8.9 mg (yield: 29%, purity: 99.5%) of Compound No. 102c.

Compound No. 102c:

$^1$H-NMR ($CDCl_3$) δ: 0.56 (s, 3 H), 0.98 (t, J=7.4 Hz, 3 H), 1.06 (d, J=5.9 Hz, 3 H), 1.14-1.74 (m, 13 H), 1.84-2.07 (m, 5 H), 2.32 (dd, J=13.4, 6.3 Hz, 1 H), 2.55-2.62 (m, 2 H), 2.80-2.85 (m, 1 H), 4.23-4.30 (m, 2 H), 4.43 (br, 1 H), 5.00 (s, 1 H), 5.33 (s, 1 H), 5.59 (d, J=2.1 Hz, 1 H), 6.01 (d, J=11.1 Hz, 1 H), 6.28 (d, J=2.5 Hz, 1 H), 6.37 (d, J=11.2 Hz, 1 H).

MS m/z 455.4 (($M+1$)$^+$)

(2-c) A reaction solution prepared by adding 0.34 ml (4.0 M, 1.36 mmol) of an aqueous lithium hydroxide solution to an anhydrous THF solution (2.0 ml) containing 34 mg (47 µmol) of Compound (D) (most polar) obtained by the above method was stirred at room temperature for 60 minutes. Water was added to the reaction solution and the resultant solution was subjected to extraction with ethyl acetate. The organic layer was washed with water and saturated brine, dried with anhydrous sodium sulfate and concentrated. The residue was dissolved in a mixed solution of toluene and acetonitrile (1:1, 2 ml) and to the resultant solution was added 13 mg (0.14 mmol) of $LiBF_4$, and the resultant solution was chilled with ice. A reaction solution prepared by adding 0.084 ml (1.0 M, 0.084 mmol) of an acetonitrile solution of sulfuric acid to this solution was stirred at 0° C. for one hour. To the reaction solution was added a saturated aqueous sodium bicarbonate solution, and the resultant solution was subjected to extraction with ethyl acetate. The organic layer was washed with saturated brine, dried with anhydrous sodium sulfate and concentrated. The residue was purified by a Sep-Pack silica Plus cartridge (Waters, hexane:ethyl acetate=1:1→hexane: ethyl acetate:methanol=3:6:1) and HPLC (reversed phase, A=95% $H_2O/CH_3CN$; B=95% $CH_3OH/H_2O$; B=85%) to obtain 9.2 mg (yield: 43%, purity: 99.7%) of Compound No. 102d.

Compound No. 102d:

$^1$H-NMR ($CDCl_3$) δ: 0.57 (s, 3 H), 0.96 (t, J=7.4 Hz, 3 H), 1.06 (d, J=6.4 Hz, 3 H), 1.23-1.79 (m, 13 H), 1.87-2.08 (m, 5 H), 2.32 (dd, J=13.4, 6.4 Hz, 1 H), 2.57-2.62 (m, 1 H), 2.80-2.85 (m, 2 H), 4.24 (br, 1 H), 4.44 (br, 1 H), 4.55-4.62 (m, 1 H), 5.00 (s, 1 H), 5.33 (s, 1H), 5.52 (d, J=1.8 Hz, 1 H), 6.02 (d, J=11.4 Hz, 1 H), 6.21 (d, J=1.8 Hz, 1 H), 6.37 (d, J=11.4 Hz, 1 H).

MS m/z 455.4 (($M+1$)$^+$)

Example 3

Synthesis of 20(R)-(tetrahydro-3-methylene-2-furanone-4-propyl-5-yl)methyl-9,10-secopregna-5(Z),7(E),10(19)-triene-1α,3β-diol (Compound No. 103a, Compound No. 103b, Compound No. 103c, and Compound No. 103d)

(1) Using 205 mg (0.349 mmol) of Compound (15) obtained in Reference Example 13, as in Example 2(1), a reaction was carried out by replacing Compound (3a) ($R^{2d}/R^{2e}$=Et/Hydrogen atom, $R^7$=Et) obtained in Reference Example 2 with the compound (3a) ($R^{2d}/R^{2e}$=Pr/Hydrogen atom, $R^7$=Et) obtained in Reference Example 3 to obtain 3 components of Compound (E). They are in the order of increasing polarity: 98 mg (yield: 38%) of the compound (E)

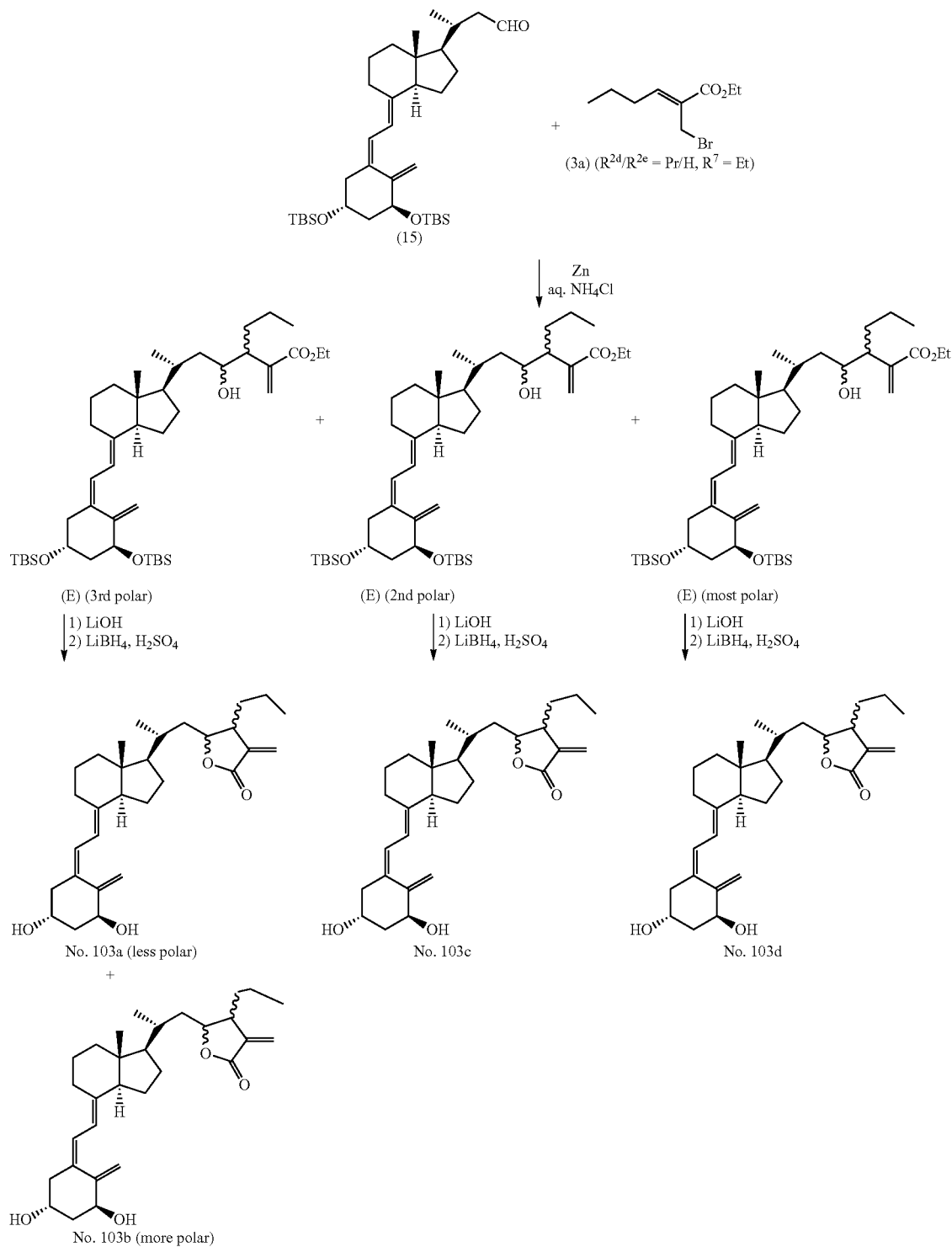

(3rd polar), 43 mg (yield: 17%) of Compound (E) (2nd polar) and 38 mg (yield: 15%) of Compound (E) (most polar). These compounds are isomers due to the steric configuration of the asymmetric carbon to which a hydroxyl group is bonded and the adjacent asymmetric carbon to which a propyl group is bonded. Compound (E) (3rd polar) is a mixture of two isomers, and Compound (E) (second polarity) and Compound (E) (most polar) each are a single isomer.

Compound (E) (3rd Polar)

$^1$H-NMR (CDCl$_3$) δ: 0.059 (s, 6 H), 0.062 (s, 6 H), 0.55 (s, 3 H), 0.876 (s, 9 H), 0.882 (s, 9 H), 0.92-2.03 (m, 28 H), 2.18-2.25 (m, 2 H), 2.41-2.66 (m, 2 H), 2.79-2.84 (m, 1 H), 3.75 (br, 1H), 4.18-4.26 (m, 3 H), 4.36-4.37 (m, 1 H), 4.87 (d, J=2.0 Hz, 1 H), 5.19 (s, 1 H), 5.54 & 5.59 (s, 1 H), 6.02 (d, J=11.2 Hz, 1 H), 6.23 (d, J=11.4 Hz, 1 H), 6.28-6.32 (m, 1 H).

MS m/z 743.5 ((M+1)$^+$)

Compound (E) (2nd Polar)

$^1$H-NMR (CDCl$_3$) δ: 0.06 (s, 6 H), 0.07 (s, 6 H), 0.53 (s, 3 H), 0.87 (s, 9 H), 0.88 (s, 9 H), 1.00 (d, J=6.8 Hz, 3 H), 1.03-1.96 (m, 26 H), 2.22-2.25 (m, 1 H), 2.41-2.45 (m, 1 H), 2.60-2.61 (m, 1 H), 2.71-2.83 (m, 1 H), 3.78 (br, 1 H), 4.18-4.26 (m, 3 H), 4.38 (br, 1 H), 4.86 (d, J=2.5 Hz, 1 H), 5.18 (s, 1 H), 5.65 (d, J=1.1 Hz, 1 H), 6.01 (d, J=11.4 Hz, 1 H), 6.23 (d, J=10.7 Hz, 1 H), 6.28 (d, J=1.3 Hz, 1 H)

MS m/z 743.5 ((M+1)$^+$)

Compound (E) (Most Polar)

$^1$H-NMR (CDCl$_3$) δ: 0.059 (s, 6 H), 0.062 (s, 6 H), 0.55 (s, 3 H), 0.876 (s, 9 H), 0.882 (s, 9 H), 1.02 (d, J=6.1 Hz, 3 H), 1.15-2.03 (m, 25 H), 2.18-2.25 (m, 1 H), 2.41-2.45 (m, 2 H), 2.64-2.69 (m, 1 H), 2.79-2.84 (m, 1 H), 3.75 (br, 1 H), 4.16-4.26 (m, 3 H), 4.36-4.40 (m, 1 H), 4.87 (d, J=2.0 Hz, 1 H), 5.19 (s, 1 H), 5.59 (s, 1 H), 6.02 (d, J=11.2 Hz, 1 H), 6.23 (d, J=11.4 Hz, 1 H), 6.31 (d, J=1.2 Hz, 1 H).

MS m/z 743.5 ((M+1)$^+$)

(2-a) Using 98 mg (132 μmol) of Compound (E) (3rd polar) obtained by the above method, a reaction similar to Example 2(2-a) was carried out to obtain 16.4 mg (yield: 27%, purity: 98%) of Compound No. 103a (less polar) and 15.7 mg (yield: 25%, purity: 99%) of Compound No. 103b (more polar). These compounds are isomers due to the steric configuration of the asymmetric carbon to which the propyl group is bonded.

Compound No. 103a (Less Polar)

$^1$H-NMR (CDCl$_3$) δ: 0.57 (s, 3 H), 0.96 (t, J=7.1 Hz, 3 H), 1.02 (d, J=6.6 Hz, 3 H), 1.21-2.05 (m, 20 H), 2.31 (dd, J=13.4, 6.6 Hz, 1 H), 2.58-2.62 (m, 2 H), 2.80-2.85 (m, 1 H), 4.23-4.30 (m, 2 H), 4.40-4.46 (m, 1 H), 5.00 (s, 1 H), 5.33 (s, 1 H), 5.57 (d, J=2.3 Hz, 1 H), 6.01 (d, J=11.2 Hz, 1 H), 6.26 (d, J=2.8 Hz, 1 H), 6.37 (d, J=11.1 Hz, 1 H).

MS m/z 469.3 ((M+1)$^+$)

Compound No. 103b (More Polar)

$^1$H-NMR (CDCl$_3$) δ: 0.57 (s, 3 H), 0.96 (t, J=6.9 Hz, 3 H), 1.00 (d, J=6.6 Hz, 3 H), 1.05-2.05 (m, 20 H), 2.31 (dd, J=13.4, 6.6 Hz, 1 H), 2.57-2.62 (m, 1 H), 2.80-2.85 (m, 1 H), 2.97-3.00 (m, 1 H), 4.23-4.24 (m, 1 H), 4.40-4.45 (m, 1 H), 4.63-6.69 (m, 1 H), 5.00 (s, 1 H), 5.33 (s, 1 H), 5.51 (d, J=2.3 Hz, 1 H), 6.01 (d, J=11.4 Hz, 1 H), 6.21 (d, J=2.6 Hz, 1 H), 6.37 (d, J=11.2 Hz, 1 H).

MS m/z 469.2 ((M+1)$^+$)

(2-b) Using 43 mg (58 μmol) of Compound (E) (2nd polar) obtained by the above method, a reaction similar to Example 2(2-b) was carried out to obtain 11.0 mg (yield: 41%, purity: 99.5%) of Compound No. 103c.

Compound No. 103c:

$^1$H-NMR (CDCl$_3$) δ: 0.56 (s, 3 H), 0.96 (t, J=7.1 Hz, 3 H), 1.06 (d, J=5.9 Hz, 3 H), 1.16-1.74 (m, 14 H), 1.84-2.08 (m, 6 H), 2.32 (dd, J=13.2, 6.4 Hz, 1 H), 2.58-2.63 (m, 2 H), 2.80-2.85 (m, 1 H), 4.24-4.28 (m, 2 H), 4.40-4.47 (m, 1 H), 5.00 (s, 1 H), 5.33 (s, 1 H), 5.58 (d, J=2.1 Hz, 1 H), 6.01 (d, J=11.2 Hz, 1 H), 6.26 (d, J=2.5 Hz, 1 H), 6.38 (d, J=10.9 Hz, 1 H).

MS m/z 469.3 ((M+1)$^+$)

(2-c) Using 38 mg (51 μmol) of Compound (E) (2nd polar) obtained by the above method, a reaction similar to Example 2(2-c) was carried out to obtain 8.5 mg (yield: 35%, purity: 99%) of Compound No. 103d.

Compound No. 103d:

$^1$H-NMR (CDCl$_3$) δ: 0.56 (s, 3 H), 0.95 (t, J=6.6 Hz, 3 H), 1.06 (d, J=6.4 Hz, 3 H), 1.29-1.76 (m, 14 H), 1.87-2.05 (m, 6 H), 2.32 (dd, J=13.5, 6.4 Hz, 1 H), 2.60 (dd, J=13.4, 3.5 Hz, 1 H), 2.80-2.92 (m, 2 H), 4.22-4.24 (m, 1 H), 4.41-4.45 (m, 1 H), 4.54-4.61 (m, 1 H), 5.00 (s, 1 H), 5.33 (t, J=1.6 Hz, 1 H), 5.50 (d, J=1.8 Hz, 1 H), 6.02 (d, J=11.1 Hz, 1 H), 6.20 (d, J=2.0 Hz, 1 H), 6.38 (d, J=11.2 Hz, 1 H).

MS m/z 469.3 ((M+1)$^+$)

Example 4

Synthesis of 20(R)-(tetrahydro-3-methylene-2-furanone-4-isopropyl-5-yl)methyl-9,10-secopregna-5 (Z),7(E),10(19)-triene-1α,3β-diol (Compound No. 104a, and Compound No. 104b)

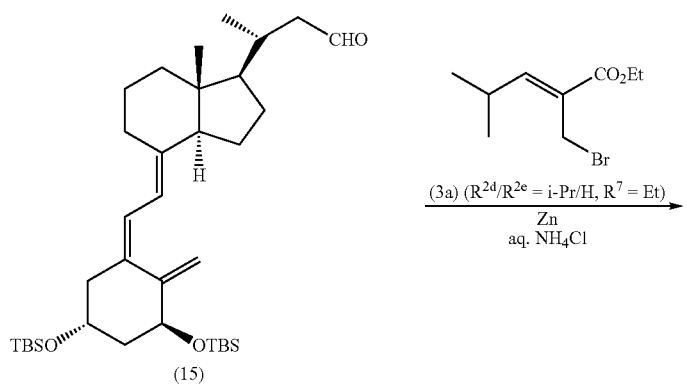

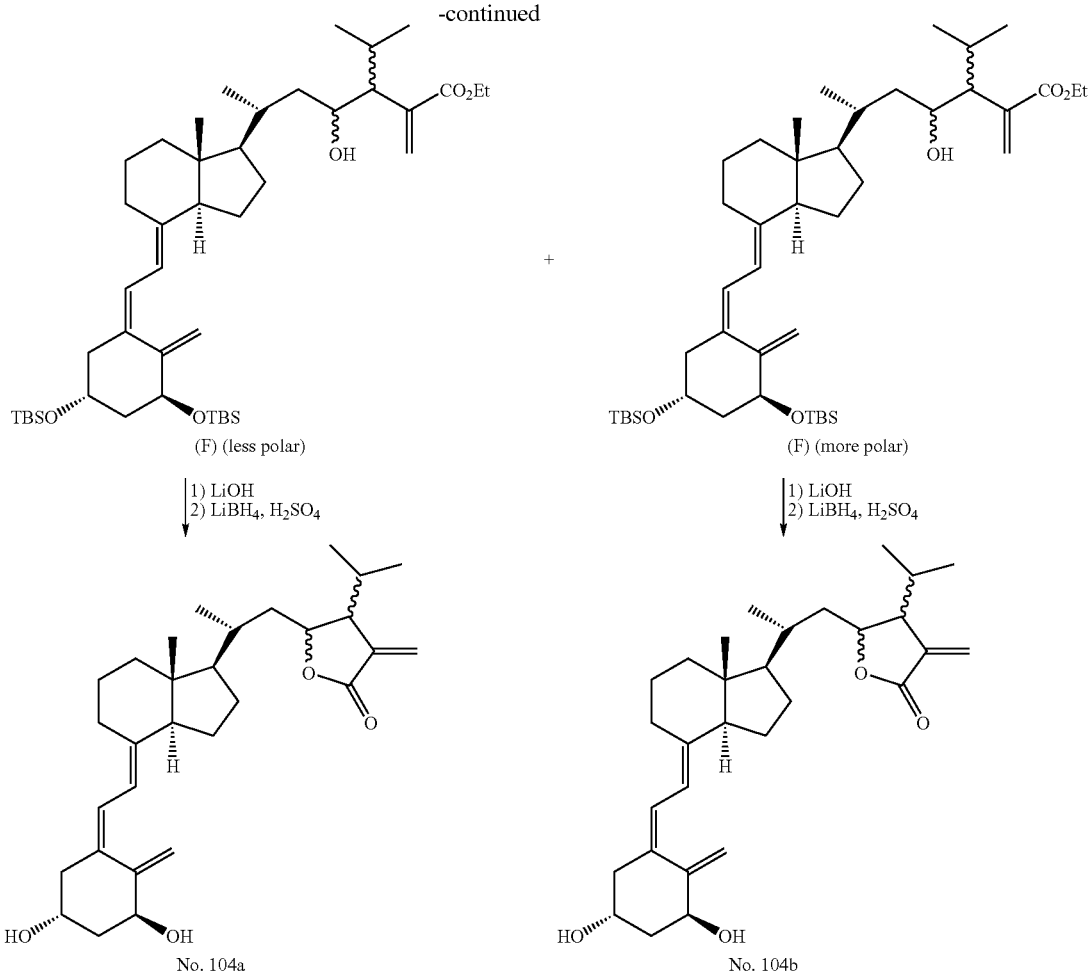

(F) (less polar)

(F) (more polar)

No. 104a

No. 104b (1) Using 205 mg (0.349 mmol) of Compound (15) obtained in Reference Example 13, as with Example 2(1), a reaction is carried out by replacing Compound (3a) ($R^{2d}/R^{2e}$=Et/Hydrogen atom, $R^7$=Et) obtained in Reference Example 2 with Compound (3a) ($R^{2d}/R^{2e}$=i-Pr/Hydrogen atom, $R^7$=Et) obtained in Reference Example 4 to obtain 46 mg (yield: 50%) of Compound (F) (less polar) and 22 mg (yield: 38%) of Compound (F) (more polar). These compounds are isomers due to the steric configuration of the asymmetric carbon to which a hydroxyl group is bonded and/or the adjacent asymmetric carbon to which a propyl group is bonded.

Compound (F) (Less Polar):

$^1$H-NMR (CDCl$_3$) δ: 0.05 (s, 6 H), 0.06 (s, 6 H), 0.54 (s, 3 H), 0.80 (d, J=6.0 Hz, 3 H), 0.86 (s, 9 H), 0.87 (s, 9 H), 0.95 (d, J=6.3 Hz, 3 H), 1.04 (d, J=6.0 Hz, 3 H), 1.05-2.10 (m, 21 H), 2.17-2.25 (m, 1 H), 2.40-2.50 (m, 1 H), 2.75-2.85 (m, 1 H), 3.00-3.10 (m, 1 H), 3.90-4.00 (m, 1 H), 4.07-4.15 (m, 3 H), 4.36 (dd, J=6.1, 3.2 Hz, 1 H), 4.85 (d, J=2.2 Hz, 1 H), 5.14-5.17 (m, 1 H), 5.50 (d, J=1.5 Hz, 1 H), 6.00 (d, J=11.0 Hz, 1 H), 6.10-6.18 (m, 2 H).

MS m/z 743 (M$^+$), 625 ((M–H$_2$O)$^+$), 611

Compound (F) (More Polar):

$^1$H-NMR (CDCl$_3$) δ: 0.06 (s, 9 H), 0.07 (s, 3 H), 0.52 (s, 3 H), 0.81 (d, J=6.3 Hz, 3 H), 0.87 (s, 9 H), 0.88 (s, 9 H), 0.98 (d, J=6.6 Hz, 3 H), 1.05 (d, J=6.3 Hz, 3 H), 1.10-2.20 (m, 21 H), 2.21 (dd, J=13.2, 7.1 Hz, 1 H), 2.40-2.50 (m, 1 H), 2.75-2.85 (m, 1 H), 3.25-3.35 (m, 1 H), 3.97-4.03 (m, 1 H), 4.15-4.30 (m, 3 H), 4.35-4.40 (m, 1 H), 4.86 (d, J=2.4 Hz, 1 H), 5.18 (d, J=1.7 Hz, 1 H), 5.65 (d, J=1.5 Hz, 1 H), 6.00 (d, J=11.7 Hz, 1 H), 6.23 (d, J=11.2 Hz, 1H), 6.28 (d, J=1.5 Hz, 1 H).

MS m/z 743 (M$^+$), 625 ((M–H$_2$O)$^+$), 611

(2-a) Using 44 mg (59 μmol) of Compound (F) (less polar) obtained by the above method, a reaction similar to Example 2(2-b) was carried out to obtain 15 mg (yield: 54%, purity: 99%) of Compound No. 104a.

Compound No. 104a:

$^1$H-NMR (CDCl$_3$) δ: 0.56 (s, 3 H), 0.94 (d, J=6.6 Hz, 3 H), 0.95 (d, J=7.1 Hz, 3 H), 1.04 (d, J=6.6 Hz, 3 H), 1.10-2.10 (m, 19 H), 2.31 (dd, J=13.4, 6.6 Hz, 1 H), 2.44-2.52 (m, 1 H), 2.60 (dd, J=13.2, 3.2 Hz, 1 H), 2.82 (dd, J=11.7, 3.7 Hz, 1 H), 4.20-4.28 (m, 1 H), 4.40-4.48 (m, 2 H), 5.00 (s, 1 H), 5.32-5.34 (m, 1 H), 5.60 (d, J=2.0 Hz, 1 H), 6.01 (d, J=11.2 Hz, 1 H), 6.34 (d, J=2.2 Hz, 1 H), 6.38 (d, J=11.5 Hz, 1 H).

MS m/z 486 ((M+H$_2$O)$^+$), 469 ((M+1)$^+$), 451 ((M+1–H$_2$O)$^+$), 433

(2-b) Using 35 mg (47 μmol) of Compound (F) (less polar) obtained by the above method, a reaction similar to Example 2(2-b) was carried out to obtain 8.7 mg (yield: 39%, purity: 99%) of Compound No. 104b.

Compound No. 104b:

$^1$H-NMR (CDCl$_3$) δ: 0.56 (s, 3 H), 0.93 (d, J=6.8 Hz, 3 H), 0.95 (d, J=6.8 Hz, 3 H), 1.06 (d, J=5.9 Hz, 3 H), 1.10-2.10 (m,

19 H), 2.32 (dd, J=13.4, 6.6 Hz, 1 H), 2.47-2.55 (m, 1 H), 2.60 (dd, J=13.7, 3.4 Hz, 1 H), 2.82 (dd, J=12.4, 4.1 Hz, 1 H), 4.18-4.28 (m, 1 H), 4.35-4.41 (m, 1 H), 4.41-4.48 (m, 1 H), 4.98-5.00 (m, 1 H), 5.32-5.34 (m, 1 H), 5.61 (d, J=1.5 Hz, 1 H), 6.01 (d, J=11.5 Hz, 1 H), 6.33 (d, J=2.0 Hz, 1 H), 6.37 (d, J=11.2 Hz, 1 H).
MS m/z 486 ((M+H$_2$O)$^+$), 469 ((M+1)$^+$), 451 ((M+1−H$_2$O)$^+$), 433
Example 5
Synthesis of 20(R)-(tetrahydro-3-methylene-2-furanone-4-butyl-5-yl)methyl-9,10-secopregna-5(Z),7(E),10(19)-triene-1α,3β-diol (Compound No. 105a, Compound No. 105b, Compound No. 105c, and Compound No. 105d)
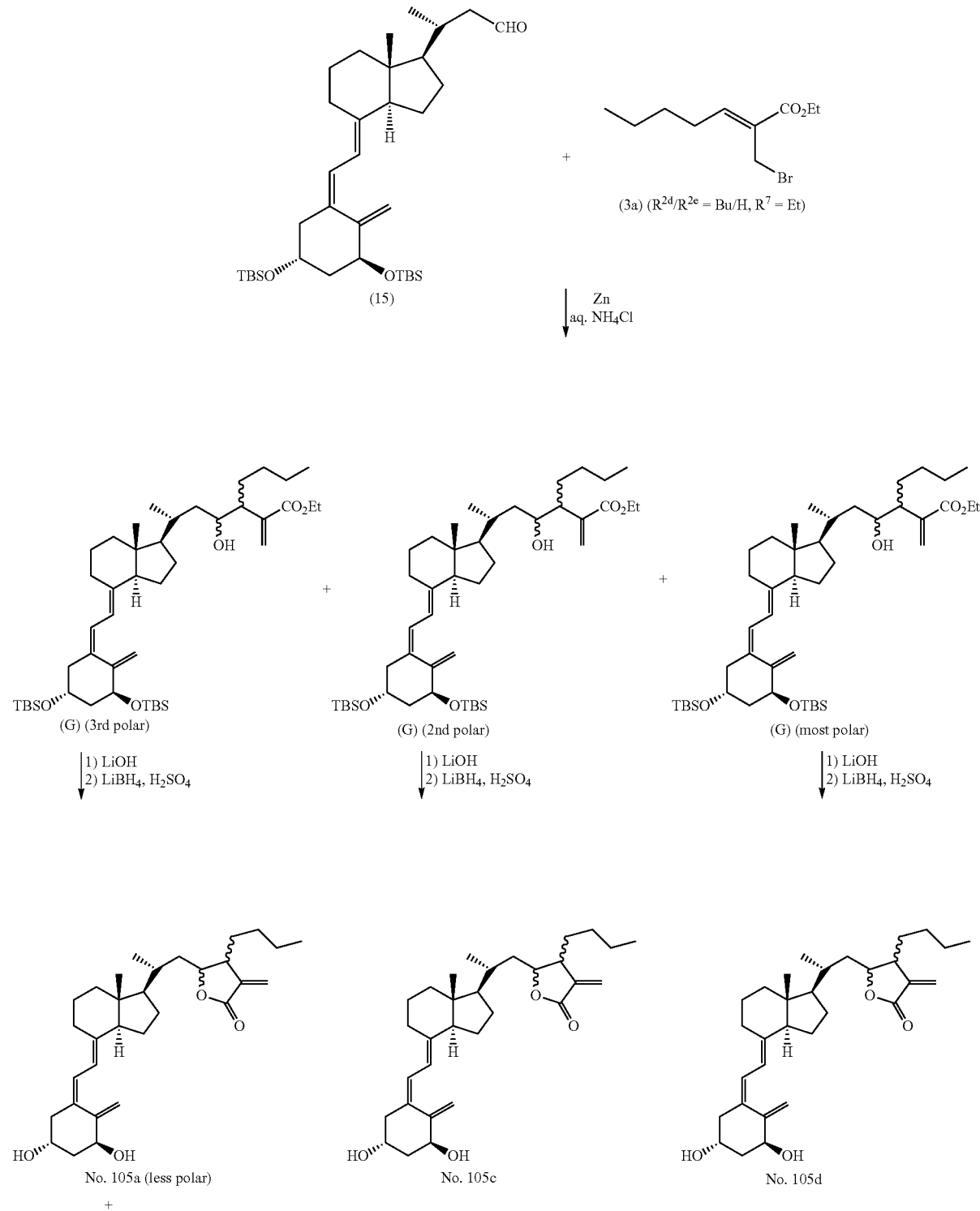

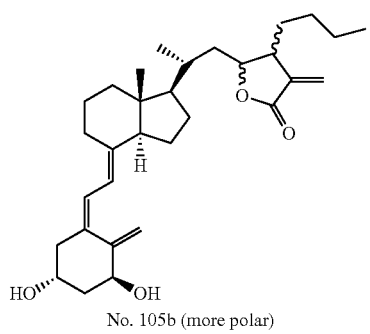

No. 105b (more polar)

(1) Using 201 mg (0.342 mmol) of Compound (15) obtained in Reference Example 13, as with Example 2(1), a reaction was carried out by replacing Compound (3a) ($R^{2d}/R^{2e}$=Et/Hydrogen atom, $R^7$=Et) obtained in Reference Example 2 with Compound (3a) ($R^{2d}/R^{2e}$=Bu/Hydrogen atom, $R^7$=Et) obtained in Reference Example 5 to obtain 3 components of Compound (G). They are in the order of increasing polarity: 108 mg (yield: 42%) of Compound (G) (3rd polar), 41 mg (yield: 16%) of Compound (G) (2nd polar) and 40 mg (yield: 15%) of Compound (G) (most polar). These compounds are isomers due to the steric configuration of the asymmetric carbon to which a hydroxyl group is bonded and the adjacent asymmetric carbon to which a butyl group is bonded. The compound (G) (3rd polar) is a mixture of two isomers, and Compound (G) (2nd polar) and Compound (G) (most polar) each are a single isomer.

Compound (G) (3rd Polar):

$^1$H-NMR (CDCl$_3$) δ: 0.05 (s, 6 H), 0.06 (s, 6 H), 0.55 (s, 3 H), 0.87 (s, 9 H), 0.88 (s, 9 H), 0.85-2.04 (m, 31 H), 2.22-2.34 (m, 1 H), 2.43-2.47 (m, 2 H), 2.80-2.84 (m, 1 H), 3.76 (br, 1H), 4.11-4.27 (m, 3 H), 4.29-4.34 (m, 1 H), 4.86 (d, J=2.3 Hz, 1 H), 5.16 (s, 1 H), 5.53 & 5.58 (s, 1 H), 6.01 (d, J=11.2 Hz, 1 H), 6.23 (d, J=10.4 Hz, 1 H), 6.25-6.27 (m, 1 H).

MS m/z 757.5 ((M+1)$^+$)

Compound (G) (2nd Polar):

$^1$H-NMR (CDCl$_3$) δ: 0.06 (s, 6 H), 0.07 (s, 6 H), 0.53 (s, 3 H), 0.87 (s, 9 H), 0.88 (s, 9 H), 0.85-1.96 (m, 31 H), 2.17-2.25 (m, 1 H), 2.43-2.46 (m, 1 H), 2.57-2.61 (m, 1 H), 2.72-2.83 (m, 1 H), 3.78 (br, 1 H), 4.11-4.26 (m, 3 H), 4.35-4.37 (m, 1 H), 4.86 (d, J=2.3 Hz, 1 H), 5.18 (s, 1 H), 5.65 (d, J=1.5 Hz, 1 H), 6.00 (d, J=11.2 Hz, 1 H), 6.23 (d, J=11.1 Hz, 1 H), 6.28 (d, J=1.3 Hz, 1 H).

MS m/z 757.5 ((M+1)$^+$)

Compound (G) (Most Polar)

$^1$H-NMR (CDCl$_3$) δ: 0.06 (s, 12 H), 0.55 (s, 3 H), 0.876 (s, 9 H), 0.879 (s, 9 H), 0.82-2.02 (m, 31 H), 2.18-2.25 (m, 1 H), 2.38-2.45 (m, 1 H), 2.63 (br, 1 H), 2.80-2.84 (m, 1 H), 3.75 (br, 1H), 4.18-4.26 (m, 3 H), 4.35-4.37 (m, 1 H), 4.87 (d, J=2.5 Hz, 1 H), 5.18 (s, 1 H), 5.59 (s, 1H), 6.02 (d, J=11.1 Hz, 1 H), 6.23 (d, J=11.4 Hz, 1 H), 6.32 (d, J=1.2 Hz, 1 H).

MS m/z 757.5 ((M+1)$^+$)

(2-a) Using 108 mg (143 μmol) of Compound (G) (3rd polar) obtained by the above method, a reaction similar to Example 2(2-a) was carried out to obtain 12.9 mg (yield: 19%, purity: 98%) of Compound No. 105a (less polar) and 14.5 mg (yield: 21%, purity: 99%) of Compound No. 105b (more polar). These compounds are isomers due to the steric configuration of the asymmetric carbon to which a butyl group is bonded on the lactone ring.

Compound No. 105a (Less Polar):

$^1$H-NMR (CDCl$_3$) δ: 0.57 (s, 3 H), 0.93 (t, J=6.6 Hz, 3 H), 1.03 (d, J=6.4 Hz, 3 H), 1.21-2.05 (m, 22 H), 2.31 (dd, J=13.4, 6.3 Hz, 1 H), 2.57-2.62 (m, 2 H), 2.81-2.85 (m, 1 H), 4.25-4.28 (m, 2 H), 4.44 (br, 1 H), 5.00 (s, 1 H), 5.33 (s, 1 H), 5.58 (d, J=2.3 Hz, 1 H), 6.02 (d, J=11.1 Hz, 1 H), 6.26 (d, J=2.6 Hz, 1 H), 6.37 (d, J=11.2 Hz, 1 H).

MS m/z 483.2 ((M+1)$^+$)

Compound No. 105b (More Polar):

$^1$H-NMR (CDCl$_3$) δ: 0.57 (s, 3 H), 0.93 (t, J=6.9 Hz, 3 H), 1.01 (d, J=6.4 Hz, 3 H), 1.06-2.05 (m, 22 H), 2.31 (dd, J=13.4, 6.3 Hz, 1 H), 2.60 (dd, J=13.2, 3.6 Hz, 1 H), 2.80-2.85 (m, 1 H), 2.92-2.97 (m, 1 H), 4.23 (br, 1 H), 4.42-4.43 (m, 1 H), 4.63-6.69 (m, 1 H), 5.00 (s, 1 H), 5.33 (d, J=1.5 Hz, 1 H), 5.51 (d, J=2.3 Hz, 1 H), 6.01 (d, J=11.2 Hz, 1 H), 6.21 (d, J=2.6 Hz, 1 H), 6.37 (d, J=11.2 Hz, 1 H).

MS m/z 483.5 ((M+1)$^+$)

(2-b) Using 41 mg (54 μmol) of Compound (G) (2nd polar) obtained by the above method, a reaction similar to Example 2(2-b) was carried out to obtain 10.3 mg (yield: 39%, purity: 98%) of Compound No. 105c.

Compound No. 105c:

$^1$H-NMR (CDCl$_3$) δ: 0.56 (s, 3 H), 0.92 (t, J=6.6 Hz, 3 H), 1.06 (d, J=5.8 Hz, 3 H), 1.13-1.74 (m, 17 H), 1.84-2.08 (m, 5 H), 2.32 (dd, J=13.5, 6.4 Hz, 1 H), 2.57-2.62 (m, 2 H), 2.80-2.85 (m, 1 H), 4.22-4.28 (m, 2 H), 4.40-4.47 (m, 1 H), 5.00 (s, 1 H), 5.33 (s, 1 H), 5.57 (d, J=2.1 Hz, 1 H), 6.01 (d, J=11.2 Hz, 1 H), 6.26 (d, J=2.5 Hz, 1 H), 6.38 (d, J=11.2 Hz, 1 H).

MS m/z 483.2 ((M+1)$^+$)

(2-c) Using 40 mg (53 μmol) of Compound (G) (most polar) obtained by the above method, a reaction similar to Example 2(2-c) was carried out to obtain 13.1 mg (yield: 51%, purity: 99%) of Compound No. 105d.

Compound No. 105d:

$^1$H-NMR (CDCl$_3$) δ: 0.56 (s, 3 H), 0.92 (t, J=6.9 Hz, 3 H), 1.06 (d, J=6.4 Hz, 3 H), 1.19-1.77 (m, 17 H), 1.87-2.05 (m, 5 H), 2.32 (dd, J=13.5, 6.6 Hz, 1 H), 2.57-2.62 (m, 1 H), 2.80-2.91 (m, 2 H), 4.22 (br, 1 H), 4.42-4.45 (m, 1 H), 4.54-4.61 (m, 1 H), 5.00 (s, 1 H), 5.33 (s, 1 H), 5.50 (d, J=1.8 Hz, 1 H), 6.02 (d, J=11.4 Hz, 1 H), 6.20 (d, J=2.0 Hz, 1 H), 6.38 (d, J=11.2 Hz, 1 H).

MS m/z 483.5 ((M+1)$^+$)

Example 6
Synthesis of 20(R)-(tetrahydro-3-methylene-2-furanone-4-isobutyl-5-yl)methyl-9,10-secopregna-5(Z),7(E),10(19)-triene-1α,3β-diol (Compound No. 106a, Compound No. 106b, Compound No. 106c, and Compound No. 106d)
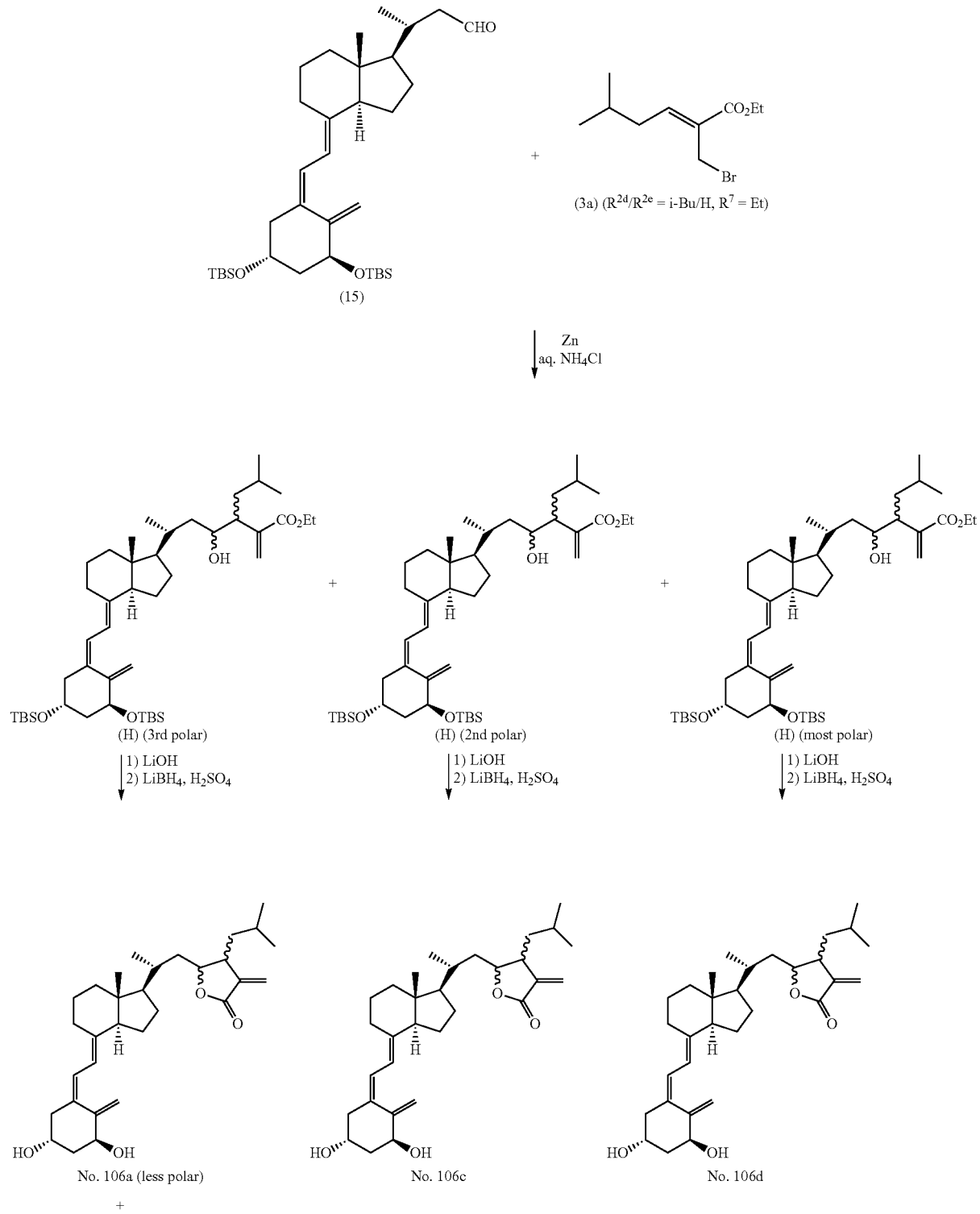

-continued

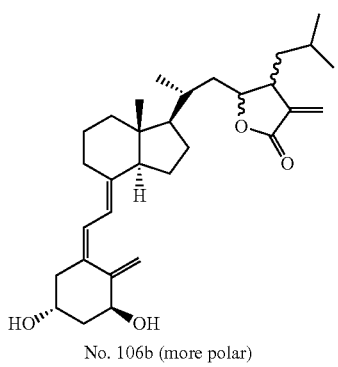
No. 106b (more polar)

(1) Using 180 mg (0.307 mmol) of Compound (15) obtained in Reference Example 13, as with Example 2(1), a reaction is carried out by replacing Compound (3a) ($R^{2d}/R^{2e}$=Et/Hydrogen atom, $R^7$=Et) obtained in Reference Example 2 with Compound (3a) ($R^{2d}/R^{2e}$=i-Bu/Hydrogen atom, $R^7$=Et) obtained in Reference Example 6 to obtain 3 components of Compound (H). They are in the order of increasing polarity: 117 mg (yield: 52%) of Compound (H) (3rd polar), 50 mg (yield: 22%) of Compound (H) (2nd polar) and 79 mg (yield: 35%) of Compound (H) (most polar). These compounds are isomers due to the steric configuration of the asymmetric carbon to which a hydroxyl group is bonded and the adjacent asymmetric carbon to which an isobutyl group is bonded. The compound (H) (3rd polar) is a mixture of two isomers, and the compound (H) (2nd polar) and the compound (H) (most polar) each are a single isomer.

Compound (H) (3rd Polar):
$^1$H-NMR (CDCl$_3$) δ: 0.05 (s, 6 H), 0.06 (s, 6 H), 0.54 (s, 1.5 H), 0.55 (s, 1.5 H), 0.80-0.98 (m, 9 H), 0.88 (s, 9 H), 0.89 (s, 9 H), 1.25-2.25 (m, 24 H), 2.42-2.50 (m, 1 H), 2.77-2.85 (m, 1 H), 3.65-3.77 (m, 1 H), 4.15-4.27 (m, 3 H), 4.36 (dd, J=6.1, 3.2 Hz, 1 H), 4.86 (d, J=2.4 Hz, 1H), 5.15 (d, J=1.7 Hz, 1 H), 5.54 (s, 0.5 H), 5.58 (d, J=1.2 Hz, 0.5 H), 6.01 (d, J=11.2 Hz, 1 H), 6.20-6.27 (m, 1.5 H), 6.28 (d, J=1.2 Hz, 0.5 H).

MS m/z 758 ((M+1)$^+$), 739 ((M−H$_2$O)$^+$), 625, 607

Compound (H) (2nd Polar):
$^1$H-NMR (CDCl$_3$) δ: 0.05 (s, 6 H), 0.06 (s, 6 H), 0.53 (s, 3 H), 0.85-0.90 (m, 6 H), 0.87 (s, 9H), 0.88 (s, 9 H), 1.00 (d, J=6.6 Hz, 3 H), 1.10-2.05 (m, 23 H), 2.21 (dd, J=12.7, 7.1 Hz, 1H), 2.42-2.47 (m, 1 H), 2.64-2.74 (m, 1 H), 2.78-2.85 (m, 1 H), 3.68-3.78 (m, 1 H), 4.15-4.30 (m, 3 H), 4.37 (dd, J=6.8, 3.9 Hz, 1 H), 4.86 (d, J=2.4 Hz, 1 H), 5.18 (d, J=1.7 Hz, 1 H), 5.65 (d, J=1.5 Hz, 1 H), 6.01 (d, J=11.0 Hz, 1 H), 6.23 (d, J=11.2 Hz, 1 H), 6.28 (d, J=1.5 Hz, 1 H).

MS m/z 757 (M$^+$), 739 ((M−H$_2$O)$^+$), 625, 607

Compound (H) (Most Polar)
$^1$H-NMR (CDCl$_3$) δ: 0.05 (s, 6 H), 0.06 (s, 6 H), 0.55 (s, 3 H), 0.84 (d, J=6.3 Hz, 3 H), 0.88 (s, 18 H), 0.90 (d, J=6.6 Hz, 3 H), 1.02 (d, J=6.6 Hz, 3 H), 1.20-2.05 (m, 22 H), 2.21 (dd, J=13.2, 7.1 Hz, 1 H), 2.35 (d, J=3.4 Hz, 1 H), 2.44 (dd, J=13.2, 3.9 Hz, 1 H), 2.75-2.85 (m, 2 H), 3.70-3.80 (m, 1 H), 4.15-4.30 (m, 3 H), 4.37 (dd, J=6.6, 3.7 Hz, 1 H), 4.87 (d, J=2.4 Hz, 1 H), 5.17-5.20 (m, 1 H), 5.60 (s, 1 H), 6.02 (d, J=11.5 Hz, 1 H), 6.24 (d, J=11.2 Hz, 1H), 6.31-6.33 (m, 1 H).

MS m/z 757 (M$^+$), 739 ((M−H$_2$O)$^+$), 625, 607

(2-a) Using 112 mg (0.154 mmol) of Compound (H) (3rd polar) obtained by the above method, a reaction similar to Example 2(2-a) was carried out to obtain 10 mg (yield: 14%, purity: 99%) of Compound No. 106a (less polar) and 16 mg (yield: 22%, purity: 99%) of Compound No. 106b (more polar). These compounds are isomers due to the steric configuration of the asymmetric carbon to which the oxygen atom is bonded on the lactone ring or the asymmetric carbon to which an isobutyl group is bonded on the lactone ring.

Compound No. 106a (Less Polar)
$^1$H-NMR (CDCl$_3$) δ: 0.57 (s, 3 H), 0.95 (d, J=6.6 Hz, 3 H), 0.96 (d, J=6.6 Hz, 3 H), 1.02 (d, J=6.3 Hz, 3 H), 1.20-2.10 (m, 21 H), 2.31 (dd, J=13.4, 6.3 Hz, 1 H), 2.53-2.68 (m, 2 H), 2.82 (dd, J=12.2, 3.9 Hz, 1 H), 4.20-4.28 (m, 2 H), 4.40-4.48 (m, 1 H), 5.00 (s, 1 H), 5.33 (s, 1 H), 5.57 (d, J=2.2 Hz, 1 H), 6.01 (d, J=11.2 Hz, 1 H), 6.24 (d, J=2.7 Hz, 1 H), 6.37 (d, J=11.2 Hz, 1 H).

MS m/z 500 ((M+H$_2$O)$^+$), 483 ((M+1)$^+$), 465 ((M+1−H$_2$O)$^+$), 447

Compound No. 106b (More Polar)
$^1$H-NMR (CDCl$_3$) δ: 0.56 (s, 3 H), 0.95 (d, J=6.6 Hz, 3 H), 0.96 (d, J=6.6 Hz, 3 H), 1.00 (d, J=6.3 Hz, 3 H), 1.03-1.13 (m, 1 H), 1.20-2.10 (m, 20 H), 2.31 (dd, J=13.4, 6.3 Hz, 1 H), 2.63 (dd, J=13.4, 3.4 Hz, 1 H), 2.82 (dd, J=12.0, 3.9 Hz, 1 H), 3.05-3.15 (m, 1 H), 4.18-4.28 (m, 1 H), 4.40-4.48 (m, 1 H), 4.67 (ddd, J=11.7, 7.1, 1.5 Hz, 1 H), 5.00 (s, 1 H), 5.32-5.34 (m, 1 H), 5.49 (d, J=2.4 Hz, 1 H), 6.01 (d, J=11.5 Hz, 1 H), 6.20 (d, J=2.7 Hz, 1H), 6.37 (d, J=11.2 Hz, 1 H).

MS m/z 500 ((M+H$_2$O)$^+$), 483 ((M+1)$^+$), 465 ((M+1−H$_2$O)$^+$), 447

(2-b) Using 46 mg (61 μmol) of Compound (H) (2nd polar) obtained in the above reaction, a reaction similar to Example 2(2-b) was carried out to obtain 12 mg (yield: 41%, purity: 99%) of Compound No. 106c.

Compound No. 106c:
$^1$H-NMR (CDCl$_3$) δ: 0.56 (s, 3 H), 0.96 (d, J=6.6 HZ, 3 H), 0.97 (d, J=6.6 Hz, 3 H), 1.06 (d, J=6.1 Hz, 3 H), 1.15-2.10 (m, 21 H), 2.32 (dd, J=13.4, 6.3 Hz, 1 H), 20.66 (dd, J=13.4, 3.4 Hz, 1 H), 2.63-2.78 (m, 1 H), 2.82 (dd, J=12.4, 4.1 Hz, 1 H), 4.17-4.27 (m, 2 H), 4.40-4.47 (m, 1 H), 5.00 (s, 1 H), 5.32-5.34 (m, 1 H), 5.58 (d, J=2.0 Hz 1 H), 6.01 (d, J=11.2 Hz, 1 H), 6.24 (d, J=2.4 Hz, 1 H), 6.38 (d, J=11.2 Hz, 1 H).

MS m/z 500 ((M+H$_2$O)$^+$), 483 ((M+1)$^+$), 465 ((M+1−H$_2$O)$^+$), 447

(2-c) Using 75 mg (99 μmol) of Compound (H) (most polar) obtained by the above method, a reaction similar to Example 2(2-c) was carried out to obtain 17 mg (yield: 36%, purity: 99%) of Compound No. 106d.

Compound No. 106d:
$^1$H-NMR (CDCl$_3$) δ: 0.56 (s, 3 H), 0.94 (d, J=6.6 Hz, 3 H), 0.95 (d, J=6.6 Hz, 3 H), 1.06 (d, J=6.3 Hz, 3 H), 1.20-2.10 (m, 21 H), 2.32 (dd, J=13.4, 6.6 Hz, 1 H), 2.60 (d, J=13.7, 3.7 Hz, 1 H), 2.82 (dd, J=13.4, 4.4 Hz, 1 H), 2.98-3.07 (m, 1 H), 4.18-4.28 (m, 1 H), 4.40-4.48 (m, 1 H), 4.59 (ddd, J=8.8, 6.3, 4.4 Hz, 1 H), 4.99-5.01 (m, 1 H), 5.32-5.34 (m, 1 H), 5.48 (d, J=1.7 Hz, 1 H), 6.02 (d, J=11.2 Hz, 1 H), 6.19 (d, J=2.2 Hz, 1 H), 6.38 (d, J=11.2 Hz, 1H).

MS m/z 500 ((M+H$_2$O)$^+$), 483 ((M+1)$^+$), 465 ((M+1−H$_2$O)$^+$), 447

Example 7
Synthesis of 20(R)-(tetrahydro-3-methylene-2-furanone-4-hexyl-5-yl)methyl-9,10-secopregna-5(Z),7(E),10(19)-triene-1α,3β-diol (Compound No. 107a, Compound No. 107b, Compound No. 107c, and Compound No. 107d)
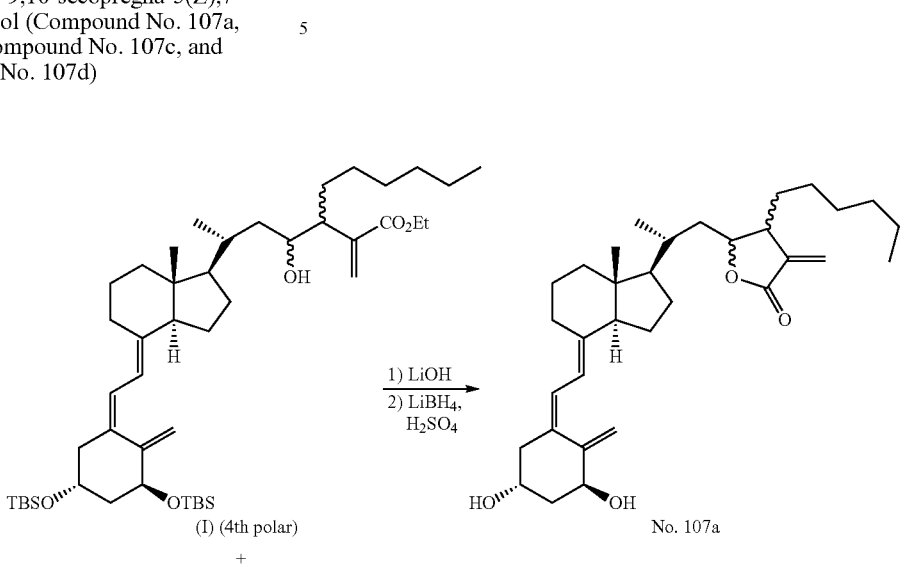
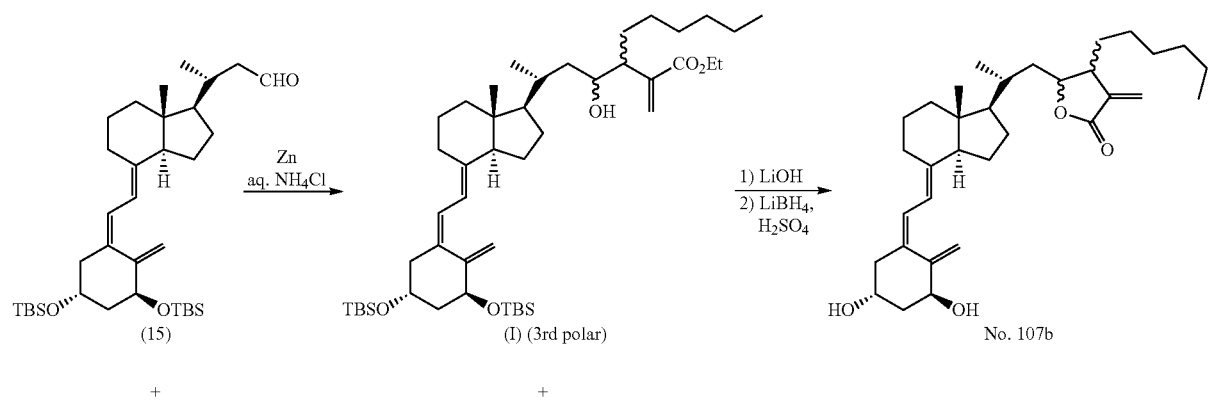
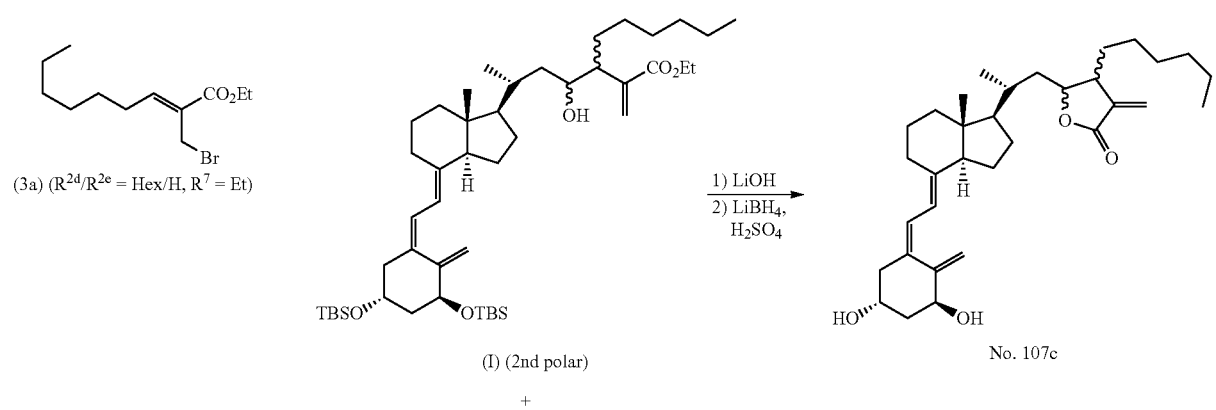

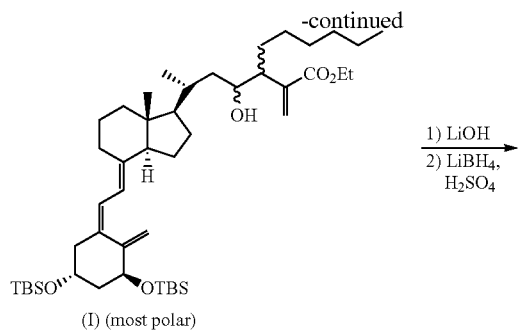
(I) (most polar)

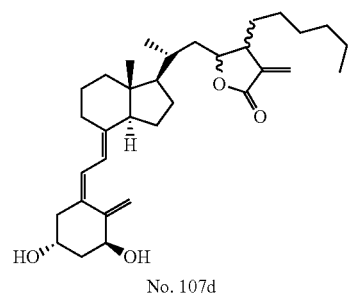
No. 107d (1) Using 202 mg (0.344 mmol) of Compound (15) obtained in Reference Example 13, as with Example 2(1), a reaction was carried out by replacing Compound (3a) ($R^{2d}/R^{2e}$=Et/Hydrogen atom, $R^7$=Et) obtained in Reference Example 2 with Compound (3a) ($R^{2d}/R^{2e}$=Hex/Hydrogen atom, $R^7$=Et) obtained in Reference Example 7 to yield 4 components of Compound (I). They are in the order of increasing polarity: 41 mg (yield: 15%) of Compound (1) (4th polar), 37 mg (yield: 14%) of Compound (I) (3rd polar), 46 mg (yield: 17%) of Compound (I) (2nd polar) and 36 mg (yield: 13%) of Compound (I) (most polar). These compounds are isomers due to the steric configuration of the asymmetric carbon to which a hydroxyl group is bonded and the adjacent asymmetric carbon to which a hexyl group is bonded.

Compound (I) (4th Polar):
$^1$H-NMR (CDCl$_3$) δ: 0.05 (s, 6 H), 0.06 (s, 6 H), 0.55 (s, 3 H), 0.87 (s, 9 H), 0.88 (s, 9 H), 0.84-2.04 (m, 32 H), 2.19-2.24 (m, 2 H), 2.44-2.47 (m, 1 H), 2.54-2.57 (m, 1 H), 2.80-2.83 (m, 1 H), 3.78 (br, 1 H), 4.19-4.24 (m, 3 H), 4.36 (br, 1 H), 4.86 (s, 1 H), 5.17 (s, 1 H), 5.52 (s, 1H), 6.01 (d, J=11.2 Hz, 1 H), 6.24 (d, J=11.7 Hz, 1 H), 6.27 (s, 1 H).

MS m/z 785.5 ((M+1)$^+$)

Compound (I) (3rd Polar):
$^1$H-NMR (CDCl$_3$) δ: 0.05 (s, 6 H), 0.06 (s, 6 H), 0.55 (s, 3 H), 0.87 (s, 9 H), 0.88 (s, 9 H), 0.82-2.04 (m, 32 H), 2.19-2.24 (m, 2 H), 2.44-2.53 (m, 2 H), 2.80-2.83 (m, 1 H), 3.75 (br, 1H), 4.19-4.23 (m, 3 H), 4.37 (br, 1 H), 4.86 (s, 1 H), 5.16 (s, 1 H), 5.57 (s, 1 H), 6.01 (d, J=11.2 Hz, 1 H), 6.24 (d, J=11.2 Hz, 1 H), 6.25 (s, 1 H).

MS m/z 785.8 ((M+1)$^+$)

Compound (I) (2nd Polar):
$^1$H-NMR (CDCl$_3$) δ: 0.06 (s, 12 H), 0.53 (s, 3 H), 0.876 (s, 9 H), 0.879 (s, 9 H) 1.00 (d, J=6.1 Hz, 3 H), 0.85-2.01 (m, 29 H), 2.21 (dd, J=13.2, 7.1 Hz, 1 H), 2.43-2.45 (m, 1 H), 2.57-2.58 (m, 1 H), 2.80-2.83 (m, 1 H), 3.77 (br, 1 H), 4.19-4.22 (m, 3 H), 4.38 (br, 1 H), 4.86 (s, 1 H), 5.18 (s, 1 H), 5.65 (s, 1 H), 6.01 (d, J=11.2 Hz, 1 H), 6.23 (d, J=11.5 Hz, 1 H), 6.28 (s, 1 H).

MS m/z 785.8 ((M+1)$^+$)

Compound (I) (Most Polar):
$^1$H-NMR (CDCl$_3$) δ: 0.06 (s, 6 H), 0.07 (s, 6 H), 0.55 (s, 3 H), 0.87 (s, 9 H), 0.88 (s, 9 H), 1.02 (d, J=6.3 Hz, 3 H), 0.84-2.08 (m, 28 H), 2.19-2.24 (m, 1 H), 2.43-2.46 (m, 2 H), 2.63-2.66 (m, 1 H), 2.80-2.84 (m, 1 H), 3.75 (br, 1 H), 4.18-4.25 (m, 3 H), 4.38 (br, 1 H), 4.87 (d, J=2.4 Hz, 1 H), 5.18 (s, 1 H), 5.59 (s, 1 H), 6.02 (d, J=11.5 Hz, 1 H), 6.24 (d, J=11.2 Hz, 1 H), 6.32 (s, 1 H).

MS m/z 785.8 ((M+1)$^+$)

(2-a) Using 41 mg (53 μmol) of Compound (1) (4rth polar) obtained by the above method, a reaction similar to Example 2(2-b) was carried out to obtain 6.7 mg (yield: 26%, purity: 99%) of Compound No. 107a.

Compound No. 107a:
$^1$H-NMR (CDCl$_3$) δ: 0.57 (s, 3 H), 0.90 (t, J=6.6 Hz, 3 H), 1.01 (d, J=6.6 Hz, 3 H), 1.24-2.05 (m, 26 H), 2.31 (dd, J=13.4, 6.3 Hz, 1 H), 2.59-2.62 (m, 1 H), 2.82-2.85 (m, 1 H), 2.96-2.97 (m, 1 H), 4.24 (br, 1 H), 4.43 (br, a H), 4.64-4.68 (m, 1 H), 5.00 (s, 1 H), 5.33 (s, 1H), 5.50 (d, J=2.4 Hz, 1 H), 6.01 (d, J=11.2 Hz, 1 H), 6.21 (d, J=2.4 Hz, 1 H), 6.37 (d, J=11.2 Hz, 1 H).

MS m/z 511.3 ((M+1)$^+$)

(2-b) Using 37 mg (47 μmol) of Compound (I) (3rd polar) obtained by the above method, a reaction similar to Example 2(2-b) was carried out to obtain 6.0 mg (yield: 26%, purity: 97%) of Compound No. 107b.

Compound No. 107b:
$^1$H-NMR (CDCl$_3$) δ: 0.57 (s, 3 H), 0.90 (t, J=6.6 Hz, 3 H), 1.03 (d, J=6.6 Hz, 3 H), 1.22-2.05 (m, 26 H), 2.31 (dd, J=13.4, 6.3 Hz, 1 H), 2.55-2.62 (m, 2 H), 2.82-2.85 (m, 1 H), 4.26-4.28 (m, 2 H), 4.44 (br, 1 H), 5.00 (s, 1 H), 5.33 (s, 1 H), 5.57 (d, J=2.2 Hz, 1 H), 6.02 (d, J=11.2 Hz, 1 H), 6.26 (d, J=2.7 Hz, 1 H), 6.37 (d, J=11.2 Hz, 1 H).

MS m/z 511.3 ((M+1)$^+$)

(2-c) Using 46 mg (59 μmol) of Compound (I) (2nd polar) obtained by the above method, a reaction similar to Example 2(2-c) was carried out to obtain 4.8 mg (yield: 16%, purity: 98%) of Compound No. 107c.

Compound No. 107c:
$^1$H-NMR (CDCl$_3$) δ: 0.57 (s, 3 H), 0.89 (t, J=6.6 Hz, 3 H), 1.06 (d, J=5.9 Hz, 3 H), 1.23-1.70 (m, 20 H), 1.88-2.05 (m, 6 H), 2.32 (dd, J=13.7, 6.6 Hz, 1 H), 2.59-2.61 (m, 2 H), 2.82-2.85 (m, 1 H), 4.24-4.27 (m, 2 H), 4.44 (br, 1 H), 5.00 (s, 1 H), 5.33 (s, 1 H), 5.58 (d, J=2.2 Hz, 1 H), 6.02 (d, J=11.5 Hz, 1 H), 6.26 (d, J=2.4 Hz, 1 H), 6.38 (d, J=11.5 Hz, 1 H).

MS m/z 511.3 ((M+1)$^+$)

(2-d) Using 36 mg (45 μmol) of Compound (I) (most polar) obtained by the above method, a reaction similar to Example 2(2-c) was carried out to obtain 6.4 mg (yield: 28%, purity: 98%) of Compound No. 107d.

Compound No. 107d:
$^1$H-NMR (CDCl$_3$) δ: 0.57 (s, 3 H), 0.89 (t, J=6.6 Hz, 3 H), 1.06 (d, J=6.6 Hz, 3 H), 1.26-1.74 (m, 20 H), 1.89-2.05 (m, 6 H), 2.32 (dd, J=13.4, 6.6 Hz, 1 H), 2.59-2.62 (m, 1 H), 2.82-2.88 (m, 2 H), 4.23 (br, 1 H), 4.44 (br, 1 H), 4.55-4.60 (m, 1 H), 5.00 (s, 1 H), 5.33 (t, J=1.6 Hz, 1 H), 5.50 (d, J=1.5 Hz, 1 H), 6.02 (d, J=11.5 Hz, 1 H), 6.19 (d, J=2.0 Hz, 1 H), 6.38 (d, J=11.2 Hz, 1 H).

MS m/z 511.2 ((M+1)$^+$)

Example 8

Synthesis of 20(R)-(tetrahydro-3-methylene-2-furanone-4-octyl-5-yl)methyl-9,10-secopregna-5(Z),7(E),10(19)-triene-1α,3β-diol (Compound No. 108a, Compound No. 108b, Compound No. 108c and Compound No. 108d)

(1) Using 201 mg (0.342 mmol) of Compound (15) obtained in Reference Example 13, as in Example 2(1), a reaction was carried out by replacing Compound (3a) ($R^{2d}/R^{2e}$=Et/Hydrogen atom, $R^7$=Et) obtained in Reference Example 2 with Compound (3a) ($R^{2d}/R^{2e}$=Octyl/Hydrogen atom, $R^7$=Et) obtained in Reference Example 8 to obtain 3 components of Compound (J). They are in the order of increasing polarity: 56 mg (yield: 20%) of Compound (J) (3rd

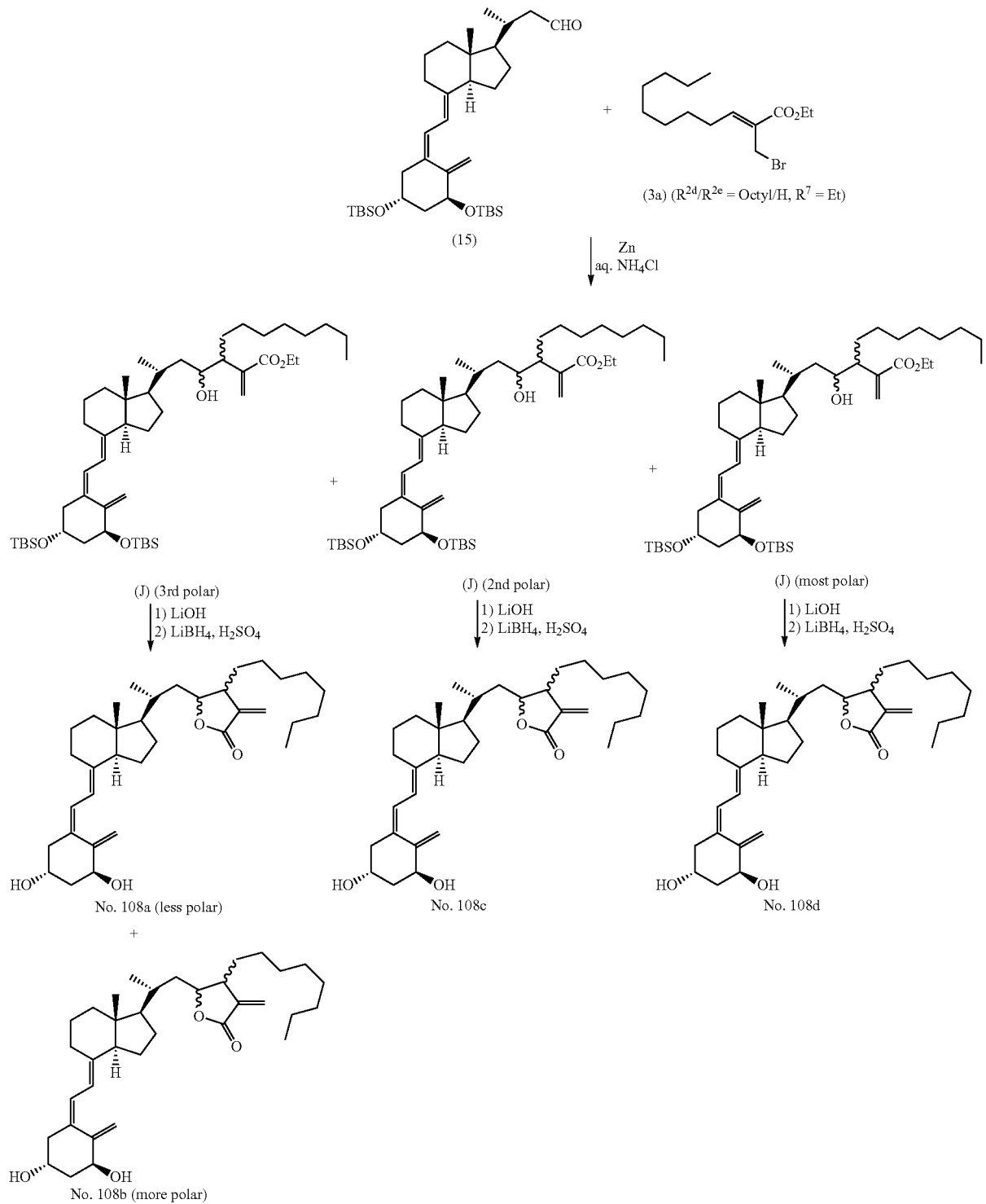

polar), 37 mg (yield: 13%) of Compound (J) (2nd polar) and 29 mg (yield: 10%) of Compound (J) (most polar). These are isomers due to the steric configuration of the asymmetric carbon to which a hydroxyl group is bonded and the adjacent asymmetric carbon to which an octyl group is bonded. Compound (J) (3rd polar) is a mixture of two isomers, and Compound (J) (2nd polar) and Compound (J) (most polar) each are a single isomer.

Compound (J) (3rd Polar):
$^1$H-NMR (CDCl$_3$) δ: 0.05 (s, 3 H), 0.06 (s, 9 H), 0.55 (s, 3 H), 0.87 (s, 9 H), 0.88 (s, 9 H), 0.83-2.04 (m, 38 H), 218-2.24 (m, 1 H), 2.43-2.45 (m, 2 H), 2.80-2.83 (m, 1 H), 3.75 (br, 1 H), 4.11-4.24 (m, 3 H), 4.37 (br, 1 H), 4.86 (d, J=2.3 Hz, 1 H), 5.16 (s, 1 H), 5.52 & 5.57 (s, 1 H), 6.01 (d, J=11.2 Hz, 1 H), 6.24 (d, J=11.2 Hz, 1 H), 6.27-6.28 (m, 1 H).
MS m/z 813.8 ((M+1)$^+$)

Compound (J) (2nd Polar):
$^1$H-NMR (CDCl$_3$) δ: 0.06 (s, 12 H), 0.53 (s, 3 H), 0.87 (s, 9 H), 0.88 (s, 9 H), 0.85-1.98 (m, 38 H), 2.22-2.24 (m, 1 H), 2.43-2.45 (m, 1 H), 2.57-2.64 (m, 1 H), 2.80-2.83 (m, 1 H), 3.77 (br, 1 H), 4.11-4.24 (m, 3 H), 4.38 (br, 1 H), 4.86 (d, J=2.3 Hz, 1 H), 5.18 (s, 1 H), 5.65 (s, 1 H), 6.01 (d, J=11.0 Hz, 1 H), 6.23 (d, J=11.1 Hz, 1 H), 6.28 (d, J=1.3 Hz, 1 H).
MS m/z 813.8 ((M+1)$^+$)

Compound (J) (Most Polar)
$^1$H-NMR (CDCl$_3$) δ: 0.06 (s, 12 H), 0.55 (s, 3 H), 0.876 (s, 9 H), 0.879 (s, 9 H), 0.72-1.99 (m, 38 H), 2.20-2.24 (m, 1 H), 2.37-2.63 (m, 2 H), 2.81-2.84 (m, 1 H), 3.74 (br, 1 H), 4.17-4.27 (m, 3 H), 4.35-4.37 (m, 1 H), 4.87 (d, J=2.5 Hz, 1 H), 5.18 (s, 1 H), 5.59 (s, 1 H), 6.02 (d, J=1.0 Hz, 1 H), 6.23 (d, J=11.5 Hz, 1 H), 6.31 (d, J=1.2 Hz, 1 H).
MS m/z 813.8 ((M+1)$^+$)

(2-a) Using 56 mg (68 µmol) of Compound (J) (3rd polar) obtained by the above method, a reaction similar to Example 2(2-a) was carried out to obtain 2.4 mg (yield: 7%, purity: 95%) of Compound No. 108a (less polar) and 3.0 mg (yield: 8%, purity: 96%) of Compound No. 108b (more polar). These compounds are isomers due to the steric configuration of the asymmetric carbon to which an octyl group is bonded on the lactone ring.

Compound No. 108a (Less Polar):
$^1$H-NMR (CDCl$_3$) δ: 0.57 (s, 3 H), 0.93 (t, J=6.8 Hz, 3 H), 1.02 (d, J=6.6 Hz, 3 H), 1.25-2.04 (m, 30 H), 2.31 (dd, J=13.4, 6.6 Hz, 1 H), 2.60 (m, 1 H), 2.82 (m, 1 H), 4.25 (m, 2H), 4.43 (br, 1 H), 4.63-6.69 (m, 1 H), 5.00 (s, 1 H), 5.33 (s, 1 H), 5.57 (d, J=2.4 Hz, 1 H), 6.01 (d, J=11.5 Hz, 1 H), 6.26 (d, J=2.7 Hz, 1 H), 6.37 (d, J=11.2 Hz, 1 H).
MS m/z 539.3 ((M+1)$^+$)

Compound No. 108b (More Polar):
$^1$H-NMR (CDCl$_3$) δ: 0.57 (s, 3 H), 0.93 (t, J=6.6 Hz, 3 H), 1.01 (d, J=6.3 Hz, 3 H), 1.10-2.05 (m, 30 H), 2.31 (dd, J=13.7, 6.6 Hz, 1 H), 2.59-2.62 (m, 1 H), 2.82-2.85 (m, 1 H), 2.95 (m, 1 H), 4.24 (br, 1 H), 4.43 (br, 1 H), 4.63-4.68 (m, 1 H), 5.00 (s, 1 H), 5.33 (s, 1 H), 5.50 (d, J=2.4 Hz, 1 H), 6.01 (d, J=11.7 Hz, 1 H), 6.21 (d, J=2.4 Hz, 1 H), 6.37 (d, J=11.5 Hz, 1 H).
MS m/z 539.3 ((M+1)$^+$)

(2-b) Using 37 mg (45 µmol) of Compound (J) (2nd polar) obtained by the above method, a reaction similar to Example 2(2-b) was carried out to obtain 2.4 mg (yield: 10%, purity: 98%) of Compound No. 108c.

Compound No. 108c:
$^1$H-NMR (CDCl$_3$) δ: 0.57 (s, 3 H), 0.88 (t, J=6.6 Hz, 3 H), 1.06 (d, J=6.1 Hz, 3 H), 1.26-1.70 (m, 25 H), 1.92-2.02 (m, 5 H), 2.32 (dd, J=13.7, 6.6 Hz, 1 H), 2.59-2.61 (m, 2 H), 2.82-2.85 (m, 1 H), 4.24-4.25 (m, 2 H), 4.44 (br, 1 H), 5.00 (s, 1 H), 5.33 (s, 1 H), 5.58 (d, J=2.0 Hz, 1 H), 6.01 (d, J=11.0 Hz, 1 H), 6.26 (d, J=2.4 Hz, 1 H), 6.38 (d, J=11.2 Hz, 1 H).
MS m/z 539.3 ((M+1)$^+$)

(2-c) Using 29 mg (36 µmol) of Compound (J) (most polar) obtained by the above method, a reaction similar to Example 2(2-c) was carried out to obtain 2.2 mg (yield: 11%, purity: 99%) of Compound No. 108d.

Compound No. 106d:
$^1$ H-NMR (CDCl$_3$) δ: 0.56 (s, 3 H), 0.88 (t, J=6.7 Hz, 3 H), 1.06 (d, J=6.3 Hz, 3 H), 1.26-1.70 (m, 25 H), 1.94-2.05 (m, 5 H), 2.32 (dd, J=13.4, 6.6 Hz, 1 H), 2.58-2.62 (m, 1 H), 2.82-2.88 (m, 2 H), 4.23 (br, 1 H), 4.44 (br, 1 H), 4.54-4.61 (m, 1 H), 5.00 (s, 1 H), 5.33 (s, 1H), 5.50 (d, J=1.7 Hz, 1 H), 6.02 (d, J=11.2 Hz, 1 H), 6.20 (d, J=2.0 Hz, 1 H), 6.38 (d, J=11.5 Hz, 1 H).
MS m/z 539.4 ((M+1)$^+$)

Example 9

Synthesis of 20(R)-(tetrahydro-3-methylene-2-furanone-4-phenethyl-5-yl)methyl-9,10-secopregna-5 (Z),7(E),10(19)-triene-1α,3β-diol (Compound No. 110a, Compound No. 110b, Compound No. 110c, and Compound No. 110d)

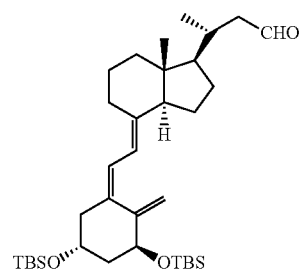

(15)

+

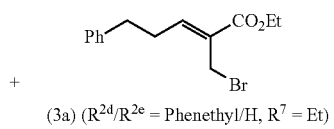

(3a) (R$^{2d}$/R$^{2e}$ = Phenethyl/H, R$^7$ = Et)

Zn
aq. NH$_4$Cl

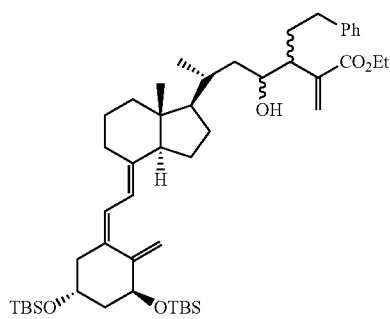 (K) (3rd polar)

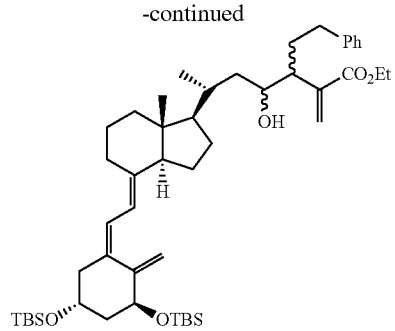 (K) (2nd polar)

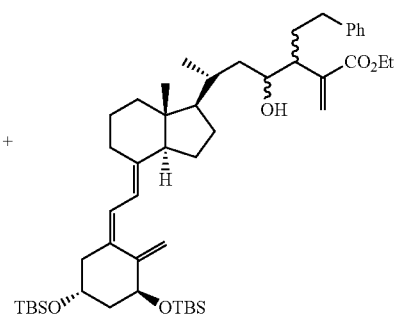 (K) (most polar)

1) LiOH
2) LiBH₄, H₂SO₄

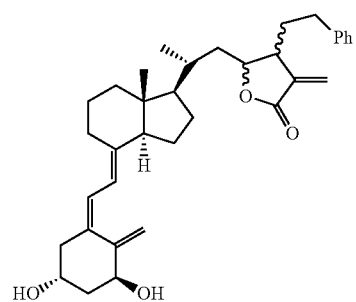 No. 110a (less polar)

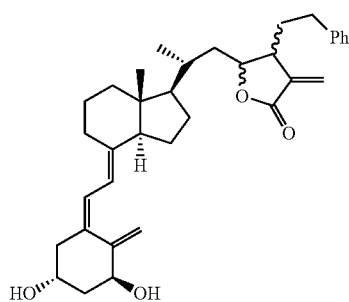 No. 110c

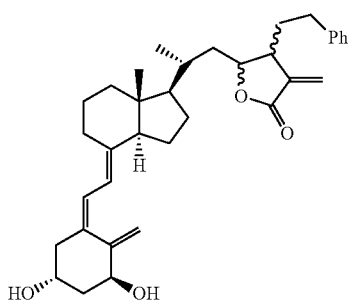 No. 110d

+

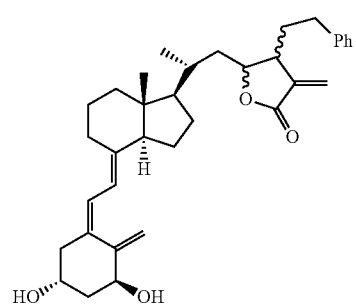 No. 110b (more polar)

(1) Using 202 mg (0.344 mmol) of Compound (15) obtained in Reference Example 13, as in Example 2(1), a reaction was carried out by replacing Compound (3a) ($R^{2d}/R^{2e}$=Et/Hydrogen atom, $R^7$=Et) obtained in Reference Example 2 with Compound (3a) ($R^{2d}/R^{2e}$=Phenethyl/Hydrogen atom, $R^7$=Et) obtained in Reference Example 10 to obtain 3 components of Compound (K). They are in the order of increasing polarity: 99 mg (yield: 36%) of Compound (K) (3rd polar), 44 mg (yield: 16%) of Compound (K) (2nd polar) and 43 mg (yield: 16%) of Compound (K) (most polar). These compounds are isomers due to the steric configuration of the asymmetric carbon to which a hydroxyl group is bonded and the adjacent asymmetric carbon to which a phenethyl group is bonded. Compound (K) (3rd polar) is a mixture of two isomers, and Compound (K) (2nd polar) and Compound (K) (most polar) each are a single isomer.

Compound (K) (3rd Polar):

$^1$H-NMR (CDCl₃) δ: 0.06 (s, 12 H), 0.54 (s, 3 H), 0.87 (s, 9 H), 0.88 (s, 9 H), 0.90-0.94 (m, 3H), 1.24-2.07 (m, 21 H), 2.18-2.24 (m, 1 H), 2.43-2.84 (m, 5 H), 3.78 (br, 1 H), 4.09-4.26 (m, 3 H), 4.34-4.36 (m, 1 H), 4.86 (d, J=2.4 Hz, 1 H), 5.17 (d, J=1.8 Hz, 1 H), 5.58 & 5.62 (s, 1H), 6.01 (d, J=11.5 Hz, 1 H), 6.23 (d, J=11.2 Hz, 1 H), 6.22-6.25 (m, 1 H), 7.14-7.29 (m, 5H).

Compound (K) (2nd Polar):

$^1$H-NMR (CDCl$_3$) δ: 0.06 (s, 12 H), 0.52 (s, 3 H), 0.876 (s, 9 H), 0.882 (s, 9 H), 0.91 (d, J=6.3 Hz, 3 H), 1.22-2.08 (m, 21 H), 2.22-2.24 (m, 1 H), 2.43-2.80 (m, 5 H), 3.81 (br, 1 H), 4.09-4.26 (m, 3 H), 4.38 (br, 1 H), 4.86 (d, J=2.4 Hz, 1 H), 5.18 (s, 1 H), 5.68 (s, 1 H), 6.00 (d, J=11.2 Hz, 1 H), 6.23 (d, J=11.2 Hz, 1 H), 6.33 (s, 1 H), 7.15-7.29 (m, 5 H).

Compound (K) (Most Polar):

$^1$H-NMR (CDCl$_3$) δ: 0.07 (s, 6 H), 9.088 (s, 3 H), 0.094 (s, 3 H), 0.46 (s, 3 H), 0.88 (s, 9 H), 0.90-0.93 (m, 12 H), 1.24-2.08 (m, 21 H), 2.23-2.25 (m, 1 H), 2.40-2.83 (m, 5 H), 3.74 (br, 1H), 4.09-4.26 (m, 3 H), 4.39 (br, 1 H), 4.89 (d, J=2.1 Hz, 1H), 5.22 (s, 1 H), 5.65 (s, 1 H), 6.02 (d, J=11.2 Hz, 1 H), 6.24 (d, J=11.2 Hz, 1 H), 6.39 (s, 1 H), 7.12-7.29 (m, 5 H).

(2-a) Using 99 mg (123 μmol) of Compound (K) (3rd polar) obtained by the above method, a reaction similar to Example 2(2-a) was carried out to obtain 3.7 mg (yield: 6%, purity: 99%) of Compound No. 110a (less polar) and 7.5 mg (yield: 12%, purity: 99%) of Compound No. 110b (more polar). These compounds are isomers due to the steric configuration of the asymmetric carbon to which a phenethyl group is bonded on the lactone ring.

Compound No. 110a (Less Polar):

$^1$H-NMR (CDCl$_3$) δ: 0.56 (s, 3 H), 1.02 (d, J=6.6 Hz, 3 H), 1.22-2.05 (m, 18 H), 2.32 (dd, J=13.4, 6.3 Hz, 1 H), 2.59-2.62 (m, 2 H), 2.70 (t, J=8.1 Hz, 2 H), 2.82-2.85 (m, 1 H), 4.22-4.25 (m, 1 H), 4.34-4.35 (m, 1 H), 4.41-4.43 (m, 1 H), 5.00 (s, 1 H), 5.33 (s, 1 H), 5.62 (d, J=2.2 Hz, 1 H), 6.01 (d, J=11.2 Hz, 1 H), 6.30 (d, J=2.7 Hz, 1 H), 6.37 (d, J=11.0 Hz, 1 H), 7.17-7.33 (m, 5 H).

MS m/z 531.3 ((M+1)$^+$)

Compound No. 110b (More Polar):

$^1$H-NMR (CDCl$_3$) δ: 0.56 (s, 3 H), 1.00 (d, J=6.6 Hz, 3 H), 1.11-1.33 (m, 4 H), 1.46-2.03 (m, 14 H), 2.31 (dd, J=13.7, 6.3 Hz, 1 H), 2.58-2.76 (m, 3 H), 2.81-2.84 (m, 1 H), 3.00-3.01 (m, 1 H), 4.23 (br, 1 H), 4.43 (br, 1 H), 4.65-4.70 (m, 1 H), 4.99 (s, 1 H), 5.33 (s, 1 H), 5.57 (d, J=2.2 Hz, 1 H), 6.01 (d, J=11.2 Hz, 1 H), 6.26 (d, J=2.2 Hz, 1 H), 6.36 (d, J=11.2 Hz, 1 H), 7.18 (d, J=7.8 Hz, 2 H), 7.21-7.33 (m, 3 H).

MS m/z 531.3 ((M+1)$^+$)

(2-b) Using 44 mg (54 μmol) of Compound (K) (2nd polar) obtained by the above method, a reaction similar to Example 2(2-b) was carried out to obtain 4.4 mg (yield: 15%, purity: 99%) of Compound No. 110c.

Compound No. 110c:

$^1$H-NMR (CDCl$_3$) δ: 0.54 (s, 3 H), 1.06 (d, J=5.9 Hz, 3 H), 1.09-2.06 (m, 18 H), 2.32 (dd, J=13.4, 6.3 Hz, 1 H), 2.59-2.72 (m, 4 H), 2.82-2.85 (m, 1 H), 4.23 (br, 1 H), 4.30-4.32 (m, 1H), 4.44 (br, 1 H), 5.00 (s, 1 H), 5.33 (t, J=1.7 Hz, 1 H), 5.64 (d, J=2.0 Hz, 1 H), 6.01 (d, J=11.2 Hz, 1 H), 6.31 (d, J=2.4 Hz, 1 H), 6.38 (d, J=11.5 Hz, 1 H), 7.17-7.33 (m, 5 H).

MS m/z 531.2 ((M+1)$^+$)

(2-c) Using 43 mg (54 μmol) of Compound (K) (most polar) obtained by the above method, a reaction similar to Example 2(2-c) was carried out to obtain 5.8 mg (yield: 20%, purity: 99%) of Compound No. 110d.

Compound No. 110d:

$^1$H-NMR (CDCl$_3$) δ: 0.56 (s, 3 H), 1.05 (d, J=6.6 Hz, 3 H), 1.07-2.05 (m, 18 H), 2.32 (dd, J=13.4, 6.6 Hz, 1 H), 2.55-2.62 (m, 2 H), 2.70-2.85 (m, 2 H), 2.92-2.94 (m, 1 H), 4.23 (br, 1H), 4.43 (br, 1 H), 4.57-4.62 (m, 1 H), 5.01 (s, 1 H), 5.33 (s, 1 H), 5.52 (d, J=1.8 Hz, 1 H), 6.02 (d, J=11.5 Hz, 1 H), 6.26 (d, J=2.0 Hz, 1 H), 6.38 (d, 3=11.2 Hz, 1 H), 7.16-7.33 (m, 5 H).

MS m/z 531.3 ((M+1)$^+$)

Example 10

Synthesis of 20(R)-(tetrahydro-3-methylene-2-furanone-4-(2-hydroxyethyl)-5-yl)methyl-9,10-secopregna-5(Z),7(E),10(19)-triene-1α,3β-diol (Compound No. 114a, Compound No. 114b, and Compound No. 114c

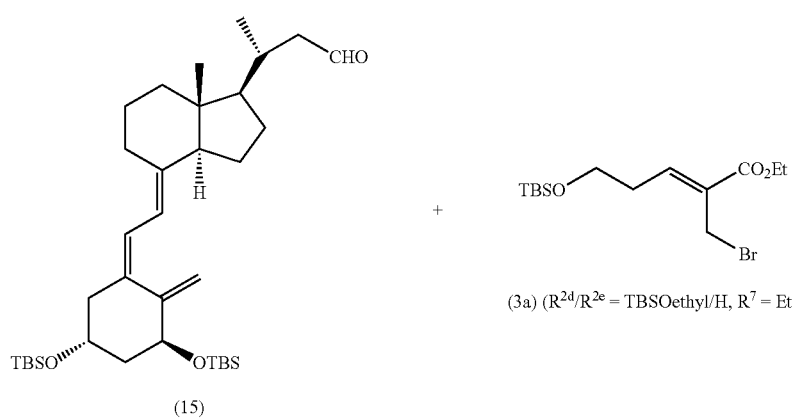

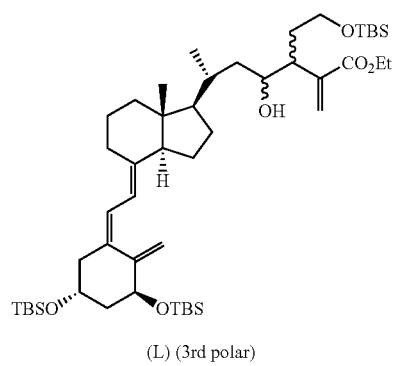

(L) (3rd polar)

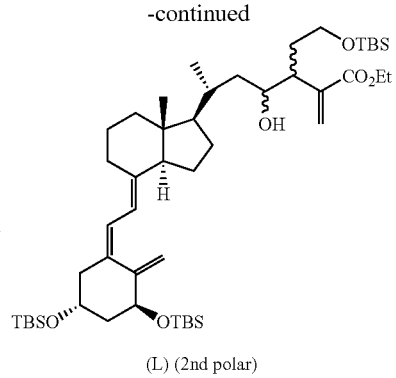

(L) (2nd polar)

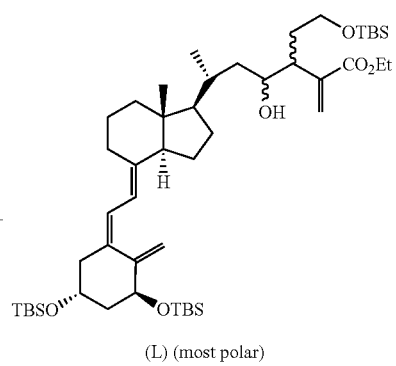

(L) (most polar)

1) LiOH
2) LiBH₄, H₂SO₄
3) HCl

1) LiOH
2) LiBH₄, H₂SO₄
3) HCl

1) LiOH
2) LiBH₄, H₂SO₄
3) HCl

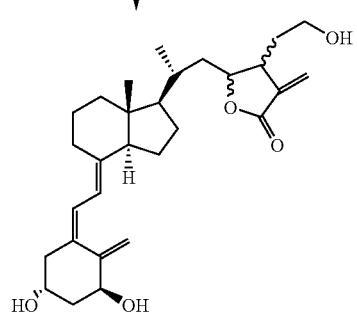

No. 114a

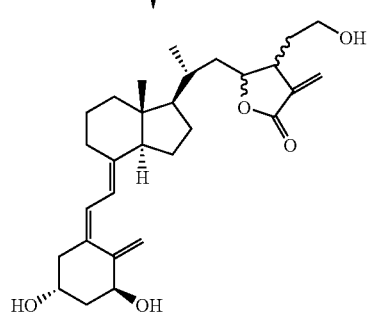

No. 114b

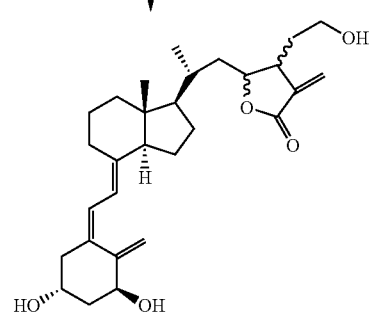

No. 114c (1) Using 202 mg (0.344 mmol) of Compound (15) obtained in Reference Example 13, as in Example 2(1), a reaction was carried out by replacing Compound (3a) ($R^{2d}/R^{2e}$=Et/Hydrogen atom, $R^7$=Et) obtained in Reference Example 2 with Compound (3a) ($R^{2d}/R^{2e}$=TBSOEt/Hydrogen atom, $R^7$=Et) obtained in Reference Example 12 to obtain 3 components of Compound (L). They are in the order of increasing polarity: 41 mg (yield: 12%) of Compound (L) (3rd polar), 40 mg (yield: 12%) of Compound (L) (2nd polar) and 23 mg (yield: 7%) of Compound (L) (most polar). These compounds are isomers due to the steric configuration of the asymmetric carbon to which a hydroxyl group is bonded and the adjacent asymmetric carbon to which a 2-(t-butyldimethylsilyloxy)ethyl group is bonded. Compound (L) (3rd polar) is a mixture of two isomers, and Compound (L) (2nd polar) and Compound (L) (most polar) each are a single isomer.

Compound (L) (3rd Polar):

¹H-NMR (CDCl₃) δ: 0.055 (s, 6 H), 0.063 (s, 6 H), 0.55 & 0.56 (s, 3 H), 0.87 (s, 9 H), 0.88 (s, 9 H), 1.05 & 1.06 (s, 9 H), 0.91-2.04 (m, 23 H), 2.19-2.24 (m, 1 H), 2.40-2.54 (m, 2 H), 2.81-2.84 (m, 1 H), 3.60-3.82 (m, 3 H), 4.16-4.29 (m, 5 H), 4.37 (br, 1 H), 4.86 (s, 1 H), 5.17 (s, 1 H), 5.46 & 5.55 (s, 1 H), 6.02 (d, J=10.7 Hz, 1 H), 6.22-6.26 (m, 2 H), 7.37-7.42 (m, 6H), 7.64-7.66 (m, 4 H).

MS m/z 983.5 ((M+1)⁺)

Compound (L) (2nd Polar):

¹H-NMR (CDCl₃) δ: 0.06 (s, 12 H), 0.54 (s, 3 H), 0.86 (s, 9 H), 0.88 (s, 9 H), 1.03 (s, 9 H), 0.81-2.04 (m, 23 H), 2.19-2.24 (m, 1 H), 2.43-2.46 (m, 1 H), 2.81-2.84 (m, 1 H), 3.00-3.03 (m, 1 H), 3.51-3.57 (m, 1 H), 3.65-3.67 (m, 1 H), 3.81 (m, 1 H), 4.15-4.23 (m, 5 H), 4.38 (br, 1 H), 4.88 (d, J=2.4 Hz, 1 H), 5.20 (s, 1 H), 5.52 (s, 1 H), 6.02 (d, J=11.2 Hz, 1 H), 6.23 (d, J=11.0 Hz, 1 H), 6.27 (s, 1 H), 7.33-7.43 (m, 6 H), 7.60-7.65 (m, 4 H).

MS m/z 983.5 ((M+1)⁺)

Compound (L) (Most Polar):

¹H-NMR (CDCl₃) δ: 0.06 (s, 12 H), 0.52 (s, 3 H), 0.88 (s, 18 H), 1.04 (s, 9 H), 0.76-2.04 (m, 23 H), 2.19-2.28 (m, 1 H), 2.43-2.45 (m, 1 H), 2.80-2.83 (m, 2 H), 3.61-3.81 (m, 3 H), 4.11-4.21 (m, 5 H), 4.37 (br, 1 H), 4.87 (s, 1 H), 5.18 (s, 1 H), 5.66 (s, 1 H), 6.01 (d, J=11.2 Hz, 1 H), 6.23 (d, J=12.0 Hz, 1 H), 6.26 (s, 1 H), 7.35-7.42 (m, 6 H), 7.60-7.65 (m, 4 H).

MS m/z 983.5 ((M+1)⁺)

(2-a) A reaction solution was prepared by adding 0.31 ml (4.0 M, 1.2 mmol) of an aqueous lithium hydroxide solution to an anhydrous THF solution (2.0 ml) containing 41 mg (0.041 mmol) of Compound (L) (3rd polar) obtained by the above method and was stirred at room temperature for 60 minutes. Water was added to the reaction solution, and extraction was performed with ethyl acetate. The organic layer was washed with water and saturated brine, dried with anhydrous sodium sulfate and concentrated. The resultant residue was dissolved in a mixed solution of toluene and acetonitrile (1:1, 2 ml). To the solution was added 16 mg (0.17 mmol) of LiBF₄ and the resultant solution was chilled with ice. A reaction solution was prepared by adding 0.016 ml (2.0 M, 0.12 mmol) of an acetonitrile solution of sulfuric acid to the above solution and was stirred for 4 hours. A saturated aqueous solution of sodium hydrogen carbonate was added to the reaction solution, and the resultant solution was subjected to extraction with ethyl acetate. The organic layer was washed with saturated brine, dried with anhydrous sodium sulfate and concentrated. The resultant residue was dissolved in methanol (2 ml). To the resultant solution was added 0.62 ml (4.0 M, 2.48 mmol) of a hydrochloric acid-dioxane solution, and stirring was continued at room temperature for 2 hours. A saturated aqueous solution of sodium hydrogen carbonate was added to this reaction solution, and extraction was performed with ethyl acetate. The organic layer was washed with saturated brine, dried with anhydrous sodium sulfate and concentrated. The residue was purified by preparative TLC (chloroform:methanol=5:1) and HPLC (reversed phase, A=95% H$_2$O/CH$_3$CN; B=60% CH$_3$OH/MeOH; B=60% (0.5% H$_2$O)) to obtain 1.6 mg (yield: 8%, purity: 98%) of Compound No. 114a. The compound is a mixture of two isomers due to the steric configuration of the asymmetric carbon to which the oxygen atom is bonded on the lactone ring or the asymmetric carbon to which a 2-hydroxyethyl group is bonded on the lactone ring.

Compound No. 114a:

$^1$H-NMR (CDCl$_3$) δ: 0.57 (s, 6 H), 1.01 (d, J=6.3 Hz, 3 H), 1.02 (d, J=6.4 Hz, 3 H), 0.83-2.05 (m, 32 H), 2.29-2.34 (m, 4 H), 2.58-2.61 (m, 2 H), 2.82 (m, 3 H), 3.25 (m, 1 H), 3.66-3.78 (m, 4 H), 4.24-4.43 (m, 7 H), 4.73 (m, 1 H), 5.00 (s, 2 H), 5.33 (s, 2 H), 5.57 (d, 3=2.2 Hz, 1 H), 5.63 (d, J=2.4 Hz, 1 H), 6.01 (d, J=11.2 Hz, 2 H), 6.26 (d, J=2.4 Hz, 1 H), 6.29 (d, J=2.9 Hz, 1 H), 6.37 (d, J=11.2 Hz, 2 H).

MS m/z 471.2 ((M+1)$^+$)

(2-b) Using 39 mg (0.040 mmol) of Compound (L) (2nd polar) obtained by the above method, a reaction similar to Example 10(2-a) was carried out to obtain 2.0 mg (yield: 11%, purity: 100%) of Compound No. 114b.

Compound No. 114:

$^1$H-NMR (CDCl$_3$) δ: 0.56 (s, 3 H), 1.06 (d, J=6.1 Hz, 3 H), 0.83-2.05 (m, 16 H), 2.29-2.33 (m, 2 H), 2.58-2.61 (m, 1 H), 2.80-2.85 (m, 2 H), 3.64-3.77 (m, 2 H), 4.23-4.34 (m, 3 H), 4.44 (br, 1 H), 5.00 (s, 1 H), 5.33 (t, J=1.7 Hz, 1 H), 5.64 (d, J=2.1 Hz, 1 H), 6.01 (d, J=11.2 Hz, 1 H), 6.30 (d, J=2.7 Hz, 1 H), 6.38 (d, J=1.0 Hz, 1 H).

MS m/z 471.3 ((M+1)$^+$)

(2-c) Using 23 mg (0.023 mmol) of Compound (L) (most polar) obtained by the above method, a reaction similar to Example 10(2-a) was carried out to obtain 1.5 mg (yield: 14%, purity: 100%) of Compound No. 114c.

Compound No. 114c:

$^1$H-NMR (CDCl$_3$) δ: 0.57 (s, 3 H), 1.06 (d, J=6.6 Hz, 3 H), 0.83-2.05 (m, 16 H), 2.17-2.34 (m, 2 H), 2.59-2.62 (m, 1 H), 2.80-2.84 (m, 1 H), 3.18 (m, 1 H), 3.65-3.80 (m, 2 H), 4.23-4.30 (m, 2 H), 4.44 (br, 1 H), 4.61 (m, 1 H), 5.00 (s, 1 H), 5.33 (s, 1 H), 5.58 (d, J=1.7 Hz, 1 H), 6.02 (d, J=11.2 Hz, 1 H), 6.25 (d, J=2.0 Hz, 1 H), 6.38 (d, J=11.2 Hz, 1 H).

MS m/z 471.3 ((M+1)$^+$)

Example 11

Synthesis of 2α-methyl-20(R)-(tetrahydro-3-methylene-2-furanone-4(R)-methyl-5(R)-yl)methyl-9,10-secopregna-5(Z),7(E),10(19)-triene-1α,3β-diol (Compound No. 201a) and 2α-methyl-20(R)-(tetrahydro-3-methylene-2-furanone-4(S)-methyl-5(S)-yl)methyl-9,10-secopregna-5(Z),7(E),10(19)-triene-1α,3β-diol (Compound No. 201 b)

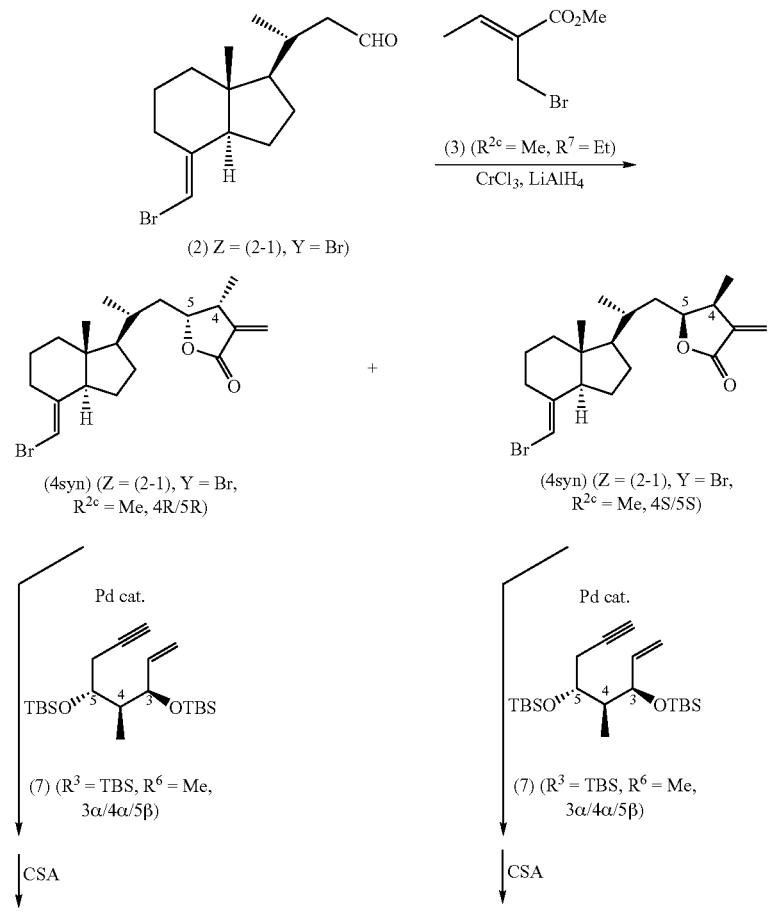

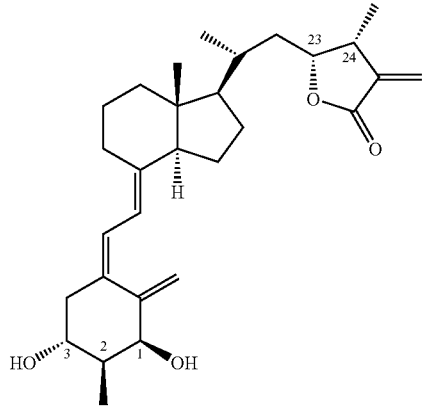

No. 201a
(1α/2α/3β/23R/24R)

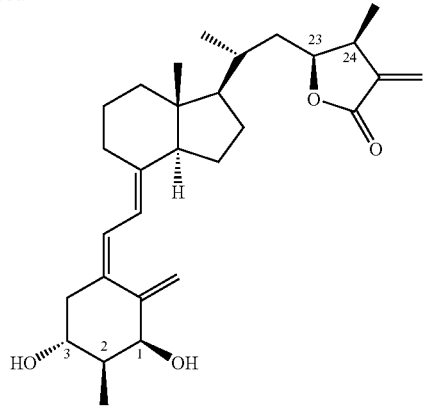

No. 201b
(1α/2α/3β/23S/24S)

(1) A solution was prepared by adding 97 mg (2.6 mmol) of LiAlH$_4$ to a THF (26 ml) suspension containing 811 mg (5.1 mmol) of chromium chloride (III) at 0° C. and was stirred at room temperature for 30 minutes. To the solution, a THF (8 ml) solution containing 494 mg (2.6 mmol) of Compound (3) ($R^{2c}$=Me, $R^7$=Me) which was obtained by using methyl acrylate in place of ethyl acrylate as in Reference Example 1 and a THF (8 ml) solution of 385 mg (1.3 mmol) of Compound (2) (Z=(2-1), Y=Br) obtained by a method known in the literature (for example, the specification of International Publication WO 95/33716) were added, and the resultant reaction solution was stirred at the same temperature for one hour. Water was added to the reaction solution, and extraction of the aqueous layer was performed with diethyl ether. The combined organic layer was washed with saturated brine, and dried with anhydrous sodium sulfate. The residue obtained by distilling off the solvent under reduced pressure was purified by preparative TLC (chloroform) to obtain 467 mg of a mixture (volume ratio of 1:1) of Compound (4syn) (Z=(2-1), Y=Br, $R^{2c}$=Me, 4R/5R) and Compound (4syn) (Z=(2-1), Y=Br, $R^{2c}$=Me, 4S/5S). Yield is 95%. These compounds were separated by HPLC (normal phase, hexane:ethyl acetate=3:1).

Compound (4syn) (Z=(2-1), Y=Br, $R^{2c}$=Me, 4R/5R):

$^1$H-NMR (CDCl$_3$) δ: 0.59 (s, 3 H), 1.01 (d, J=6.6 Hz, 3 H), 1.10 (ddd, J=13.3, 10.8, 1.9 Hz, 1 H), 1.13 (d, J=7.1 Hz, 3 H), 1.20-1.35 (m, 3 H), 1.40-1.71 (m, 6 H), 1.75 (m, 1 H), 1.86 (m, 1 H), 1.97 (ddd, J=12.4, 6.7, 1.1 Hz, 1 H), 2.03 (br d, J=12.4 Hz, 1 H), 5.76 (m, 1 H), 3.17 (ddq, J=2.5, 7.7, 7.1 Hz, 1 H), 4.68 (ddd, J=11.8, 7.7, 1.9 Hz, 1 H), 5.53 (d, J=2.8 Hz, 1 H), 5.65 (s, 1 H), 6.22 (d, J=2.8 Hz, 1 H).

LRMS m/z 380 (M$^+$), 301, 227, 147, 105

HRMS calcd for C$_{20}$H$_{29}$O$_2$$^{79}$Br 380.1350, found 380.1353

Compound (4syn) (Z=(2-1), Y=Br, $R^{2c}$=Me, 4S/5S):

$^1$H-NMR (CDCl$_3$) δ: 0.58 (s, 3 H), 1.06 (d, J=6.9 Hz, 3 H), 1.14 (d, J=7.0 Hz, 3 H), 1.22-1.51 (m, 5 H), 1.52-1.72 (m, 6 H), 1.96 (m, 1 H), 1.98-2.05 (m, 2 H), 2.88 (m, 1 H), 3.11 (dddq, J=2.0, 2.0, 6.8, 7.0 Hz, 1 H), 4.60 (ddd, J=8.3, 6.8, 5.2 Hz, 1 H), 5.84 (d, J=2.1 Hz, 1 H), 5.65 (s, 1 H), 6.19 (d, J=2.1 Hz, 1 H).

LRMS m/z 380 (M$^+$), 301, 227, 147, 105

HRMS calcd for C$_{20}$H$_{29}$O$_2$$^{79}$Br 380.1351, found 380.1347

(2-a) A reaction solution was prepared by adding triethylamine (1.5 ml) and 33 mg (29 μmol) of tetrakis(triphenylphosphine) palladium (0) to a toluene solution (3 ml) containing 37 mg (96 μmol) of Compound (4syn) (Z=(2-1), Y=Br, $R^{2c}$=Me, 4R/5R) obtained by the above method and 46 mg (0.12 mmol) of Compound (7) ($R^3$=TBS, $R^6$=Me, 3α/4α/5β) obtained by a method known in the literature (for example, Fujishima et al., Bioorg. Med. Chem. Vol. 8, 123, 2000) and was stirred at 110° C. for 1.5 hours. The reaction solution was filtered through a silica gel pad (and eluted with hexane-ethyl acetate 5:1) to obtain a crude product (45 mg). The crude product was dissolved in 3 ml of methanol, and 47 mg (0.2 mmol) of camphor sulfuric acid was added to the solution at 0° C. The resultant solution was stirred at room temperature for 45 minutes. A saturated aqueous solution of sodium hydrogen carbonate was added to the solution, and extraction of the aqueous layer was performed with ethyl acetate. The organic layer was washed with saturated brine, and dried with anhydrous sodium sulfate. The residue obtained by distilling off the solvent under reduced pressure was purified by silica gel column chromatography (hexane:ethyl acetate=1:2) to obtain 24 mg of Compound 201a. Yield: 57%.

Compound No. 201a:

$^1$H-NMR (CDCl$_3$) δ: 0.57 (s, 3 H), 1.02 (d, J=6.4 Hz, 3 H), 1.08 (m, 1 H), 1.13 (d, J=7.3 Hz, 3 H), 1.15-1.35 (m, 3 H), 1.40-2.10 (m, 14 H), 2.31 (dd, J=13.4, 6.6 Hz, 1 H), 2.59 (dd, J=13.4, 3.3 Hz, 1 H), 2.83 (dd, J=12.1, 3.8 Hz, 1 H), 3.16 (dq, J=7.8, 7.3 Hz, 1 H), 4.23 (m, 1H), 4.43 (m, 1 H), 4.67 (ddd, J=11.8, 7.8, 2.0 Hz, 1 H), 4.99 (s, 1 H), 5.33 (s, 1 H), 5.52 (d, J=2.7 Hz, 1 H), 6.01 (d, J=11.3 Hz, 1 H), 6.21 (d, J=2.7 Hz, 1 H), 6.36 (d, J=11.3 Hz, 1 H).

LRMS m/z 440 (M$^+$), 422, 404, 378, 289, 209, 105

HRMS calcd for C$_{28}$H$_{40}$O$_4$ 440.2927, found 440.2935

(2-b) Using 35 mg (92 μmol) of Compound (4syn) (Z=(2-1), Y=Br, $R^{2c}$=Me, 4S/5S) obtained by the above method and 44 mg (0.12 mmol) of Compound (7) ($R^3$=TBS, $R^6$=Me, 3α/4α/5β), a reaction similar to Example 11(2-a) was carried out to obtain 20 mg of Compound No. 201b. Yield: 48%.

Compound No. 201b:

$^1$H-NMR (CDCl$_3$) δ: 0.56 (s, 3 H), 1.05 (d, J=6.6 Hz, 3 H), 1.13 (d, J=7.1 Hz, 3 H), 1.20-1.75 (m, 13 H), 1.87-1.95 (m, 2 H), 1.96-2.08 (m, 3 H), 2.31 (dd, J=13.4, 6.6 Hz, 1 H), 2.59 (dd, J=13.4, 3.4 Hz, 1 H), 2.82 (dd, J=12.5, 4.4 Hz, 1 H), 3.11 (dddq, J=2.2, 2.2, 6.8, 7.1 Hz, 1 H), 4.22 (m, 1 H), 4.43 (m, 1 H), 4.59 (ddd, J=8.2, 6.8, 5.3 Hz, 1 H), 4.99 (dd, J=1.5, 1.5 Hz, 1 H), 5.32 (dd, J=1.5, 1.5 Hz, 1 H), 5.53 (d, J=2.2 Hz, 1 H), 6.01 (d, J=11.2 Hz, 1 H), 6.18 (d, J=2.2 Hz, 1 H), 6.37 (d, J=11.2 Hz, 1 H).

LRMS m/z 440 (M+), 422, 404, 251, 105
HRMS calcd for $C_{28}H_{40}O_4$ 440.2987, found 440.2932

Example 12

Synthesis of 2α-methyl-20(R)-(tetrahydro-3-methylene-2-furanone-4(R)-methyl-5(S)-yl)methyl-9,10-secopregna-5(Z),7(E),10(19)-triene-1α,3β-diol (Compound No. 201c)

extracted with ethyl acetate, the organic layer was washed with saturated brine and was then dried with anhydrous sodium sulfate. The residue obtained by distilling off the solvent under reduced pressure was purified by silica gel column chromatography (hexane:ethyl acetate=3:1) to obtain 14 mg of Compound (M) (4R/5R). Yield: 93%, a colorless oily substance.

$^1$H-NMR (CDCl$_3$) δ: 0.59 (s, 3 H), 0.96 (d, J=6.6 Hz, 3 H), 1.03 (m, 1 H), 1.07 (d, J=7.0 Hz, 3 H), 1.20-1.38 (m, 3 H), 1.40-1.73 (m, 7 H), 1.85-2.06 (m, 3 H), 2.30 (dq, J=3.9, 7.0 Hz, 1 H), 2.53 (br s, 2 H), 2.88 (m, 1 H), 3.71 (ddd, J=10.6, 3.9, 1.8 Hz, 1 H), 4.06 (br d, J=12.9, 1 H), 4.13 (br d, J=12.9 Hz, 1 H), 4.93 (s, 1 H), 5.17 (br s, 1 H), 5.64 (s, 1 H).

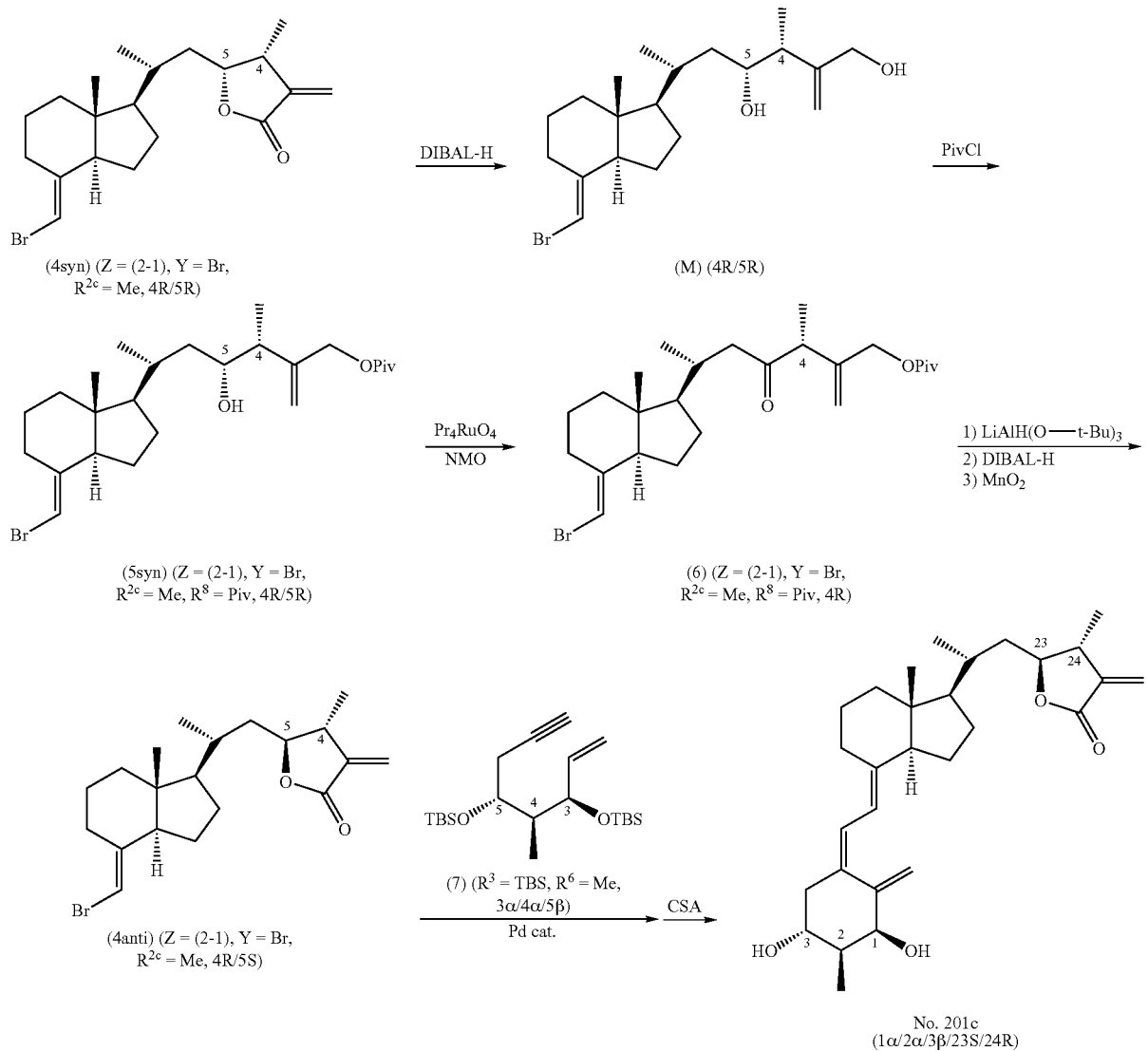

(1) A reaction solution was prepared by adding 0.15 ml (1.04 M, 0.16 mmol) of a toluene solution of DIBAL-H to a toluene solution containing 15.1 mg (0.04 mmol) of Compound (4syn) (Z=(2-1), Y=Br, R$^{2c}$=Me, 4R/5R) obtained in Example 11(1) at 0° C. and was stirred at room temperature for 2 hours. After the reaction solution was diluted with diethyl ether, a 10% aqueous solution of sodium potassium tartrate was added and the resultant solution was stirred at room temperature for one hour. After the aqueous layer was extracted with ethyl acetate, the organic layer was washed LRMS m/z 384 (M+), 254, 227, 175, 147, 106, 86
HRMS calcd for $C_{20}H_{33}O_2{}^{79}Br$ 384.1664, found 384.1667

(2) A reaction solution was prepared by adding 0.22 ml (2.7 mmol) of pyridine and 0.11 ml (0.89 mmol) of pivaloyl chloride to a methylene chloride (3.4 ml) solution containing 261 mg (0.68 mmol) of Compound (M) (4R/5R) obtained by the above method at 0° C. and was stirred at room temperature for 16 hours. After water was added to the reaction solution, the aqueous layer was extracted with diethyl ether. The organic layer was washed with saturated brine, and dried with anhydrous sodium sulfate. The residue obtained by distilling off the solvent under reduced pressure was purified by silica gel column chromatography (hexane:ethyl acetate=10:1) to obtain 272 mg of Compound (5syn) (Z=(2-1), Y=Br, $R^{2c}$=Me, $R^8$=Piv, 4R/5R). Yield: 86%, a colorless oily substance.

$^1$H-NMR (CDCl$_3$) δ: 0.58 (s, 3 H), 0.95 (d, J=6.6 Hz, 3 H), 1.02 (m, 1 H), 1.09 (d, J=6.9 Hz, 3 H), 1.14-1.73 (m, 11 H), 1.22 (s, 9 H), 1.85-2.06 (m, 3 H), 2.15 (dq, J=5.3, 6.9 Hz, 1 H), 2.86 (m, 1 H), 3.71 (m, 1 H), 4.54 (s, 2 H), 4.97 (s, 1 H), 5.12 (s, 1 H), 5.63 (s, 1 H).

LRMS m/z 468 (M$^+$), 389, 299, 269, 227, 170, 147

HRMS calcd for C$_{25}$H$_{41}$O$_3$$^{79}$Br 468.2239, found 468.2234

(3) A reaction solution was prepared by adding 20 mg (0.058 mmol) of tetrapropylammonium perruthenate (Pr$_4$NRuO$_4$) and 102 mg (0.88 mmol) of N-methylmorphorine N-oxide (NMO) to a methylene chloride (2.9 ml) solution containing 273 mg (0.58 mmol) of Compound (5syn) (Z=(2-1), Y=Br, $R^{2c}$=Me, $R^8$=Piv, 4R/5R) obtained by the above method and was stirred at room temperature for 4 hours. After the reaction solution was filtered, the filtrate was concentrated. The resultant crude product was purified by silica gel column chromatography (hexane:ethyl acetate=30:1) to obtain 252 mg of Compound (6) (Z=(2-1), Y=Br, $R^{2c}$=Me, $R^8$=Piv, 4R). Yield: 93%, a colorless oily substance.

$^1$H-NMR (CDCl$_3$) δ: 0.55 (s, 3 H), 0.85 (d, J=6.6 Hz, 3 H), 1.17 (d, J=7.1 Hz, 3 H), 1.18 (s, 9 H), 1.19-1.30 (m, 3 H), 1.35-1.70 (m, 5 H), 1.79 (m, 1 H), 1.88-2.05 (m, 3 H), 2.22 (dd, J=16.7, 9.9 Hz, 1 H), 2.45 (dd, J=16.7, 2.4 Hz, 1 H), 2.82 (m, 1 H), 3.18 (q, J=7.1 Hz, 1 H), 4.46 (d, J=14.7 Hz, 1 H), 4.50 (d, J=14.7 Hz, 1 H), 4.99 (s, 1 H), 5.16 (s, 1 H), 5.59 (s, 1H).

LRMS m/z 466 (M$^+$), 387, 364, 279, 237, 175, 137

HRMS calcd for C$_{25}$H$_{39}$$^{79}$BrO$_3$ 466.2082, found 466.2086

(4) A reaction solution was prepared by adding 0.33 ml (1.0 M, 0.33 mmol) of a THF solution of LiAlH (O-t-Bu)$_3$ to a THF (1 ml) solution containing 51 mg (0.11 mmol) of Compound (6) (Z=(2-1), Y=Br, $R^{2c}$=Me, $R^8$=Piv, 4R) obtained by the above method at 0° C. and was stirred at the same temperature for 9 hours. After a saturated aqueous solution of ammonium chloride was added to the reaction solution, the aqueous layer was extracted with ethyl acetate. The organic layer was washed with saturated brine, and dried with anhydrous sodium sulfate. The residue obtained by distilling off the solvent under reduced pressure was dissolved in toluene (1 ml). To the solution was added 0.41 ml (1.0 M, 0.41 mmol) of a toluene solution of DIBAL-H at 0° C. and the resultant solution was stirred at 0° C. for one hour. A 10% aqueous solution of sodium potassium tartrate was added to the reaction solution, and the resultant solution was stirred at 0° C. for one hour. Then the aqueous layer was extracted with ethyl acetate. The organic layer was washed with saturated brine, and dried with anhydrous sodium sulfate. The residue obtained by distilling off the solvent under reduced pressure was dissolved in methylene chloride (2 ml). To the solution was added 150 mg (1.7 mmol) of MnO$_2$ and the resultant solution was stirred at room temperature for 29 hours. After the solution was filtered, the residue obtained by concentrating the filtrate was purified by preparative TLC (hexane:ethyl acetate=10:1) to obtain 12 mg of Compound (4anti) (Z=(2-1), Y=Br, $R^{2c}$=Me, 4R/5S). Yield: 29%, a colorless oily substance.

$^1$H-NMR (CDCl$_3$) δ: 0.58 (s, 3 H), 1.07 (d, J=6.1 Hz, 3 H), 1.25 (d, J=6.8 Hz, 3 H), 1.20-1.75 (m, 11 H), 1.90-2.16 (m, 3 H), 2.64 (m, 1 H), 2.88 (m, 1 H), 4.07 (dt, J=6.3, 5.6 Hz, 1 H), 5.53 (d, J=3.1 Hz, 1 H), 5.65 (s, 1 H), 6.22 (d, J=3.1 Hz, 1 H).

LRMS m/z 380 (M$^+$), 301, 227, 147

HRMS calcd for C$_{20}$H$_{29}$O$_2$$^{79}$Br 380.1351, found 380.1354

(5) Using 14 mg (37 μmol) of Compound (4anti) (Z=(2-1), Y=Br, $R^{2c}$=Me, 4R/5S) obtained by the above method and 17 mg (48 μmol) of Compound (7) (R$^3$=TBS, R$^6$=Me, 3α/4α/5β), a reaction similar to Example 11(2-a) was carried out to obtain 7.8 mg of Compound No. 201c. Yield: 48%.

Compound No. 201c:

$^1$H-NMR (CDCl$_3$) δ: 0.57 (s, 3 H), 1.06 (d, J=5.9 Hz, 3 H), 1.28 (d, J=6.8 Hz, 3 H), 1.25-1.80 (m, 13 H), 1.85-2.10 (m, 5 H), 2.32 (dd, J=13.6, 6.4 Hz, 1 H), 2.55-2.70 (m, 2 H), 2.83 (m, 1 H), 4.07 (dt, J=5.9, 6.4 Hz, 1 H), 4.23 (m, 1 H), 4.43 (m, 1 H), 5.00 (s, 1 H), 5.33 (s, 1 H), 5.53 (d, J=2.9 Hz, 1 H), 6.01 (d, J=11.1 Hz, 1 H), 6.22 (d, J=2.9 Hz, 1 H), 6.37 (d, J=11.1 Hz, 1 H).

LRMS m/z 440 (M$^+$), 422, 404, 251, 105

HRMS calcd for C$_{28}$H$_{40}$O$_4$ 440.2927, found 440.2929

Example 13

Synthesis of 2α-methyl-20(R)-(tetrahydro-3-methylene-2-furanone-4(S)-methyl-5(R)-yl)methyl-9,10-secopregna-5(Z),7(E),10(19)-triene-1α,3β-diol (Compound No. 201 d

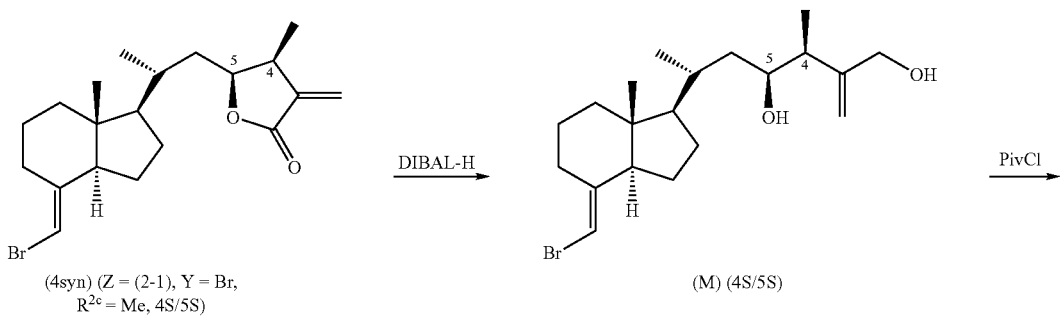

(4syn) (Z = (2-1), Y = Br, $R^{2c}$ = Me, 4S/5S)

(M) (4S/5S)

-continued

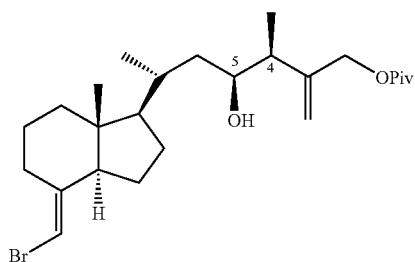

(5syn) (Z = (2-1), Y = Br, R²ᶜ = Me, R⁸ = Piv, 4S/5S)

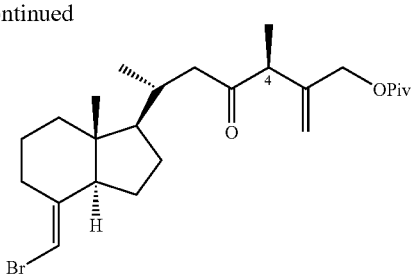

(6) (Z = (2-1), Y = Br, R²ᶜ = Me, R⁸ = Piv, 4S)

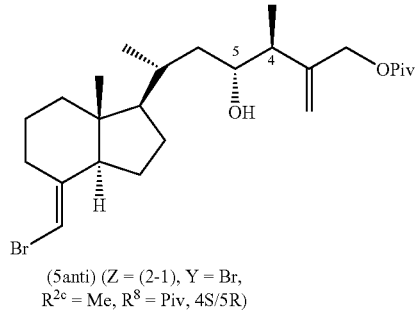

(5anti) (Z = (2-1), Y = Br, R²ᶜ = Me, R⁸ = Piv, 4S/5R)

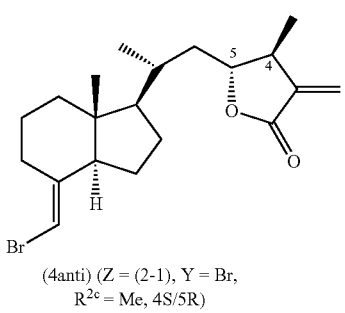

(4anti) (Z = (2-1), Y = Br, R²ᶜ = Me, 4S/5R)

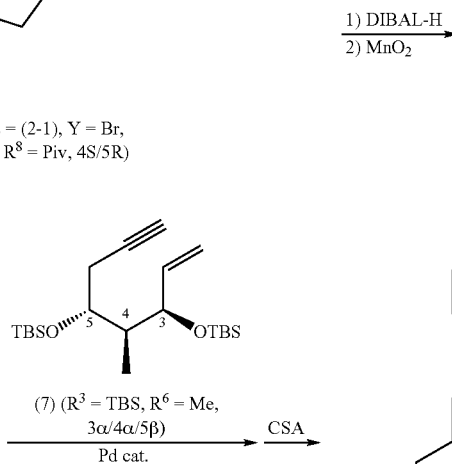

(7) (R³ = TBS, R⁶ = Me, 3α/4α/5β)

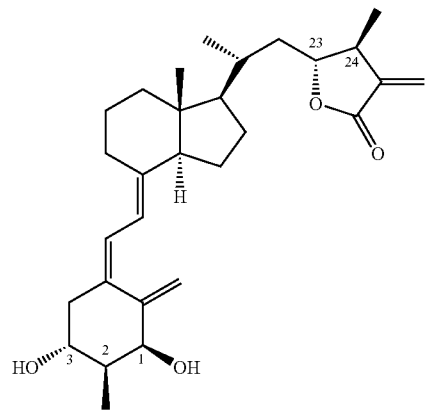

No. 201d
(1α/2α/3β/23R/24S)

(1) Using 18 mg of Compound (4syn) (Z=(2-1), Y=Br, R²ᶜ=Me, 4S/5S) obtained in Example 11(1), a reaction similar to Example 12(1) was carried out to obtain 17 mg of Compound (M) (4S/5S). Yield: 95%, a colorless oily substance.

$^1$H-NMR (CDCl$_3$) δ: 0.57 (s, 3 H), 1.00 (d, J=6.6 Hz, 3 H), 1.02 (d, J=7.1 Hz, 3 H), 1.15-1.72 (m, 11 H), 1.86-2.06 (m, 3 H), 2.01 (dq, J=2.1, 7.1 Hz, 1 H), 2.70-3.05 (m, 3 H), 3.56 (ddd, J=7.4, 6.0, 2.4 Hz, 1 H), 4.04 (dd, J=12.9, 0.49 Hz, 1 H), 4.13 (dd, J=12.9, 0.73 Hz, 1 H), 4.96 (s, 1 H), 6.26 (br d, J=0.98 Hz, 1 H), 5.63 (br s, 1 H).

LRMS m/z 384 (M⁺), 298, 254, 227, 175, 147

HRMS calcd for C$_{20}$H$_{33}$O$_2$$^{79}$Br 384.1664, found 384.1664

(2) Using 220 mg (0.57 mmol) of Compound (M) (4S/5S) obtained by the above method, a reaction similar to Example 12(2) was carried out to obtain 226 mg of Compound (5syn) (Z=(2-1), Y=Br, R²ᶜ=Me, R⁸=Piv, 4S/5S). Yield: 84%, a colorless oily substance $^1$H-NMR (CDCl$_3$) δ: 0.56 (s, 3 H), 1.05 (d, J=6.6 Hz, 3 H), 1.04 (d, J=6.9 Hz, 3 H), 1.15-1.80 (m, 12 H), 1.23 (s, 9 H), 1.90-2.10 (m, 3 H), 2.26 (dq, J=2.8, 6.9 Hz, 1 H), 2.87 (m, 1 H), 3.79 (m, 1 H), 4.52 (d, J=13.7 Hz, 1 H), 4.59 (d, J=13.7 Hz, 1 H), 5.02 (s, 1 H), 5.17 (d, J=1.2 Hz, 1 H), 5.63 (s, 1 H).

LRMS m/z 468 (M⁺), 389, 299, 269, 227, 170, 147

HRMS calcd for C$_{25}$H$_{41}$O$_3$$^{79}$Br 468.2239, found 468.2240

(3) Using 210 mg (0.45 mmol) of Compound (5syn) (Z=(2-1), Y=Br, R²ᶜ=Me, R⁸=Piv, 4S/5S) obtained by the above method, a reaction similar to Example 12(3) was carried out to obtain 196 mg of Compound (6) (Z=(2-1), Y=Br, R²ᶜ=Me, R⁸=Piv, 4S). Yield: 94%, a colorless oily substance.

$^1$H-NMR (CDCl$_3$) δ: 0.59 (s, 3 H), 0.92 (d, J=6.4 Hz, 3 H), 1.20 (d, J=7.1 Hz, 3 H), 1.22 (s, 9H), 1.29 (m, 1 H), 1.35-1.75 (m, 7 H), 1.83 (m, 1 H), 1.93-2.10 (m, 3 H), 2.26 (dd, J=16.4, 9.9 Hz, 1 H), 2.52 (d, J=16.4, 2.8 Hz, 1 H), 2.88 (m, 1 H), 3.18 (q, J=7.1 Hz, 1 H), 4.53 (s, 2 H), 5.06 (s, 1 H), 5.21 (s, 1 H), 5.64 (s, 1 H).

LRMS m/z 466 (M⁺, $^{79}$Br), 387, 366, 279, 237, 175

HRMS calcd for C$_{25}$H$_{39}$$^{79}$BrO$_3$ 466.2083, found 466.2083

(4) A reaction solution was prepared by adding 0.24 ml (1.0 M, 0.24 mmol) of a THF solution of LiAlH(O-t-Bu)$_3$ to a THF (1 ml) solution containing 36 mg (0.076 mmol) of Compound (6) (Z=(2-1), Y=Br, R²ᶜ=Me, R⁸=Piv, 4S) obtained by the above method at −78° C. and then the temperature of the reaction solution was increased to 0° C. over a period of 1.5 hours. The reaction solution was further stirred at 0° C. and then a saturated aqueous solution of ammonium chloride was added to the solution. The aqueous layer was extracted with ethyl acetate, and the organic layer was washed with saturated brine and dried with anhydrous sodium sulfate. The residue obtained by distilling off the solvent under reduced pressure was purified by silica gel flash column chromatography (hexane:ethyl acetate=10:1) to obtain 27 mg of Compound (5anti) (Z=(2-1), Y=Br, $R^{2c}$=Me, $R^8$=Piv, 4S/5R). Yield: 74%, a colorless oily substance.

$^1$H-NMR (CDCl$_3$) δ: 0.59 (s, 3 H), 0.96 (d, J=6.6 Hz, 3 H), 1.03 (d, J=7.1 Hz, 3 H), 1.16 (m, 1 H), 1.22 (s, 9 H), 1.20-1.80 (m, 10 H), 1.91 (m, 1 H), 1.98 (ddd, J=12.4, 6.8, 1.5 Hz, 1 H), 2.03 (m, 1 H), 2.16 (m, 1 H), 2.21 (br s, 1 H), 2.87 (m, 1 H), 3.59 (m, 1 H), 4.50 (d, J=13.9 Hz, 1 H), 4.58 (d, J=13.9 Hz, 1 H), 5.04 (s, 1 H), 5.11 (d, J=1.2 Hz, 1 H), 5.63 (s, 1 H).

LRMS m/z 468 (M$^+$), 390, 229, 178, 68, 57

HRMS calcd for $C_{25}H_{41}{}^{79}BrO_3$ 468.2239, found 468.2243

(5) A reaction solution was prepared by adding 0.22 ml (1.04 M, 0.23 mmol) of a toluene solution of DIBAL-H to toluene (1 ml) containing 27 mg (0.057 mmol) of Compound (5anti) (Z=(2-1), Y=Br, $R^{2c}$=Me, $R^8$=Piv, 4S/5R) obtained by the above method at 0° C. and was stirred at the same temperature for 2 hours. After the reaction solution was diluted with diethyl ether, a 10% aqueous solution of sodium potassium tartrate was added, and the resultant solution was stirred at room temperature for one hour. The aqueous layer was extracted with ethyl acetate, and the organic layer was washed with saturated brine and dried with anhydrous sodium sulfate. The residue obtained by distilling off the solvent under reduced pressure was dissolved in methylene chloride (1 ml). To the solution was added 74 mg (0.85 mmol) of MnO$_2$ and the resultant solution was stirred at room temperature for 24 hours. After the resultant reaction solution was filtered, the residue obtained by concentrating the filtrate was purified by preparative TLC (hexane:ethyl acetate=10:1) to obtain 11 mg of Compound (4anti) (Z=(2-1), Y=Br, $R^{2c}$=Me, 4S/5R). Yield: 52%.

$^1$H-NMR (CDCl$_3$) δ: 0.59 (s, 3 H), 1.02 (d, J=6.6 Hz, 3 H), 1.23 (d, J=6.6 Hz, 3 H), 1.20-1.95 (m, 12 H), 1.98 (ddd, J=12.2, 5.4, 1.7 Hz, 1 H), 2.03 (br d, J=13.2 Hz, 1 H), 2.61 (m, 1 H), 2.89 (m, 1 H), 4.07 (ddd, J=10.7, 7.3, 2.2 Hz, 1 H), 5.53 (d, J=3.1 Hz, 1 H), 5.65 (d, J=1.7 Hz, 1 H), 6.22 (d, J=3.1 Hz, 1 H).

LRMS m/z 380 (M$^+$), 301, 227, 147

HRMS calcd for $C_{20}H_{29}{}^{79}BrO_2$ 380.1351, found 380.1345

(6) Using 19 mg (49 μmol) of Compound (4anti) (Z=(2-1), Y=Br, $R^{2c}$=Me, 4S/5R) obtained by the above method and 27 mg (74 mmol) of Compound (7) ($R^3$=TBS, $R^6$=Me, 3α/4α/5β), a reaction similar to Example 11(2-a) was carried out to obtain 11 mg of Compound No. 201d. Yield: 52%.

Compound No. 201d:

$^1$H-NMR (CDCl$_3$) δ: 0.57 (s, 3 H), 1.01 (d, J=6.4 Hz, 3 H), 1.22 (d, J=6.8 Hz, 3 H), 1.20-1.38 (m, 4 H), 1.40-2.10 (m, 14 H), 2.31 (dd, J=13.4, 6.4 Hz, 1 H), 2.55-2.65 (m, 2 H), 2.82 (dd, J=12.2, 3.9 Hz, 1 H), 4.07 (ddd, J=10.5, 7.3, 2.0 Hz, 1 H), 4.22 (m, 1 H), 4.42 (dd, J=7.6, 4.4 Hz, 1 H), 4.99 (s, 1 H), 5.32 (dd, J=1.7, 1.4 Hz, 1 H), 5.52 (d, J=2.9 Hz, 1 H), 6.01 (d, J=11.2 Hz, 1 H), 6.21 (d, J=2.9 Hz, 1 H), 6.36 (d, J=11.2 Hz, 1 H).

LRMS m/z 440 (M$^+$), 422, 404, 251, 105

HRMS calcd for $C_{28}H_{44}O_4$ 440.2927, found 440.2920

Example 14

Synthesis of 2α-methyl-20(R)-(tetrahydro-3-methylene-2-furanone-4(R)-ethyl-5(R)-yl)methyl-9,10-secopregna-5(Z),7(E),10(19)-triene-1α,3β-diol (Compound No. 202a) and 2α-methyl-20(R)-(tetrahydro-3-methylene-2-furanone-4(S)-ethyl-5(S)-yl)methyl-9,10-secopregna-5 (Z),7(E),10(19)-triene-1α,3β-diol (Compound No. 202b)

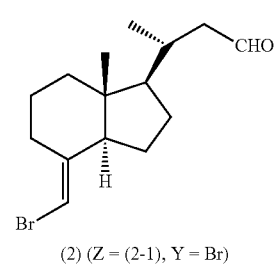

(2) (Z = (2-1), Y = Br)

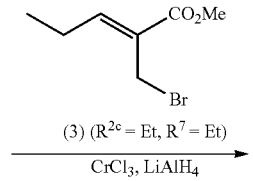

(3) ($R^{2c}$ = Et, $R^7$ = Et)

CrCl$_3$, LiAlH$_4$

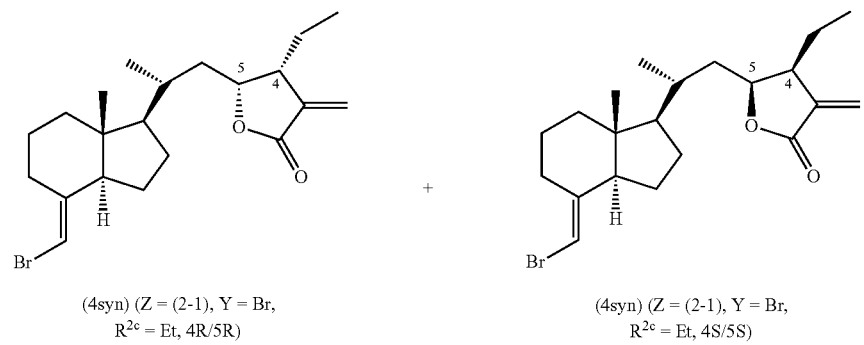

(4syn) (Z = (2-1), Y = Br, $R^{2c}$ = Et, 4R/5R)

+

(4syn) (Z = (2-1), Y = Br, $R^{2c}$ = Et, 4S/5S)

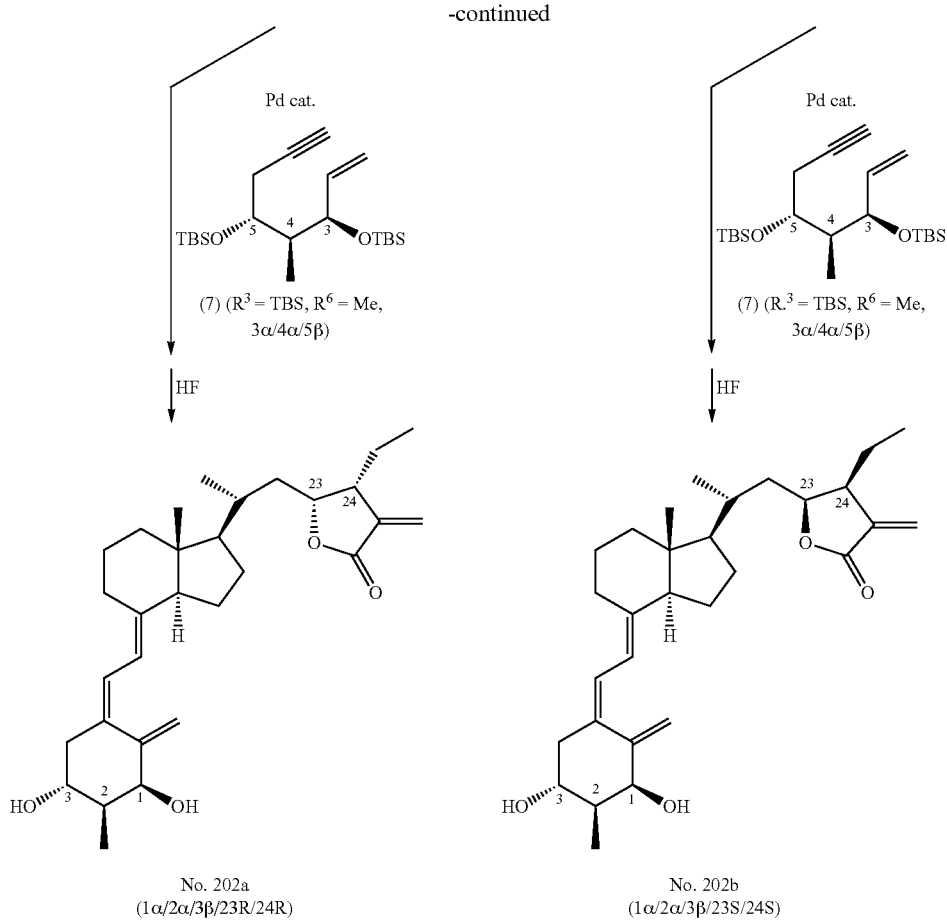

No. 202a
(1α/2α/3β/23R/24R)

No. 202b
(1α/2α/3β/23S/24S)

(1) Using 660 mg (2.3 mmol) of Compound (2) (Z=(2-1), Y=Br) obtained by a method known in the literature (for example, the specification of International Publication WO 95/33716), a reaction similar to Example 11 (1) was carried out to obtain 439 mg (yield: 50%) of Compound (4syn) (Z=(2-1), Y=Br, $R^{2c}$=Et, 4R/5R) and 366 mg (yield: 42%) of Compound (4syn) (Z=(2-1), Y=Br, $R^{2c}$=Et, 4S/5S). However, instead of Compound (3) ($R^{2c}$=Me, $R^7$=Me) in Example 11(1), used was Compound (3) ($R^{2c}$=Et, $R^7$=Me) which was obtained by using methyl acrylate in place of ethyl acrylate as in Reference Example 2. Compound (4syn) (Z=(2-1), Y=Br, $R^{2c}$=Et, 4R/5R):

$^1$H-NMR (CDCl$_3$) δ: 0.59 (s, 3 H), 0.98 (t, J=7.4 Hz, 3 H), 1.01 (d, J=6.6 Hz, 3 H), 1.13 (ddd, J=14.2, 10.7, 2.0, Hz, 1 H), 1.24-1.34 (m, 3 H), 1.40-1.79 (m, 9 H), 1.84 (m, 1 H), 1.95 (ddd, J=4.0, 5.6, 11.9 Hz, 1 H), 2.02 (m, 1 H), 2.86-2.92 (m, 2 H), 4.67 (ddd, J=11.7, 7.0, 1.8 Hz, 1 H), 5.52 (d, J=2.4 Hz, 1 H), 5.65 (s, 1 H), 6.22 (d, J=2.4 Hz, 1 H).

LRMS m/z 394 (M$^+$) 315, 227, 202, 175, 147

HRMS calcd for C$_{21}$H$_{31}$O$_2$$^{79}$Br 394.1507, found 394.1507
Compound (4syn) (Z=(2-1), Y=Br, $R^{2c}$=Et, 4S/5S):

$^1$H-NMR (CDCl$_3$) δ: 0.58 (s, 3 H), 0.96 (t, J=7.3 Hz, 3 H), 1.06 (d, J=6.6 Hz, 3 H), 1.26-1.48 (m, 6 H), 1.53-1.76 (m, 7 H), 1.92-2.05 (m, 3 H), 2.81 (m, 1 H), 2.88 (m, 1 H), 4.59 (ddd, J=8.7, 6.2, 4.9 Hz, 1 H), 5.52 (d, J=2.0 Hz, 1 H), 5.65 (s, 1 H), 6.21 (d, J=2.0 Hz, 1 H).

LRMS m/z 394 (M$^+$) 315, 227, 202, 175, 147

HRMS calcd for C$_{21}$H$_{31}$O$_2$$^{79}$Br 394.1507, found 394.1507

(2-a) A reaction solution was prepared by adding triethylamine (1.8 ml) and 21 mg (18 μmol) of tetrakis(triphenylphosphine)palladium (0) to 24 mg (61 μmol) of Compound (4syn) (Z=(2-1), Y=Br, $R^{2c}$=Et, 4R/5R) obtained by the above method and a toluene solution (3 ml) containing 35 mg (91 μmol) of Compound (7) ($R^3$=TBS, $R^6$=Me, 3α/4α/5β) obtained by a method known in the literature (for example, Fujishima et al., Bioorg. Med. Chem., Vol. 8, 123, 2000), and was stirred at 110° C. for 1.5 hours. After a crude product obtained by concentrating the reaction solution was dissolved in 1.5 ml of acetonitrile, a mixed solution (mixing ratio of 1:9, 1.5 ml) of concentrated hydrogen fluoride and acetonitrile was added to the acetonitrile solution and the resultant solution was stirred at room temperature for 3 hours. A saturated aqueous solution of sodium hydrogen carbonate was added to the resultant solution, and extraction of the aqueous layer was performed with ethyl acetate. The organic layer was washed with saturated brine, and dried with anhydrous sodium sulfate. The residue obtained by distilling off the solvent under reduced pressure was purified by preparative thin-layer chromatography (hexane:ethyl acetate=1:1) to obtain 18 mg of Compound No. 202a. Yield: 63%.
Compound No. 202a:

$^1$H-NMR (CDCl$_3$) δ: 0.55 (s, 3 H), 0.97 (t, J=7.6 Hz, 3 H), 1.00 (d, J=6.3 Hz, 3 H), 1.07 (d, J=6.8 Hz, 3 H), 1.12 (ddd, J=14.2, 10.6, 1.8 Hz, 1 H), 1.23-1.34 (m, 3 H), 1.44-1.85 (m, 12H), 1.88-2.04 (m, 3 H), 2.22 (dd, J=13.6, 7.7 Hz, 1 H), 2.66 (dd, J=13.6, 4.1 Hz, 1 H), 2.80-2.91 (m, 2 H), 3.85 (ddd, J=7.7, 7.6, 4.1 Hz, 1 H), 4.31 (m, 1 H), 4.66 (ddd, J=11.7, 7.0, 1.8 Hz, 1 H), 5.00 (d, J=1.7 Hz, 1 H), 5.28 (s, 1 H), 5.51 (d, J=2.5 Hz, 1 H), 6.00 (d, J=11.2 Hz, 1 H), 6.21 (d, J=2.5 Hz, 1 H), 6.37 (d, J=11.2 Hz, 1 H).

LRMS m/z 468 (M+) 450, 432, 265, 223, 211, 171, 148
HRMS calcd for $C_{29}H_{42}O_4$ 468.3240, found 468.3241

(2-b) Using 24 mg (61 µmol) of Compound (4syn) (Z=(2-1), Y=Br, $R^{2c}$=Et, 4S/5S) obtained by the above method and 35 mg (91 µmol) of Compound (7) ($R^3$=TBS, $R^6$=Me, 3α/4α/5β), a reaction similar to Example 14(2-a) was carried out to obtain 32 mg of Compound No. 202b. Yield: 57%.

Compound No. 202b:

$^1$H-NMR (CDCl$_3$) δ: 0.55 (s, 3 H), 0.95 (t, J=7.3 Hz, 3 H), 1.05 (d, J=6.3 Hz, 3 H), 1.07 (d, J=6.8 Hz, 3 H), 1.21-1.77 (m, 15 H), 1.88-1.96 (m, 2 H), 1.99-2.01 (m, 2 H), 2.23 (dd, J=13.4, 7.7 Hz, 1 H), 2.66 (dd, J=13.4, 4.1 Hz, 1 H), 2.77-2.84 (m, 2 H), 3.84 (ddd, J=7.7, 7.4, 4.1 Hz, 1 H), 4.30 (m, 1 H), 4.57 (m, 1 H), 5.00 (d, J=1.7 Hz, 1 H), 5.27 (s, 1 H), 5.51 (d, J=1.8 Hz, 1 H), 6.01 (d, J=11.2 Hz, 1 H), 6.20 (d, J=1.8 Hz, 1 H), 6.38 (d, J=11.2 Hz, 1 H).

LRMS m/z 468 (M+) 450, 432, 265, 223, 211, 171, 148
HRMS calcd for $C_{30}H_{44}O_4$ 468.3240, found 468.3239

Example 15

Synthesis of 2α-methyl-20(R)-(tetrahydro-3-methylene-2-furanone-4(R)-ethyl-5(S)-yl)methyl-9,10-secopregna-5(Z),7(E),10(19)-triene-1α,3β-diol (Compound No. 202c)

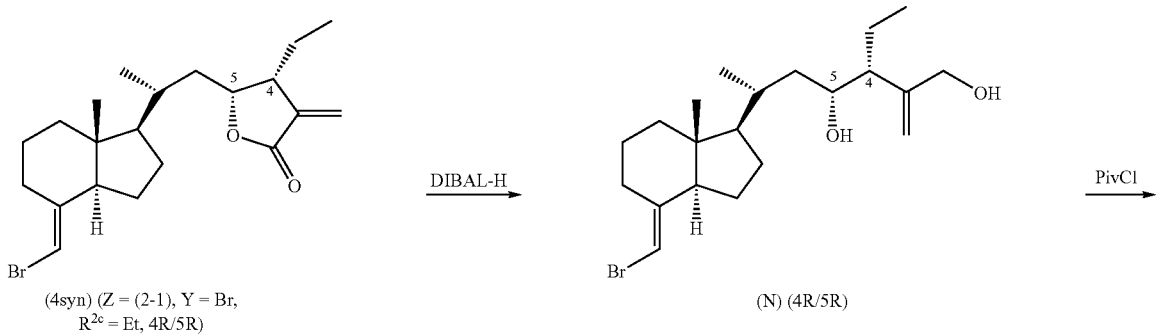

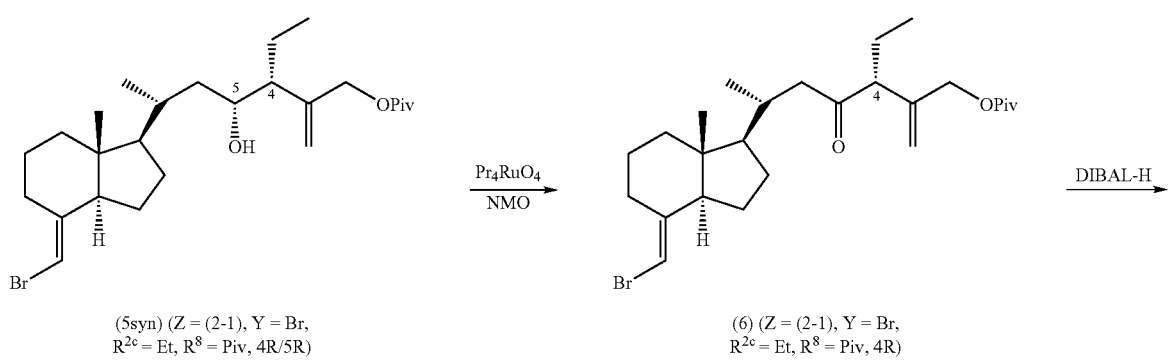

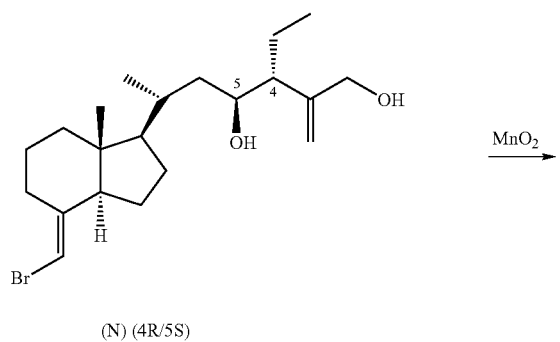

-continued

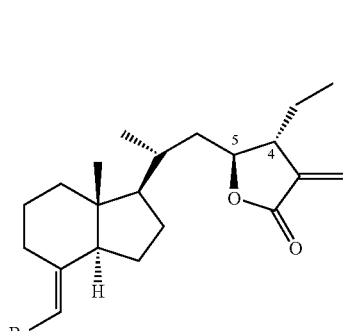

(4anti) (Z = (2-1), Y = Br, R²ᶜ = Et, 4R/5S)

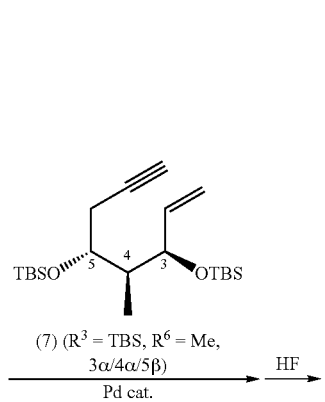

(7) (R³ = TBS, R⁶ = Me, 3α/4α/5β)

$\xrightarrow{\text{HF}}_{\text{Pd cat.}}$

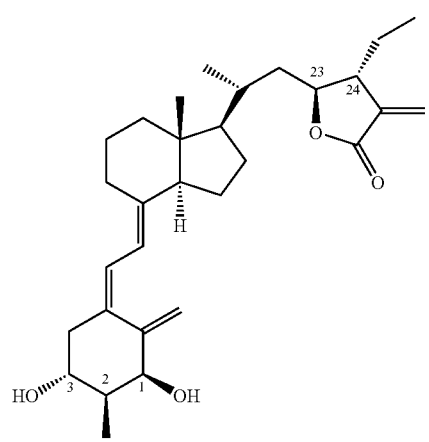

No. 202c
(1α/2α/3β/23S/24R)

(1) Using 55 mg (0.139 mmol) of Compound (4syn) (Z=(2-1), Y=Br, R²ᶜ=Et, 4R/5R) obtained in Example 14(1), a reaction similar to Example 12(1) was carried out to obtain 49 mg of Compound (N) (4R/5R). Yield: 88%, a colorless solid substance.

¹H-NMR (CDCl₃) δ: 0.59 (s, 3 H), 0.86 (t, J=7.4 Hz, 3 H), 0.95 (d, J=6.6 Hz, 3 H), 1.03 (br dd, J=11.6, 11.6 Hz, 1 H), 1.22-1.35 (m, 3 H), 1.40-1.69 (m, 9 H), 1.88-2.05 (m, 4 H), 2.34 (br s, 2 H), 2.88 (m, 1 H), 3.71 (br dd, J=4.0, 9.9 Hz, 1 H), 4.03 (d, J=13.3 Hz, 1 H), 4.08 (d, J=13.3 Hz, 1 H), 4.91 (s, 1 H), 5.20 (s, 1 H), 5.65 (s, 1 H).

LRMS m/z 398 (M⁺) 382, 353, 298, 281, 255, 175

HRMS calcd for C₂₁H₃₁O₂⁷⁹Br 398.1820, found 398.1825.

(2) Using 267 mg (0.668 mmol) of Compound (N) (4R/5R) obtained by the above method, a reaction similar to Example 12(2) was carried out to obtain 300 mg of Compound (5syn) (Z=(2-1), Y=Br, R²ᶜ=Et, R⁸=Piv, 4R/5R). Yield: 93%, a colorless oily substance.

¹H-NMR (CDCl₃) δ: 0.57 (s, 3 H), 0.88 (t, J=7.3 Hz, 3 H), 1.02 (d, J=6.3 Hz, 3 H), 1.18-1.37 (m, 4 H), 1.23 (s, 9 H), 1.39-1.71 (m, 10 H), 1.91-2.03 (m, 4 H), 2.88 (m, 1 H), 3.70 (m, 1 H), 4.49 (d, J=13.9 Hz, 1 H), 4.55 (d, J=13.9 Hz, 1 H), 5.00 (s, 1 H), 5.23 (s, 1 H), 5.65 (s, 1 H).

LRMS m/z 482 (M⁺) 382, 301, 283, 175

HRMS calcd for C₂₁H₃₁O₂⁷⁹Br 482.2396, found 482.2399

(3) Using 220 mg (0.454 mmol) of the compound (5syn) (Z=(2-1), Y=Br, R²ᶜ=Et, R⁸=Piv, 4R/5R) obtained by the above method, a reaction similar to Example 12(3) was carried out to obtain 189 mg of Compound (6) (Z=(2-1), Y=Br, R²ᶜ=Et, R⁸=Piv, 4R). Yield: 86%, a colorless oily substance.

¹H-NMR (CDCl₃) δ: 0.59 (s, 3 H), 0.86 (t, J=7.3 Hz, 3 H), 0.88 (d, J=6.3 Hz, 3 H), 1.18-1.33 (m, 3 H), 1.22 (s, 9 H), 1.42-1.68 (m, 6 H), 1.77-1.88 (m, 2 H), 1.96-2.02 (m, 3 H), 2.25 (dd, J=16.8, 9.9 Hz, 1 H), 2.46 (dd, J=16.8, 2.9 Hz, 1 H), 2.88 (m, 1 H), 3.01 (t, J=7.3 Hz, 1 H), 4.48 (dd, J=13.9 Hz, 1 H), 4.52 (dd, J=13.9 Hz, 1 H) 5.06 (s, 1 H), 5.21 (s, 1 H), 5.64 (s, 1 H).

LRMS m/z 480 (M⁺) 401, 300, 175

HRMS calcd for C₂₆H₄₁O₃⁷⁹Br 480.2239, found 480.2241

(4) A reaction solution was prepared by adding 0.98 ml (1.04 M, 1.0 mmol) of a toluene solution of DIBAL-H to a toluene solution (0.73 ml) containing 70 mg (0.145 mmol) of Compound (6) (Z=(2-1), Y=Br, R²ᶜ=Et, R⁸=Piv, 4R) obtained by the above method at 0° C. and was stirred at the same temperature for 4 hours. After methanol and a 10% aqueous solution of sodium potassium tartrate were added to the reaction solution, the resultant solution was stirred at room temperature for one hour. The solution was subjected to extraction with ethyl acetate, and the organic layer was washed with saturated brine and dried with anhydrous sodium sulfate. The residue obtained by distilling off the solvent under reduced pressure was purified by silica gel flash column chromatography (hexane:ethyl acetate=6:1) to obtain 29 mg of Compound (N) (4R/5S). Yield: 50%, a colorless solid substance.

¹H-NMR (CDCl₃) δ: 0.57 (s, 3 H), 0.85 (t, J=7.3 Hz, 3 H), 1.00 (d, J=6.6 Hz, 3 H), 1.17 (ddd, J=14.3, 8.5, 6.1 Hz, 1 H), 1.25-1.34 (m, 3 H), 1.39-1.71 (m, 9 H), 1.87-2.02 (m, 3 H), 2.10 (ddd, J=9.4, 4.8, 4.8 Hz, 1 H), 2.87 (m, 1 H), 3.04 (br s, 2 H), 3.71 (br dd, J=10.9, 6.2 Hz, 1 H), 3.97 (d, J=12.6 Hz, 1 H), 4.08 (d, J=12.6 Hz, 1 H), 4.96 (s, 1 H), 5.21 (s, 1 H), 5.64 (s, 1 H).

LRMS m/z 398 (M⁺) 380, 300, 256, 175

HRMS calcd for C₂₁H₃₅O₂⁷⁹Br 398.1820, found 398.1835

(5) A solution was prepared by dissolving 83 mg (0.208 mmol) of Compound (N) (4R/5S) obtained by the above method in methylene chloride (2 ml). A reaction solution was prepared by adding 432 mg (5.0 mmol) of MnO₂ to the above solution and was stirred at room temperature for 2.5 days. After the reaction solution was filtered, the residue obtained by concentrating the filtrate was purified by silica gel flash column chromatography (hexane:ethyl acetate=19:1) to obtain 77 mg of Compound (4anti) (Z=(2-1), Y=Br, R²ᶜ=Et, 4R/5S). Yield: 94%, a colorless solid substance.

¹H-NMR (CDCl₃) δ: 0.57 (s, 3 H), 0.97 (t, J=7.4 Hz, 3 H), 1.06 (d, J=6.1 Hz, 3 H), 1.18-1.71 (m, 13 H), 1.88-2.03 (m, 3 H), 2.55 (m, 1 H), 2.87 (m, 1 H), 4.26 (ddd, J=6.5, 6.5, 4.3 Hz, 1 H), 5.58 (d, J=2.3 Hz, 1 H), 5.64 (br s, 1 H), 6.27 (d, J=2.3 Hz, 1 H).

LRMS m/z 394 (M⁺) 315, 227, 202, 175, 147

HRMS calcd for C₂₁H₃₁O₂⁷⁹Br 394.1507, found 394.1508

(6) Using 16 mg (40 μmol) of Compound (4anti) (Z=(2-1), Y=Br, R²ᶜ=Et, 4R/5S) obtained by the above method and 23 mg (61 μmol) of Compound (7) (R³=TBS, R⁶=Me, 3α/4α/5β), a reaction similar to Example 14(2-a) was carried out to obtain 23 mg of Compound No. 202c. Yield: 51%.

Compound No. 202c:
¹H-NMR (CDCl₃) δ: 0.55 (s, 3 H), 0.97 (t, J=7.4 Hz, 3 H), 1.05-1.08 (m, 6 H), 1.15-1.73 (m, 15 H), 1.86-1.96 (m, 2 H), 1.98-2.03 (m, 2 H), 2.23 (dd, J=13.5, 8.1 Hz, 1 H), 2.56 (m, 1 H), 2.67 (dd, J=13.5, 4.0 Hz, 1 H), 2.82 (m, 1 H), 3.84 (m, 1 H), 4.26 (m, 1 H), 4.31 (m, 1 H), 5.00 (d, J=2.0 Hz, 1 H), 5.27 (br s, 1 H), 5.58 (d, J=2.3 Hz, 1 H), 6.00 (d, J=11.2 Hz, 1 H), 6.27 (d, J=2.3 Hz, 1 H), 6.38 (d, J=11.2 Hz, 1 H).
LRMS m/z 468 (M⁺) 450, 432, 265, 223, 211, 171, 148
HRMS calcd for $C_{30}H_{44}O_4$ 468.3240, found 468.3241
Example 16
Synthesis of 2α-methyl-20(R)-(tetrahydro-3-methylene-2-furanone-4(S)-ethyl-5(R)-yl)methyl-9,10-secopregna-5(Z),7(E),10(19)-triene-1α,3β-diol (Compound No. 202d)
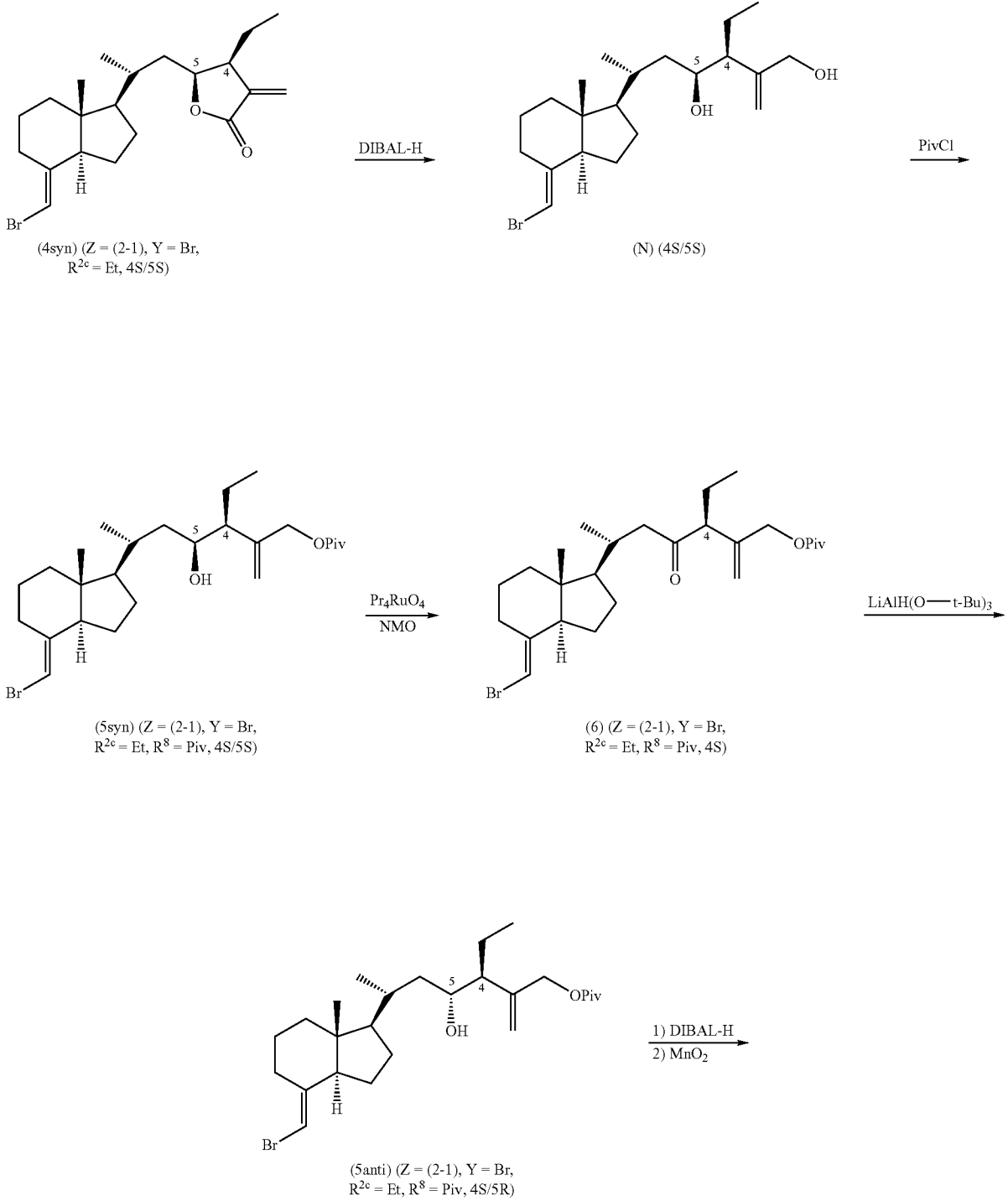

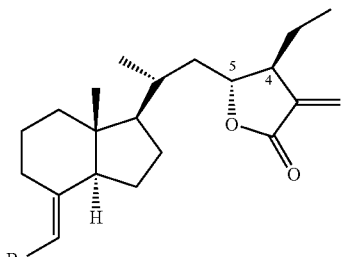

(4anti) (Z = (2-1), Y = Br, $R^{2c}$ = Et, 4S/5R)

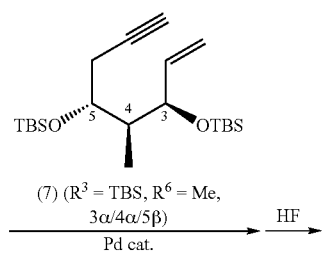

(7) ($R^3$ = TBS, $R^6$ = Me, 3α/4α/5β)

$\xrightarrow[\text{Pd cat.}]{\text{HF}}$

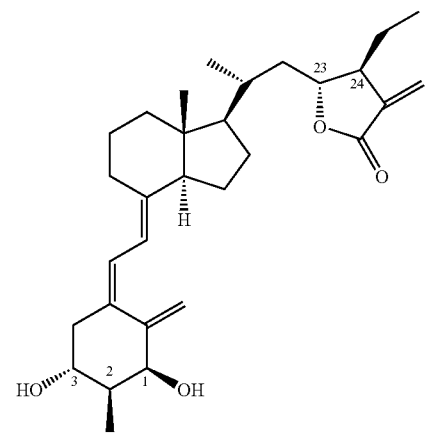

No. 202d
(1α/2α/3β/23R/24S)

(1) Using 27 mg (0.068 mmol) of Compound (4syn) (Z=(2-1), Y=Br, $R^{2c}$=Et/Hydrogen atom, 4S/5S) obtained in Example 14(1), a reaction similar to Example 12(1) was carried out to obtain 27 mg of Compound (N) (4S/5S). Yield: 99%, a colorless solid substance.

$^1$H-NMR (CDCl$_3$) δ: 0.58 (s, 3 H), 0.85 (t, J=7.4 Hz, 3 H), 1.02 (d, J=6.3 Hz, 3 H), 1.17-1.37 (m, 5 H), 1.42-1.71 (m, 8 H), 1.92-2.03 (m, 3 H), 2.09 (ddd, J=10.6, 3.3, 3.3 Hz, 1H), 2.56 (br s, 2 H), 2.88 (m, 1 H), 3.74 (ddd, J=6.5, 6.5, 2.5 Hz, 1 H), 4.04 (d, J=12.9 Hz, 1H), 4.11 (d, J=12.9 Hz, 1 H), 4.96 (s, 1 H), 5.20 (s, 1 H), 5.65 (s, 1 H).

LRMS m/z 398 (M$^+$) 382, 353, 298, 281, 255, 175

HRMS calcd for C$_{21}$H$_{31}$O$_2$$^{79}$Br 398.1820, found 398.1794

(2) Using 189 mg (0.473 mmol) of Compound (N) (4S/5S) obtained by the above method, a reaction similar to Example 12(2) was carried out to obtain 210 mg of Compound (5syn) (Z=(2-1), Y=Br, $R^{2c}$=Et, $R^8$=Piv, 4S/5S). Yield: 92%, a colorless oily substance.

$^1$H-NMR (CDCl$_3$) δ: 0.59 (s, 3 H), 0.88 (t, J=7.3 Hz, 3 H), 0.95 (d, J=6.3 Hz, 3 H), 1.08 (ddd, J=2.1, 11.1, 13.5 Hz, 1 H), 1.20-1.36 (m, 3 H), 1.24 (s, 9 H), 1.40-1.75 (m, 10 H), 1.89-2.05 (m, 4 H), 2.88 (m, 1 H), 3.66 (m, 1 H), 4.49 (s, 2 H), 4.94 (s, 1 H), 5.17 (d, J=1.2 Hz, 1 H), 5.65 (s, 1 H).

LRMS m/z 482 (M$^+$) 382, 301, 283, 175

HRMS calcd for C$_{21}$H$_{31}$O$_2$$^{79}$Br 482.2396, found 482.2402

(3) Using 210 mg (0.434 mmol) of Compound (5syn) (Z=(2-1), Y=Br, $R^{2c}$=Et, $R^8$=Piv, 4S/5S) obtained by the above method, a reaction similar to Example 12(3) was carried out to obtain 170 mg of Compound (6) (Z=(2-1), Y=Br, $R^{2c}$=Et, $R^8$=Piv, 4S). Yield: 81%, a colorless oily substance.

$^1$H-NMR (CDCl$_3$) δ: 0.57 (s, 3 H), 0.86 (t, J=7.5 Hz, 3 H), 0.91 (d, J=6.3 Hz, 3 H), 1.21 (s, 9 H), 1.24-1.34 (m, 3 H), 1.39-1.68 (m, 6 H), 1.77-1.88 (m, 2 H), 1.94-2.02 (m, 3 H), 2.22 (dd, J=16.8, 9.8 Hz, 1 H), 2.50 (dd, J=16.8, 2.5 Hz, 1 H), 2.86 (m, 1 H), 2.97 (t, J=7.3 Hz, 1 H), 4.49 (s, 2 H), 4.52 (dd, J=13.9 Hz, 1 H) 5.06 (s, 1 H), 5.20 (s, 1 H), 5.62 (s, 1 H).

LRMS m/z 480 (M$^+$) 401, 300, 175

HRMS calcd for C$_{26}$H$_{41}$O$_3$$^{79}$Br 480.2239, found 480.2238

(4) Using 70 mg (0.145 mmol) of Compound (6) (Z=(2-1), Y=Br, $R^{2c}$=Et, $R^8$=Piv, 4S) obtained by the above method, a reaction similar to Example 13(4) was carried out to obtain 53 mg of Compound (5anti) (Z=(2-1), Y=Br, $R^{2c}$=Et, $R^8$=Piv, 4S/5R). Yield: 75%, a colorless oily substance.

$^1$H-NMR (CDCl$_3$) δ: 0.58 (s, 3 H), 0.86 (t, J=7.3 Hz, 3 H), 0.96 (d, J=6.6 Hz, 3 H), 1.14 (m, 1 H), 1.22 (s, 9 H), 1.25-1.39 (m, 4 H), 1.41-1.58 (m, 5 H), 1.60-1.77 (m, 3 H), 1.85-2.05 (m, 4 H), 2.17 (m, 1 H), 2.87 (m, 1 H), 3.63 (m. 1 H), 4.45 (d, J=13.9 Hz, 1 H), 4.56 (d, J=13.9 Hz, 1 H), 5.03 (s, 1 H), 5.20 (s, 1 H), 5.64 (s, 1 H).

LRMS m/z 482 (M$^+$) 382, 301, 283, 175

HRMS calcd for C$_{21}$H$_{31}$O$_2$$^{79}$Br 482.2396, found 482.2393

(5) Using 40 mg (0.083 mmol) of Compound (5anti) (Z=(2-1), Y=Br, $R^{2c}$=Et, $R^5$=Piv, 4S/5R) obtained by the above method, a reaction similar to Example 13(5) was carried out to obtain 77 mg of Compound (4anti) (Z=(2-1), Y=Br, $R^{2c}$=Et, 4S/5R). Yield: 94%, a colorless solid substance.

$^1$H-NMR (CDCl$_3$) δ: 0.58 (s, 3 H), 0.98 (t, J=7.3 Hz, 3 H), 1.03 (d, J=6.6 Hz, 3 H), 1.21-1.90 (m, 14 H), 1.95-2.04 (m, 2 H), 2.50 (m, 1 H), 2.88 (m, 1 H), 4.28 (ddd, J=11.0, 4.9, 2.2 Hz, 1 H), 5.58 (d, J=2.6 Hz, 1 H), 5.64 (br s, 1 H), 6.27 (d, J=2.6 Hz, 1 H).

LRMS m/z 394 (M$^+$) 315, 227, 202, 175, 147

HRMS calcd for C$_{21}$H$_3$O$_2$$^{79}$Br 394.1507, found 394.1510

(6) Using 14 mg (25 μmol) of Compound (4anti) (Z=(2-1), Y Br, $R^{2c}$=Et, 4S/5R) obtained by the above method and 15 mg (38 μmol) of Compound (7) ($R^3$=TBS, $R^6$=Me, 3α/4α/5β), a reaction similar to Example 14(2-a) was carried out to obtain 8 mg of Compound No. 202d. Yield: 67%.

Compound No. 202d:

$^1$H-NMR (CDCl$_3$) δ: 0.55 (s, 3 H), 0.98 (t, J=7.4 Hz, 3 H), 1.02 (d, J=6.6 Hz, 3 H), 1.08 (d, J=6.8 Hz, 3 H), 1.22-1.76 (m, 17 H), 2.23 (dd, J=13.5, 7.9 Hz, 1 H), 2.51 (m, 1 H), 2.67 (dd, J=13.5, 4.0 Hz, 1 H), 2.82 (m, 1 H), 3.85 (m, 1 H), 4.27-4.31 (m, 2 H), 5.00 (d, J=1.5 Hz, 1H), 5.28 (s, 1 H), 5.58 (d, J=2.4 Hz, 1 H), 6.00 (d, J=11.2 Hz, 1 H), 6.27 (d, J=2.4 Hz, 1H), 6.38 (d, J=11.2 Hz, 1 H).

LRMS m/z 468 (M$^+$) 450, 432, 265, 223, 211, 171, 148

HRMS calcd for C$_{30}$H$_{44}$O$_4$ 468.3240, found 468.3244

Example 17
Synthesis of 2α-methyl-20(R)-(tetrahydro-3-methylene-2-furanone-4(R)-butyl-5(R)-yl)methyl-9,10-secopregna-5(Z),7(E),10(19)-triene-1α,3β-diol (Compound No. 205a) and 2α-methyl-20(R)-(tetrahydro-3-methylene-2-furanone-4(S)-butyl-5(S)-yl)methyl-9,10-secopregna-5(Z),7(E),10(19)-triene-1α,3β-diol (Compound No. 205b)
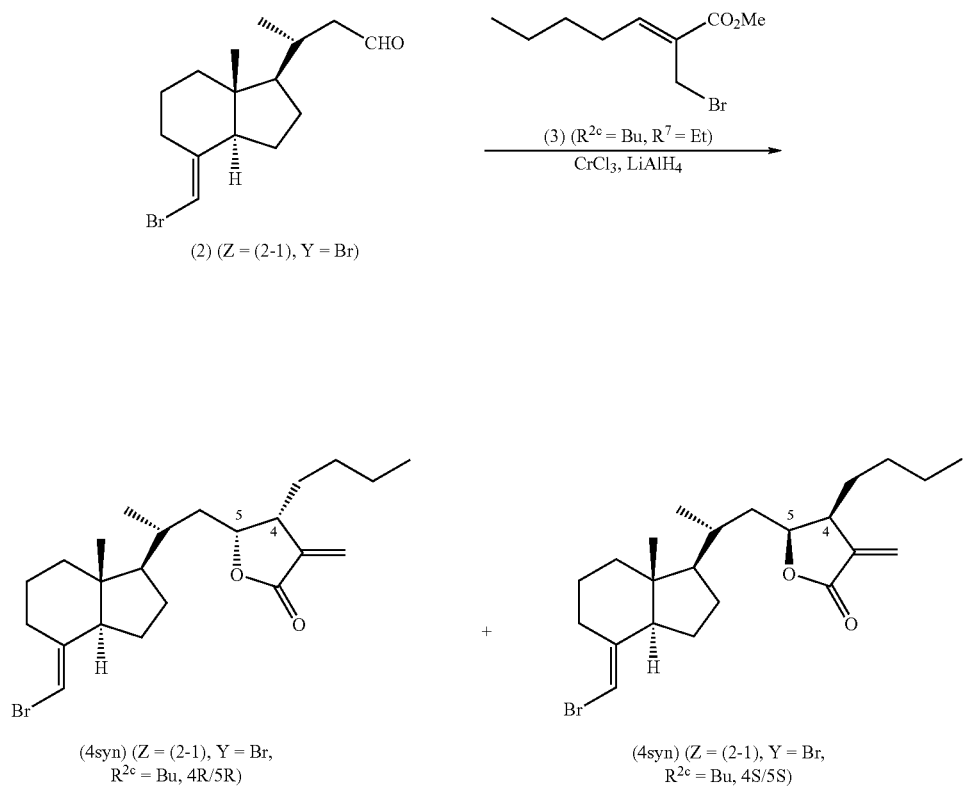
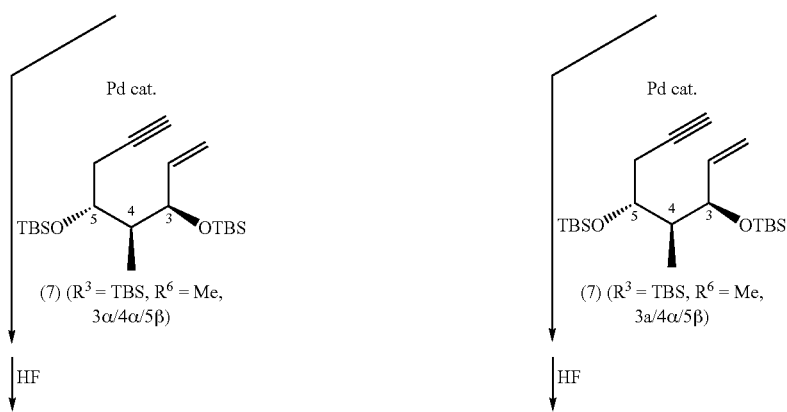

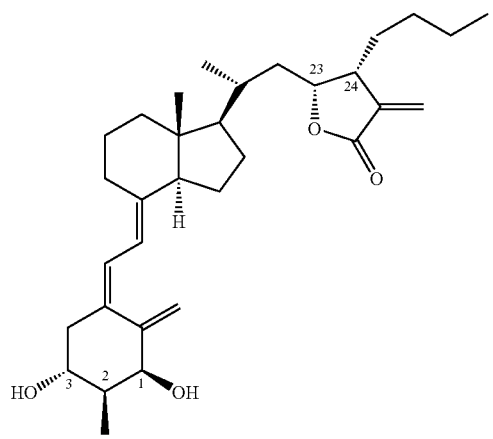

No. 205a
(1α/2α/3β/23R/24R)

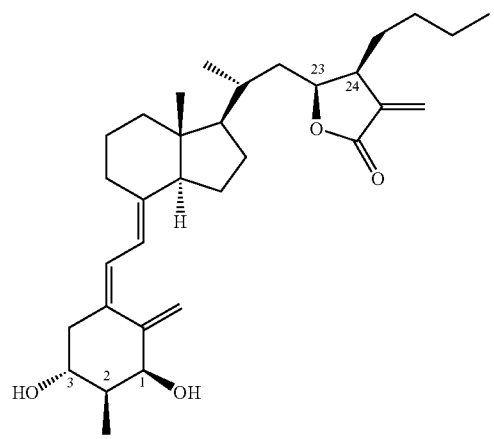

No. 205b
(1α/2α/3β/23S/24S)

(1) Using 30 mg (0.101 mmol) of Compound (2) (Z=(2-1), Y=Br) obtained by a method known in the literature (for example, the specification of International Publication WO 95/33716), a reaction similar to Example 11(1) was carried out to obtain 21 mg (yield: 50%) of Compound (4syn) (Z=(2-1), Y=Br, $R^{2c}$=Bu, 4R/5R) and 18 mg (yield: 42%) of compound (4syn) (Z=(2-1), Y=Br, $R^{2c}$=Bu, 4S/5S). However, instead of Compound (3) ($R^{2c}$=Me, $R^7$=Me) in Example 11(1), used was Compound (3) ($R^{2c}$=Bu, $R^7$=Me) which was obtained by using methyl acrylate in place of ethyl acrylate as in Reference Example 5. Compound (4syn) (Z=(2-1), Y=Br, $R^{2c}$=Bu, 4R/5R):

$^1$H-NMR (CDCl$_3$) δ: 0.59 (s, 3 H), 0.93 (t, J=7.1 Hz, 3 H), 1.01 (d, J=6.3 Hz, 3 H), 1.12 (ddd, J=14.2, 10.5, 2.0 Hz, 1 H), 1.24-1.70 (m, 15 H), 1.75 (m, 1 H), 1.87 (m, 1 H), 1.97 (ddd, J=12.5, 6.6, 1.6 Hz, 1 H), 2.03 (br d, J=12.5 Hz, 1 H), 2.88 (m, 1 H), 2.98 (m, 1 H), 4.66 (ddd, J=11.8, 7.2, 1.9 Hz, 1 H), 5.51 (d, J=2.3 Hz, 1 H), 5.65 (dd, J=1.7, 1.7 Hz, 1 H), 6.21 (d, J=2.3 Hz, 1 H).

LRMS m/z 422 (M$^+$), 343, 281, 227

HRMS calcd for $C_{23}H_{35}O_2{}^{79}Br$ 422.1820, found 422.1826
Compound (4syn) (Z=(2-1), Y=Br, $R^{2c}$=Bu, 4S/5S):

$^1$H-NMR (CDCl$_3$) δ: 0.58 (s, 3 H), 0.92 (t, J=7.2 Hz, 3 H), 1.06 (d, J=6.6 Hz, 3 H), 1.20-1.75 (m, 17 H), 1.92-2.05 (m, 3 H), 2.87 (m, 1 H), 2.90 (m, 1 H), 4.58 (ddd, J=8.8, 6.3, 4.7 Hz, 1 H), 5.51 (d, J=2.0 Hz, 1 H), 5.65 (dd, J=1.7, 1.4 Hz, 1 H), 6.20 (d, J=2.0 Hz, 1H).

EI-LRMS m/z 422 (M$^+$), 343, 281, 227

EI-HRMS calcd for $C_{23}H_{35}O_2{}^{79}Br$ 422.1820, found 422.1820

(2-a) Using 51 mg (121 μmol) of Compound (4syn) (Z=(2-1), Y=Br, $R^{2c}$=Bu, 4R/5R) obtained by the above method and 70 mg (182 μmol) of Compound (7) ($R^3$=TBS, $R^6$=Me, 3α/4α/5β), a reaction similar to Example 14(2-a) was carried out to obtain 39 mg of Compound No. 205a. Yield: 66%.

Compound No. 205a:

$^1$H-NMR (CDCl$_3$) δ: 0.56 (s, 3 H), 0.93 (t, J=7.0 Hz, 3 H), 1.00 (d, J=6.6 Hz, 3 H), 1.08 (d, J=6.8 Hz, 3 H), 1.11 (ddd, J=14.2, 11.0, 1.5 Hz, 1 H), 1.20-2.05 (m, 22 H), 2.23 (dd, J=13.4, 7.8 Hz, 1 H), 2.67 (dd, J=13.4, 4.0 Hz, 1 H), 2.83 (m, 1 H), 2.96 (m, 1 H), 3.85 (m, 1H), 4.31 (s, 1 H), 4.66 (ddd, J=11.5, 7.1, 1.5 Hz, 1 H), 5.00 (d, J=1.7 Hz, 1 H), 5.28 (s, 1 H), 5.51 (d, J=2.4 Hz, 1 H), 6.01 (d, J=11.2 Hz, 1 H), 6.21 (d, J=2.4 Hz, 1 H), 6.37 (d, J=11.2 Hz, 1 H).

LRMS m/z 496 (M$^+$), 478, 460, 434, 265

HRMS calcd for $C_{32}H_{48}O_4$ 496.3553, found 496.3534

(2-b) Using 49 mg (115 μmol) of Compound (4syn) (Z=(2-1), Y=Br, $R^{2c}$=Bu, 4S/5S) obtained by the above method and 66 mg (172 μmol) of Compound (7) ($R^3$=TBS, $R^6$=Me, 3α/4α/5β), a reaction similar to Example 14(2-a) was carried out to obtain 32 mg of Compound No. 205b. Yield: 57%.

Compound No. 205b:

$^1$H-NMR (CDCl$_3$) δ: 0.53 (s, 3 H), 0.92 (t, J=7.0 Hz, 3 H), 1.05 (d, J=6.6 Hz, 3 H), 1.08 (d, J=6.8 Hz, 3 H), 1.20-1.78 (m, 19 H), 1.88-2.07 (m, 4 H), 2.23 (dd, J=13.5, 7.9 Hz, 1 H), 2.67 (dd, J=13.5, 3.9 Hz, 1 H), 2.82 (m, 1 H), 2.89 (m, 1 H), 3.84 (m, 1 H), 4.30 (m, 1 H), 4.57 (ddd, J=11.5, 8.6, 6.1 Hz, 1 H), 5.00 (d, J=1.5 Hz, 1 H), 5.28 (s, 1 H), 5.50 (d, J=1.6 Hz, 1 H), 6.01 (d, J=11.2 Hz, 1 H), 6.19 (d, J=1.6 Hz, 1 H), 6.38 (d, J=11.2 Hz, 1 H).

LRMS m/z 496 (M$^+$), 478, 460, 434, 265

HRMS calcd for $C_{32}H_{48}O_4$ 496.3553, found 496.3557

Example 18
Synthesis of 2α-methyl-20(R)-(tetrahydro-3-methylene-2-furanone-4(R)-butyl-5(S)-yl)methyl-9,10-secopregna-5(Z),7(E),10(19)-triene-1α,3β-diol (Compound No. 205c)
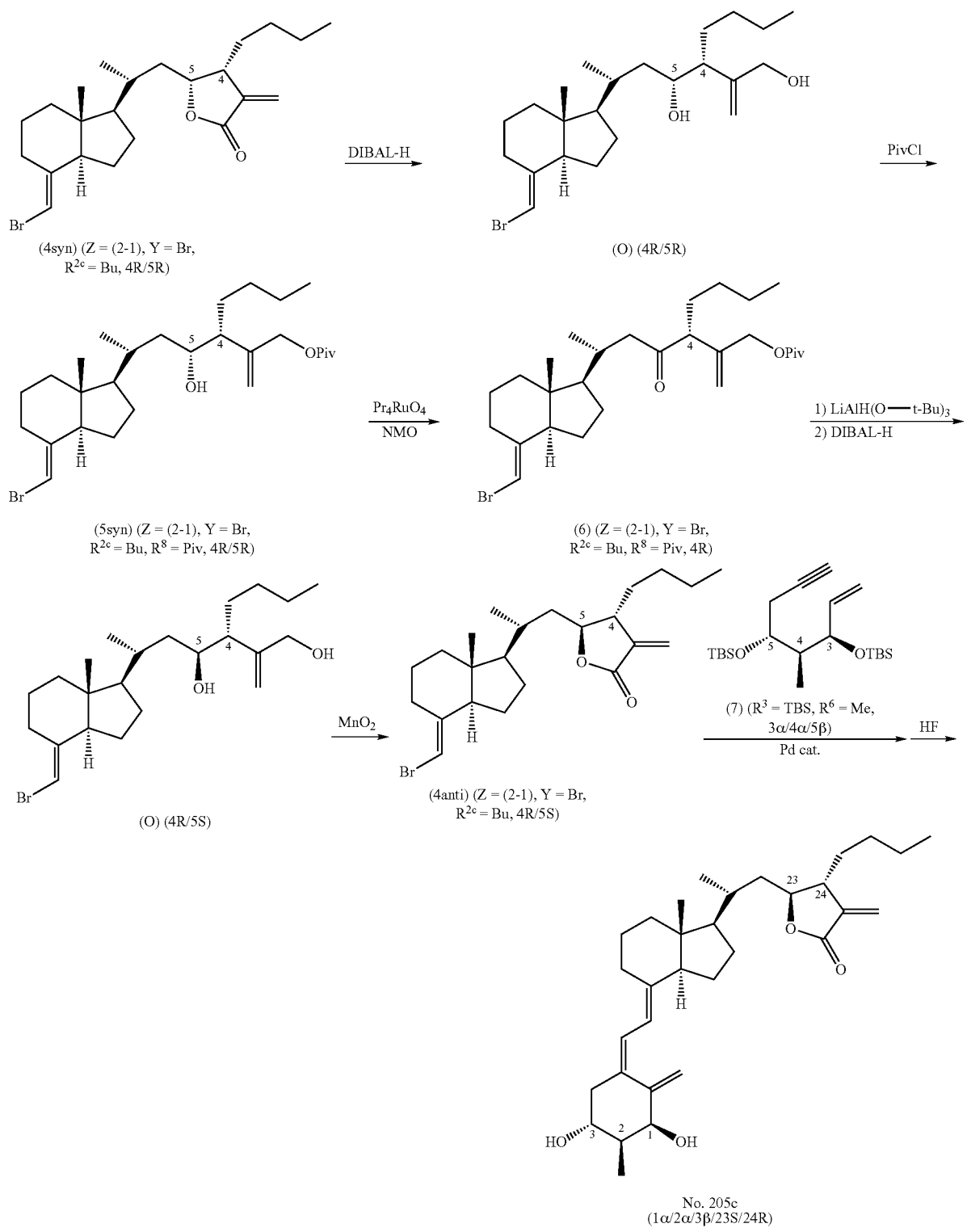

(1) Using 15 mg (0.036 mmol) of Compound (4syn) (Z=(2-1), Y=Br, $R^{2c}$=Bu, 4R/5R) obtained in Example 17(1), a reaction similar to Example 12(1) was carried out to obtain 15 mg of Compound (O) (4R/5R). Yield: 98%, a colorless solid substance.

$^1$H-NMR (CDCl$_3$) δ: 0.56 (s, 3 H), 0.88 (t, J=7.1 Hz, 3 H), 0.95 (d, J=6.6 Hz, 3 H), 1.03 (m, 1 H), 1.10-1.72 (m, 16 H), 1.85-2.05 (m, 3 H), 2.11 (ddd, J=8.8, 4.2, 4.6 Hz, 1 H), 2.32 (br s, 2 H), 2.87 (m, 1 H), 3.69 (ddd, J=6.4, 4.2, 3.2 Hz, 1 H), 4.02 (d, J=13.2 Hz, 1 H), 4.08 (d, J=13.2 Hz, 1 H), 4.92 (s, 1 H), 5.18 (s, 1 H), 5.64 (s, 1 H).

LRMS m/z 426 (M$^+$), 409, 329, 298, 256, 227, 175

HRMS calcd for C$_{23}$H$_{39}$O$_2$$^{79}$Br 426.2134, found 426.2111

(2) Using 455 mg (1.06 mmol) of Compound (O) (4R/5R) obtained by the above method, a reaction similar to Example 12(2) was carried out to obtain 455 mg of Compound (5syn) (Z=(2-1), Y=Br, $R^{2c}$=Bu, $R^8$=Piv, 4R/5R). Yield: 84%, a colorless oily substance.

$^1$H-NMR (CDCl$_3$) δ: 0.56 (s, 3 H), 0.88 (t, J=7.1 Hz, 3 H), 0.95 (d, J=6.6 Hz, 3 H), 1.06 (ddd, J=14.0, 10.8, 1.6 Hz, 1 H), 1.13-1.73 (m, 17 H), 1.24 (s, 9 H), 1.85-2.06 (m, 4 H), 2.87 (m, 1 H), 3.65 (m, 1 H), 4.49 (s, 2 H), 4.94 (s, 1 H), 5.16 (d, J=1.2 Hz, 1 H), 5.66 (s, 1 H).

LRMS m/z 510 (M$^+$), 492, 212, 175, 110

HRMS calcd for C$_{28}$H$_{47}$O$_3$$^{79}$Br 510.2709, found 510.2709

(3) Using 455 mg (0.89 mmol) of Compound (5syn) (Z=(2-1), Y=Br, $R^{2c}$=Bu, $R^8$=Piv, 4R/5R) obtained by the above method, a reaction similar to Example 12(3) was carried out to obtain 391 mg of Compound (6) (Z=(2-1), Y=Br, $R^{2c}$=Bu, $R^8$=Piv, 4R). Yield: 86%, a colorless oily substance.

$^1$H-NMR (CDCl$_3$) δ: 0.60 (s, 3 H), 0.88 (t, J=6.4 Hz, 3 H), 0.89 (d, J=6.8 Hz, 3 H), 1.23 (s, 9 H), 1.15-1.72 (m, 13 H), 1.75-1.88 (m, 2 H), 1.92-2.05 (m, 3 H), 2.26 (dd, J=16.9, 10.0 Hz, 1 H), 2.54 (dd, J=16.9, 2.7 Hz, 1 H), 2.88 (m, 1 H), 3.9 (t, J=7.2 Hz, 1 H), 4.48 (d, J=13.9 Hz, 1 H), 5.52 (d, J=13.9 Hz, 1 H), 5.05 (s. 1 H), 5.20 (s, 1 H), 5.64 (s, 1 H).

LRMS m/z 508 (M$^+$), 423, 407, 351, 279, 237, 175

HRMS calcd for C$_{28}$H$_{45}$O$_3$$^{79}$Br 508.2552, found 508.2556

(4) A reaction solution was prepared by adding 7.5 ml (1.0 M, 7.5 mmol) of a THF solution of LiAlH(O-t-Bu)$_3$ to a THF (1.5 ml) solution containing 380 mg (0.745 mmol) of Compound (6) (Z=(2-1), Y=Br, $R^{2c}$=Bu, $R^8$=Piv, 4R) obtained by the above method at 0° C. and was stirred at the same temperature for 19 hours. A saturated aqueous ammonium chloride solution was added to the reaction solution at 0° C., and extraction of the aqueous layer was performed with ethyl acetate. The organic layer was washed with saturated brine, and dried with anhydrous sodium sulfate. The residue obtained by distilling off the solvent under reduced pressure was dissolved in toluene (2.5 ml). To the solution was added 2.9 ml (1.04 M, 3.0 mmol) of a toluene solution of DIBAL-H at 0° C. and the resultant solution was stirred at the same temperature for 1.5 hours. A 10% aqueous solution of sodium potassium tartrate was added to the reaction solution, and extraction of the aqueous layer was performed with ethyl acetate. The organic layer was washed with saturated brine, and dried with anhydrous sodium sulfate. The residue obtained by distilling off the solvent under reduced pressure was purified by silica gel flash column chromatography (hexane:ethyl acetate=10:1) to obtain 207 mg of Compound (O) (4R/5S). Yield: 65%, an amorphous solid substance.

$^1$H-NMR (CDCl$_3$) δ: 0.57 (s, 3 H), 0.89 (t, J=7.2 Hz, 3 H), 1.01 (d, J=6.6 Hz 3 H), 1.10-1.75 (m, 17 H), 1.85-2.05 (m, 3 H), 2.20 (dt, J=10.0, 4.8 Hz, 1 H), 2.81 (br s, 2 H), 2.88 (m, 1 H), 3.70 (dt, J=10.0, 6.2 Hz, 1 H), 3.98 (d, J=12.5 Hz, 1 H), 4.10 (d, J=12.5 Hz, 1 H), 4.96 (d, J=1.7 Hz, 1 H), 5.21 (s, 1 H), 5.64 (s, 1 H).

LRMS m/z 426 (M$^+$), 408, 329, 298, 256, 227, 175

HRMS calcd for C$_{23}$H$_{39}$O$_2$$^{79}$Br 426.2134, found 426.2117

(5) Using 283 mg (0.556 mmol) of Compound (O) (4R/5S) obtained by the above method, a reaction similar to Example 14(5) was carried out to obtain 171 mg of Compound (4anti) (Z=(2-1), Y=Br, $R^{2c}$=Bu, 4R/5S). Yield: 98%, a colorless oily substance.

$^1$H-NMR (CDCl$_3$) δ: 0.58 (s, 3 H), 0.92 (d, J=6.8 Hz, 3 H), 1.07 (d, J=6.1 Hz, 3 H), 1.18-1.74 (m, 17 H), 1.88-2.08 (m, 3 H), 2.60 (m, 1 H), 2.88 (m, 1 H), 4.25 (dt, J=4.2, 6.2 Hz, 1 H), 5.58 (d, J=2.3 Hz, 1 H), 5.65 (s, 1 H), 6.26 (d, J=2.3 Hz, 1 H).

LRMS m/z 422 (M$^+$), 343, 281, 227

HRMS calcd for C$_{23}$H$_{35}$O$_2$$^{79}$Br 422.1820, found 422.1820

(6) Using 38 mg (90 μmol) of the compound (4anti) (Z=(2-1), Y=Br, $R^{2c}$=Bu, 4R/5S) obtained by the above method and 52 mg (135 μmol) of the compound (7) ($R^3$=TBS, $R^6$=Me, 3α/4α/5β), a reaction similar to Example 14(2-a) was carried out to obtain 23 mg of Compound No. 205c. Yield: 51%.

Compound No. 205c:

$^1$H-NMR (CDCl$_3$) δ: 0.55 (s, 3 H), 0.92 (t, J=6.7 Hz, 3 H), 1.06 (d, J=6.8 Hz, 3 H), 1.07 (d, J=7.1 Hz, 3 H), 1.20 (m, 1 H), 1.25-1.75 (m, 18 H), 1.85-2.06 (m, 4 H), 2.23 (dd, J=13.4, 7.8 Hz, 1 H), 2.60 (m, 1 H), 2.67 (dd, J=13.4, 4.0 Hz, 1 H), 2.82 (m, 1 H), 3.61 (m, 1 H), 4.25 (dt, J=3.5, 6.2 Hz, 1 H), 4.31 (m, 1 H), 5.00 (d, J=1.7 Hz, 1 H), 5.27 (s, 1 H), 5.58 (d, J=2.3 Hz, 1 H), 6.01 (d, J=11.2 Hz, 1 H), 6.25 (d, J=2.3 Hz, 1 H), 6.38 (d, J=11.2 Hz, 1 H).

LRMS m/z 496 (M$^+$), 478, 460, 434, 265

HRMS calcd for C$_{32}$H$_{48}$O$_4$ 496.3553, found 496.3545

Example 19

Synthesis of 2α-methyl-20(R)-(tetrahydro-3-methylene-2-furanone-4(S)-butyl-5(R)-yl)methyl-9,10-secopregna-5(Z),7(E), 10(19)-triene-1α,3β-diol (Compound No. 205d)

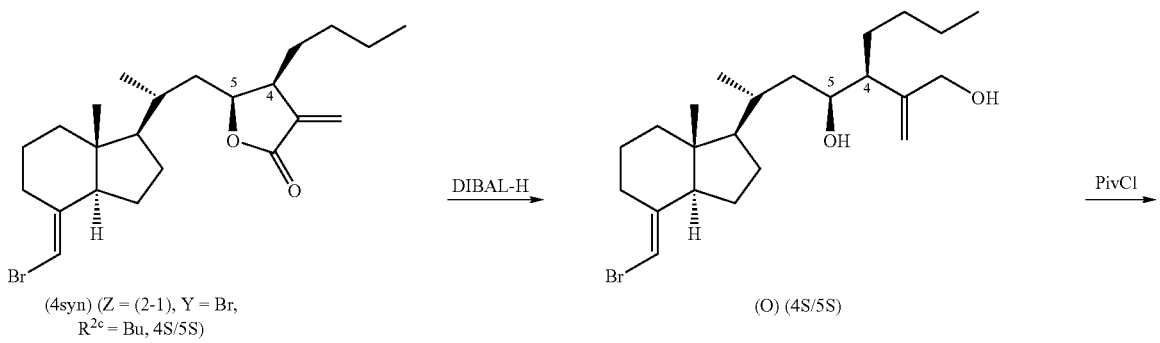

-continued

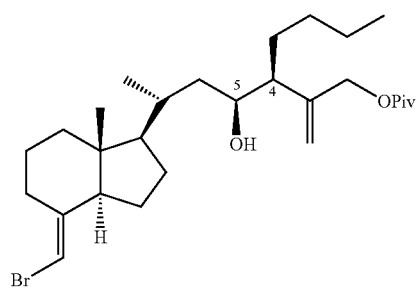

(5syn) (Z = (2-1), Y = Br, R²ᶜ = Bu, R⁸ = Piv, 4S/5S)

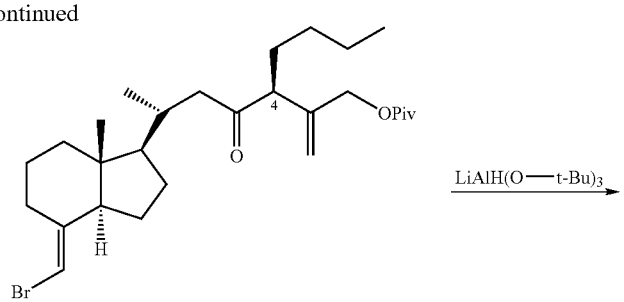

(6) (Z = (2-1), Y = Br, R²ᶜ = Bu, R⁸ = Piv, 4S)

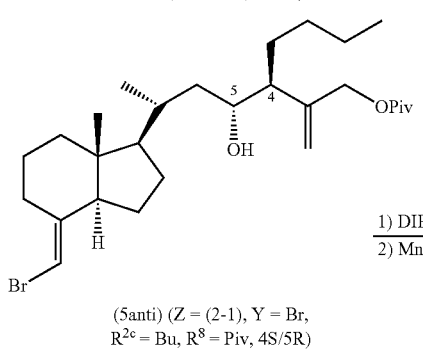

(5anti) (Z = (2-1), Y = Br, R²ᶜ = Bu, R⁸ = Piv, 4S/5R)

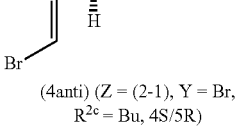

(4anti) (Z = (2-1), Y = Br, R²ᶜ = Bu, 4S/5R)

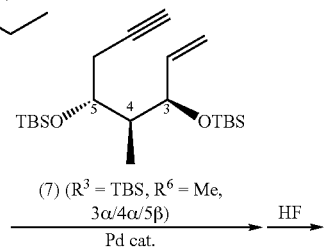

(7) (R³ = TBS, R⁶ = Me, 3α/4α/5β)

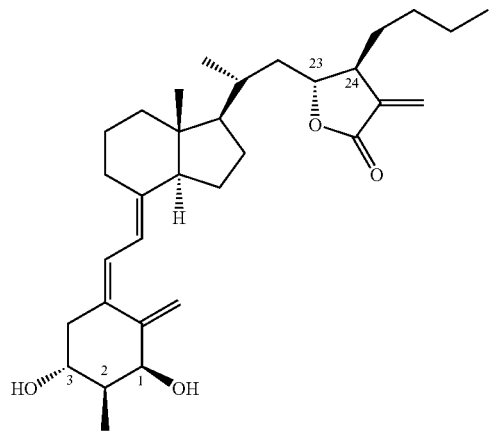

No. 205d
(1α/2α/3β/23R/24S)

(1) Using 20 mg (0.048-mmol) of Compound (4syn) (Z=(2-1), Y=Br, R²ᶜ=Bu (原原の誤り) atom, 4S/5S) obtained in Example 17(1), a reaction similar to Example 12(1) was carried out to obtain 19 mg of Compound (O) (4S/5S). Yield: 93%, a colorless solid substance.

¹H-NMR (CDCl₃) δ: 0.58 (s, 3 H), 0.89 (t, J=7.1 Hz, 3 H), 1.01 (d, J=6.3 Hz, 3 H), 0.95-1.75 (m, 17 H), 1.90-2.05 (m, 3 H), 2.18 (ddd, J=8.8, 5.4, 2.7 Hz, 1 H), 2.55 (br s, 2 H), 2.88 (m, 1 H), 3.73 (dt, J=2.7, 6.6 Hz, 1 H), 4.03 (d, J=12.9 Hz, 1 H), 4.11 (d, J=12.9 Hz, 1 H), 4.96 (d, J=1.1 Hz, 1 H), 5.18 (d, J=1.1 Hz, 1 H), 5.65 (s, 1 H).

EI-LRMS m/z 426 (M⁺), 409, 329, 298, 256, 227, 175

HRMS calcd for C₂₃H₃₉O₂⁷⁹Br 426.2134, found 426.2151

(2) Using 355 mg (0.831 mmol) of Compound (O) (4S/5S) obtained by the above method, a reaction similar to Example 12(2) was carried out to obtain 346 mg of Compound (5syn) (Z=(2-1), Y=Br, R²ᶜ=Bu, R⁸=Piv, 4S/5S). Yield: 81%, a colorless oily substance.

¹H-NMR (CDCl₃) δ: 0.57 (s, 3 H), 0.89 (t, J=7.1 Hz, 3 H), 1.02 (d, J=6.4 Hz, 3 H), 1.10-1.73 (m, 17 H), 1.23 (s, 9 H), 1.78 (br d, J=4.4 Hz, 1 H), 1.90-2.04 (m, 3 H), 2.07 (ddd, J=10.6, 3.9, 3.9 Hz, 1 H), 2.88 (m, 1 H), 3.70 (m, 1 H), 4.48 (d, J=13.9 Hz, 1 H), 4.56 (d, J=13.9 Hz, 1 H), 5.00 (s, 1 H), 5.21 (d, J=0.98 Hz, 1 H), 5.64 (s, 1 H).

LRMS m/z 510 (M⁺), 492, 212, 175, 110

HRMS calcd for C₂₈H₄₇O₃⁷⁹Br 510.2709, found 510.2737

(3) Using 346 mg (0.676 mmol) of Compound (5syn) (Z=(2-1), Y=Br, R²ᶜ=Bu, R⁸=Piv, 4S/5S) obtained by the above method, a reaction similar to Example 12(3) was carried out to obtain 294 mg of Compound (6) (Z=(2-1), Y=Br, R²ᶜ=Bu, R⁸=Piv, 4S). Yield: 85%, a colorless oily substance.

¹H-NMR (CDCl₃) δ: 0.59 (s, 3 H), 0.88 (t, J=7.2 Hz, 3 H), 0.92 (d, J=6.4 Hz, 3 H), 1.22 (s, 9 H), 1.15-1.72 (m, 13 H), 1.75-1.88 (m, 2 H), 1.94-2.05 (m, 3 H), 2.23 (dd, J=16.8, 10.0 Hz, 1 H), 2.52 (dd, J=16.8, 2.9 Hz, 1 H), 2.88 (m, 1 H), 3.06 (t, J=7.3 Hz, 1 H), 4.50 (s, 2 H), 5.07 (s, 1 H), 5.20 (s, 1 H), 5.64 (s, 1 H).

LRMS m/z 568 (M⁺), 423, 407, 351, 279, 237, 175

HRMS calcd for C₂₈H₄₅O₃⁷⁹Br 508.2552, found 508.2534

(4) Using 283 mg (0.556 mmol) of Compound (6) (Z=(2-1), Y=Br, $R^{2c}$=Bu, $R^8$=Piv, 4S) obtained by the above method, a reaction similar to Example 13(4) was carried out to obtain 53 mg of Compound (5anti) (Z=(2-1), Y=Br, $R^{2c}$=Bu, $R^8$=Piv, 4S/5R). Yield: 75%, a colorless oily substance.

$^1$H-NMR (CDCl$_3$) δ: 0.59 (s, 3 H), 0.88 (t, J=6.8 Hz, 3 H), 0.96 (d, J=6.4 Hz, 3 H), 1.10-1.80 (m, 17 H), 1.23 (s, 9 H), 1.85-2.10 (m, 4 H), 2.19 (d, J=3.4 Hz, 1 H), 2.87 (m, 1 H), 3.62 (m, 1 H), 4.45 (d, J=13.9 Hz, 1 H), 4.57 (d, J=13.9 Hz, 1 H), 5.03 (s, 1 H), 5.18 (s, 1H), 5.64 (s, 1 H).

LRMS m/z 510 (M$^+$), 477, 409, 311, 212, 175, 110

HRMS calcd for $C_{28}H_{47}O_3{}^{79}Br$ 510.2709, found 510.2708

(5) Using 260 mg (0.506 mmol) of Compound (5anti) (Z=(2-1), Y=Br, $R^{2c}$=Bu, $R^8$=Piv, 4S/5R) obtained by the above method, a reaction similar to Example 13(5) was carried out to obtain 197 mg of Compound (4anti) (Z=(2-1), Y=Br, $R^{2c}$=Bu, 4S/5R). Yield: 98%, a colorless, amorphous substance.

$^1$H-NMR (CDCl$_3$) δ: 0.59 (s, 3 H), 0.93 (t, J=6.8 Hz, 3 H), 1.03 (d, J=6.3 Hz, 3 H), 1.20-1.92 (m, 18 H), 1.98 (dd, J=12.5, 7.2 Hz, 1 H), 2.03 (br d, J=12.5 Hz, 1 H), 2.55 (m, 1H), 2.88 (m, 1 H), 4.27 (ddd, J=11.0, 4.9, 2.0 Hz, 1 H), 5.58 (d, J=2.4 Hz, 1 H), 5.65 (s, 1H), 6.26 (d, J=2.4 Hz, 1 H).

LRMS m/z 422 (M$^+$), 343, 281, 227

HRMS calcd for $C_{23}H_{35}O_2{}^{79}Br$ 422.1820, found 422.1819

(6) Using 35 mg (82 μmol) of Compound (4anti) (Z=(2-1), Y=Br, $R^{2c}$=Bu, 4S/5R) obtained by the above method and 47 mg (123 μmol) of Compound (7) ($R^3$=TBS, $R^6$=Me, 3α/4α/5β), a reaction similar to Example 14(2-a) was carried out to obtain 20 mg of Compound No. 205d. Yield: 50%.

Compound No. 205d:

$^1$H-NMR (CDCl$_3$) δ: 0.57 (s, 3 H), 0.93 (t, J=7.0 Hz, 3 H), 1.03 (d, J=6.6 Hz, 3 H), 1.20-2.08 (m, 24 H), 2.31 (dd, J=13.6, 6.4 Hz, 1 H), 2.55 (m, 1 H), 2.60 (dd, J=13.6, 3.1 Hz, 1 H), 2.83 (m, 1 H), 4.23 (m, 1 H), 4.27 (ddd, J=11.1, 4.9, 2.1 Hz, 1 H), 4.43 (m, 1 H), 5.00 (s, 1 H), 5.33 (s, 1 H), 5.57 (d, J=2.6 Hz, 1 H), 6.01 (d, J=11.2 Hz, 1 H), 6.26 (d, J=2.6 Hz, 1 H), 6.37 (d, J=11.2 Hz, 1 H).

LRMS m/z 482 (M$^+$), 464, 446, 251, 153

HRMS calcd for $C_{31}H_{46}O_4$ 482.3396, found 482.3398

Example 20

Synthesis of 2α-methyl-20(R)-(tetrahydro-3-methylene-2-furanone-4(R)-isobutyl-5(R)-yl)methyl-9,10-secopregna-5(Z),7(E),10(19)-triene-1α,3β-diol (Compound No. 206a) and 2α-methyl-20(R)-(tetrahydro-3-methylene-2-furanone-4(S)-isobutyl-5(S)-yl) methyl-9,10-secopregna-5(Z),7(E),10(19)-triene-1α,3β-diol (Compound No. 206b)

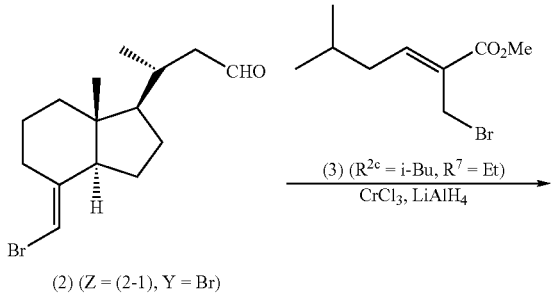

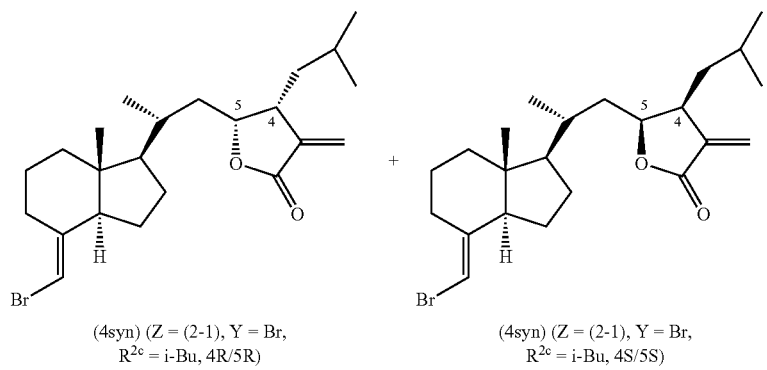

-continued

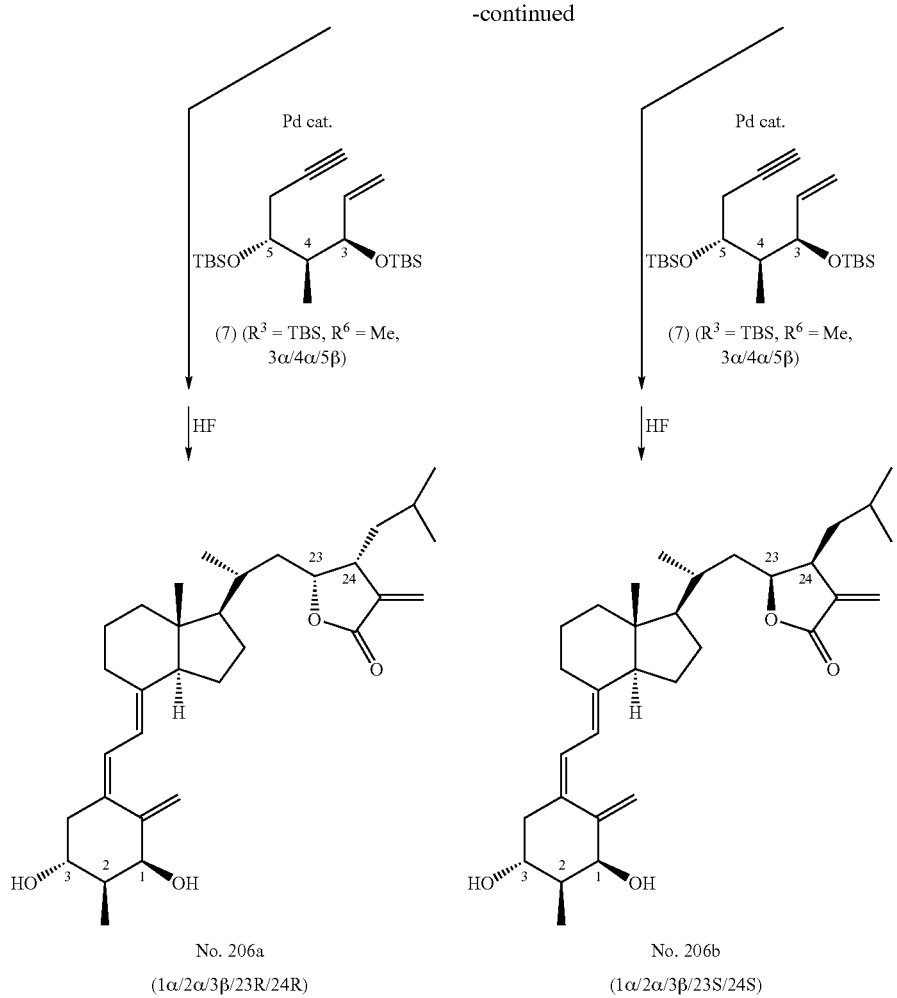

No. 206a
(1α/2α/3β/23R/24R)

No. 206b
(1α/2α/3β/23S/24S)

(1) Using 30 mg (0.101 μmmol) of Compound (2) (Z=(2-1), Y=Br) obtained by a method known in the literature (for example, the specification of International Publication WO 95/33716), a reaction similar to Example 11(1) was carried out to obtain 23.5 mg (yield: 55%) of Compound (4syn) (Z=(2-1), Y=Br, $R^{2c}$=i-Bu, 4R/5R) and 16.9 mg (yield: 39%) of Compound (4syn) (Z=(2-1), Y=Br, $R^{2c}$=i-Bu, 4S/5S). However, instead of Compound (3) ($R^{2c}$=Me, $R^7$=Me) in Example 11(1), used was Compound (3) ($R^{2c}$=i-Bu, $R^7$=Me) which was obtained by using methyl acrylate in place of ethyl acrylate, as in Reference Example 6.

Compound (4syn) (Z=(2-1), Y=Br, $R^{2c}$=i-Bu, 4R/5R):

$[\alpha]_D^{24}$+146.2 (c 1.55, CHCl$_3$)

$^1$H-NMR (CDCl$_3$) δ: 0.56 (s, 3 H), 0.95 (d, J=2.5 Hz, 3 H), 0.96 (d, J=2.4 Hz, 3 H), 1.01 (d, J=6.3 Hz, 3 H), 1.09 (ddd, J=14.3, 10.7, 2.0 Hz, 1 H), 1.20-1.92 (m, 14 H), 1.95-2.05 (m, 2 H), 2.88 (m, 1 H), 3.09 (m, 1 H), 4.66 (ddd, J=11.8, 7.1, 1.8 Hz, 1 H), 5.48 (d, J=2.6 Hz, 1 H), 5.65 (br s, 1 H), 6.21 (d, J=2.6 Hz, 1 H).

$^{13}$C-NMR (CDCl$_3$) δ: 11.9, 18.5, 22.0, 22.5 (2 C), 22.7, 24.9, 27.6, 31.0, 32.6, 36.3, 36.7, 40.0, 41.2, 45.6, 55.9, 56.3, 78.2, 97.7, 120.6, 139.6, 144.8, 170.6.

LRMS m/z 422 (M$^+$), 343, 257, 227

HRMS calcd for $C_{23}H_{35}O_2{}^{79}$Br 422.1820, found 422.1820

Compound (4syn) (Z=(2-1), Y=Br, $R^{2c}$=i-Bu, 4S/5S):

$[\alpha]_D^{24}$+35.6 (c 0.76, CHCl$_3$)

$^1$H-NMR (CDCl$_3$) δ: 0.58 (s, 3 H), 0.95 (d, J=6.6 Hz, 6 H), 1.06 (d, J=6.6 Hz, 3 H), 1.22-1.75 (m, 14 H), 1.89-2.06 (m, 3 H), 2.88 (m, 1 H), 3.02 (m, 1 H), 4.59 (m, 1 H), 5.48 (d, J=2.1 Hz, 1 H), 5.65 (s, 1 H), 6.19 (d, J=2.1 Hz, 1 H).

$^{13}$C-NMR (CDCl$_3$) δ: 11.7, 19.8, 22.0 (2 C), 22.5, 23.0, 24.4, 27.7, 30.9, 34.5, 36.0, 36.1, 39.7, 41.5, 45.6, 55.7, 56.0, 80.4, 97.5, 120.6, 139.7, 144.9, 170.6.

LRMS m/z 422 (M$^+$), 343, 257, 227

HRMS calcd for $C_{23}H_{35}O_2{}^{79}$Br 422.1821, found 422.1819

(2-a) Using 21 mg (50 μmol) of Compound (4syn) (Z=(2-1), Y=Br, $R^{2c}$=i-Bu, 4R/5R) obtained by the above method and 29 mg (75 μmol) of Compound (7) ($R^3$=TBS, $R^6$=Me, 3α/4α/5β), a reaction similar to Example 14(2-a) was carried out to obtain 13.3 mg of Compound No. 206a. Yield: 53%.

Compound No. 206a:

$[\alpha]_D^{23}$+112.6 (c 1.02, CHCl$_3$)

$^1$H-NMR (CDCl$_3$) δ: 0.56 (s, 3 H), 0.95 (d, J=6.6 Hz, 3 H), 0.96 (d, J=6.6 Hz, 3 H), 1.00 (d, J=6.6 Hz, 3 H), 1.07 (d, J=6.8 Hz, 3 H), 1.08 (m, 1 H), 1.18-2.05 (m, 19 H), 2.23 (dd, J=13.5, 7.8 Hz, 1 H), 2.67 (d, J=13.5, 4.0 Hz, 1 H), 2.82 (m, 1 H), 3.09 (m, 1 H), 3.85 (m, 1 H), 4.31 (m, 1 H), 4.66 (ddd, J=11.6, 7.2, 1.6 Hz, 1 H), 5.00 (d, J=2.0 Hz, 1 H), 5.28 (s, 1 H), 5.48 (d, J=2.6 Hz, 1 H), 6.00 (d, J=11.4 Hz, 1 H), 6.20 (d, J=2.6 Hz, 1 H), 6.37 (d, J=11.4 Hz, 1 H).

$^{13}$C-NMR (CDCl$_3$) δ: 12.1, 12.5, 18.5, 22.2, 22.5, 22.7, 23.5, 24.9, 27.6, 29.0, 32.6, 36.2, 36.7, 40.5, 41.2, 43.4, 44.1, 46.0, 56.3, 57.0, 71.7, 75.3, 78.3, 113.2, 117.1, 120.6, 124.6, 133.2, 139.6, 142.7, 146.5, 170.6.

LRMS m/z 496 (M$^+$), 478, 460, 434, 265

HRMS calcd for C$_{32}$H$_{48}$O$_4$ 496.3552, found 496.3570

(2-b) Using 21 mg (49 μmol) of Compound (4syn) (Z=(2-1), Y=Br, R$^{2c}$=i-Bu, 4S/5S) obtained by the above method and 28 mg (74 μmol) of Compound (7) (R$^3$=TBS, R$^6$=Me, 3α/4α/5β), a reaction similar to Example 14(2-a) was carried out to obtain 12 mg of Compound No. 206b. Yield: 49%.

Compound No. 206b:

[α]$_D^{24}$+11.9 (c 0.92, CHCl$_3$)

$^1$H-NMR (CDCl$_3$) δ: 0.55 (s, 3 H), 0.94 (d, J=6.4 Hz, 3 H), 0.95 (d, J=6.6 Hz, 3 H), 1.05 (d, J=6.6 Hz, 3 H), 1.08 (d, J=6.8 Hz, 3 H), 1.20-1.7 (m, 16 H), 1.88-2.08 (m, 4 H), 2.23 (dd, J=13.6, 7.8 Hz, 1 H), 2.67 (dd, J=13.6, 3.9 Hz, 1 H), 2.83 (m, 1 H), 3.02 (m, 1 H), 3.84 (m, 1H), 4.30 (br s, 1), 4.58 (ddd, J=8.7, 6.4, 4.6 Hz, 1 H), 5.00 (d, J=2.0 Hz, 1 H), 5.28 (d, J=2.0 Hz, 1 H), 5.48 (d, J=2.1 Hz, 1 H), 6.01 (d, J=11.4 Hz, 1 H), 6.19 (d, J=2.1 Hz, 1 H), 6.38 (d, J=11.4 Hz, 1 H).

$^{13}$C-NMR (CDCl$_3$) δ: 11.9, 12.5, 19.8, 22.0, 22.2, 23.1, 23.5, 24.4, 27.9, 29.0, 34.5, 35.9, 36.1, 40.4, 41.4, 43.5, 44.2, 46.0, 56.1, 56.9, 71.7, 75.4, 80.6, 113.2, 117.1, 120.6, 124.7, 133.2, 139.8, 142.8, 146.5, 170.7.

LRMS m/z 496 (M$^+$), 478, 460, 434, 265

HRMS calcd for C$_{32}$H$_{48}$O$_4$ 496.3553, found 496.3553

Example 21

Synthesis of 2α-methyl-20(R)-(tetrahydro-3-methylene-2-furanone-4(R)-isobutyl-5(S)-yl)methyl-9,10-secopregna-5(Z),7(E),10(19)-triene-1α,3β-diol (Compound No. 206c)

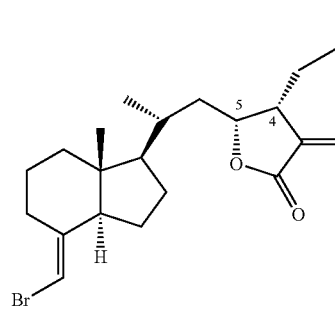

(4syn) (Z = (2-1), Y = Br, R$^{2c}$ = i-Bu, 4R/5R)

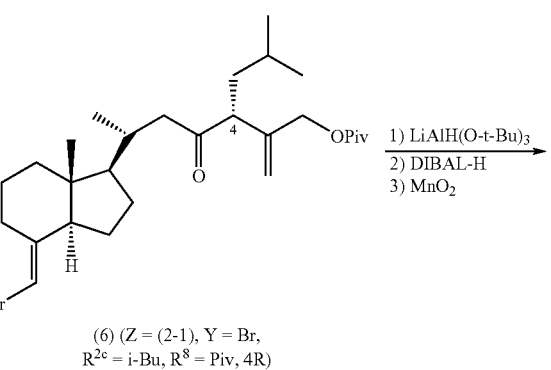

(P) (4R/5R)

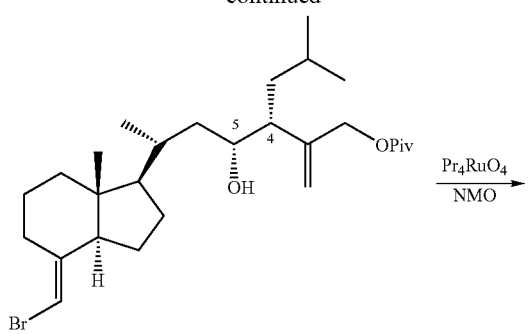

(5syn) (Z = (2-1), Y = Br, R$^{2c}$ = i-Bu, R$^8$ = Piv, 4R/5R)

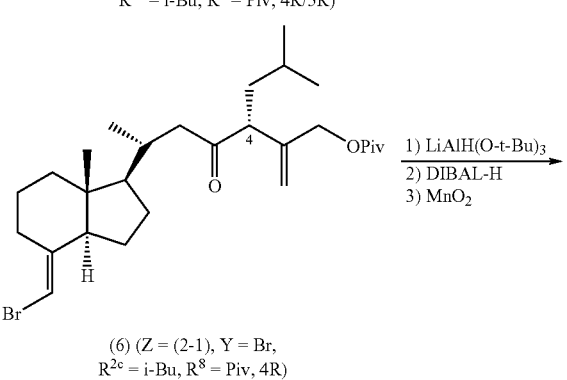

(6) (Z = (2-1), Y = Br, R$^{2c}$ = i-Bu, R$^8$ = Piv, 4R)

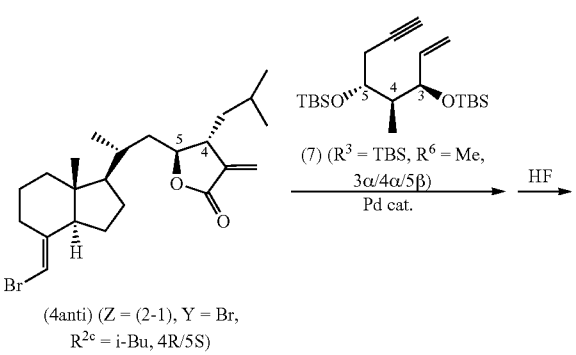

(4anti) (Z = (2-1), Y = Br, R$^{2c}$ = i-Bu, 4R/5S)

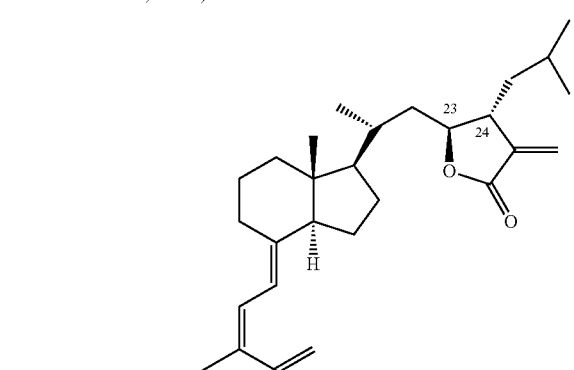

No. 206c (1α/2α/3β/23S/24R)

(1) Using 10 mg (0.024 mmol) of Compound (4syn) (Z=(2-1), Y=Br, R$^{2c}$=i-Bu, 4R/5R) obtained in Example 20(1), a reaction similar to Example 12(1) was carried out to obtain 10 mg of Compound (P) (4R/5R). Yield: 96%, a colorless oily substance.

$[\alpha]_D^{18}$+99.7 (c 0.86, CHCl$_3$)

$^1$H-NMR (CDCl$_3$) δ: 0.59 (s, 3 H), 0.83 (d, J=6.4 Hz, 3 H), 0.90 (d, J=6.4 Hz, 3 H), 0.96 (d, J=6.6 Hz, 3 H), 1.01 (m, 1 H), 1.20-1.35 (m, 4 H), 1.40-1.75 (m, 9 H), 1.85-2.05 (m, 3 H), 2.24 (dt, J=10.6, 3.9 Hz, 1 H), 2.36 (br s, 2 H), 2.88 (m, 1 H), 3.68 (ddd, J=10.6, 4.2, 1.8 Hz, 1 H), 4.04 (dd, J=13.2, 0.7 Hz, 1 H), 4.09 (dd, J=13.2, 0.7 Hz, 1 H), 4.92 (s, 1 H), 5.18 (d, J=1.2 Hz, 1 H), 5.64 (s, 1 H).

$^{13}$C-NMR (CDCl$_3$) δ: 11.8, 18.7, 21.4, 21.9, 22.4, 23.9, 25.3, 27.7, 30.9, 32.8, 37.2, 39.8, 40.5, 45.5, 48.6, 55.9, 56.3, 65.6, 71.5, 97.4, 114.1, 144.9, 149.1.

LRMS m/z 426 (M$^+$), 408, 365, 351, 329, 298, 256, 227, 175, 147

HRMS calcd for C$_{23}$ H$_{39}$O$_2$$^{79}$Br 426.2134, found 426.2146

(2) Using 219 mg (0.513 mmol) of Compound (P) (4R/5R) obtained by the above method, a reaction similar to Example 12(2) was carried out to obtain 222 mg of Compound (5syn) (Z=(2-1), Y=Br, R$^{2c}$=i-Bu, R$^8$=Piv, 4R/5R). Yield: 84%, a colorless oily substance.

$[\alpha]_D^{24}$+84.6 (c 1.16, CHCl$_3$)

$^1$H-NMR (CDCl$_3$) δ: 0.56 (s, 3 H), 0.85 (d, J=6.6 Hz, 3 H), 0.90 (d, J=6.6 Hz, 3 H), 0.95 (d, J=6.6 Hz, 3 H), 1.03 (ddd, J=13.7, 11.0, 1.7 Hz, 1 H), 1.24 (s, 9 H), 1.20-1.75 (m, 14 H), 1.87-2.05 (m, 3 H), 2.16 (ddd, J=11.1, 4.6, 4.6 Hz, 1 H), 2.87 (m, 1 H), 3.64 (ddd, J=10.0, 4.5, 4.5 Hz, 1 H), 4.51 (s, 2 H), 4.95 (s, 1 H), 5.16 (s, 1 H), 5.64 (s, 1 H).

$^{13}$C-NMR (CDCl$_3$) δ: 11.9, 18.7, 21.5, 22.0, 22.5, 24.0, 25.3, 27.2 (3 C), 27.8, 31.0, 32.9, 37.7, 38.8, 39.9, 40.9, 45.6, 48.1, 55.9, 56.3, 66.1, 70.9, 97.4, 112.6, 144.9, 145.0, 178.2.

LRMS m/z 510 (M$^+$), 492, 408, 212, 156

HRMS calcd for C$_{28}$H$_{47}$O$_3$$^{79}$Br 510.2709, found 510.2695

(3) Using 202 mg (0.394 mmol) of Compound (5syn) (Z=(2-1), Y=Br, R$^{2c}$=i-Bu, R$^8$=Piv, 4R/5R) obtained by the above method, a reaction similar to Example 12(3) was carried out to obtain 168 mg of Compound (6) (Z=(2-1), Y=Br, R$^{2c}$=i-Bu, R$^8$=Piv, 4R). Yield: 84%, a colorless oily substance.

$[\alpha]_D^{26}$+6.44 (c 0.82, CHCl$_3$)

$^1$H-NMR (CDCl$_3$) δ: 0.56 (s, 3 H), 0.87 (d, J=6.7 Hz, 3 H), 0.88 (d, J=6.4 Hz, 3 H), 0.89 (d, J=6.8 Hz, 3 H), 1.23 (s, 9 H), 1.20-1.75 (m, 11 H), 1.84 (m, 1 H), 1.95-2.05 (m, 3 H), 2.27 (dd, J=16.9, 10.0 Hz, 1 H), 2.47 (dd, J=16.9, 2.5 Hz, 1 H), 2.87 (m, 1 H), 3.23 (t, J=7.3 Hz, 1 H), 4.47 (d, J=13.9 Hz, 1 H), 4.55 (d, J=13.9 Hz, 1 H), 5.05 (s, 1 H), 5.20 (s, 1 H), 5.64 (s, 1 H).

$^{13}$C-NMR (CDCl$_3$) δ: 11.9, 19.7, 22.0, 22.4, 22.5, 22.6, 25.9, 27.2 (3 C), 27.7, 31.0, 32.1, 38.8, 39.1, 39.7, 45.5, 48.5, 54.3, 55.4, 55.8, 65.6, 97.5, 115.2, 141.6, 144.7, 177.7, 208.7.

LRMS m/z 508 (M$^+$), 429, 406, 350, 297, 227

HRMS calcd for C$_{28}$H$_{45}$O$_3$$^{79}$Br 508.2552, found 508.2542

(4) Using 153 mg (0.30 mmol) of Compound (6) (Z=(2-1), Y=Br, R$^{2c}$=i-Bu, R$^8$=Piv, 4R) obtained by the above method, a reaction similar to Example 12(4) was carried out to obtain 84 mg of Compound (4anti) (Z=(2-1), Y=Br, R$^{2c}$=i-Bu, 4R/5S). Yield: 69%, a colorless oily substance.

$[\alpha]_D^{25}$+77.6 (c 0.82, CHCl$_3$)

$^1$H-NMR (CDCl$_3$) δ: 0.58 (s, 3 H), 0.96 (d, J=6.6 Hz, 3 H), 0.97 (d, J=6.6 Hz, 3 H), 1.07 (d, J=6.4 Hz, 3 H), 1.15-1.75 (m, 14 H), 1.88-2.05 (m, 3 H), 2.66 (m, 1 H), 2.88 (m, 1 H), 4.20 (ddd, J=6.8, 5.6, 3.9 Hz, 1 H), 5.57 (d, J=2.3 Hz, 1 H), 5.65 (s, 1 H), 6.24 (d, J=2.3 Hz, 1H).

$^{13}$C-NMR (CDCl$_3$) δ: 11.8, 19.6, 22.0, 22.3, 22.5, 22.7, 25.2, 27.9, 31.0, 34.3, 39.7, 42.3, 43.1, 43.9, 45.5, 55.7 (2 C), 82.8, 97.5, 121.9, 139.5, 144.7, 170.2.

LRMS m/z 422 (M$^+$), 343, 257, 227

HRMS calcd for C$_{23}$ H$_{35}$O$_2$$^{79}$Br 422.1820, found 422.1820

(5) Using 21 mg (49 μmol) of Compound (4anti) (Z=(2-1), Y=Br, R$^{2c}$=i-Bu, 4R/5S) obtained by the above method and 28 mg (74 μmol) of Compound (7) (R$^3$=TBS, R$^6$=Me, 3α/4α/5β), a reaction similar to Example 14(2-a) was carried out to obtain 13.1 mg of Compound No. 206c. Yield: 54%.

Compound No. 206c:

$[\alpha]_D^{24}$+55.8 (c 1.01, CHCl$_3$)

$^1$H-NMR (CDCl$_3$) δ: 0.55 (s, 3 H), 0.95 (d, J=6.3 Hz, 3 H), 0.96 (d, J=6.6 Hz, 3 H), 1.06 (d, J=6.1 Hz, 3 H), 1.08 (d, J=6.8 Hz, 3 H), 1.15-1.75 (m, 16 H), 1.85-2.05 (m, 4 H), 2.23 (dd, J=13.4, 7.8 Hz, 1 H), 2.63-2.71 (m, 2 H), 2.82 (m, 1 H), 3.84 (ddd, J=7.6, 7.6, 4.2 Hz, 1 H), 4.20 (m, 1 H), 4.30 (br s, 1 H), 5.00 (d, J=2.0 Hz, 1 H), 5.27 (dd, J=1.7, 1.0 Hz, 1 H), 5.57 (d, J=2.3 Hz, 1 H), 6.01 (d, J=11.2 Hz, 1 H), 6.24 (d, J=2.3 Hz, 1 H), 6.38 (d, J=11.2 Hz, 1 H).

$^{13}$C-NMR (CDCl$_3$) δ: 11.9, 12.5, 19.6, 22.2, 22.3, 22.7, 23.4, 25.1, 27.9, 29.0, 34.3, 40.3, 42.3, 43.0, 43.4, 43.9, 44.2, 45.9, 56.2, 56.5, 71.7, 75.4, 83.0, 113.2, 117.1, 122.1, 124.7, 133.2, 139.7, 142.7, 146.5, 170.5.

LRMS m/z 496 (M$^+$), 478, 460, 434, 265

HRMS calcd for C$_{32}$H$_{48}$O$_4$ 496.3553, found 496.3539

Example 22

Synthesis of 2α-methyl-20(R)-(tetrahydro-3-methylene-2-furanone-4(S)-isobutyl-5(R)-yl)methyl-9,10-secopregna-5(Z),7(E),10(19)-triene-1α,3β-diol (Compound No. 206d)

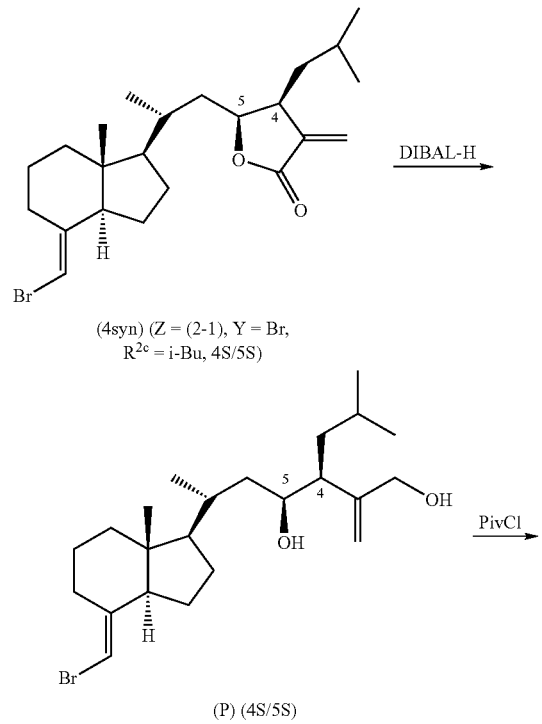

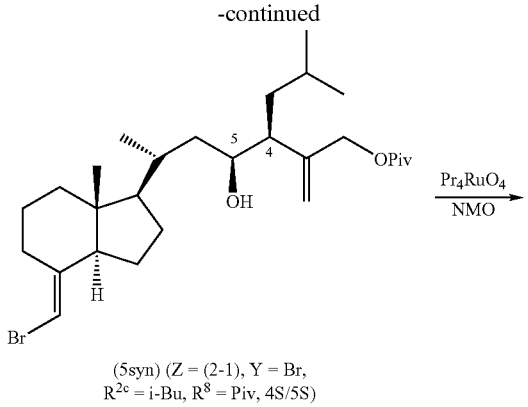

(5syn) (Z = (2-1), Y = Br,
R²ᶜ = i-Bu, R⁸ = Piv, 4S/5S)

Pr₄RuO₄ / NMO →

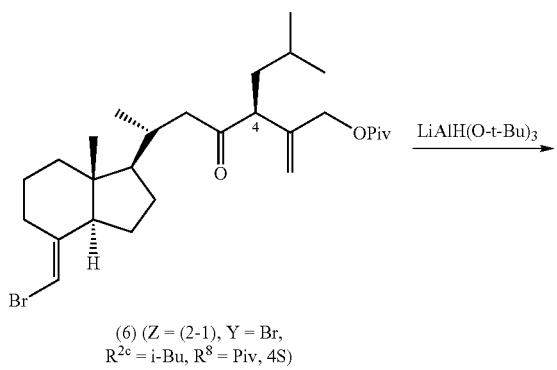

(6) (Z = (2-1), Y = Br,
R²ᶜ = i-Bu, R⁸ = Piv, 4S)

LiAlH(O-t-Bu)₃ →

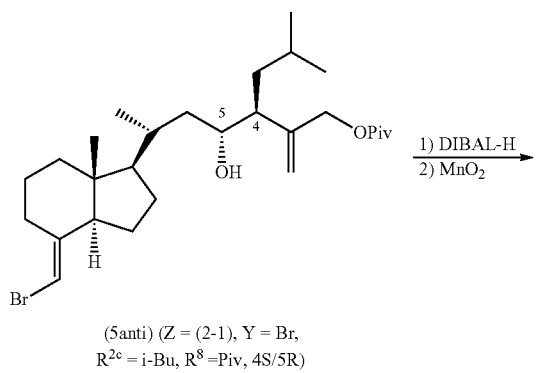

(5anti) (Z = (2-1), Y = Br,
R²ᶜ = i-Bu, R⁸ = Piv, 4S/5R)

1) DIBAL-H
2) MnO₂ →

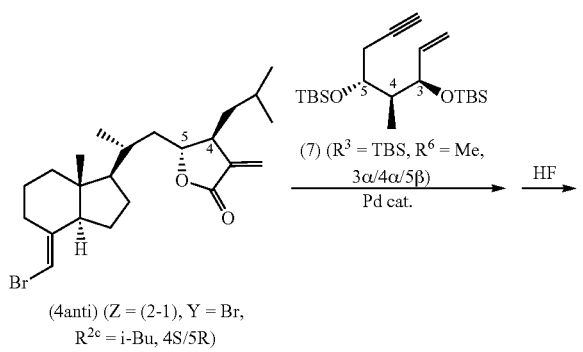

(4anti) (Z = (2-1), Y = Br,
R²ᶜ = i-Bu, 4S/5R)

(7) (R³ = TBS, R⁶ = Me, 3α/4α/5β)
HF
Pd cat. →

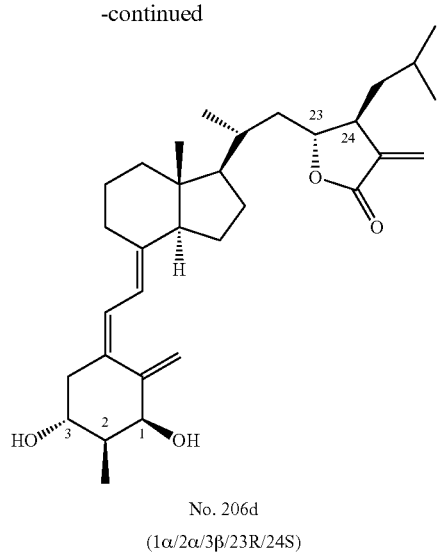

No. 206d
(1α/2α/3β/23R/24S)

(1) Using 11 mg (0.026 mmol) of Compound (4syn) (Z=(2-1), Y=Br, R²ᶜ=i-Bu (原原の誤り) atom, 4S/5S) obtained in Example 20(1), a reaction similar to Example 12(1) was carried out to obtain 11 mg of Compound (P) (4S/5S). Yield: 95%, an amorphous solid substance.

$[\alpha]_D^{24}$ +83.7 (c 0.83, CHCl₃)

¹H-NMR (CDCl₃) δ: 0.58 (s, 3 H), 0.83 (d, J=6.4 Hz, 3 H), 0.91 (d, J=6.6 Hz, 3 H), 1.01 (d, J=6.3 Hz, 3 H), 1.10-1.73 (m, 14 H), 1.90-2.05 (m, 3 H), 2.32 (br d, J=11.7 Hz, 1 H), 2.87 (m, 1 H), 3.03 (br s, 2 H), 3.74 (m, 1 H), 4.02 (d, J=12.8 Hz, 1 H), 4.11 (d, J=12.8 Hz, 1 H), 4.96 (s, 1 H), 5.17 (s, 1 H), 5.65 (s, 1 H).

¹³C-NMR (CDCl₃) δ: 11.8, 19.4, 21.4, 22.0, 22.5, 24.2, 25.3, 27.8, 31.0, 34.2, 34.5, 39.8, 40.4, 45.5, 46.2, 55.8, 56.5, 65.0, 73.2, 97.5, 114.8, 144.9, 149.8.

LRMS m/z 409 ((M−OH)⁺), 408, 351, 329, 298, 256, 227, 175, 147

HRMS calcd for $C_{23}H_{38}O^{79}Br$ (M−OH)⁺ 409.2106, found 409.2107

(2) Using 147 mg (0.343 mmol) of Compound (P) (4S/5S) obtained by the above method, a reaction similar to Example 12(2) was carried out to obtain 173 mg of Compound (5syn) (Z=(2-1), Y=Br, R²ᶜ=i-Bu, R⁸=Piv, 4S/5S). Yield: 99%, a colorless oily substance.

$[\alpha]_D^{23}$ +67.0 (c 1.17, CHCl₃)

¹H-NMR (CDCl₃) δ: 0.56 (s, 3 H), 0.84 (d, J=6.4 Hz, 3 H), 0.91 (d, J=6.3 Hz, 3 H), 1.01 (d, J=6.4 Hz, 3 H), 1.15-1.70 (m, 14 H), 1.23 (s, 9 H), 1.80 (br s, 1 H), 1.90-2.05 (m, 3 H), 2,21 (br d, J=11.7 Hz, 1 H), 2.87 (m, 1 H), 3.71 (m, 1 H), 4.49 (d, J=14.2 Hz, 1 H), 4.58 (d, J=14.2 Hz, 1 H), 5.01 (s, 1 H), 5.21 (s, 1 H), 5.65 (s, 1 H).

¹³C-NMR (CDCl₃) δ: 11.7, 19.5, 21.6, 22.0, 22.5, 24.2, 25.2, 27.2 (3 C), 27.8, 31.0, 34.5, 34.6, 38.8, 39.8, 40.3, 45.1, 45.5, 55.8, 56.4, 66.2, 71.9, 97.5, 112.9, 145.0, 145.2, 178.2.

LRMS m/z 510 (M⁺), 492, 408, 391, 212, 110

HRMS calcd for $C_{28}H_{47}O_3^{79}Br$ 510.2708, found 510.2713

(3) Using 140 mg (0.273 mmol) of Compound (5syn) (Z=(2-1), Y=Br, R²ᶜ=i-Bu, R⁸=Piv, 4S/5S) obtained by the above method, a reaction similar to Example 12(3) was carried out to obtain 117 mg of Compound (6) (Z=(2-1), Y=Br, R²ᶜ=i-Bu, R⁸=Piv, 4S). Yield: 84%, a colorless oily substance.

$[\alpha]_D^{26}$ +128.7 (c 0.78, CHCl₃)

119

$^1$H-NMR (CDCl$_3$) δ: 0.59 (s, 3 H), 0.87 (d, J=6.8 Hz, 3 H), 0.89 (d, J=6.8 Hz, 3 H), 0.92 (d, J=6.6 Hz, 3 H), 1.22 (s, 9 H), 1.20-1.75 (m, 11 H), 1.84 (m, 1 H), 1.95-2.05 (m, 3 H), 2.24 (dd, J=16.8, 9.8 Hz, 1 H), 2.53 (dd, J=16.8, 2.7 Hz, 1 H), 2.88 (m, 1 H), 3.20 (t, J=7.1 Hz, 1 H), 4.48 (d, J=15.0 Hz, 1 H), 4.52 (d, J=15.0 Hz, 1 H), 5.07, (s, 1 H), 5.20 (s, 1 H), 5.64 (s, 1 H).

$^{13}$C-NMR (CDCl$_3$) δ: 11.9, 20.1, 22.0, 22.4, 22.5, 22.7, 25.8, 27.2 (5 C), 27.6, 31.0, 32.6, 38.9, 39.8, 45.6, 48.1, 55.5, 55.9, 65.6, 97.5, 115.3, 141.7, 144.7, 177.7, 209.4.

LRMS m/z 508 (M$^+$), 429, 406, 350, 297, 227

HRMS calcd for C$_{28}$H$_{45}$O$_3$$^{79}$Br 508.2552, found 508.2556

(4) Using 103 mg (0.20 mmol) of Compound (6) (Z=(2-1), Y=Br, R$^{2c}$=i-Bu, R$^8$=Piv, 4S) obtained by the above method, a reaction similar to Example 13(4) was carried out to obtain 103 mg of Compound (5anti) (Z=(2-1), Y=Br, R$^{2c}$=i-Bu, 4S/5R). Yield: 100%, a colorless oily substance.

[α]$_D^{25}$+81.7 (c 0.82, CHCl$_3$)

$^1$H-NMR (CDCl$_3$) δ: 0.59 (s, 3 H), 0.85 (d, J=6.6 Hz, 3 H), 0.89 (d, J=6.6 Hz, 3 H), 0.93 (d, J=6.6 Hz, 3 H), 1.10-1.80 (m, 14 H), 1.23 (s, 9 H), 1.92 (m, 1 H), 1.98 (ddd, J=12.9, 6.6, 1.5 Hz, 1 H), 2.03 (ddd, J=12.9, 2.7, 2.7 Hz, 1 H), 2.15 (ddd, J=11.5, 7.6, 4.2 Hz, 1 H), 2.24 (br d, J=3.4 Hz, 1 H), 2.87 (m, 1 H), 3.59 (m, 1 H), 4.45 (d, J=14.2 Hz, 1 H), 2.47 (d, J=14.2 Hz, 1 H), 5.04 (s, 1 H), 5.18 (s, 1 H), 5.64 (s, 1 H).

$^{13}$C-NMR (CDCl$_3$) δ: 11.9, 18.8, 21.5, 22.1, 22.6, 24.0, 25.6, 27.2 (3 C), 27.8, 31.0, 32.8, 38.7, 38.8, 39.9, 41.5, 45.6, 50.6, 56.0, 56.5, 64.9, 70.2, 97.4, 114.6, 144.0, 144.9, 178.3.

LRMS m/z 510 (M$^+$), 492, 408, 212, 156

HRMS calcd for C$_{28}$H$_{47}$O$_3$$^{79}$Br 510.2708, found 510.2701

(5) Using 103 mg (0.201 mmol) of Compound (5anti) (Z=(2-1), Y=Br, R$^{2c}$=i-Bu, 4S/5R) obtained by the above method, a reaction similar to Example 13(5) was carried out to obtain 77 mg of Compound (4anti) (Z=(2-1), Y=Br, R$^{2c}$=i-Bu, 4S/5R). Yield: 90%.

[α]$_D^{25}$+119.2 (c 0.73, CHCl$_3$)

$^1$H-NMR (CDCl$_3$) δ: 0.59 (s, 3 H), 0.95 (d, J=6.6 Hz, 3 H), 0.96 (d, J=6.6 Hz, 3 H), 1.02 (d, J=6.6 Hz, 3 H), 1.20-1.95 (m, 15 H), 1.97 (ddd, J=12.3, 6.8, 1.7 Hz, 1 H), 2.02 (ddd, J=12.3, 2.9, 2.4 Hz, 1 H), 2.62 (m, 1 H), 2.89 (m, 1 H), 4.24 (ddd, J=11.1, 4.6, 2.2 Hz, 1 H), 5.56 (d, J=2.6 Hz, 1 H), 5.65 (s, 1 H), 6.24 (d, J=2.6 Hz, 1 H).

$^{13}$C-NMR (CDCl$_3$) δ: 11.9, 18.5, 22.0, 22.2, 22.5, 22.9, 25.3, 27.6, 31.0, 32.9, 39.9, 43.0, 43.1, 43.5, 45.6, 55.8, 56.1, 81.2, 97.5, 121.7, 139.8, 144.6, 170.2.

LRMS m/z 422 (M$^+$), 343, 257, 227

HRMS calcd for C$_{23}$ H$_{35}$O$_2$$^{79}$Br 422.1821, found 422.1820

(6) Using 23 mg (53 µmol) of Compound (4anti) (Z=(2-1), Y=Br, R$^{2c}$=i-Bu, 4S/5R) obtained by the above method and 31 mg (80 µmol) of Compound (7) (R$^3$=TBS, R$^6$=Me, 3α/4α/5β), a reaction similar to Example 14(2-a) was carried out to obtain 13.1 mg of Compound 206d. Yield: 49%.

[α]$_D^{24}$+85.3 (c 0.60, CHCl$_3$)

$^1$H-NMR (CDCl$_3$) δ: 0.56 (s, 3 H), 0.95 (d, J=6.6 Hz, 3 H), 0.96 (d, J=6.3 Hz, 3 H), 1.02 (d, J=6.6 Hz, 3 H), 1.05 (d, J=6.8 Hz, 3 H), 1.18-1.35 (m, 4 H), 1.40-208 (m, 16 H), 2.23 (dd, J=13.6, 7.9 Hz, 1 H), 2.62 (m, 1 H), 2.67 (dd, J=13.6, 3.8 Hz, 1 H), 2.83 (m, 1 H), 3.85 (m, 1H), 4.24 (ddd, J=10.9, 4.8, 2.0 Hz, 1 H), 4.31 (m, 1 H), 5.00 (d, J=1.7 Hz, 1 H), 5.28 (s, 1H), 5.56 (d, J=2.2 Hz, 1 H), 6.50 (d, J=11.4 Hz, 1 H), 6.24 (d, J=11.2 Hz, 1 H), 6.38 (d, J=11.4 Hz, 1 H).

$^{13}$C-NMR (CDCl$_3$) δ: 12.1, 12.5, 18.5, 22.1, 22.2, 22.9, 23.5, 25.2, 27.5, 29.0, 33.0, 40.5, 43.0, 43.1, 43.4, 43.5, 44.2, 46.0, 56.3, 56.9, 71.7, 75.4, 81.4, 113.2, 117.1, 121.8, 124.6, 133.2, 140.0, 142.7, 146.5, 170.5.

LRMS m/z 496 (M$^+$), 478, 460, 434, 265

HRMS calcd for C$_{32}$H$_{48}$O$_4$ 496.3552, found 496.3554

120

Example 23

Synthesis of 2α-(3-hydroxypropyl)-20(R)-(tetrahydro-3-methylene-2-furanone-5(R)-yl)methyl-9,10-secopregna-5(Z),7(E),10(19)-triene-1α,3β-diol (Compound No. 801a)

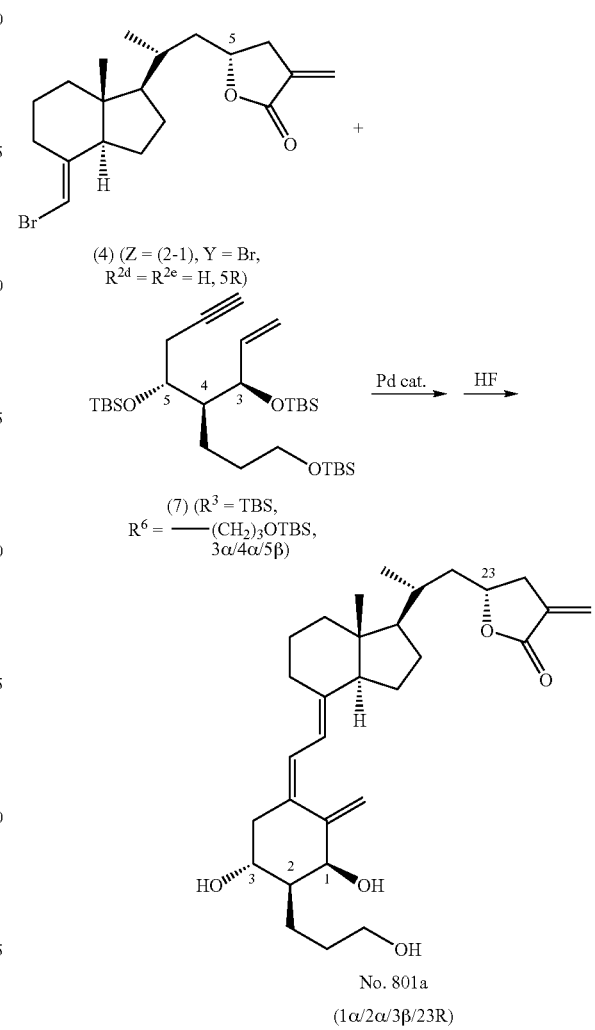

Using 14 mg (38 µmol) of Compound (4) (Z=(2-1), Y=Br, R$^{2d}$=R$^{2e}$=H, 5R) obtained by a method known in the literature (for example, the specification of International Publication WO 95/33716) and 31 mg (57 µmol) of Compound (7) (R$^3$=TBS, R$^6$=—(CH$_2$)$_3$OTBS, 3α/4α/5β), a reaction similar to Example 14(2-a) was carried out to obtain 10 mg of Compound No. 801a. Yield: 56%.

$^1$H-NMR (CDCl$_3$) δ: 0.55 (s, 3 H), 1.02 (d, J=6.3 Hz, 3 H), 1.26-1.82 (m, 19 H), 1.96-2.04 (m, 3 H), 2.25 (dd, J=13.1, 8.3 Hz, 1 H), 2.52 (m, 1 H), 2.67 (dd, J=13.1, 4.0 Hz, 1 H), 2.84 (m, 1 H), 3.03 (m, 1 H), 3.71 (t, J=5.3 Hz, 2 H), 3.90 (ddd, J=8.3, 8.3, 4.5 Hz, 1 H), 4.38 (d, J=2.0 Hz, 1 H), 4.64 (m, 1 H), 4.99 (s, 1 H), 5.28 (s, 1 H), 5.62 (s, 1 H), 6.00 (d, J=11.2 Hz, 1 H), 6.23 (s, 1 H), 6.39 (d, J=11.2 Hz, 1 H).

LRMS m/z 484 (M$^+$), 466, 448, 438, 389, 338, 309, 253

HRMS calcd for C$_{30}$H$_{44}$O$_5$ 484.3189, found 484.3174

Example 24

Synthesis of 2α-(3-hydroxypropyl)-20(R)-(tetrahydro-3-methylene-2-furanone-5(S)-yl)methyl-9,10-secopregna-5(Z),7(E),10(19)-triene-1α,3β-diol (Compound No. 801 b)

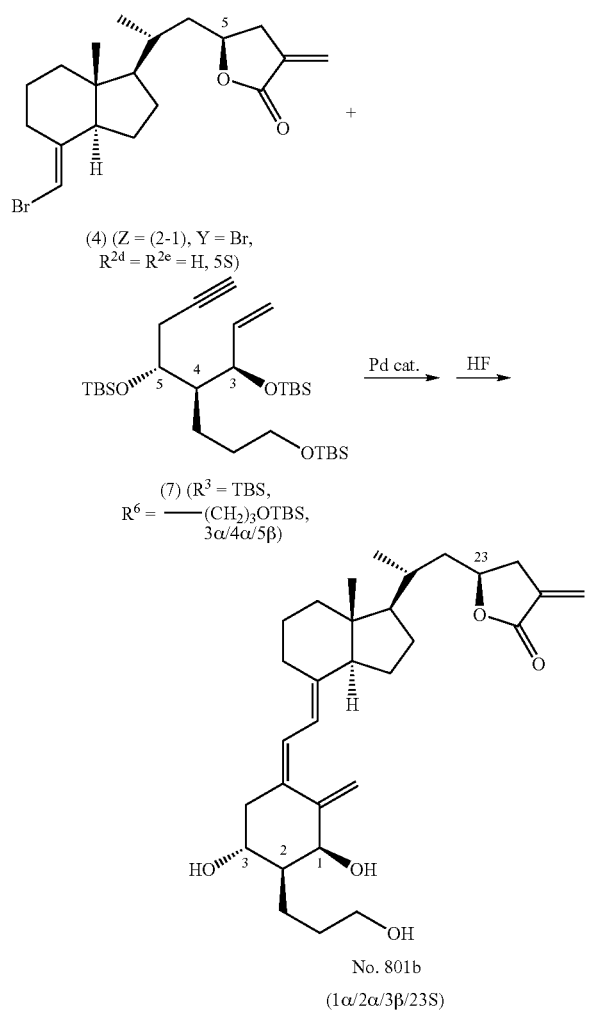

Using 12 mg (33 µmol) of Compound (4) (Z=(2-1), Y=Br, $R^{2d}=R^{2e}$=H, 5S) obtained by a method known in the literature (for example, the specification of International Publication WO 95/33716) and 27 mg (49 µmol) of Compound (7) ($R^3$=TBS, $R^6$=—(CH$_2$)$_3$OTBS, 3α/4α/5β), a reaction similar to Example 14(2-a) was carried out to obtain 7.0 mg of Compound No. 801b. Yield: 45%.

$^1$H-NMR (CDCl$_3$) δ: 0.55 (s, 3 H), 1.03 (d, J=6.3 Hz, 3 H), 1.22-1.73 (m, 19 H), 1.88-2.04 (m, 3 H), 2.25 (dd, J=13.0, 8.8 Hz, 1 H), 2.54 (dddd, J=16.8, 6.3, 3.1, 3.1 Hz, 1 H), 2.66 (dd, J=13.0, 4.4 Hz, 1 H), 2.83 (m, 1H), 3.05 (dddd, J=16.8, 7.4, 2.3, 2.3 Hz, 1 H), 3.70 (t, J=5.0 Hz, 2 H), 3.89 (ddd, J=8.3, 8.3, 4.3 Hz, 1 H), 4.38 (d, J=2.4 Hz, 1 H), 4.59 (ddt, J=6.4, 6.3, 5.0 Hz, 1 H), 4.99 (d, J=2.0 Hz, 1 H), 5.28 (m, 1 H), 5.62 (dd, J=3.1, 2.3 Hz, 1 H), 5.99 (d, J=11.4 Hz, 1 H), 6.22 (dd, J=3.1, 2.3 Hz, 1 H), 6.40 (d, J=11.4 Hz, 1 H).

LRMS m/z 484 (M$^+$), 466, 448, 438, 389, 338, 309, 253

HRMS calcd for C$_{30}$H$_{44}$O$_5$ 484.3189, found 484.3176

Example 25

Synthesis of 2α-(3-hydroxypropyl)-20(R)-(tetrahydro-3-methylene-2-furanone-4(R)-methyl-5(R)-yl) methyl-9,10-secopregna-5(Z),7(E),10(19)-triene-1α, 3β-diol (Compound No. 802a)

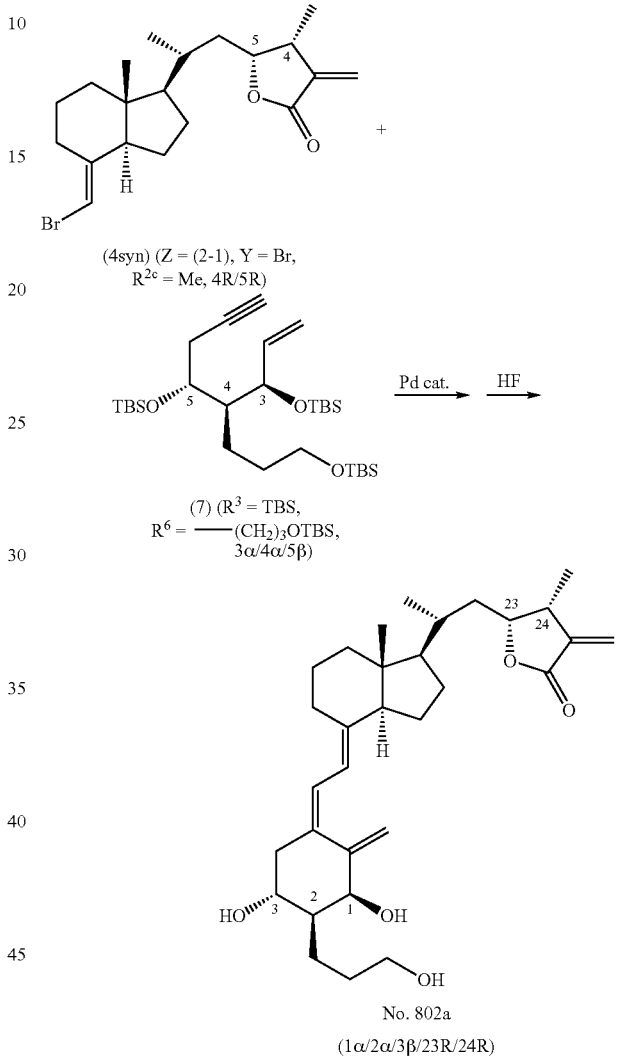

Using 19 mg (44 µmol) of Compound (4syn) (Z=(2-1), Y=Br, $R^{2c}$=Me, 4R/5R) obtained in Example 11 (1) and 41 mg (76 µmol) of Compound (7) ($R^3$=TBS, $R^6$=—(CH$_2$)$_3$OTBS, 3α/4α/5β), a reaction similar to Example 14(2-a) was carried out to obtain 16.6 mg of Compound No. 802a. Yield: 66%.

$^1$H-NMR (CDCl$_3$) δ: 0.55 (s, 3 H), 1.00 (d, J=6.6 Hz, 3 H), 1.09 (m, 1 H), 1.13 (d, J=7.1 Hz, 3 H), 1.20-1.85 (m, 16 H), 1.90-2.10 (m, 3 H), 2.24 (dd, J=13.3, 8.8 Hz, 1 H), 2.35 (br s, 2H), 2.65 (dd, J=13.3, 4.2 Hz, 1 H), 2.82 (m, 1 H), 3.16 (m, 1 H), 3.60-3.75 (m, 2 H), 2.89 (ddd, J=8.8, 8.3, 4.2 Hz, 1 H), 4.37 (d, J=2.7 Hz, 1 H), 4.68 (ddd, J=11.7, 7.6, 1.8 Hz, 1 H), 4.98 (d, J=1.9 Hz, 1 H), 5.27 (d, J=1.5 Hz, 1 H), 5.53 (d, J=2.6 Hz, 1 H), 5.99 (d, J=11.2 Hz, 1 H), 6.21 (d, J=2.6 Hz, 1 H), 6.38 (d, J=11.2 Hz, 1 H).

LRMS m/z 498 (M$^+$), 480, 462

HRMS calcd for C$_{31}$H$_{46}$O$_5$ 498.3345, found 498.3337

Example 26

Synthesis of 2α-(3-hydroxypropyl)-20(R)-(tetrahydro-3-methylene-2-furanone-4(S)-methyl-5(S)-yl)methyl-9,10-secopregna-5(Z),7(E),10(19)-triene-1α,3β-diol (Compound No. 802b)

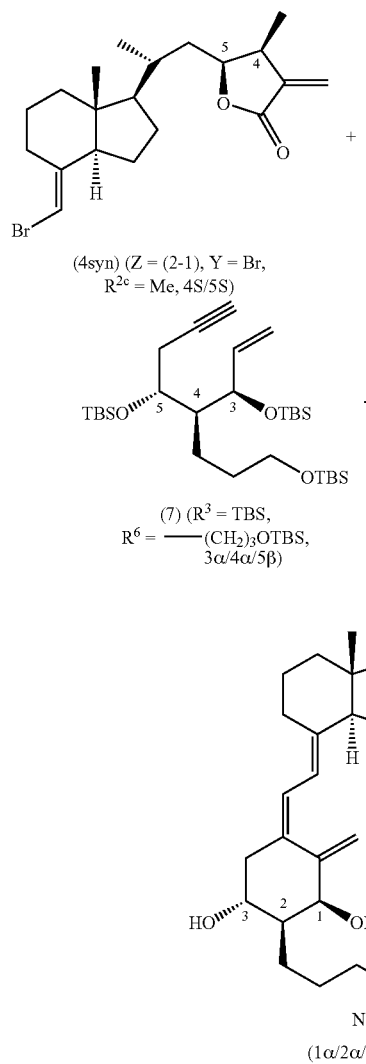

No. 802b
(1α/2α/3β/23S/24S)

Example 27

Synthesis of 2α-(3-hydroxypropyl)-20(R)-(tetrahydro-3-methylene-2-furanone-4(R)-methyl-5(S)-yl)methyl-9,10-secopregna-5(Z),7(E),10(19)-triene-1α,3β-diol (Compound No. 802c)

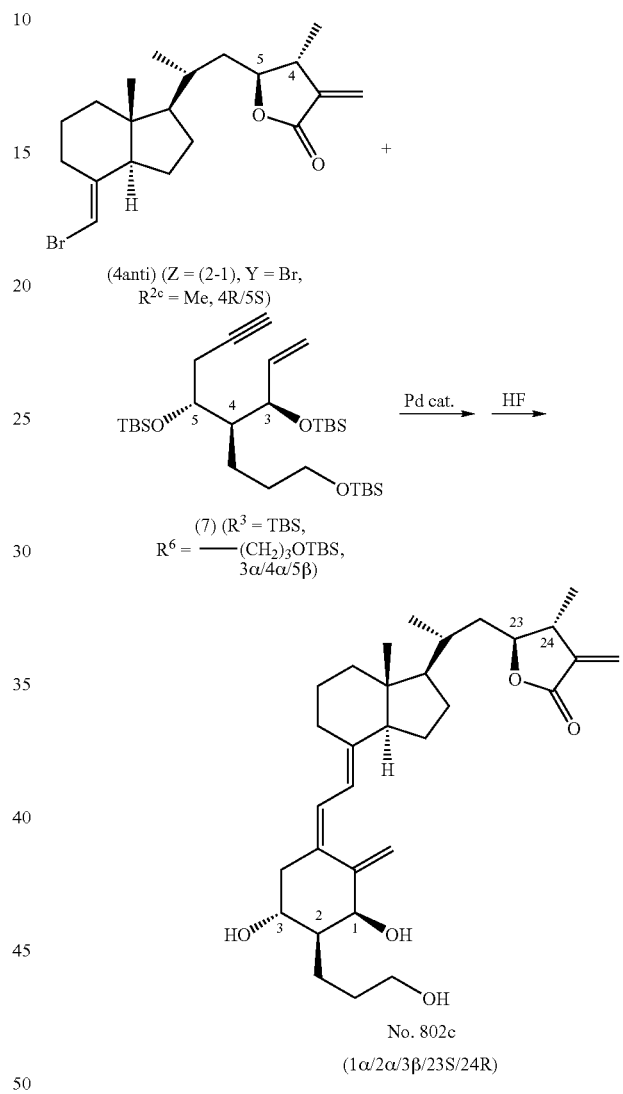

No. 802c
(1α/2α/3β/23S/24R)

Using 18 mg (46 μmol) of Compound (4syn) (Z=(2-1), Y=Br, $R^{2c}$=Me, 4S/5S) obtained in Example 11(1) and 38 mg (70 μmol) of Compound (7) ($R^3$=TBS, $R^6$=—$(CH_2)_3$OTBS, 3α/4α/5β), a reaction similar to Example 14(2-a) was carried out to obtain 14.1 mg of Compound No. 802b. Yield: 61%.

$^1$H-NMR (CDCl$_3$) δ: 0.54 (s, 3 H), 1.04 (d, J=6.4 Hz, 3 H), 1.13 (d, J=7.1 Hz, 3 H), 1.20-2.20 (m, 22 H), 2.24 (dd, J=13.1, 8.9 Hz, 1 H), 2.65 (dd, J=13.1, 2.9 Hz, 1 H), 2.82 (m, 1 H), 3.10 (m, 1 H), 3.60-3.75 (m, 2 H), 3.88 (m, 1 H), 4.37 (br d, J=2.4 Hz, 1 H), 4.58 (m, 1H), 4.98 (s, 1 H), 5.26 (s, 1 H), 5.53 (d, J=1.8 Hz, 1 H), 5.99 (d, J=11.2 Hz, 1 H), 6.18 (d, J=1.8 Hz, 1 H), 6.38 (d, J=11.2 Hz, 1 H).

LRMS m/z 498 (M$^+$), 480, 462, 452

HRMS calcd for C$_{31}$H$_{46}$O$_5$ 498.3345, found 498.3350

Using 21 mg (56 μmol) of Compound (4anti) (Z=(2-1), Y=Br, $R^{2c}$=Me, 4R/5S) obtained in Example 12(4) and 45 mg (83 μmol) of Compound (7) ($R^3$=TBS, $R^6$=—$(CH_2)_3$OTBS, 3α/4α/5β), a reaction similar to Example 14(2-a) was carried out to obtain 15.1 mg of Compound No. 802c. Yield: 54%.

$^1$H-NMR (CDCl$_3$) δ: 0.55 (s, 3 H), 1.05 (d, J=5.9 Hz, 3 H), 1.24 (d, J=6.8 Hz, 3 H), 1.20-1.75 (m, 15 H), 1.85-2.05 (m, 5 H), 2.24 (dd, J=13.3, 8.9 Hz, 1 H), 2.31 (br s, 2 H), 2.58-2.70 (m, 2 H), 2.82 (m, 1 H), 3.60-3.75 (m, 2 H), 3.87 (m, 1 H), 4.07 (dt, J=5.9, 6.4 Hz, 1 H), 4.36 (br d, J=2.7 Hz, 1 H), 4.98 (d, J=1.7 Hz, 1 H), 5.26 (d, J=1.7 Hz, 1 H), 5.52 (d, J=2.8 Hz, 1 H), 5.99 (d, J=11.5 Hz, 1 H), 6.21 (d, J=2.8 Hz, 1 H), 6.38 (d, J=11.5 Hz, 1H).

LRMS m/z 498 (M$^+$), 480, 462

HRMS calcd for C$_{31}$H$_{46}$O$_5$ 498.3345, found 498.3344

Example 28

Synthesis of 2α-(3-hydroxypropyl)-20(R)-(tetrahydro-3-methylene-2-furanone-4(S)-methyl-5(R)-yl)methyl-9,10-secopregna-5(Z),7(E),10(19)-triene-1α,3β-diol (Compound No. 802d)

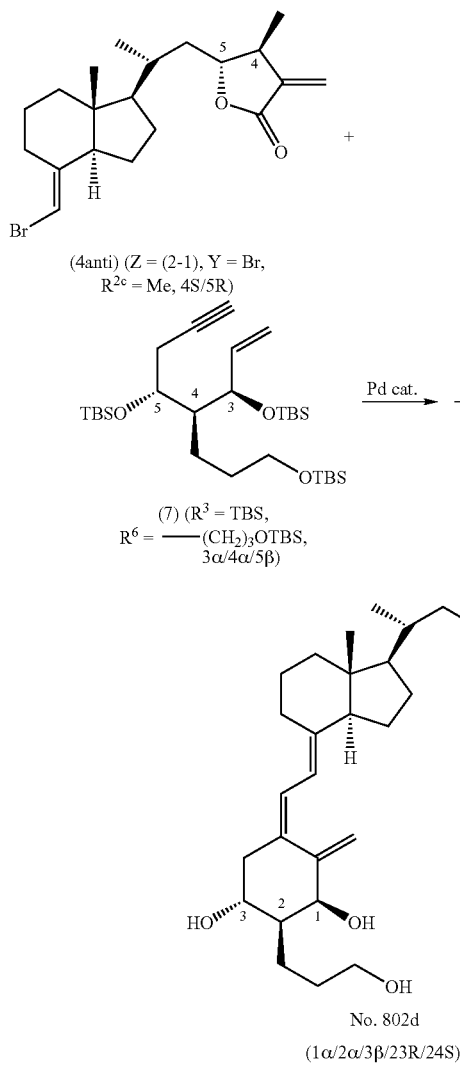

Example 29

Synthesis of 2α-(3-hydroxypropyl)-20(R)-(tetrahydro-3-methylene-2-furanone-4(R)-ethyl-5(R)-yl)methyl-9,10-secopregna-5(Z),7(E),10(19)-triene-1α,3β-diol (Compound No. 803a)

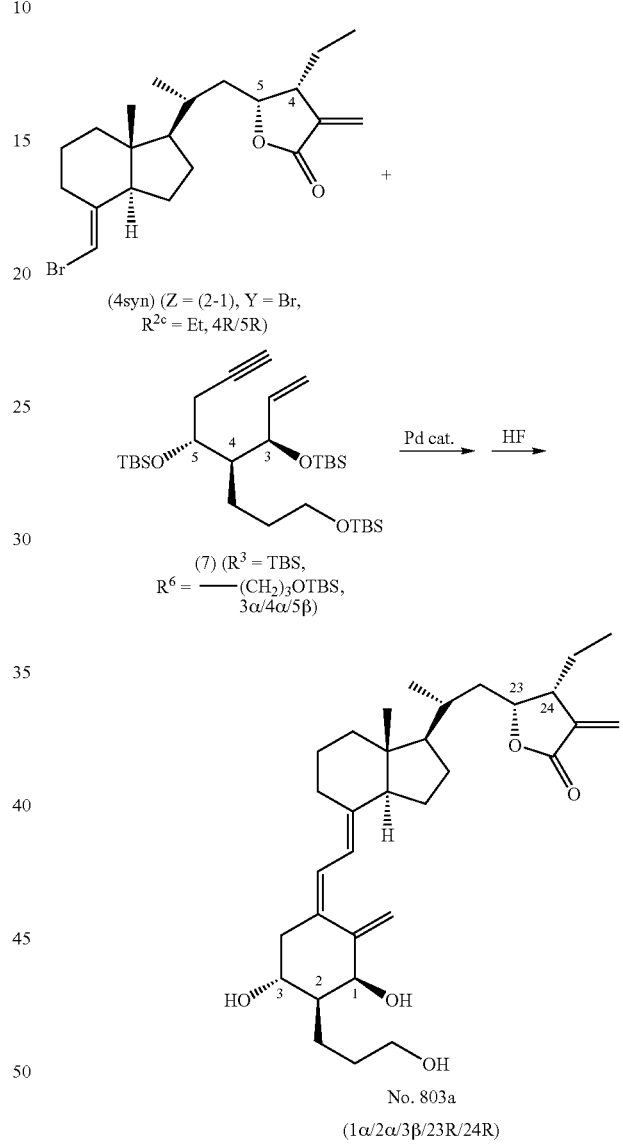

Using 10 mg (26 μmol) of Compound (4anti) (Z=(2-1), Y=Br, $R^{2c}$=Me, 4S/5R) obtained in Example 13(5) and 21 mg (39 μmol) of Compound (7) ($R^3$=TBS, $R^6$=—$(CH_2)_3OTBS$, 3α/4α/5β), a reaction similar to Example 14(2-a) was carried out to obtain 2.3 mg of Compound No. 802d. Yield: 26%.

[1] H-NMR (10% $CD_3OD$ in $CDCl_3$) δ: 0.47 (s, 3 H), 0.93 (d, J=6.4 Hz, 3 H), 1.15 (d, J=6.8 Hz, 3 H), 1.12-1.80 (m, 20 H), 1.85-2.00 (m, 2 H), 2.15 (dd, J=13.2, 9.3 Hz, 1 H), 2.50-2.60 (m, 2 H), 2.75 (m, 1 H), 3.50-3.60 (m, 2 H), 3.73 (ddd, J=8.4, 8.4, 4.2 Hz, 1 H), 4.02 (m, 1H), 4.22 (d, J=2.4 Hz, 1 H), 4.88 (d, J=2.0 Hz, 1 H), 5.17 (d, J=2.0 Hz, 1 H), 5.48 (d, J=2.9 Hz, 1 H), 5.95 (d, J=11.2 Hz, 1 H), 6.13 (d, J=2.9 Hz, 1 H), 6.29 (d, J=11.2 Hz, 1 H).

LRMS m/z 498 ($M^+$), 481, 480, 462, 391

HRMS calcd for $C_{31}H_{46}O_5$ 498.3346 found 498.3346

Using 10 mg (25 μmol) of Compound (4syn) (Z=(2-1), Y=Br, $R^{2c}$=Et, 4R/5R) obtained in Example 14(1) and 21 mg (38 μmol) of Compound (7) ($R^3$=TBS, $R^6$=—$(CH_2)_3OTBS$, 3α/4α/5β), a reaction similar to Example 14(2-a) was carried out to obtain 7 mg of Compound No. 803a. Yield: 54%.

[1] H-NMR ($CDCl_3$) δ: 0.55 (s, 3 H), 0.98 (t, J=7.3 Hz, 3 H), 1.00 (d, J=6.3 Hz, 3 H), 1.12 (ddd, J=14.2, 10.5, 2.0 Hz, 1 H), 1.22-1.89 (m, 21 H), 1.97 (dd, J=12.5, 7.4 Hz, 1 H), 2.02 (br d, J=12.4 Hz, 1 H), 2.25 (dd, J=13.4, 8.8 Hz, 1 H), 2.66 (dd, J=13.4, 4.4 Hz, 1 H), 2.83 (m, 1 H), 2.88 (m, 1 H), 3.69 (m, 2 H), 3.90 (ddd, J=8.4, 8.4, 4.4 Hz, 1 H), 4.38 (d, J=3.3 Hz, 1 H), 4.66 (ddd, J=11.7, 4.0, 1.8 Hz, 1 H), 4.98 (d, J=1.6 Hz, 1 H), 5.27 (d, J=1.6 Hz, 1 H), 5.52 (d, J=2.2 Hz, 1 H), 5.99 (d, J=11.9 Hz, 1 H), 6.21 (d, J=12.4 Hz, 1 H), 6.38 (d, J=11.9 Hz, 1 H).

LRMS m/z 512 (M+) 494, 476, 417, 309, 211, 133
HRMS calcd for $C_{32}H_{48}O_5$ 512.3502, found 512.3522

Example 30

Synthesis of 2α-(3-hydroxypropyl)-20(R)-(tetrahydro-3-methylene-2-furanone-4(S)-ethyl-5(S)-yl)methyl-9,10-secopregna-5(Z),7(E),10(19)-triene-1α,3β-diol (Compound No. 803b)

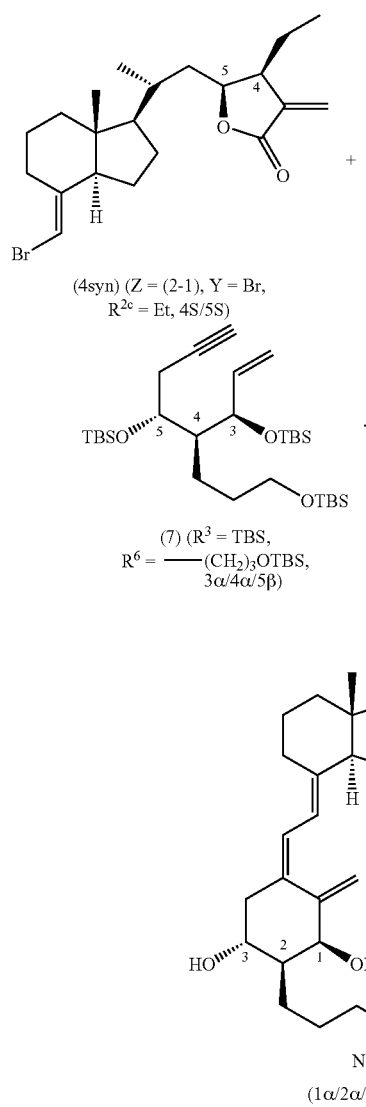

Using 21 mg (53 μmol) of Compound (4syn) (Z=(2-1), Y=Br, $R^{2c}$=Et, 4S/5S) obtained in Example 14(1) and 43 mg (80 μmol) of Compound (7) ($R^3$=TBS, $R^6$=—$(CH_2)_3$OTBS, 3α/4α/5β), a reaction similar to Example 14(2-a) was carried out to obtain 17 mg of Compound No. 803b. Yield: 62%.

$^1$H-NMR (CDCl₃) δ: 0.55 (s, 3 H), 0.95 (t, J=7.3 Hz, 3 H), 1.04 (d, J=6.3 Hz, 3 H), 1.25-2.04 (m, 22 H), 2.22-2.27 (m, 3 H), 2.65 (dd, J=13.4, 4.3 Hz, 1 H), 2.77-2.84 (m, 2 H), 3.68 (m, 2 H), 3.88 (ddd, J=8.0, 8.0, 4.2 Hz, 1 H), 4.37 (d, J=2.2 Hz, 1 H), 4.57 (dt, J=8.2, 5.7 Hz, 1 H), 4.98 (d, J=1.4 Hz, 1 H), 5.26 (d, J=1.4 Hz, 1 H), 5.51 (d, J=1.6 Hz, 1 H), 6.00 (d, J=11.1 Hz, 1 H), 6.20 (d, J=1.6 Hz. 1 H), 6.39 (d, J=11.1 Hz, 1 H).

LRMS m/z 512 (M+) 494, 476, 417, 309, 211, 133
HRMS calcd for $C_{32}H_{48}O_5$ 512.3502, found 512.3506

Example 31

Synthesis of 2α-(3-hydroxypropyl)-20(R)-(tetrahydro-3-methylene-2-furanone-4(R)-ethyl-5(S)-yl)methyl-9,10-secopregna-5(Z),7(E),10(19)-triene-1α,3β-diol (Compound No. 803c)

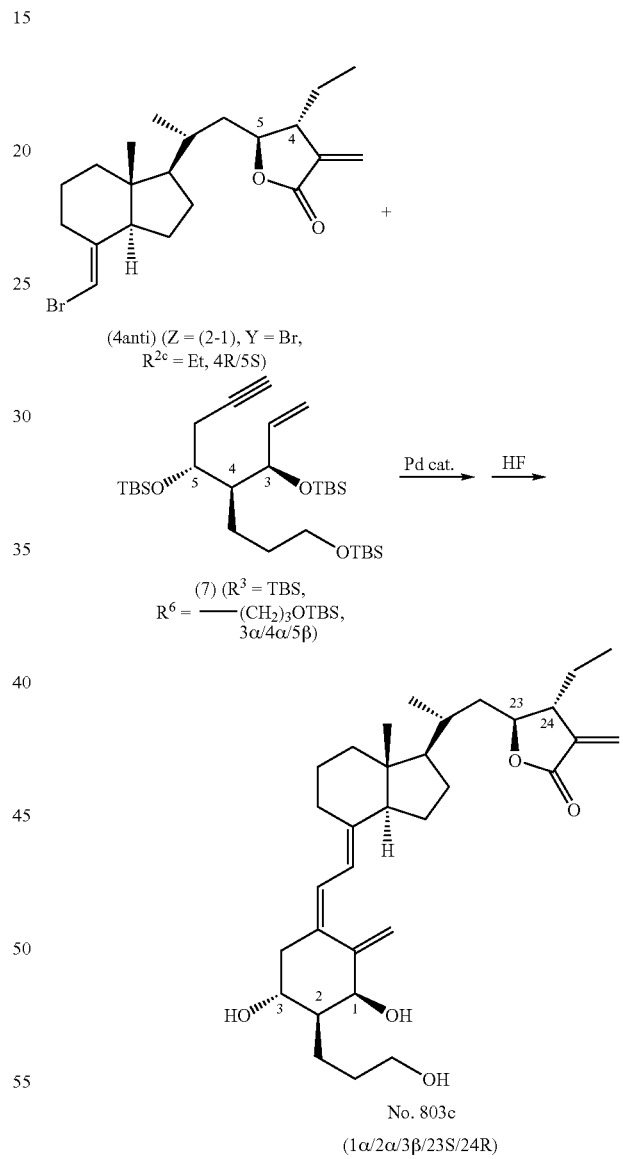

Using 21 mg (53 μmol) of Compound (4anti) (Z=(2-1), Y=Br, $R^{2c}$=Et, 4R/5S) obtained in Example 15(5) and 43 mg (80 μmol) of Compound (7) ($R^3$=TBS, $R^6$=—$(CH_2)_3$OTBS, 3α/4α/5β), a reaction similar to Example 14(2-a) was carried out to obtain 17 mg of Compound No. 803c. Yield: 62%.

$^1$H-NMR (CDCl₃) δ: 0.54 (s, 3 H), 0.97 (t, J=7.3 Hz, 3 H), 1.05 (d, J=5.9 Hz, 3 H), 1.17-1.76 (m, 21 H), 1.85-2.27 (m, 7 H), 3.64-3.71 (m, 2 H), 3.88 (ddd, J=8.3, 8.3, 4.4 Hz, 1H), 4.26 (m, 1 H), 4.37 (d, J=2.9 Hz, 1 H), 4.98 (d, J=1.7 Hz, 1 H), 5.26 (d, J=1.7 Hz, 1 H), 5.58 (d, J=2.4 Hz, 1 H), 5.97 (d, J=11.2 Hz, 1 H), 6.27 (d, J=2.4 Hz, 1 H), 6.38 (d, J=11.2 Hz. 1 H).

LRMS m/z 512 (M+) 494, 476, 417, 309, 211, 133
HRMS calcd for $C_{32}H_{48}O_5$ 512.3502, found 512.3501

Example 32

Synthesis of 2α-(3-hydroxypropyl)-20(R)-(tetrahydro-3-methylene-2-furanone-4(S)-ethyl-5(R)-yl) methyl-9,10-secopregna-5(Z),7(E),10(19)-triene-1α, 3β-diol (Compound No. 803d)

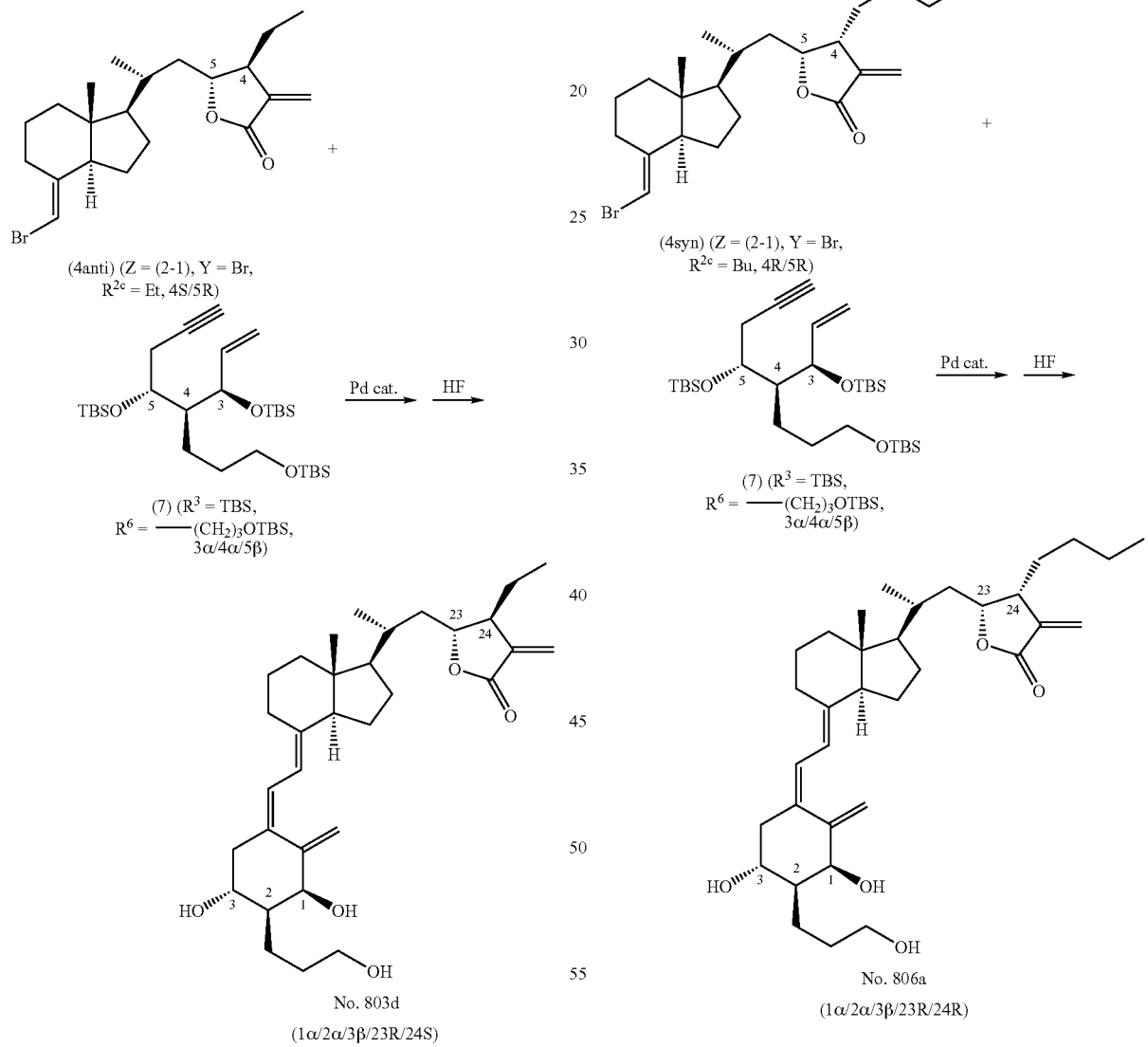

(m, 2 H), 3.88 (ddd, J=8.0, 8.0, 4.5 Hz, 1 H), 4.28 (br dd, J=10.5, 3.8 Hz, 1 H), 4.36 (J=2.2 Hz, 1 H), 4.97 (s, 1 H), 5.26 (s, 1 H), 5.57 (d, J=2.3 Hz, 1 H), 5.99 (d, J=11.4 Hz, 1 H), 6.26 (d, J=2.3 Hz, 1 H), 6.34 (d, J=11.4 Hz, 1 H).

HRMS calcd for $C_{32}H_{48}O_5$ 512.3502, found 512.3506

Example 33

Synthesis of 2α-(3-hydroxypropyl)-20(R)-(tetrahydro-3-methylene-2-furanone-4(R)-butyl-5(R)-yl) methyl-9,10-secopregna-5(Z),7(E),10(19)-triene-1α, 3β-diol (Compound No. 806a)

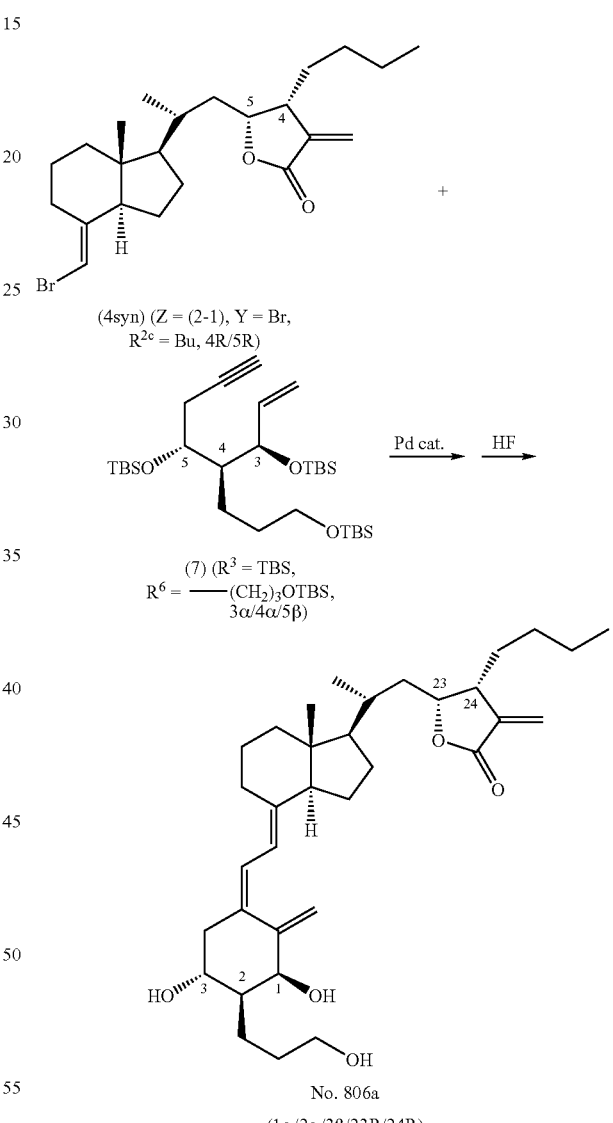

Using 29 mg (73 μmol) of Compound (4anti) (Z=(2-1), Y=Br, $R^{2c}$=Et, 4S/5R) obtained in Example 16(5) and 60 mg (110 μmol) of Compound (7) ($R^3$=TBS, $R^6$=—(CH$_2$)$_3$OTBS, 3α/4α/5β), a reaction similar to Example 14(2-a) was carried out to obtain 20 mg of Compound No. 803d. Yield: 53%.

$^1$H-NMR (CDCl$_3$) δ: 0.55 (s, 3 H), 0.97 (t, J=7.4 Hz, 3 H), 1.02 (d, J=6.6 Hz, 3 H), 1.22-2.03 (m, 22 H), 2.21-2.51 (m, 4 H), 2.65 (dd, J=13.5, 4.3 Hz, 1 H), 2.82 (m, 1 H), 3.64-3.72

Using 60 mg (142 μmol) of Compound (4syn) (Z=(2-1), Y=Br, $R^{2c}$=Bu, 4R/5R) obtained in Example 17(1) and 115 mg (213 μmol) of Compound (7) ($R^3$=TBS, $R^6$=—(CH$_2$)$_3$OTBS, 3α/4α/5β), a reaction similar to Example 14(2-a) was carried out to obtain 40 mg of Compound No. 806a. Yield: 52%.

$^1$H-NMR (CDCl$_3$) δ: 0.55 (s, 3 H), 0.93 (t, J=7.0 Hz, 3 H), 1.00 (d, J=6.6 Hz, 3 H), 1.11 (ddd, J=14.0, 10.7, 1.6 Hz, 1 H), 1.20-2.05 (m, 24 H), 2.11 (br s, 1 H), 2.24 (dd, J=13.3, 8.7 Hz, 1 H), 2.49 (br s, 2 H), 2.65 (dd, J=13.3, 4.2 Hz, 1 H), 2.83 (m, 1 H), 2.96 (m, 1 H), 3.63-3.73 (m, 2 H), 3.89 (m, 1 H), 4.37 (br d, J=1.9 Hz, 1 H), 4.65 (ddd, J=11.5, 7.1, 1.5 Hz, 1 H), 4.97 (d, J=2.0 Hz, 1 H), 5.27 (d, J=1.5 Hz, 1 H), 5.51 (d, J=2.3 Hz, 1 H), 6.00 (d, J=11.1 Hz, 1 H), 6.20 (d, J=2.3 Hz, 1 H), 6.37 (d, J=11.1 Hz, 1 H).

LRMS m/z 540 (M$^+$), 522, 504

HRMS calcd for $C_{34}H_{52}O_5$ 540.3815, found 540.3818

Example 34

Synthesis of 2α-(3-hydroxypropyl)-20(R)-(tetrahydro-3-methylene-2-furanone-4(S)-butyl-5(S)-yl)methyl-9,10-secopregna-5(Z),7(E),10(19)-triene-1α,3β-diol (Compound No. 806b)

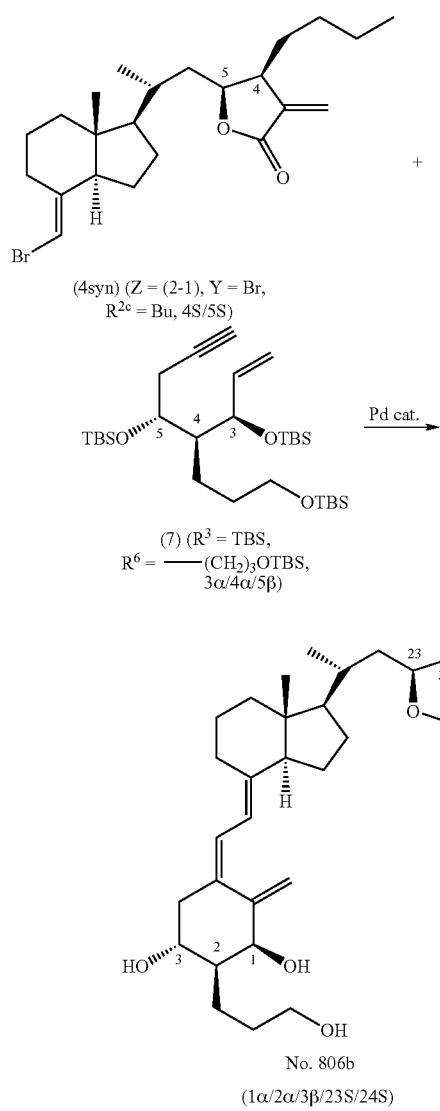

Using 42 mg (95 μmol) of Compound (4syn) (Z=(2-1), Y=Br, R$^{2c}$=Bu, 4S/5S) obtained as in Example 17(1) and 80 mg (148 μmol) of Compound (7) (R$^3$=TBS, R$^6$=—(CH$_2$)$_3$OTBS, 3α/4α/5β), a reaction similar to Example 14(2-a) was carried out to obtain 27 mg of Compound No. 806b. Yield: 52%.

$^1$H-NMR (CDCl$_3$) δ: 0.55 (s, 3 H), 0.92 (t, J=7.1 Hz, 3 H), 1.05 (d, J=6.6 Hz, 3 H), 1.15-1.80 (m, 21 H), 1.83-2.08 (m, 5 H), 2.25 (dd, J=13.3, 8.8 Hz, 1 H), 2.48 (br s, 2 H), 2.65 (dd, J=13.3, 4.2 Hz, 1 H), 2.83 (m, 1 H), 2.89 (m, 1 H), 3.63-3.75 (m, 2 H), 3.88 (ddd, J=8.1, 8.1, 4.3 Hz, 1 H), 4.37 (br d, J=2.7 Hz, 1 H), 4.57 (ddd, J=8.3, 6.0, 5.2 Hz, 1 H), 4.98 (d, J=2.0 Hz, 1 H), 5.27 (d, J=1.5 Hz, 1 H), 5.50 (d, J=1.8 Hz, 1 H), 6.00 (d, J=11.2 Hz, 1H), 6.19 (d, J=1.8 Hz, 1 H), 6.39 (d, J=11.2 Hz, 1 H).

LRMS m/z 540 (M$^+$), 522, 504

HRMS calcd for $C_{34}H_{52}O_5$ 540.3815, found 540.3812

Example 35

Synthesis of 2α-(3-hydroxypropyl)-20(R)-(tetrahydro-3-methylene-2-furanone-4(R)-butyl-5(S)-yl)methyl-9,10-secopregna-5(Z),7(E),10(19)-triene-1α,3β-diol (Compound No. 806c)

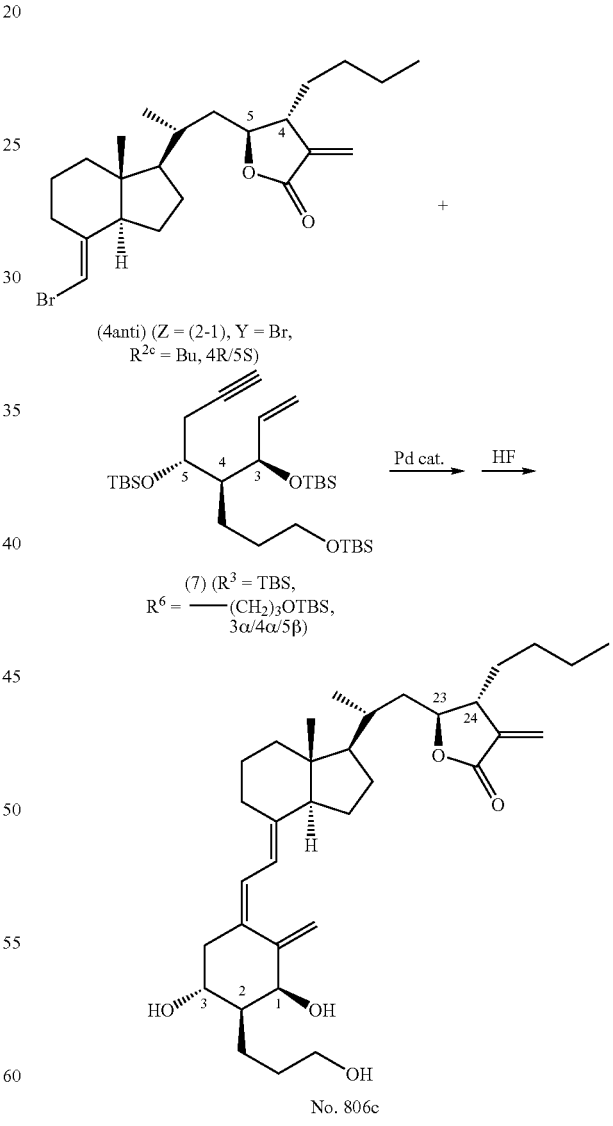

Using 40 mg (95 μmol) of Compound (4anti) (Z=(2-1), Y=Br, R$^{2c}$=Bu, 4R/5S) obtained in Example 18(5) and 77 mg (142 μmol) of Compound (7) (R$^3$=TBS, R$^6$=—(CH$_2$)$_3$OTBS, 3α/4α/5β), a reaction similar to Example 14(2-a) was carried out to obtain 28 mg of Compound No. 806c. Yield: 54%.

$^1$H-NMR (CDCl$_3$) δ: 0.55 (s, 3 H), 0.92 (t, J=7.0 Hz, 3 H), 1.06 (d, J=6.0 Hz, 3 H), 1.13-1.80 (m, 22 H), 1.83-2.08 (m, 4 H), 2.25 (dd, J=13.4, 8.4 Hz, 1 H), 2.43 (br s, 2 H), 2.60 (m, 1 H), 2.65 (dd, J=13.4, 4.3 Hz, 1 H), 2.83 (m, 1 H), 3.63-3.75 (m, 2 H), 3.99 (ddd, J=8.4, 8.4, 4.3 Hz, 1 H), 4.25 (ddd, J=6.2, 6.2, 4.4 Hz, 1 H), 4.37 (br d, J=2.9 Hz, 1 H), 4.98 (d, J=2.0 Hz, 1 H), 5.27 (d, J=1.7 Hz, 1 H), 5.59 (d, J=2.2 Hz, 1 H), 6.00 (d, J=11.2 Hz, 1H), 6.26 (d, J=2.2 Hz, 1 H), 6.39 (d, J=11.2 Hz, 1 H).

LRMS m/z 540 (M$^+$), 522, 504

HRMS calcd for C$_{34}$H$_{52}$O$_5$ 540.3815, found 540.3815

Example 36

Synthesis of 2α-(3-hydroxypropyl)-20(R)-(tetrahydro-3-methylene-2-furanone-4(S)-butyl-5(R)-yl) methyl-9,10-secopregna-5(Z),7(E),10(19)-triene-1α,3β-diol (Compound No. 806d)

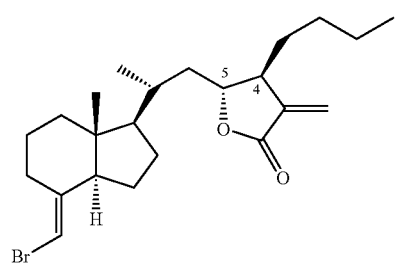

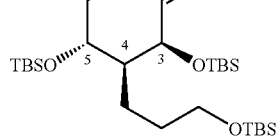

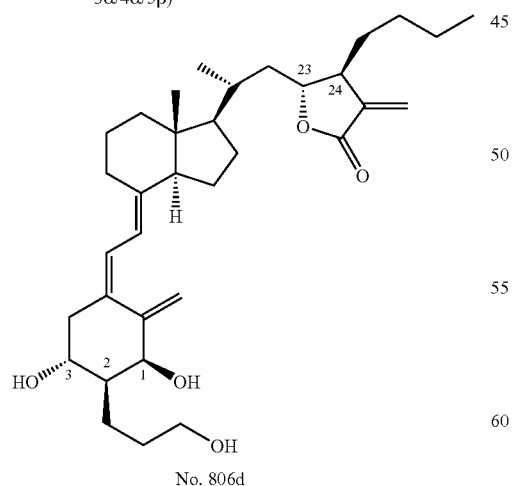

No. 806d
(1α/2α/3β/23R/24S)

Using 30 mg (105 μmol) of Compound (4anti) (Z=(2-1), Y=Br, R$^{2c}$=Bu, 4S/5R) obtained in Example 19(5) and 57 mg (105 μmol) of Compound (7) (R$^3$=TBS, R$^6$=—(CH$_2$)$_3$OTBS, 3α/4α/5β), a reaction similar to Example 14(2-a) was carried out to obtain 16 mg of Compound No. 806d. Yield: 40%.

$^1$H-NMR (CDCl$_3$) δ: 0.54 (s, 3 H), 0.92 (t, J=6.8 Hz, 3 H), 1.01 (d, J=6.3 Hz, 3 H), 1.20-1.85 (m, 23 H), 1.90-2.50 (m, 5 H), 2.24 (dd, J=13.2, 8.4 Hz, 1 H), 2.54 (m, 1 H), 2.65 (dd, J=13.2, 4.2 Hz, 1 H), 2.82 (m, 1 H), 3.63-3.73 (m, 2 H), 3.88 (ddd, J=8.4, 8.4, 4.2 Hz, 1 H), 4.26 (ddd, J=10.8, 4.8, 1.8 Hz, 1 H), 4.36 (br d, J=2.7 Hz, 1 H), 4.97 (d, J=1.7 Hz, 1H), 5.26 (d, J=1.5 Hz, 1 H), 5.57 (d, J=2.4 Hz, 1 H), 5.99 (d, J=11.2 Hz, 1 H), 6.24 (d, J=2.4 Hz, 1 H), 6.37 (d, J=11.2 Hz, 1 H).

LRMS m/z 540 (M$^+$), 522, 504

HRMS calcd for C$_{34}$H$_{52}$O$_5$ 540.38515, found 540.3815

Example 37

Synthesis of 2α-(3-hydroxypropyl)-20(R)-(tetrahydro-3-methylene-2-furanone-4(R)-isobutyl-5(R)-yl) methyl-9,10-secopregna-5(Z),7(E),10(19)-triene-1α,3β-diol (Compound No. 807a)

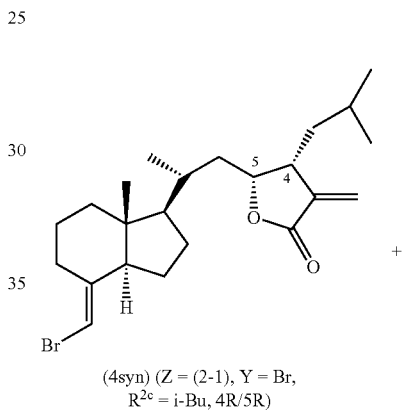

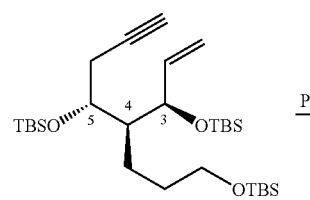

No. 807a (1α/2α/3β/23R/24R)

Using 19 mg (45 µmol) of Compound (4syn) (Z=(2-1), Y=Br, $R^{2c}$=i-Bu, 4R/5R) obtained in Example 20(1) and 37 mg (68 µmol) of Compound (7) ($R^3$=TBS, $R^6$=—$(CH_2)_3$OTBS, 3α/4α/5β), a reaction similar to Example 14(2-a) was carried out to obtain 12 mg of Compound No. 807a. Yield: 49%.

$^1$H-NMR (CDCl$_3$) δ: 0.55 (s, 3 H), 0.95 (d, J=6.4 Hz, 3 H), 0.96 (d, J=6.3 Hz, 3 H), 0.99 (d, J=6.6 Hz, 3 H), 1.68 (ddd, J=13.9, 10.9, 1.6 Hz, 1 H), 1.20-2.10 (m, 24 H), 2.25 (dd, J=13.3, 8.8 Hz, 1 H), 2.66 (dd, J=13.3, 4.2 Hz, 1 H), 2.83 (m, 1 H), 3.09 (m, 1 H), 3.65-3.75 (m, 2 H), 3.90 (ddd, J=8.1, 8.1, 4.2 Hz, 1 H), 4.38 (br d, J=2.7 Hz, 1 H), 4.66 (ddd, J=11.5, 7.0, 1.4 Hz, 1 H), 4.98 (d, J=2.0 Hz, 1 H), 5.27 (d, J=1.5 Hz, 1 H), 5.48 (d, J=2.6 Hz, 1 H), 5.99 (d, J=11.2 Hz, 1 H), 6.20 (d, J=2.6 Hz, 1 H), 6.38 (d, J=11.2 Hz, 1 H).

LRMS m/z 540 (M$^+$), 522, 504

HRMS calcd for $C_{34}H_{52}O_5$ 540.3815, found 540.3818

Example 38

Synthesis of 2α-(3-hydroxypropyl)-20(R)-(tetrahydro-3-methylene-2-furanone-4(S)-isobutyl-5(S)-yl)methyl-9,10-secopregna-5(Z),7(E),10(19)-triene-1α,3β-diol (Compound No. 807b)

(4syn) (Z = (2-1), Y = Br, $R^{2c}$ = i-Bu, 4S/5S)

+

(7) ($R^3$ = TBS, $R^6$ = —$(CH_2)_3$OTBS, 3α/4α/5β)

Pd cat. → HF →

No. 807b (1α/2α/3β/23S/24S)

Using 20 mg (47 µmol) of Compound (4syn) (Z=(2-1), Y=Br, $R^{2c}$=i-Bu, 4S/5S) obtained in Example 20(1) and 38 mg (70 µmol) of Compound (7) ($R^3$=TBS, $R^6$=—$(CH_2)_3$OTBS, 3α/4α/5β), a reaction similar to Example 14(2-a) was carried out to obtain 15 mg of Compound No. 807b. Yield: 59%.

$^1$H-NMR (CDCl$_3$) δ: 0.55 (s, 3 H), 0.94 (d, J=6.6 Hz, 3 H), 0.95 (d, J=6.2 Hz, 3 H), 1.05 (d, J=6.4 Hz, 3 H), 1.20-2.08 (m, 23 H), 2.10-2.40 (m, 2 H), 2.25 (dd, J=13.1, 8.2 Hz, 1 H), 2.65 (dd, J=13.1, 4.4 Hz, 1 H), 2.82 (m, 1 H), 3.02 (m, 1 H), 3.62-3.75 (m, 2 H), 3.88 (ddd, J=8.1, 8.1, 4.3 Hz, 1 H), 4.37 (br d, J=2.9 Hz, 1 H), 4.58 (ddd, J=8.1, 6.3, 4.5 Hz, 1 H), 4.99 (d, J=1.7 Hz, 1 H), 5.27 (d, J=1.7 Hz, 1 H), 5.48 (d, J=2.1 Hz, 1 H), 6.00 (d, J=11.2 Hz, 1H), 6.19 (d, J=2.1 Hz, 1 H), 6.39 (d, J=11.2 Hz, 1 H).

LRMS m/z 540 (M$^+$), 522, 504

HRMS calcd for $C_{34}H_{52}O_5$ 540.3814, found 540.3813

Example 39

Synthesis of 2α-(3-hydroxypropyl)-20(R)-(tetrahydro-3-methylene-2-furanone-4(R)-isobutyl-5(S)-yl)methyl-9,10-secoprejna-5(Z),7(E),10(19)-triene-1α,3β-diol (Compound No. 807c)

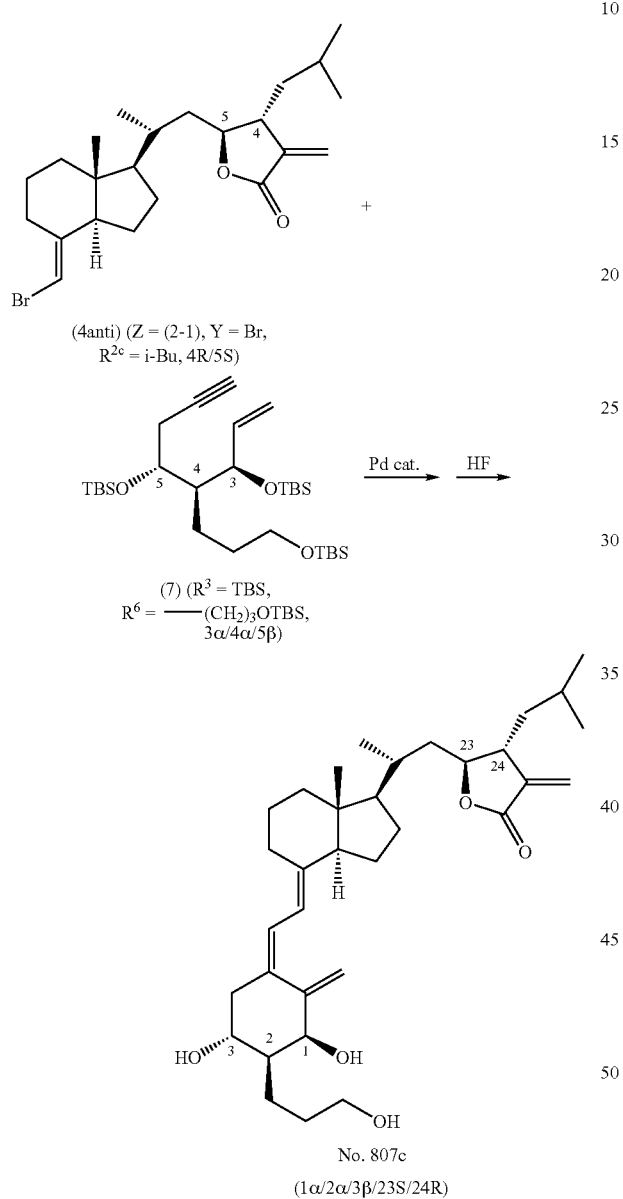

Using 21 mg (50 μmol) of Compound (4anti) (Z=(2-1), Y=Br, $R^{2c}$=i-Bu, 4R/5S) obtained in Example 21(4) and 40 mg (74 μmol) of Compound (7) ($R^3$=TBS, $R^6$=—$(CH_2)_3$OTBS, 3α/4α/5β), a reaction similar to Example 14(2-a) was carried out to obtain 15 mg of Compound No. 807c. Yield: 57%.

$^1$H-NMR (CDCl$_3$) δ: 0.55 (s, 3 H), 0.95 (d, J=6.7 Hz, 3 H), 0.96 (d, J=6.6 Hz, 3 H), 1.06 (d, J=6.1 Hz, 3 H), 1.15-2.10 (m, 23 H), 2.18-2.40 (m, 2 H), 2.25 (dd, J=12.9, 8.5 Hz, 1 H), 2.60-2.72 (m, 2 H), 2.82 (m, 1 H), 3.62-3.75 (m, 2 H), 3.88 (ddd, J=8.1, 8.1, 4.3 Hz, 1 H), 4.20 (m, 1 H), 4.37 (br d, J=2.7 Hz, 1 H), 4.98 (d, J=1.8 Hz, 1 H), 5.27 (d, J=1.8 Hz, 1 H), 5.57 (d, J=2.2 Hz, 1 H), 6.00 (d, J=11.2 Hz, 1 H), 6.24 (d, J=2.2 Hz, 1 H), 6.39 (d, J=11.2 Hz, 1 H).

LRMS m/z 540 (M$^+$), 522, 504
HRMS calcd for $C_{34}H_{52}O_5$ 540.3815, found 540.3816

Example 40

Synthesis of 2α-(3-hydroxypropyl)-20(R)-(tetrahydro-3-methylene-2-furanone-4(S)-isobutyl-5(R)-yl)methyl-9,10-secopregna-5(Z),7(E),10(19)-triene-1α,3β-diol (Compound No. 807d)

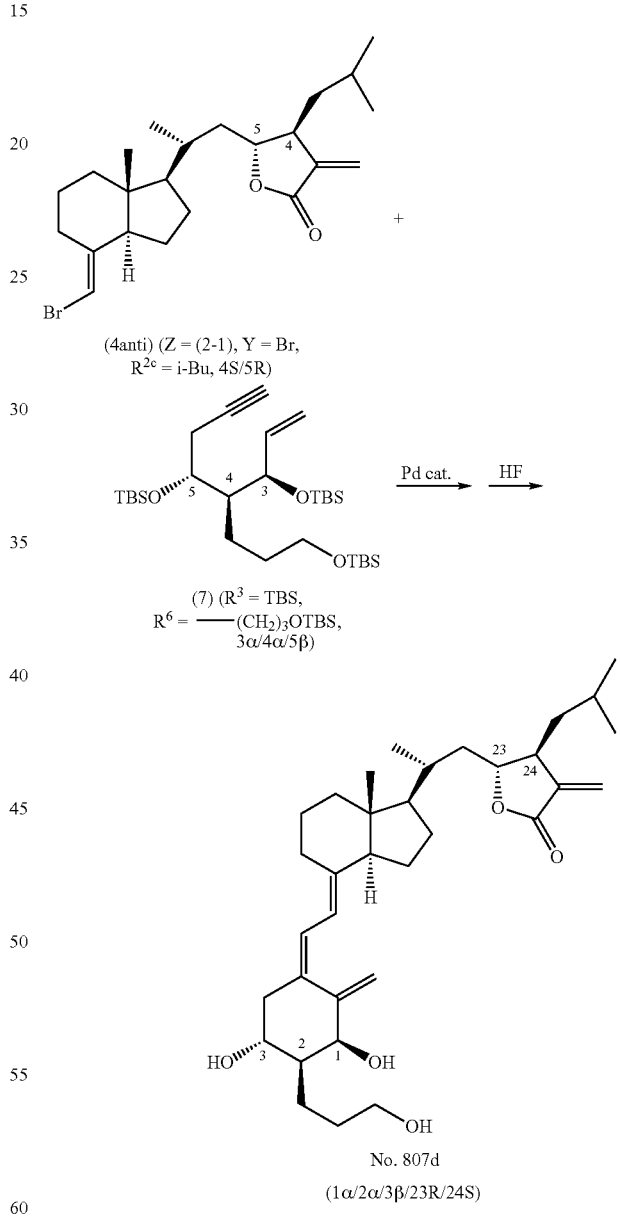

Using 18 mg (42 μmol) of Compound (4anti) (Z=(2-1), Y=Br, $R^{2c}$=i-Bu, 4S/5R) obtained in Example 22(5) and 34 mg (63 μmol) of Compound (7) ($R^3$=TBS, $R^6$=—$(CH_2)_3$OTBS, 3α/4α/5β), a reaction similar to Example 14(2-a) was carried out to obtain 10 mg of Compound No. 807d. Yield: 44%.

$^1$H-NMR (CDCl$_3$) δ: 0.55 (s, 3 H), 0.95 (d, J=6.6 Hz, 3 H), 0.96 (d, J=6.4 Hz, 3 H), 1.01 (d, J=6.6 Hz, 3 H), 1.15-2.20 (m, 25 H), 2.25 (dd, J=13.1, 9.2 Hz, 1 H), 2.62 (m, 1 H), 2.66 (dd, J=13.1, 4.1 Hz, 1 H), 2.83 (m, 1 H), 3.65-3.75 (m, 2 H), 3.90 (ddd, J=7.9, 7.9, 4.4 Hz, 1 H), 4.24 (ddd, J=10.8, 4.5, 1.9 Hz, 1 H), 4.37 (br d, J=2.4 Hz, 1 H), 4.98 (d, J=1.7 Hz, 1 H), 5.27 (d, 1.7 Hz, 1 H), 5.56 (d, J=2.4 Hz, 1 H), 5.99 (d, J=11.2 Hz, 1 H), 6.24 (d, J=2.4 Hz, 1 H), 6.38 (d, J=11.2 Hz, 1 H).

LRMS m/z 540 (M$^+$), 522, 504

HRMS calcd for C$_{34}$H$_{52}$O$_5$ 540.3815, found 540.3814

Example 41

Synthesis of 2α-(3-hydroxypropoxy)-20(R)-(tetrahydro-3-methylene-2-furanone-5(R)-yl)methyl-9,10-secopregna-5(Z),7(E),10(19)-triene-1α,3β-diol (Compound No. 101a)

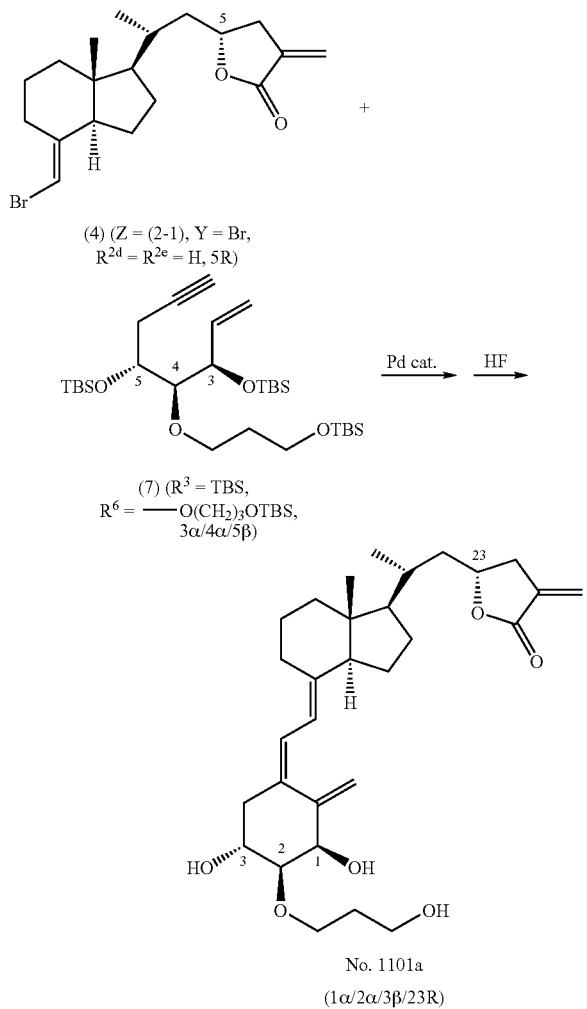

Using 16 mg (44 μmol) of Compound (4) (Z=(2-1), Y=Br, R$^{2d}$=R$^{2e}$=H, 5R) obtained by a method known in the literature (for example, the specification of International Publication WO 95/33716) and 36 mg (65 μmol) of Compound (7) (R$^3$=TBS, R$^6$=—O(CH$_2$)$_3$OTBS, 3α/4α/5β) obtained by a method known in the literature (for example, Org. Lett., Vol. 2, 2619-2622, 2000), a reaction similar to Example 14(2-a) was carried out to obtain 10 mg of Compound No. 1101a. Yield: 46%.

$^1$H-NMR (CDCl$_3$) δ: 0.56 (s, 3 H), 1.01 (d, J=6.3 Hz, 3 H), 1.26-2.03 (m, 16 H), 2.23 (dd, J=9.0, 13.2 Hz, 1 H), 2.35 (br s, 1 H), 2.54 (m, 2 H), 2.61 (d, J=3.9 Hz, 1 H), 2.68 (dd, J=13.2, 4.2 Hz, 1 H), 2.81-2.84 (m, 1 H), 3.03-3.09 (br dd, J=7.6, 17.3 Hz, 1 H), 3.37 (dd, J=3.1, 7.2 Hz, 1 H), 3.76-3.90 (m, 4 H), 4.06 (m, 1 H), 4.44 (br s, 1 H), 4.63-4.64 (m, 1 H), 5.01 (br s, 1 H), 5.39 (br s, 1 H), 5.61 (br s, 1 H), 6.01 (d, J=11.0 Hz, 1 H), 6.22 (br s, 1 H), 6.41 (d, J=11.0 Hz, 1 H).

LRMS m/z 500 (M$^+$) 482, 464, 406, 390, 352

HRMS calcd for C$_{30}$H$_{44}$O$_6$ 500.3138, found 500.3134

Example 42

Synthesis of 2α-(3-hydroxypropoxy)-20(R)-(tetrahydro-3-methylene-2-furanone-5(S)-yl)methyl-9,10-secopregna-5(Z),7(E),10(19)-triene-1α,3β-diol (Compound No. 1101b)

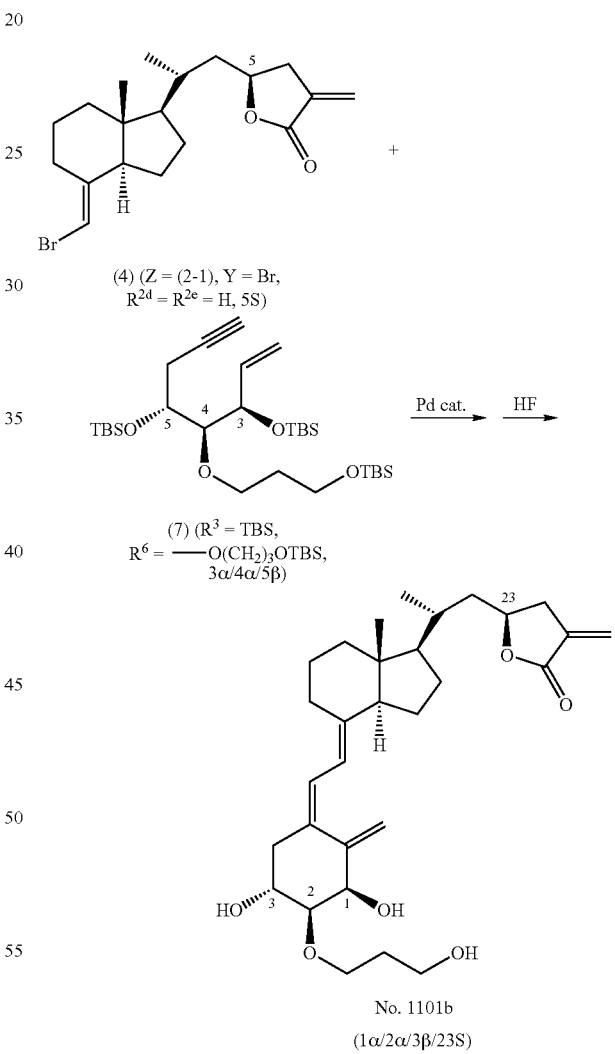

Using 11 mg (29 μmol) of Compound (4) (Z=(2-1), Y=Br, R$^{2d}$=R$^{2e}$=H, 5S) obtained by a method known in the literature (for example, the specification of International Publication WO 95/33716) and 25 mg (45 μmol) of Compound (7) (R$^3$=TBS, R$^6$=—O(CH$_2$)$_3$OTBS, 3α/4α/5β), a reaction similar to Example 14(2-a) was carried out to obtain 11 mg of Compound No. 1101b. Yield: 73%.

$^1$H-NMR (CDCl$_3$) δ: 0.55 (s, 3 H), 1.02 (d, J=6.4 Hz, 3 H), 1.21-2.01 (m, 16 H), 2.17 (t, J=5.0 Hz, 1 H), 2.24 (dd, J=9.3, 13.0 Hz, 1 H), 2.47 (d, J=3.4 Hz, 1 H), 2.54 (d, J=4.4 Hz, 1H), 2.56 (m, 1 H), 2.69 (dd, J=4.6, 13.0 Hz, 1 H), 2.81-2.84 (m, 1 H), 3.05 (dddd, J=2.3, 2.6, 7.4, 16.9 Hz, 1 H), 3.38 (dd, J=3.5, 7.5 Hz, 1 H), 3.75-3.90 (m, 4 H), 4.06 (m, 1 H), 4.45 (dd, J=3.5, 3.5 Hz, 1 H), 4.59 (dddd, J=7.4, 7.0, 7.0, 7.0 Hz, 1 H), 5.09 (br s, 1 H), 5.39 (br s, 1 H), 5.62 (dd, J=2.3, 2.3 Hz, 1 H), 6.01 (d, J=11.4 Hz, 1 H), 6.22 (dd, J=2.6, 2.7 Hz, 1 H), 6.42 (d, J=11.4 Hz, 1 H).

LRMS m/z 500 (M$^+$) 482, 464, 406, 390, 352

HRMS calcd for C$_{30}$H$_{44}$O$_6$ 500.3138, found 500.3033

Example 43

Synthesis of 2α-(3-hydroxypropoxy)-20(R)-(tetrahydro-3-methylene-2-furanone-4(R)-methyl-5(R)-yl)methyl-9,10-secopregna-5(Z),7(E),10(19)-triene-1α,3β-diol (Compound No. 1102a)

OTBS, 3α/4α/5β), a reaction similar to Example 14(2-a) was carried out to obtain 12.1 mg of Compound No. 1102a. Yield: 51%.

$^1$H-NMR (CDCl$_3$) δ: 0.55 (s, 3 H), 0.99 (d, J=6.6 Hz, 3 H), 1.06 (m, 1 H), 1.13 (d, J=7.1 Hz, 3 H), 1.15-1.90 (m, 13 H), 1.93-2.05 (m, 2 H), 2.23 (dd, J=13.4, 9.2 Hz, 1 H), 2.40-2.75 (m, 3 H), 2.67 (dd, J=13.4, 4.6 Hz, 1 H), 2.82 (m, 1 H), 3.15 (m, 1 H), 3.37 (dd, J=7.3, 3.0 Hz, 1 H), 3.54-3.90 (m, 4 H), 4.06 (ddd, J=9.2, 7.3, 4.6 Hz, 1 H), 4.43 (d, J=3.0 Hz, 1 H), 4.67 (ddd, J=11.7, 7.7, 1.7 Hz, 1 H), 5.07 (d, J=1.7 Hz, 1 H), 5.38 (br s, 1 H), 5.52 (d, J=2.6 Hz, 1 H), 6.00 (d, J=11.1 Hz, 1 H), 6.20 (d, =2.6 Hz, 1 H), 6.40 (d, J=11.1 Hz, 1 H).

LRMS m/z 514 (M$^+$), 496, 478, 420, 249

HRMS calcd for C$_{31}$H$_{46}$O$_6$ 514.3295, found 514.3304

Example 44

Synthesis of 2α-(3-hydroxypropoxy)-20(R)-(tetrahydro-3-methylene-2-furanone-4(S)-methyl-5(S)-yl)methyl-9,10-secopregna-5(Z),7(E),10(19)-triene-1α,3β-diol (Compound No. 1102b)

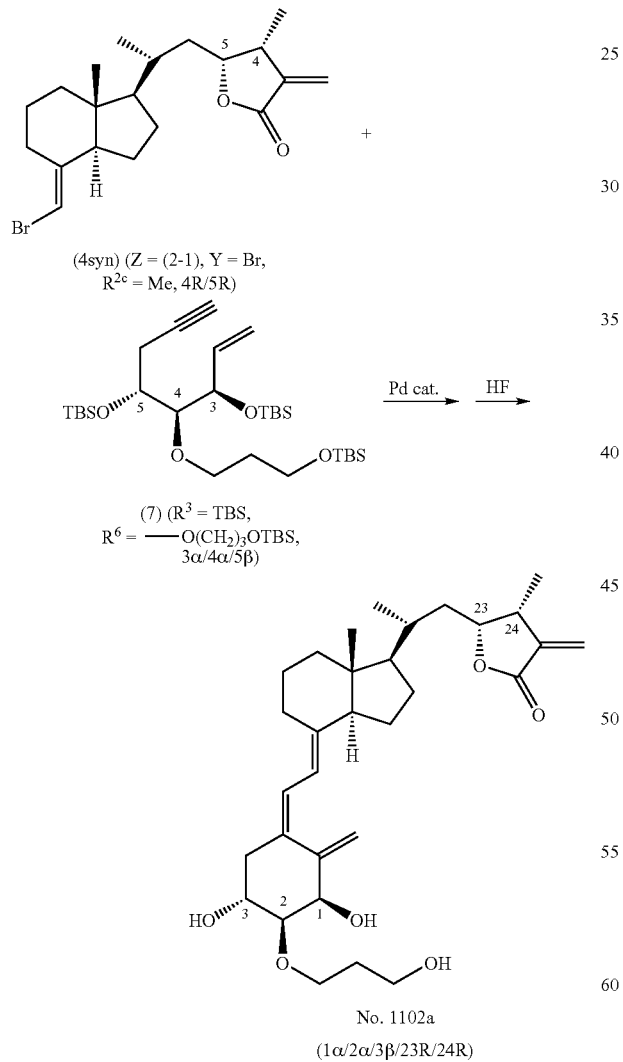

Using 18 mg (46 μmol) of Compound (4syn) (Z=(2-1), Y=Br, R$^{2c}$=Me, 4R/5R) obtained in Example 11(1) and 39 mg (70 μmol) of Compound (7) (R$^3$=TBS, R$^6$=—O(CH$_2$)$_3$ Using 19 mg (49 μmol) of Compound (4syn) (Z=(2-1), Y=Br, R$^{2c}$=Me, 4S/5S) obtained in Example 11(1) and 41 mg (73 µmol) of Compound (7) ($R^3$=TBS, $R^6$=—O(CH$_2$)$_3$OTBS, 3α/4α/5β), a reaction similar to Example 14(2-a) was carried out to obtain 10.3 mg of Compound No. 1102b. Yield: 41%.

$^1$H-NMR (CDCl$_3$) δ: 0.55 (s, 3 H), 1.04 (d, J=6.6 Hz, 3 H), 1.12 (d, J=7.1 Hz, 3 H), 1.20-1.75 (m, 11 H), 1.80-2.05 (m, 5 H), 2.23 (dd, J=13.4, 9.0 Hz, 1 H), 2.57 (br s, 3 H), 2.67 (dd, J=13.4, 4.6 Hz, 1 H), 2.82 (m, 1 H), 3.10 (m, 1 H), 3.37 (dd, J=7.3, 3.0 Hz, 1 H), 3.75-3.93 (m, 4 H), 4.05 (ddd, J=9.0, 7.3, 4.6 Hz, 1 H), 4.43 (br d, J=3.0 Hz, 1 H), 4.58 (dt, J=5.9, 7.2 Hz, 1 H), 5.08 (d, J=1.5 Hz, 1H), 6.28 (d, J=1.5 Hz, 1 H), 5.53 (d, J=2.1 Hz, 1H), 6.00 (d, J=11.2 Hz, 1 H), 6.18 (d, J=2.2 Hz, 1 H), 6.41 (d, J=11.2 Hz, 1 H).

LRMS m/z 514 (M$^+$), 496, 478, 420, 249

HRMS calcd for $C_{31}H_{46}O_6$ 514.3294, found 514.3298

Example 45

Synthesis of 2α-(3-hydroxypropoxy)-20(R)-(tetrahydro-3-methylene-2-furanone-4(R)-methyl-5(S)-yl)methyl-9,10-secopregna-5(Z),7(E),10(19)-triene-1α,3β-diol (Compound No. 1102c)

Using 17 mg (44 µmol) of Compound (4anti) (Z=(2-1), Y=Br, $R^{2c}$=Me, 4R/5S) obtained in Example 12(4) and 37 mg (66 µmol) of Compound (7) ($R^3$=TBS, $R^6$=—O(CH$_2$)$_3$OTBS, 3α/4α/5β), a reaction similar to Example 14(2-a) was carried out to obtain 12.1 mg of Compound No. 1102c. Yield: 54%.

$^1$H-NMR (CDCl$_3$) δ: 0.55 (s, 3 H), 1.05 (d, J=6.1 Hz, 3 H), 1.24 (d, J=6.8 Hz, 3 H), 1.15-1.75 (m, 12 H), 1.80-2.05 (m, 5 H), 2.23 (dd, J=13.7, 9.2 Hz, 1 H), 2.40-2.75 (m, 3 H), 2.67 (dd, J=13.7, 4.7 Hz, 1 H), 2.82 (m, 1 H), 3.37 (dd, J=7.4, 3.3 Hz, 1 H), 3.75-3.93 (m, 4H), 4.00-4.10 (m, 2 H), 4.44 (d, J=3.3 Hz, 1 H), 5.08 (d, J=1.5 Hz, 1 H), 5.38 (d, J=1.5 Hz, 1 H), 5.53 (d, J=2.9 Hz, 1 H), 6.00 (d, J=11.2 Hz, 1 H), 6.22 (d, J=2.9 Hz, 1 H), 6.41 (d, J=11.2 Hz, 1 H).

LRMS m/z 514 (M$^+$), 476, 478, 420, 402

HRMS calcd for $C_{31}H_{46}O_6$ 514.3294, found 514.3286

Example 46

Synthesis of 2α-(3-hydroxypropoxy)-20(R)-(tetrahydro-3-methylene-2-furanone-4(S)-methyl-5(R)-yl)methyl-9,10-secopregna-5(Z),7(E),10(19)-triene-1α,3β-diol (Compound No. 1102d)

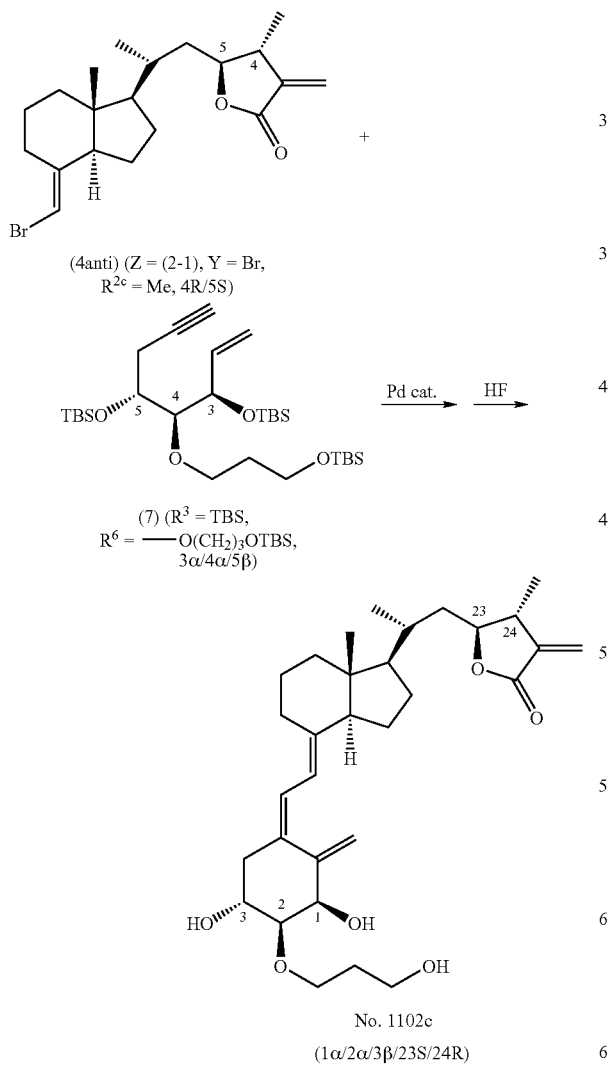

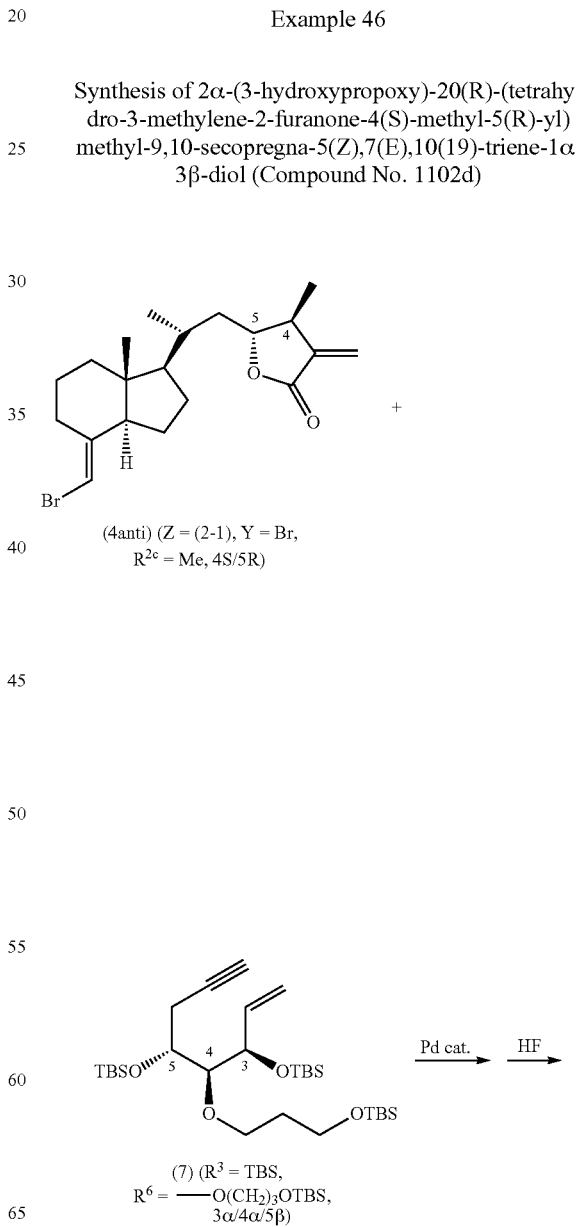

145

-continued

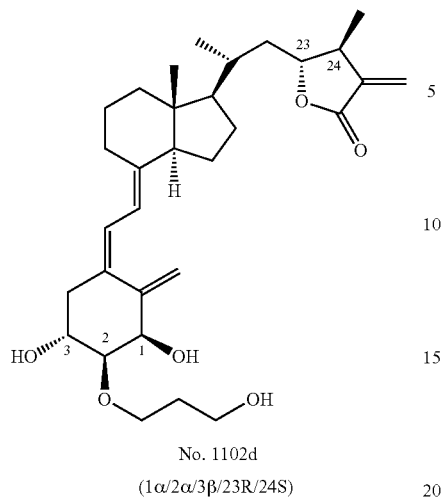

No. 1102d
(1α/2α/3β/23R/24S)

Using 11 mg (26 μmol) of Compound (4anti) (Z=(2-1), Y=Br, R$^{2c}$=Me, 4S/5R) obtained in Example 13(5) and 24 mg (42 μmol) of Compound (7) (R$^3$=TBS, R$^6$=—O(CH$_2$)$_3$OTBS, 3α/4α/5β), a reaction similar to Example 14(2-a) was carried out to obtain 7.6 mg of Compound No. 1102d. Yield: 52%.

$^1$H-NMR (CDCl$_3$) δ: 0.56 (s, 3 H), 1.00 (d, J=6.6 Hz, 3 H), 1.22 (d, J=6.8 Hz, 3 H), 1.20-1.90 (m, 14 H), 1.93-2.05 (m, 2 H), 2.23 (dd, J=13.4, 9.3 Hz, 1 H), 2.35-2.70 (m, 4 H), 2.68 (dd, J=13.4, 4.5 Hz, 1 H), 2.82 (m, 1 H), 3.37 (dd, J=7.5, 3.2 Hz, 1 H), 3.73-3.93 (m, 4H), 4.00-4.13 (m, 2 H), 4.44 (d, J=3.2 Hz, 1 H), 5.68 (d, J=1.7 Hz, 1 H), 5.38 (d, J=1.7 Hz, 1 H), 5.51 (d, J=3:1 Hz, 1 H), 6.01 (d, J=11.1 Hz, 1 H), 6.21 (d, J=3.1 Hz, 1 H), 6.40 (d, J=11.1 Hz, 1 H).

LRMS m/z 514 (M$^+$), 497, 496, 478, 420, 402, 249

HRMS calcd for C$_{31}$H$_{46}$O$_6$ 514.3294, found 514.3297

Example 47

Synthesis of 2α-(3-hydroxypropoxy)-20(R)-(tetrahydro-3-methylene-2-furanone-4(R)-ethyl-5(R)-yl)methyl-9,10-secopregna-5(Z),7(E),10(19)-triene-1α,3β-diol (Compound No. 1103a)

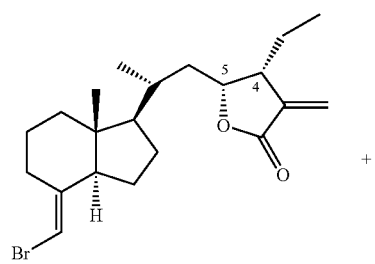

(4syn) (Z = (2-1), Y = Br, R$^{2c}$ = Et, 4R/5R)

146

-continued

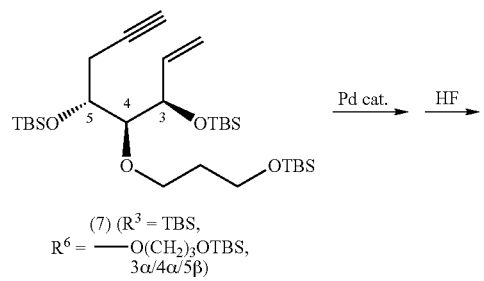

(7) (R$^3$ = TBS, R$^6$ = —O(CH$_2$)$_3$OTBS, 3α/4α/5β)

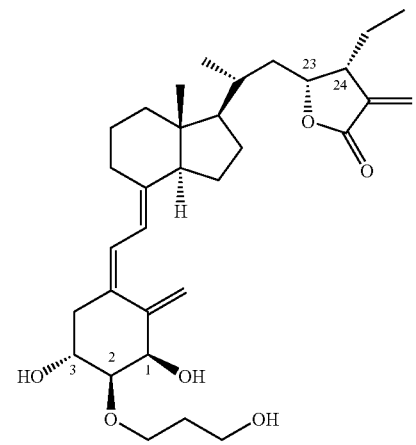

No. 1103a
(1α/2α/3β/23R/24R)

Using 13 mg (33 μmol) of Compound (4syn) (Z=(2-1), Y=Br, R$^{2c}$=Et, 4R/5R) obtained in Example 14(1) and 27 mg (49 μmol) of Compound (7) (R$^3$=TBS, R$^6$=—O(CH$_2$)$_3$OTBS, 3α/4α/5β), a reaction similar to Example 14(2-a) was carried out to obtain 10 mg of Compound No. 1103a. Yield: 58%.

$^1$H-NMR (CDCl$_3$) δ: 0.55 (s, 3 H), 0.97 (t, J=7.4 Hz, 3 H), 1.00 (d, J=6.3 Hz, 3 H), 1.12 (ddd, J=14.1, 10.7, 1.7 Hz, 1 H), 1.22-1.89 (m, 15 H), 1.97 (dd, J=12.1, 7.1 Hz, 1 H), 2.02 (br d, J=12.4 Hz, 1 H), 2.23 (dd, J=13.6, 8.8 Hz, 1 H), 2.51 (br, 3 H), 2.68 (dd, J=13.6, 4.5 Hz, 1 H), 2.82 (m, 1 H), 2.87 (m, 1 H), 3.37 (dd, J=7.4, 3.3 Hz, 1 H), 3.77 (m, 1 H), 3.80-3.85 (m, 2 H), 4.06 (m, 1 H), 4.44 (d, J=3.0 Hz, 1 H), 4.66 (ddd, J=11.5, 7.0, 1.5 Hz, 1H), 5.08 (d, J=1.7 Hz, 1 H), 5.39 (s, 1 H), 5.51 (d, J=2.4 Hz, 1 H), 6.01 (d, J=11.3 Hz, 1H), 6.21 (d, J=2.4 Hz, 1 H), 6.40 (d, J=11.3 Hz, 1 H).

LRMS m/z 528 (M$^+$) 510, 492, 466, 434, 419, 265, 249

HRMS calcd for C$_{32}$H$_{48}$O$_6$ 528.3451, found 528.3451

Example 48

Synthesis of 2α-(3-hydroxypropoxy)-20(R)-(tetrahydro-3-methylene-2-furanone-4(S)-ethyl-5(S)-yl)methyl-9,10-secopregna-5(Z),7(E),10(19)-triene-1α,3β-diol (Compound No. 1103b)

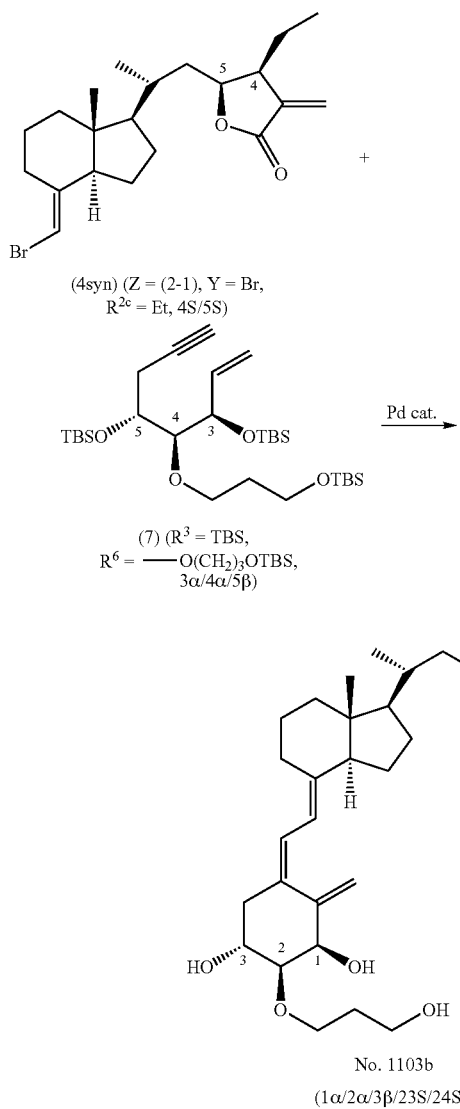

No. 1103b
(1α/2α/3β/23S/24S)

Using 27 mg (68 μmol) of Compound (4syn) (Z=(2-1), Y=Br, $R^{2c}$=Et, 4S/5S) obtained in Example 14(1) and 57 mg (102 μmol) of Compound (7) ($R^3$=TBS, $R^6$=—O(CH$_2$)$_3$OTBS, 3α/4α/5β), a reaction similar to Example 14(2-a) was carried out to obtain 22 mg of Compound No. 1103b. Yield: 61%.

$^1$H-NMR (CDCl$_3$) δ: 0.55 (s, 3 H), 0.94 (t, J=7.3 Hz, 3 H), 1.04 (d, J=6.6 Hz, 3 H), 1.24-2.01 (m, 18 H), 2.23 (dd, J=13.2, 9.0 Hz, 1 H), 2.64-2.83 (m, 6 H), 3.37 (dd, J=7.4, 3.3 Hz, 1 H), 3.76 (m, 1 H), 3.80-3.83 (m, 2 H), 3.87 (m, 1 H), 4.04 (m, 1 H), 4.44 (d, J=2.9 Hz, 1 H), 4.57 (m, 1 H), 5.08 (d, J=1.3 Hz, 1 H), 5.38 (d, J=1.3 Hz, 1 H), 5.51 (d, J=1.8 Hz, 1H), 6.01 (d, J=11.2 Hz, 1 H), 6.20 (d, J=1.8 Hz, 1 H), 6.40 (d, J=11.2 Hz, 1 H).

LRMS m/z 528 (M$^+$) 510, 492, 466, 434, 419, 265, 249
HRMS calcd for $C_{32}H_{48}O_6$ 528.3451, found 528.3453

Example 49

Synthesis of 2α-(3-hydroxypropoxy)-20(R)-(tetrahydro-3-methylene-2-furanone-4(R)-ethyl-5(S)-yl)methyl-9,10-secopregna-5(Z),7(E),10(19)-triene-1α,3β-diol (Compound No. 1103c)

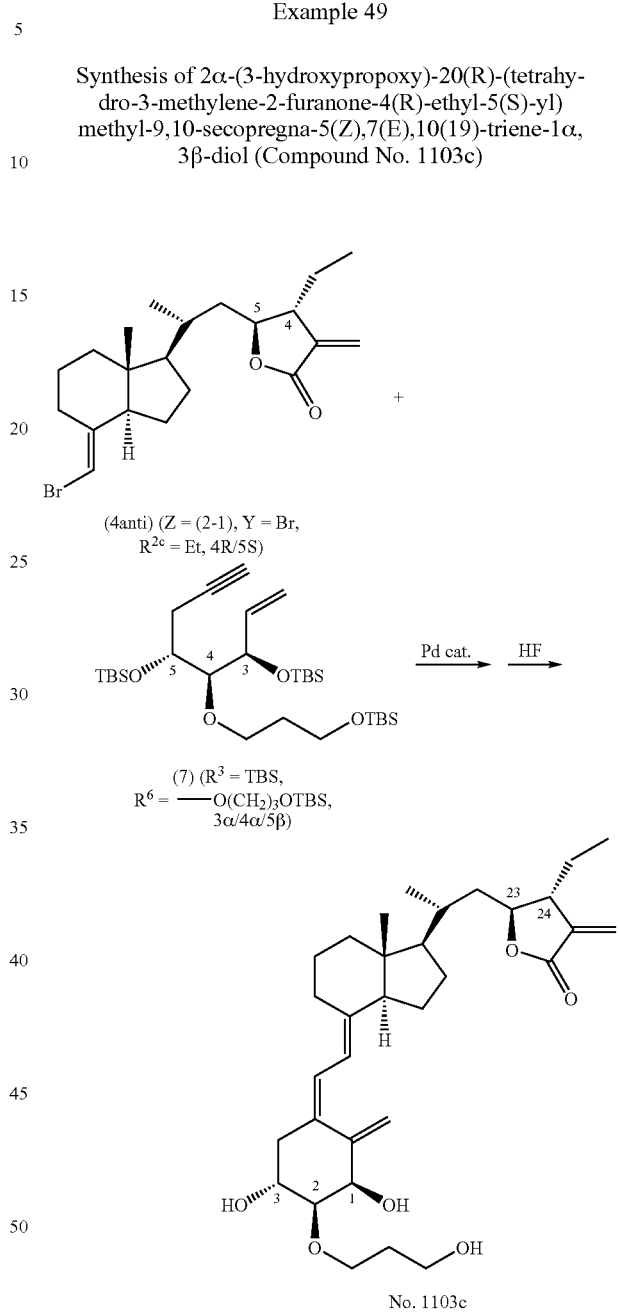

No. 1103c
(1α/2α/3β/23S/24R)

Using 21 mg (53 μmol) of Compound (4anti) (Z=(2-1), Y=Br, $R^{2c}$=Et, 4R/5S) obtained in Example 15 (5) and 44 mg (80 μmol) of Compound (7) ($R^3$=TBS, $R^6$=—O(CH$_2$)$_3$OTBS, 3α/4α/5β), a reaction similar to Example 14(2-a) was carried out to obtain 19 mg of Compound No. 1103c. Yield: 68%.

$^1$H-NMR (400 MHz, CDCl$_3$) δ: 0.55 (s, 3 H), 0.97 (t, J=7.4 Hz, 3 H), 1.05 (d, J=6.1 Hz, 3H), 1.14-1.71 (m, 13 H), 1.84-1.92 (m, 3 H), 1.98-2.00 (m, 2 H), 2.23 (dd, J=13.1, 9.2 Hz, 1H), 2.53-2.83 (m, 6 H), 3.37 (dd, J=7.6, 3.2 Hz, 1 H), 3.74-3.90 (m, 4 H), 4.05 (m, 1 H), 4.26 (m, 1 H), 4.44 (d, J=2.9

Hz, 1 H), 5.08 (d, J=2.0 Hz, 1 H), 5.38 (br s, 1 H), 5.59 (d, J=2.3 Hz, 1 H), 6.00 (d, J=11.2 Hz, 1 H), 6.27 (d, J=2.3 Hz, 1 H), 6.40 (d, J=11.2 Hz, 1 H).

LRMS m/z 528 (M$^+$) 510, 492, 466, 434, 419, 265, 249
HRMS calcd for $C_{32}H_{48}O_6$ 528.3451, found 528.3451

Example 50

Synthesis of 2α-(3-hydroxypropoxy)-20(R)-(tetrahydro-3-methylene-2-furanone-4(S)-ethyl-5(R)-yl)methyl-9,10-secopregna-5(Z),7(E),10(19)-triene-1α,3β-diol (Compound No. 1103d)

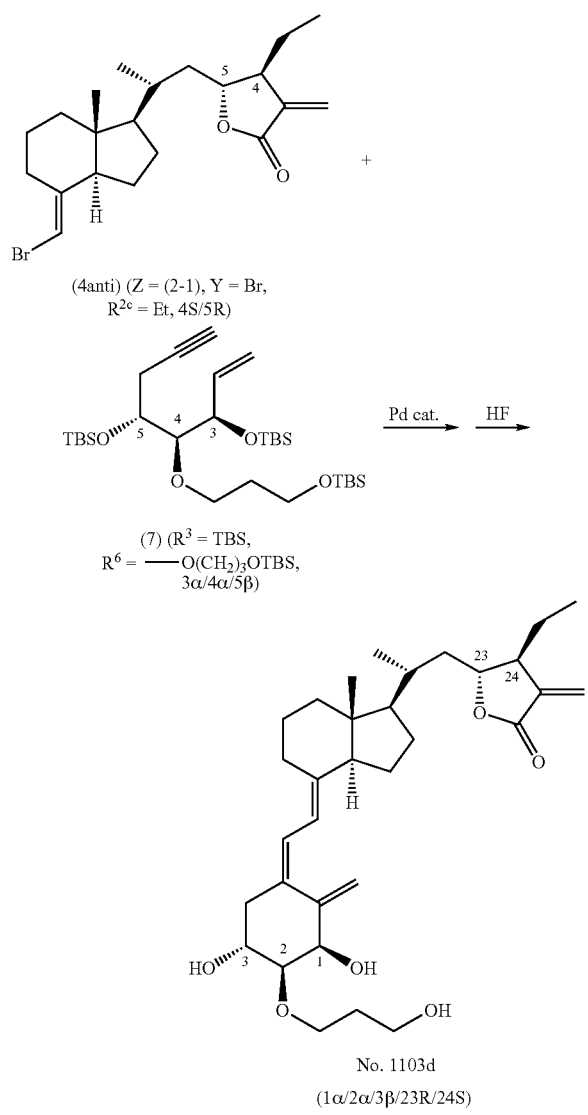

No. 1103d
(1α/2α/3β/23R/24S)

Using 32 mg (81 µmol) of Compound (4anti) (Z=(2-1), Y=Br, $R^{2c}$=Et, 4S/5R) obtained in Example 16(5) and 68 mg (121 µmol) of Compound (7) ($R^3$=TBS, $R^6$=—O(CH$_2$)$_3$OTBS, 3α/4α/5β), a reaction similar to Example 14(2-a) was carried out to obtain 26 mg of Compound No. 1103d. Yield: 61%.

$^1$H-NMR (CDCl$_3$) δ: 0.55 (s, 3 H), 0.97 (t, J=7.4 Hz, 3 H), 1.05 (d, J=6.1 Hz, 3 H), 1.14-1.71 (m, 13 H), 1.84-1.92 (m, 3 H), 1.98-2.00 (m, 2 H), 2.23 (dd, J=13.1, 9.2 Hz, 1 H), 2.53-2.83 (m, 6 H), 3.37 (dd, J=7.6, 3.2 Hz, 1 H), 3.74-3.90 (m, 4 H), 4.05 (m, 1 H), 4.26 (m, 1 H), 4.44 (d, J=2.9 Hz, 1 H), 5.08 (d, J=2.0 Hz, 1 H), 5.38 (br s, 1 H), 5.59 (d, J=2.3 Hz, 1 H), 6.00 (d, J=11.2 Hz, 1 H), 6.27 (d, J=2.3 Hz, 1 H), 6.40 (d, J=11.2 Hz, 1 H).

LRMS m/z 528 (M$^+$) 510, 492; 466, 434, 419, 265, 249
HRMS calcd for $C_{32}H_{48}O_6$ 528.3451, found 528.3451

Example 51

Synthesis of 2α-(3-hydroxypropoxy)-20(R)-(tetrahydro-3-methylene-2-furanone-4(R)-butyl-5(R)-yl)methyl-9,10-secopregna-5(Z),7(E),10(19)-triene-1α,3β-diol (Compound No. 1106a)

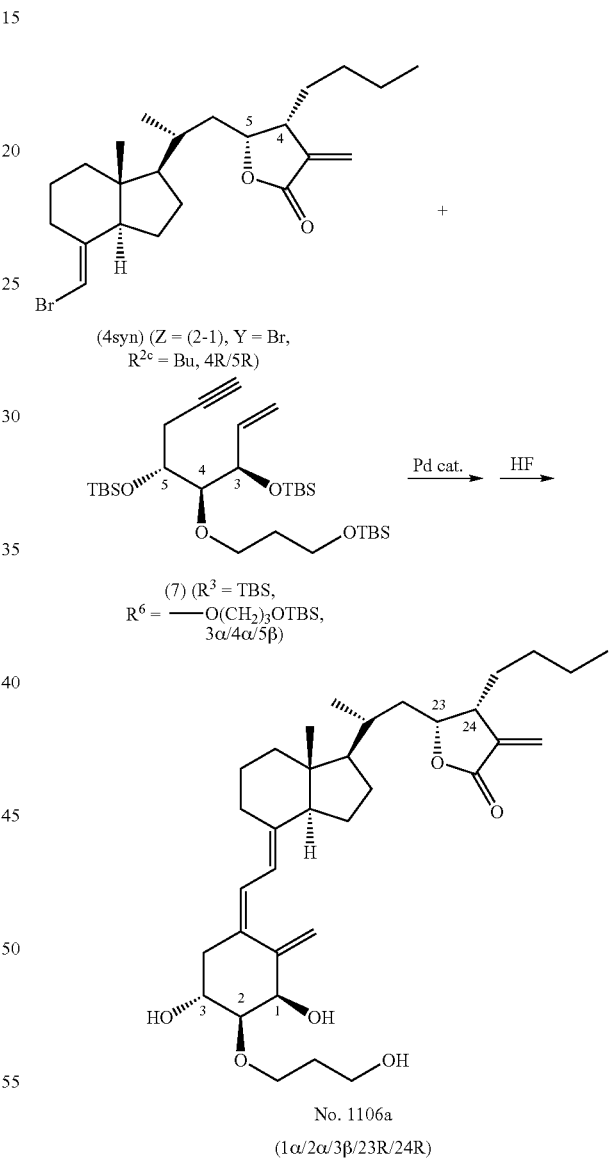

No. 1106a
(1α/2α/3β/23R/24R)

Using 60 mg (142 µmol) of Compound (4syn) (Z=(2-1), Y=Br, $R^{2c}$=Bu, 4R/5R) obtained in Example 17 (1) and 118 mg (213 µmol) of Compound (7) ($R^3$=TBS, $R^6$=—O(CH$_2$)$_3$OTBS, 3α/4α/5β), a reaction similar to Example 14(2-a) was carried out to obtain 45 mg of Compound No. 1106a. Yield: 57%.

$^1$H-NMR (CDCl$_3$) δ: 0.56 (s, 3 H), 0.93 (t, J=7.0 Hz, 3 H), 1.00 (d, J=6.4 Hz, 3 H), 1.11 (ddd, J=13.7, 11.0, 1.2 Hz, 1 H), 120-2.08 (m, 21 H), 2.23 (dd, J=13.4, 9.0 Hz, 1 H), 2.67 (dd, J=13.4, 4.4 Hz, 1 H), 2.72-2.90 (m, 4 H), 2.96 (m, 1 H), 3.37 (dd, J=7.3, 3.2 Hz, 1 H), 3.70-3.95 (m, 4 H), 4.05 (m, 1 H), 4.45 (br s, 1 H), 4.65 (ddd, J=10.4, 7.2, 1.1 Hz, 1 H), 5.08 (s, 1 H), 5.38 (s, 1 H), 5.51 (d, J=2.3 Hz, 1 H), 6.10 (d, J=11.2 Hz, 1 H), 6.21 (d, J=2.3 Hz, 1 H), 6.40 (d, J=11.2 Hz, 1 H).

LRMS m/z 556 (M+), 538, 520, 462, 444

HRMS calcd for $C_{34}H_{52}O_6$ 556.3764, found 556.3762

Example 52

Synthesis of 2α-(3-hydroxypropoxy)-20(R)-(tetrahydro-3-methylene-2-furanone-4(S)-butyl-5(S)-yl)methyl-9,10-secopregna-5(Z),7(E),10(19)-triene-1α,3β-diol (Compound No. 1106b)

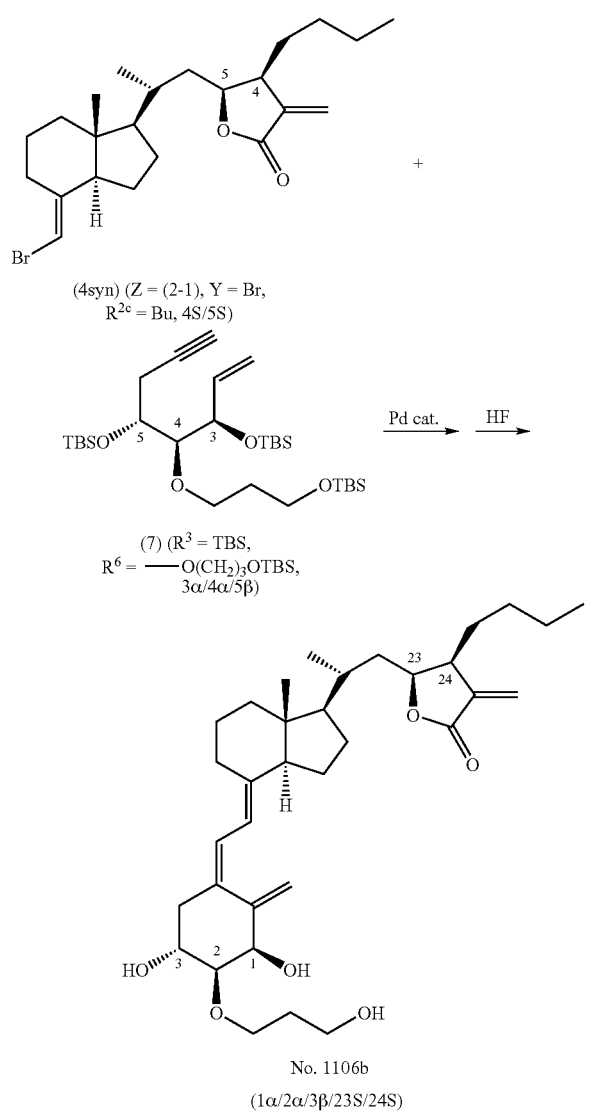

Using 42 mg (100 μmol) of Compound (4syn) (Z=(2-1), Y=Br, $R^{2c}$=Bu, 4S/5S) obtained in Example 17(1) and 84 mg (150 μmol) of Compound (7) ($R^3$=TBS, $R^6$=—O(CH$_2$)$_3$OTBS, 3α/4α/5β), a reaction similar to Example 14(2-a) was carried out to obtain 31 mg of Compound No. 1106b. Yield: 56%.

$^1$H-NMR (CDCl$_3$) δ: 0.55 (s, 3 H), 0.92 (t, J=7.0 Hz, 3 H), 1.05 (d, J=6.6 Hz, 3 H), 1.18-2.08 (m, 22 H), 1.24 (dd, J=13.4, 8.8 Hz, 1 H), 2.68 (dd, J=13.4, 4.7 Hz, 1 H), 2.70 (br s, 3 H), 2.83 (m, 1 H), 2.89 (m, 1 H), 3.37 (dd, J=7.7, 3.1 Hz, 1 H), 3.74-3.93 (m, 4 H), 4.05 (ddd, J=8.8, 7.7, 4.7 Hz, 1 H), 4.44 (br d, J=3.1 Hz, 1 H), 4.57 (ddd, J=8.3, 6.0, 5.3 Hz, 1H), 5.09 (d, J=2.0 Hz, 1 H), 5.38 (d, J=1.2 Hz, 1 H), 5.50 (d, J=1.8 Hz, 1 H), 6.01 (d, J=11.2 Hz, 1 H), 6.19 (d, J=1.8 Hz, 1 H), 6.41 (d, J=11.2 Hz, 1 H).

LRMS m/z 556 (M+), 538, 520, 462, 444

HRMS calcd for $C_{34}H_{52}O_6$ 556.3764, found 556.3760

Example 53

Synthesis of 2α-(3-hydroxypropoxy)-20(R)-(tetrahydro-3-methylene-2-furanone-4(R)-butyl-5(S)-yl)methyl-9,10-secoprejna-5(Z),7(E),10(19)-triene-1α,3β-diol (Compound No. 1106c)

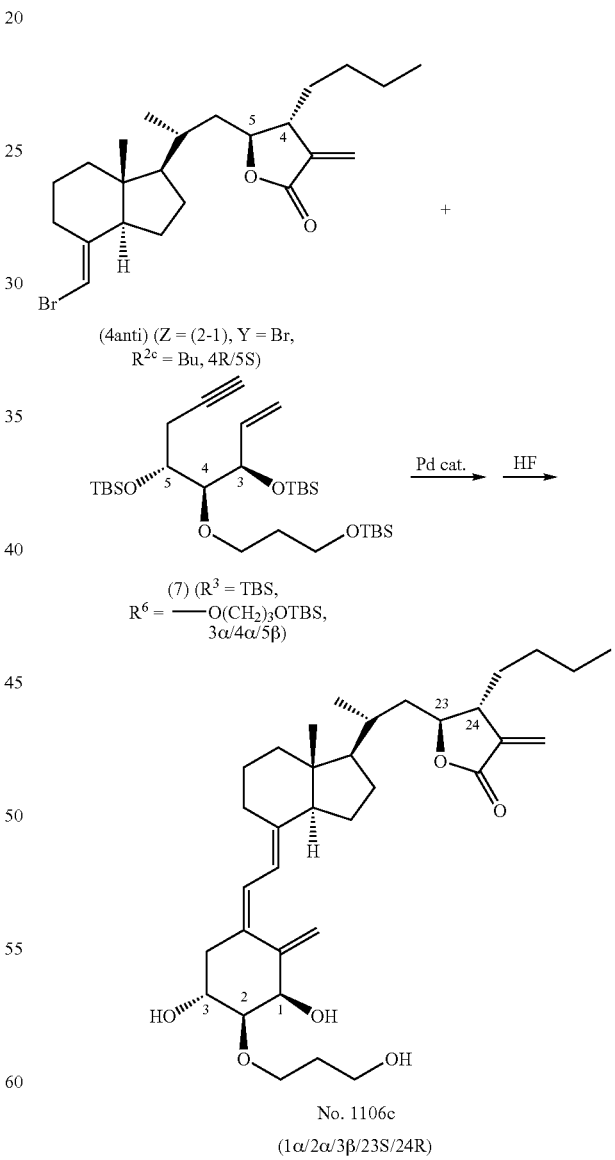

Using 39 mg (92 μmol) of Compound (4anti) (Z=(2-1), Y=Br, $R^{2c}$=Bu, 4R/5S) obtained in Example 18(5) and 77 mg (138 μmol) of Compound (7) ($R^3$=TBS, $R^6$=—O(CH$_2$)$_3$ OTBS, 3α/4α/5β), a reaction similar to Example 14(2-a) was carried out to obtain 26 mg of Compound No. 1106c. Yield: 51%.

$^1$H-NMR (CDCl$_3$) δ: 0.55 (s, 3 H), 0.92 (t, J=6.5 Hz, 3 H), 1.05 (d, J=5.4 Hz, 3 H), 1.15-2.05 (m, 22 H), 2.24 (dd, J=13.2, 9.3 Hz, 1 H), 2.40-2.78 (m, 4 H), 2.68 (dd, J=13.2, 4.2 Hz, 1 H), 2.82 (m, 1 H), 3.38 (dd, J=7.5, 2.8 Hz, 1 H), 3.73-3.93 (m, 4 H), 4.05 (m, 1 H), 4.24 (m, 1 H), 4.44 (br s, 1 H), 5.51 (s, 1 H), 5.38 (s, 1 H), 5.58 (br d, J=1.6 Hz, 1 H), 6.01 (d, J=11.1 Hz, 1 H), 6.26 (brd, J=1.6 Hz, 1 H), 6.41 (d, J=11.1 Hz, 1 H).

LRMS m/z 556 (M$^+$), 538, 520, 462, 444

HRMS calcd for C$_{34}$H$_{52}$O$_6$ 556.3764, found 556.3768

Example 54

Synthesis of 2α-(3-hydroxypropoxy)-20(R)-(tetrahydro-3-methylene-2-furanone-4(S)-butyl-5(R)-yl)methyl-9,10-secopregna-5(Z),7(E),10(19)-triene-1α,3β-diol (Compound No. 1106d)

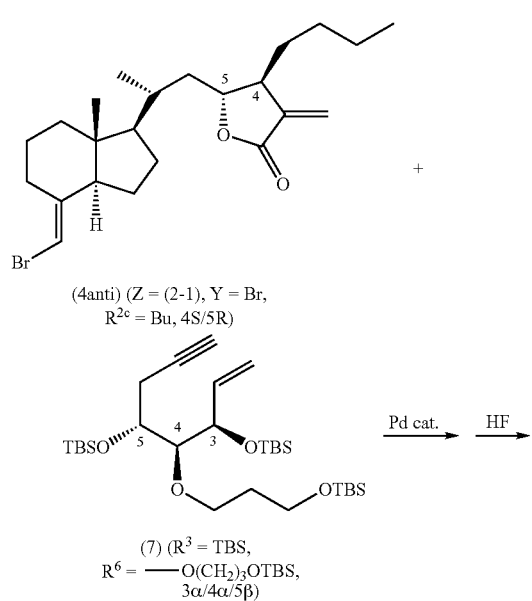

(4anti) (Z = (2-1), Y = Br, R$^{2c}$ = Bu, 4S/5R)

+

(7) (R$^3$ = TBS, R$^6$ = —O(CH$_2$)$_3$OTBS, 3α/4α/5β)

Pd cat. → HF →

No. 1106d
(1α/2α/3β/23R/24S)

Using 39 mg (92 μmol) of Compound (4anti) (Z=(2-1), Y=Br, R$^{2c}$=Bu, 4S/5R) obtained in Example 19(5) and 77 mg (138 μmol) of Compound (7) (R$^3$=TBS, R$^6$=—O(CH$_2$)$_3$OTBS, 3α/4α/5β), a reaction similar to Example 14(2-a) was carried out to obtain 23 mg of Compound No. 1106d. Yield: 44%.

$^1$H-NMR (CDCl$_3$) δ: 0.56 (s, 3 H), 0.92 (t, J=7.0 Hz, 3 H), 1.02 (d, J=6.3 Hz, 3 H), 1.20-1.90 (m, 20 H), 1.92-2.08 (m, 2 H), 2.23 (dd, J=13.4, 9.0 Hz, 1 H), 2.50-2.78 (m, 4 H), 2.68 (dd, J=13.4, 4.6 Hz, 1 H), 2.83 (m, 1 H), 3.37 (dd, J=7.5, 3.2 Hz, 1 H), 3.73-3.95 (m, 4H), 4.06 (ddd, J=9.0, 7.5, 4.6 Hz, 1 H), 4.27 (ddd, J=10.8, 4.8, 2.0 Hz, 1 H), 4.45 (br d, J=2.4 Hz, 1 H), 5.08 (d, J=1.7 Hz, 1 H), 5.39 (s, 1 H), 5.57 (d, J=2.2 Hz, 1 H), 6.01 (d, J=11.1 Hz, 1 H), 6.25 (d, J=2.9 Hz, 1 H), 6.40 (d, J=11.1 Hz, 1 H).

LRMS m/z 556 (M$^+$), 538, 520, 462, 444

HRMS calcd for C$_{34}$H$_{52}$O$_6$ 556.3764, found 556.3757

Example 55

Synthesis of 2α-(3-hydroxypropoxy)-20(R)-(tetrahydro-3-methylene-2-furanone-4(R)-isobutyl-5(R)-yl)methyl-9,10-secopregna-5(Z),7(E),10(19)-triene-1α,3β-diol (Compound No. 1107a)

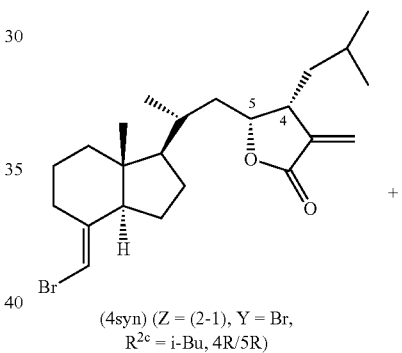

(4syn) (Z = (2-1), Y = Br, R$^{2c}$ = i-Bu, 4R/5R)

+

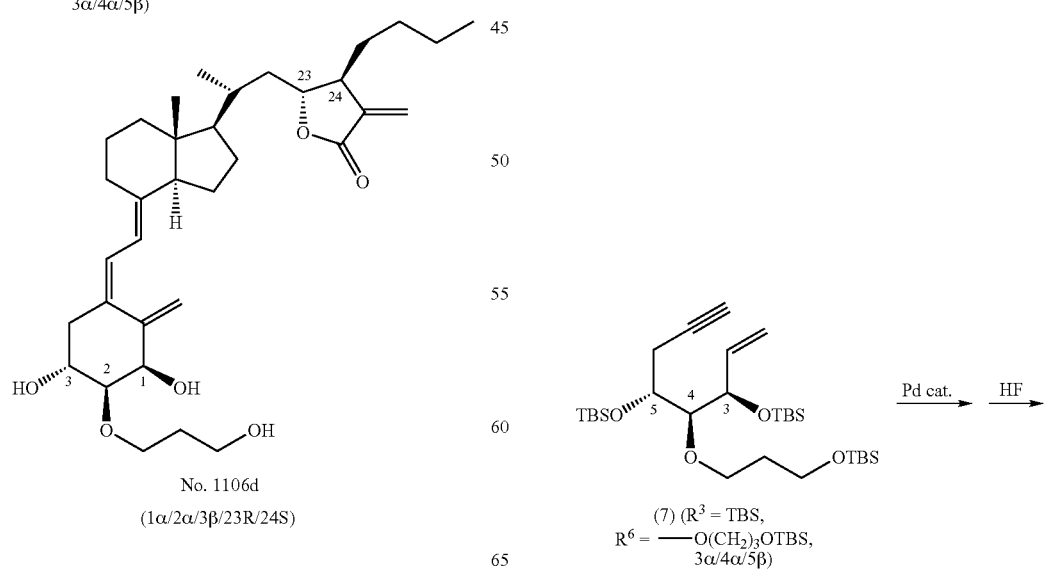

(7) (R$^3$ = TBS, R$^6$ = —O(CH$_2$)$_3$OTBS, 3α/4α/5β)

Pd cat. → HF →

155
-continued

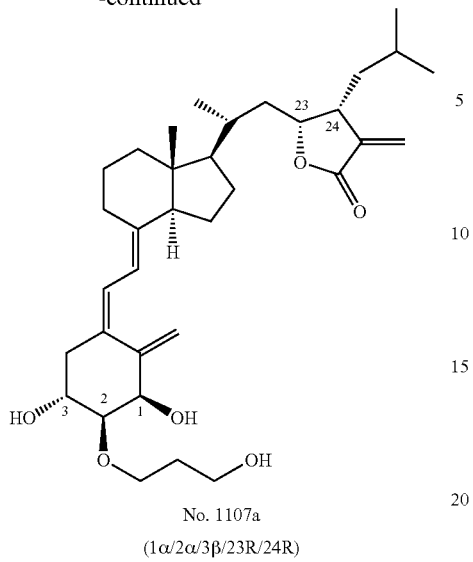

No. 1107a
(1α/2α/3β/23R/24R)

Using 18 mg (43 μmol) of Compound (4syn) (Z=(2-1), Y=Br, R$^{2c}$=i-Bu, 4R/5R) obtained in Example 20(1) and 34 mg (64 μmol) of Compound (7) (R$^3$=TBS, R$^6$=—O(CH$_2$)$_3$OTBS, 3α/4α/5β), a reaction similar to Example 14(2-a) was carried out to obtain 11 mg of Compound No. 1107a. Yield: 47%.

$^1$H-NMR (CDCl$_3$) δ: 0.56 (s, 3 H), 0.95 (d, J=6.6 Hz, 3 H), 0.96 (d, J=6.6 Hz, 3 H), 1.00 (d, J=6.6 Hz, 3 H), 1.08 (ddd, J=14.2, 10.7, 1.8 Hz, 1 H), 1.18-1.92 (m, 16 H), 1.93-2.08 (m, 2H), 2.23 (dd, J=13.4, 8.9 Hz, 1 H), 2.40-2.75 (m, 3 H), 2.68 (dd, J=13.4, 4.5 Hz, 1 H), 2.83 (m, 1 H), 3.08 (m, 1 H), 3.37 (dd, J=7.4, 3.3 Hz, 1 H), 3.73-3.93 (m, 4 H), 4.06 (ddd, J=8.1, 7.4, 4.4 Hz, 1 H), 4.45 (br d, J=2.7 Hz, 1 H), 4.66 (ddd, J=11.5, 7.1, 1.5 Hz, 1 H), 5.08 (d, J=1.7 Hz, 1 H), 5.39 (br s, 1 H), 5.48 (d, J=2.6 Hz, 1 H), 6.01 (d, J=11.2 Hz, 1 H), 6.20 (d, J=2.6 Hz, 1 H), 6.40 (d, J=11.2 Hz, 1 H).

LRMS m/z 556 (M$^+$), 538, 520, 462, 408

HRMS calcd for C$_{34}$H$_{52}$O$_6$ 556.3764, found 556.3768

Example 56

Synthesis of 2α-(3-hydroxypropoxy)-20(R)-(tetrahydro-3-methylene-2-furanone-4(S)-isobutyl-5(S)-yl) methyl-9,10-secopregna-5(Z),7(E),10(19)-triene-1α, 3β-diol (Compound No. 1107b)

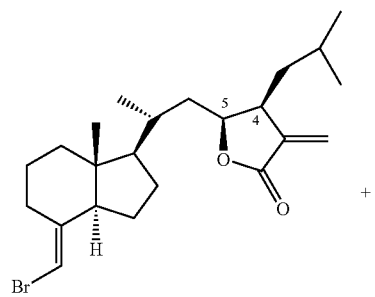

(4syn) (Z = (2-1), Y = Br,
R$^{2c}$ = i-Bu, 4S/5S)

156
-continued

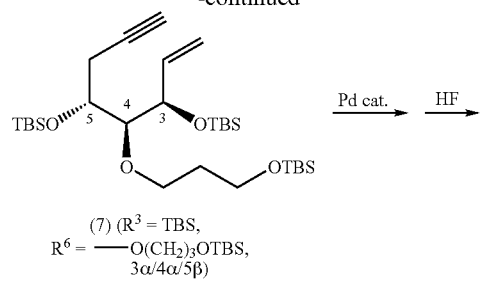

(7) (R$^3$ = TBS,
R$^6$ = —O(CH$_2$)$_3$OTBS,
3α/4α/5β)

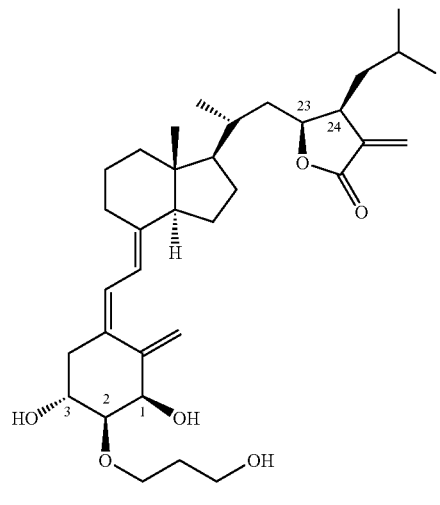

No. 1107b
(1α/2α/3β/23S/24S)

Using 22 mg (51 μmol) of Compound (4syn) (Z (2-1), Y=Br, R$^{2c}$=i-Bu, 4S/5S) obtained in Example 20(1) and 43 mg (77 mmol) of Compound (7) (R$^3$=TBS, R$^6$=—O(CH$_2$)$_3$OTBS, 3α/4α/5β), a reaction similar to Example 14(2-a) was carried out to obtain 16 mg of Compound No. 1107b. Yield: 56%.

$^1$H-NMR (CDCl$_3$) δ: 0.55 (s, 3 H), 0.94 (d, J=6.4 Hz, 3 H), 0.95 (d, J=6.4 Hz, 3 H), 1.05 (d, J=6.4 Hz, 3 H), 1.19-2.05 (m, 19 H), 2.23 (dd, J=13.3, 9.3 Hz, 1 H), 2.67 (dd, J=13.3, 4.4 Hz, 1 H), 2.73 (br s, 3 H), 2.83 (m, 1 H), 3.02 (m, 1 H), 3.37 (dd, J=7.9, 3.1 Hz, 1 H), 3.73-3.93 (m, 4 H), 4.05 (ddd, J=7.9, 7.9, 4.5 Hz, 1 H), 4.45 (br d, J=2.4 Hz, 1 H), 4.58 (ddd, J=8.5, 6.5, 4.1 Hz, 1 H), 5.09 (d, J=1.5 Hz, 1 H), 5.38 (br s, 1 H), 5.48 (d, J=1.9 Hz, 1 H), 6.01 (d, J=11.2 Hz, 1 H), 6.19 (d, J=1.9 Hz, 1 H), 6.41 (d, J=11.2 Hz, 1 H).

LRMS m/z 556 (M$^+$), 538, 520, 462, 444, 408, 393, 249

HRMS calcd for C$_{34}$H$_{52}$O$_6$ 556.3764, found 556.3762

Example 57

Synthesis of 2α-(3-hydroxypropoxy)-20(R)-(tetrahydro-3-methylene-2-furanone-4(R)-isobutyl-5(S)-yl)methyl-9,10-secopregna-5(Z),7(E), 10(19)-triene-1α,3β-diol (Compound No. 1107c)

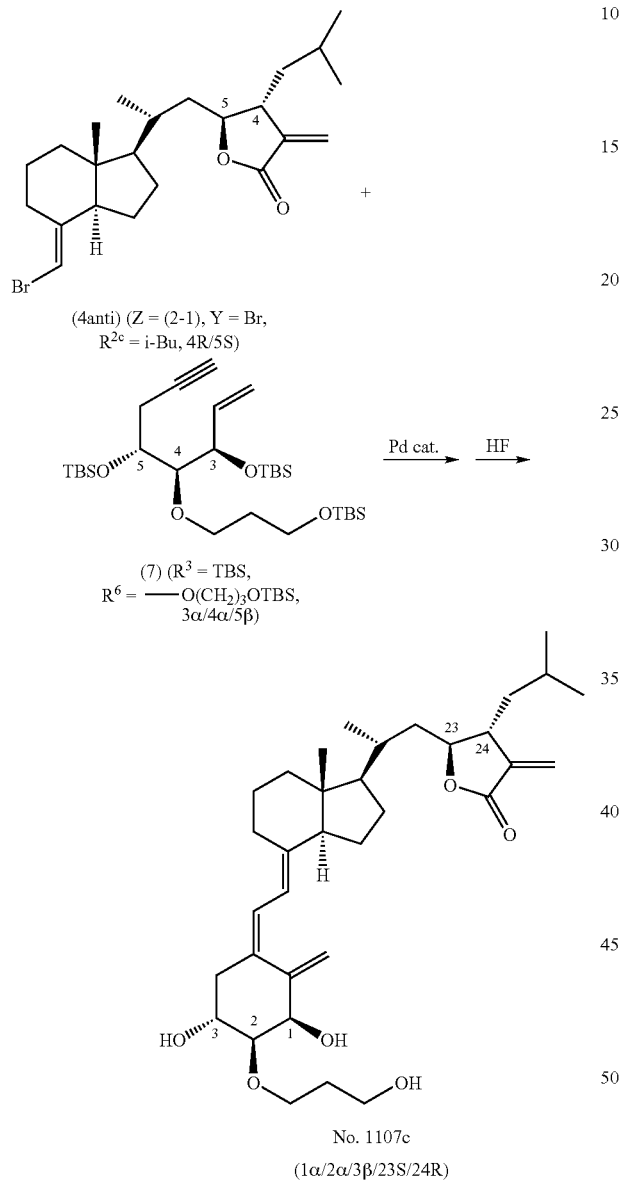

Using 19 mg (44 μmol) of Compound (4anti) (Z=(2-1), Y=Br, R$^{2c}$=i-Bu, 4R/5S) obtained in Example 21(4) and 37 mg (67 μmol) of Compound (7) (R$^3$=TBS, R$^6$=—O(CH$_2$)$_3$OTBS, 3α/4α/5β, a reaction similar to Example 14(2-a) was carried out to obtain 11 mg of Compound No. 1107c. Yield: 43%.

$^1$H-NMR (CDCl$_3$) δ: 0.55 (s, 3 H), 0.95 (d, J=6.4 Hz, 3 H), 0.96 (d, J=6.6 Hz, 3 H), 1.05 (d, J=5.9 Hz, 3 H), 1.10-1.75 (m, 14 H), 1.82-1.93 (m, 3 H), 1.95-2.05 (m, 2 H), 2.24 (dd, J=13.1, 9.4 Hz, 1 H), 2.30-2.70 (m, 4 H), 2.68 (dd, J=13.1, 4.2 Hz, 1 H), 2.83 (m, 1 H), 3.38 (dd, J=7.6, 3.2 Hz, 1 H), 3.73-3.93 (m, 4 H), 4.05 (ddd, J=8.7, 7.6, 4.5 Hz, 1 H), 4.20 (m, 1H), 4.44 (br d, J=3.2 Hz, 1 H), 5.09 (d, J=1.5 Hz, 1 H), 5.38 (d, J=1.5 Hz, 1 H), 5.57 (d, J=2.1 Hz, 1 H), 6.01 (d, J=11.2 Hz, 1 H), 6.13 (d, J=2.1 Hz, 1 H), 6.41 (d, J=11.2 Hz, 1 H).

LRMS m/z 556 (M$^+$), 538, 520, 462, 444, 408, 393, 249
HRMS calcd for C$_{34}$H$_{52}$O$_6$ 556.3764, found 556.3770

Example 58

Synthesis of 2α-(3-hydroxypropoxy)-20(R)-(tetrahydro-3-methylene-2-furanone-4(S)-isobutyl-5(R)-yl)methyl-9,10-secopregna-5(Z),7(E),10(19)-triene-1α,3β-diol (Compound No. 1107d)

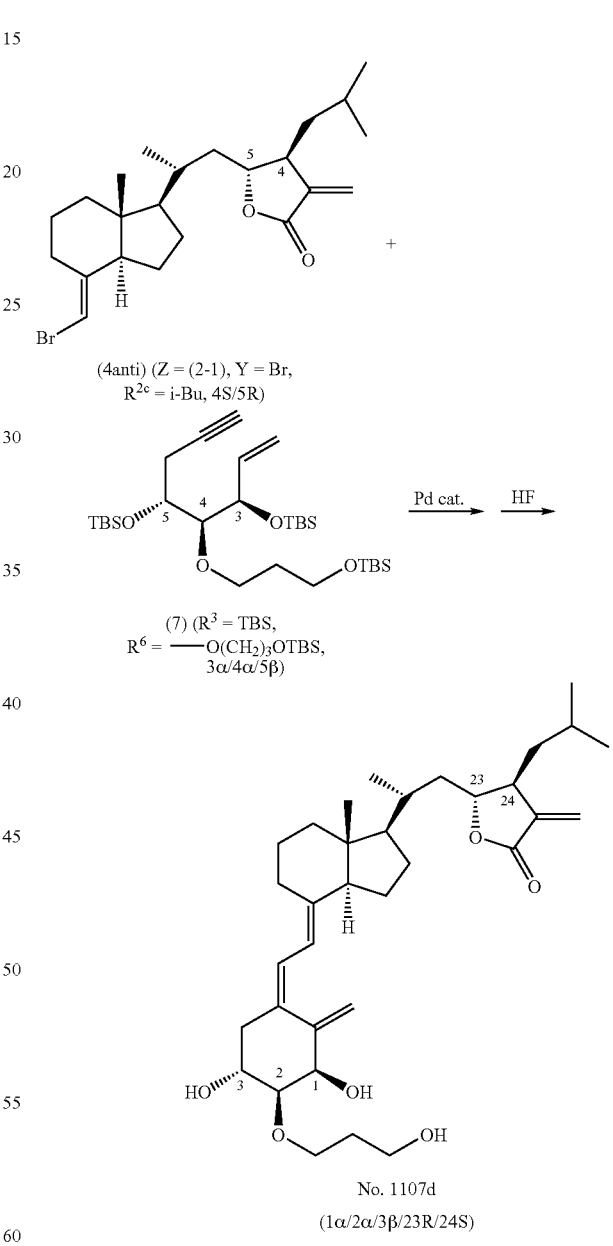

Using 10 mg (22 μmol) of Compound (4anti) (Z=(2-1), Y=Br, R$^{2c}$=i-Bu, 4S/5R) obtained in Example 22(5) and 19 mg (34 μmol) of Compound (7) (R$^3$=TBS, R$^6$=—O(CH$_2$)$_3$OTBS, 3α/4α/5β, a reaction similar to Example 14(2-a) was carried out to obtain 6 mg of Compound No. 1107d. Yield: 50%.

¹H-NMR (CDCl₃) δ: 0.56 (s, 3 H), 0.95 (d, J=6.6 Hz, 3 H), 0.96 (d, J=6.6 Hz, 3 H), 1.01 (d, J=6.6 Hz, 3 H), 1.20-1.90 (m, 17 H), 1.93-2.06 (m, 2 H), 2.23 (dd, J=13.6, 8.7 Hz, 1 H), 2.30-2.73 (m, 3 H), 2.62 (m, 1 H), 2.68 (dd, J=13.6, 4.4 Hz, 1 H), 2.83 (m, 1 H), 3.37 (dd, J=7.5, 3.2 Hz, 1 H), 3.75-3.92 (m, 4 H), 4.06 (ddd, J=8.6, 7.5, 3.2 Hz, 1 H), 4.24 (ddd, J=11.0, 4.8, 2.1 Hz, 1 H), 4.44 (d, J=3.2 Hz, 1 H), 5.08 (d, J=2.0 Hz, 1 H), 5.39 (s, 1 H), 5.56 (d, J=2.6 Hz, 1 H), 6.01 (d, J=11.4 Hz, 1 H), 6.24 (d, J=2.6 Hz, 1 H), 6.41 (d, J=11.4 Hz, 1 H).

LRMS m/z 556 (M⁺), 538, 520, 462, 444, 408, 393, 249
HRMS calcd for $C_{34}H_{52}O_6$ 556.3764, found 556.3765

Example 59

Synthesis of 20(R)-(tetrahydro-3-methylene-2-furanone-4(R)-phenyl-5(R)-yl)methyl-9,10-secopregna-5(Z),7(E),10(19)-triene-1α,3β-diol (Compound No. 109a) and 20(R)-(tetrahydro-3-methylene-2-furanone-4(S)-phenyl-5(S)-yl)methyl-9,10-secopregna-5(Z),7(E),10(19)-triene-1α,3β-diol (Compound No. 109b)

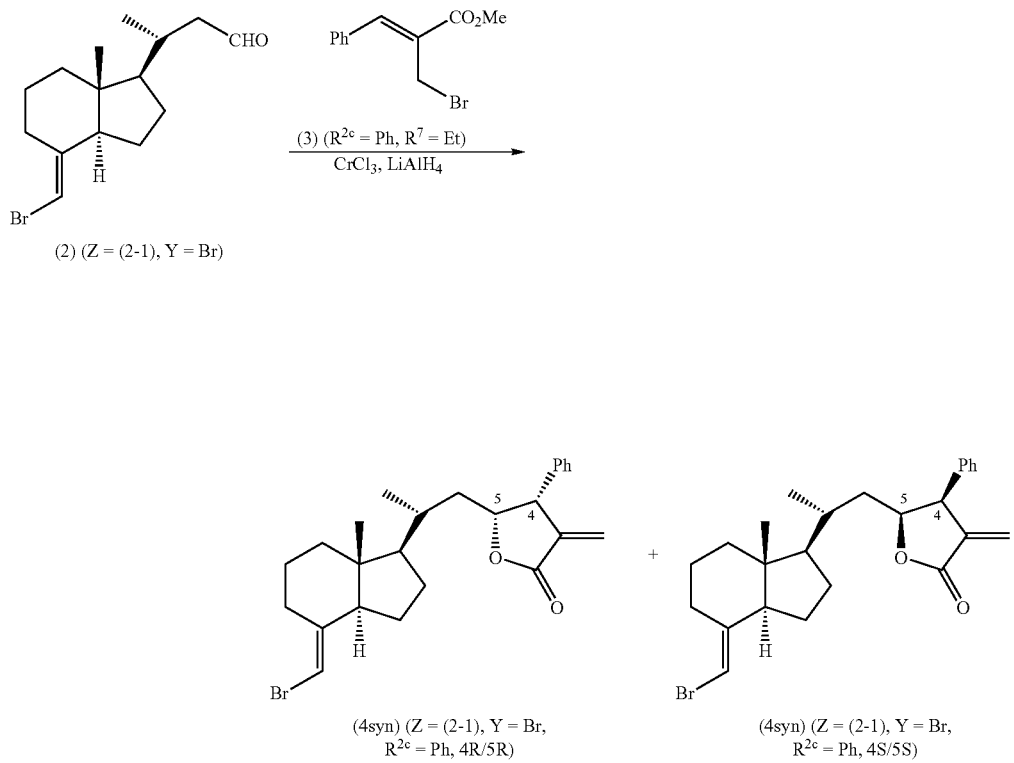

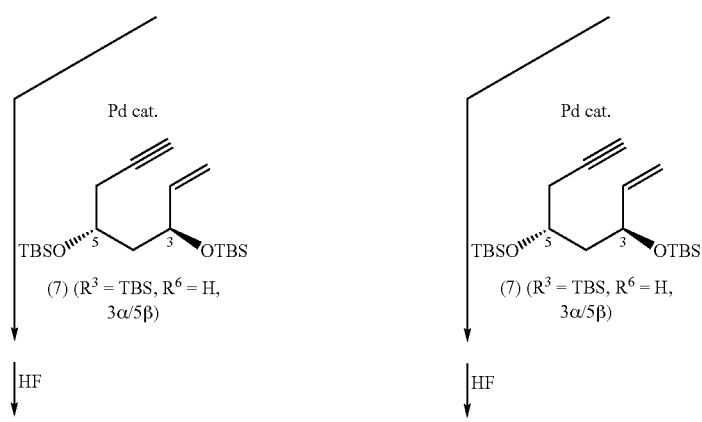

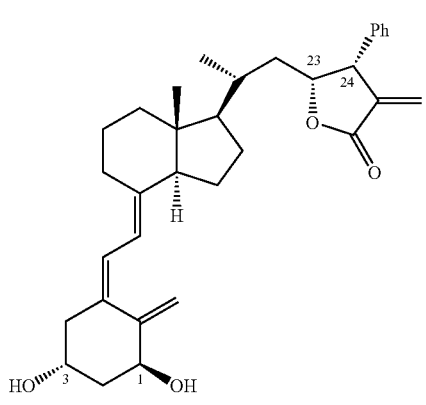

No. 109a (1α/3β/23R/24R)

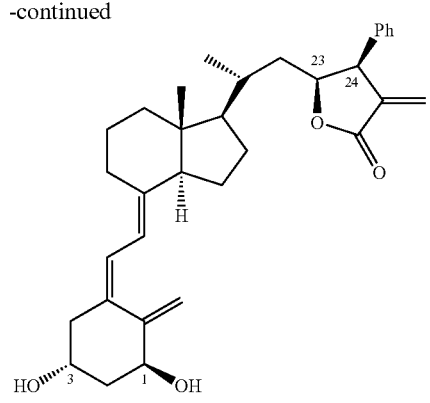

No. 109b (1α/3β/23S/24S)

(1) Using 30 mg (0.101 mmol) of Compound (2) (Z=(2-1), Y=Br) obtained by a method known in the literature (for example, the specification of International Publication WO 95/33716), a reaction similar to Example 11(1) was carried out to obtain 513 mg (yield: 49%) of Compound (4syn) (Z=(2-1), Y=Br, $R^{2c}$=Ph, 4R/5R) and 486 mg (yield: 47%) of Compound (4syn) (Z=(2-1), Y=Br, $R^{2c}$=Ph, 4S/5S). However, instead of Compound (3) ($R^{2c}$=Me, $R^7$=Me) in Example 11(1), used was Compound (3) ($R^{2c}$=Ph, $R^7$=Me) which was obtained by using methyl acrylate in place of ethyl acrylate, as in Reference Example 9. Compound (4syn) (Z=(2-1), Y=Br, $R^{2c}$=Ph, 4R/5R):

$[\alpha]_D^{23}$+266.7 (c 1.08, CHCl$_3$)

$^1$H-NMR (CDCl$_3$) δ: 0.54 (s, 3 H), 0.61 (ddd, J=2.0, 10.7, 14.6 Hz, 1 H), 0.93 (d, J=6.6 Hz, 3 H), 1.09 (dddd, J=9.6, 9.6, 9.6, 9.6 Hz, 1 H), 1.14-1.26 (m, 2 H), 1.34 (ddd, J=2.3, 12.0, 14.4 Hz, 1 H), 1.37-1.45 (m, 2 H), 1.53 (m, 1 H), 1.59-1.65 (m, 3 H), 1.70 (m, 1 H), 1.87 (ddd, J=1.6, 6.8, 12.3 Hz, 1 H), 1.95 (br d, J=12.4 Hz, 1 H), 2.85 (m, 1 H), 4.36 (ddd, J=8.0, 2.6, 2.6 Hz, 1 H), 4.86 (ddd, J=2.2, 8.0, 11.8 Hz, 1 H), 5.615 (s, 1 H), 5.617 (d, J=2.6 Hz, 1 H), 6.46 (d, J=2.6 Hz, 1 H), 7.11-7.13 (m, 2 H), 7.30 (tt, J=1.7, 7.3 Hz, 1 H), 7.35 (br t, J=7.3 Hz, 2 H).

$^{13}$C-NMR (CDCl$_3$) δ: 11.8, 18.3, 21.9, 22.4, 27.4, 30.9, 32.6, 39.0, 39.8, 45.5, 49.6, 55.8, 56.0, 88.8, 97.6, 124.3, 127.7, 128.7 (2 C), 129.0 (2 C), 137.6, 139.0, 144.8, 170.4.

LRMS m/z 442 (M$^+$), 363, 201, 175, 147

HRMS calcd for C$_{25}$H$_{31}$O$_2$$^{79}$Br 442.1507, found 442.1506

Compound (4syn) (Z=(2-1), Y=Br, $R^{2c}$=Ph, 4S/5S):

$[\alpha]_D^{24}$−24.8 (c 0.69, CHCl$_3$)

$^1$H-NMR (CDCl$_3$) δ: 0.38 (s, 3 H), 0.52 (m, 1 H), 0.97 (d, J=6.0 Hz, 3 H), 1.16-1.28 (m, 5 H), 1.36-1.42 (m, 2 H), 1.48-1.55 (m, 2 H), 1.59-1.64 (m, 2 H), 1.88 (ddd, J=1.5, 6.6, 12.5 Hz, 1H), 1.91 (br d, J=14.0 Hz, 1 H), 2.83 (m, 1 H), 4.26 (ddd, J=2.2, 2.2, 7.2 Hz, 1 H), 4.82 (ddd, J=7.2, 7.2, 7.2 Hz, 1 H), 5.58 (dd, J=1.6, 1.6 Hz, 1 H), 5.61 (d, J=2.1 Hz, 1 H), 6.41 (d, J=2.1 Hz, 1 H), 7.12-7.13 (m, 2 H), 7.29 (tt, J=1.7, 7.3 Hz, 1 H), 7.33 (br t, J=7.3 Hz, 2H).

$^{13}$C-NMR (CDCl$_3$) δ: 11.7, 19.1, 21.8, 22.4, 26.6, 30.9, 33.1, 37.5, 39.7, 45.4, 49.6, 55.6, 55.8, 80.3, 97.5, 124.2, 127.7, 128.7 (2 C), 129.0 (2 C), 138.4, 139.8, 144.9, 170.5.

LRMS m/z 442 (M$^+$), 363, 201, 175, 147

HRMS calcd for C$_{25}$H$_{31}$O$_2$$^{79}$Br 442.1507, found 442.1499

(2-a) Using 15 mg (34 μmol) of Compound (4syn) (Z=(2-1), Y=Br, $R^{2c}$=Ph, 4R/5R) obtained by the above method and 19 mg (51 μmol) of Compound (7) ($R^3$=TBS, $R^6$=hydrogen atom, 3α/5β), a reaction similar to Example 14(2-a) was carried out to obtain 8 mg of Compound No. 109a. Yield: 47%.

Compound No. 109a:

$[\alpha]_D^{28}$+191.6 (c 0.58, CHCl$_3$)

$^1$H-NMR (CDCl$_3$) δ: 0.52 (s, 3 H), 0.61 (ddd, J=2.0, 10.6, 14.6 Hz, 1 H), 0.92 (d, J=6.6 Hz, 3 Hz), 1.09-1.15 (m, 2 H), 1.18-1.43 (m, 5 H), 1.47-1.70 (m, 6 H), 1.86-2.05 (m, 4 H), 2.30 (dd, J=6.6, 13.4 Hz, 1 H), 2.59 (dd, J=3.4, 12.9 Hz, 1 H), 2.79 (dd, J=3.9, 12.0 Hz, 1 H), 4.22 (m, 1 H), 4.36 (ddd, J=2.7, 2.7, 7.9 Hz, 1 H), 4.42 (ddd, J=4.3, 4.3, 8.5 Hz, 1 H), 4.90 (ddd, J=1.9, 7.9, 11.8 Hz, 1 H), 5.00 (br s, 1 H), 5.32 (br s, 1 H), 5.61 (d, J=2.7 Hz, 1 H), 5.98 (d, J=12.3 Hz, 1 H), 6.35 (d, J=12.3 Hz, 1 H), 6.46 (d, J=2.7 Hz, 1 H), 7.11-7.13 (m, 2 H), 7.29-7.37 (m, 3 H).

$^{13}$C-NMR (CDCl$_3$) δ: 12.0, 18.3, 22.1, 23.5, 27.4, 29.0, 32.7, 39.1, 40.4, 42.8, 45.2, 45.9, 49.7, 56.3, 56.8, 66.8, 70.7, 78.9, 111.7, 117.1, 124.3, 124.8, 127.7, 128.7 (2 C), 129.1 (2 C), 133.0, 137.6, 139.0, 142.8, 147.6, 170.5.

LRMS m/z 502 (M$^+$), 484, 466, 451, 278, 251, 209

HRMS calcd for C$_{33}$H$_{42}$O$_4$ 502.3083, found 502.3078

(2-b) Using 27 mg (61 μmol) of Compound (4syn) (Z=(2-1), Y=Br, $R^{2c}$=Ph, 4S/5S) obtained by the above method and 34 mg (92 μmol) of Compound (7) ($R^3$=TBS, $R^6$=Hydrogen atom, 3α/5β), a reaction similar to Example 14(2-a) was carried out to obtain 18 mg of Compound No. 109b. Yield: 59%.

Compound No. 109b:

$[\alpha]_D^{26}$−35.5 (c 1.00, CHCl$_3$)

$^1$H-NMR (CDCl$_3$) δ: 0.37 (s, 3 H), 0.52 (m, 1 H), 0.96 (d, J=5.6 Hz, 3 H), 1.15-1.35 (m, 7 H), 1.41 (dd, J=7.0, 11.4 Hz, 1 H), 1.47-1.66 (m, 6 H), 1.85-2.04 (m, 4 H), 2.30 (dd, J=7.0, 13.3 Hz, 1 H), 2.59 (dd, J=3.3, 13.3 Hz, 1 H), 2.78 (dd, J=3.8, 12.6 Hz, 1 H), 4.22 (m, 1 H), 4.26 (ddd, J=2.2, 2.2, 7.2 Hz, 1 H), 4.23 (m, 1 H), 4.82 (ddd, J=7.2, 7.2, 14.7 Hz, 1 H), 4.98 (s, 1H), 5.32 (s, 1 H), 5.60 (d, J=2.2 Hz, 1 H), 5.94 (d, J=11.2 Hz, 1 H), 6.35 (d, J=11.2 Hz, 1H), 6.40 (d, J=2.2 Hz, 1 H), 7.11-7.13 (m, 2 H), 7.29-7.36 (m, 3 H).

$^{13}$C-NMR (CDCl$_3$) δ: 11.9, 19.2, 22.1, 23.5, 26.8, 29.0, 33.3, 37.6, 40.4, 42.9, 45.3, 45.8, 49.7, 56.1, 56.6, 66.8, 70.9, 80.5, 111.9, 117.0, 124.0, 124.9, 127.6, 128.7 (2 C), 128.9 (2 C), 132.8, 138.3, 139.8, 142.8, 147.4, 170.432.

LRMS m/z 502 (M$^+$), 484, 466, 451, 278, 251, 209

HRMS calcd for C$_{33}$H$_{42}$O$_4$ 502.3083, found 502.3081

Example 60

Synthesis of 20(R)-(tetrahydro-3-methylene-2-furanone-4(R)-phenyl-5(S)-yl)methyl-9,10-secopregna-5(Z),7(E),10(19)-triene-1α,3β-diol (Compound No. 109c)

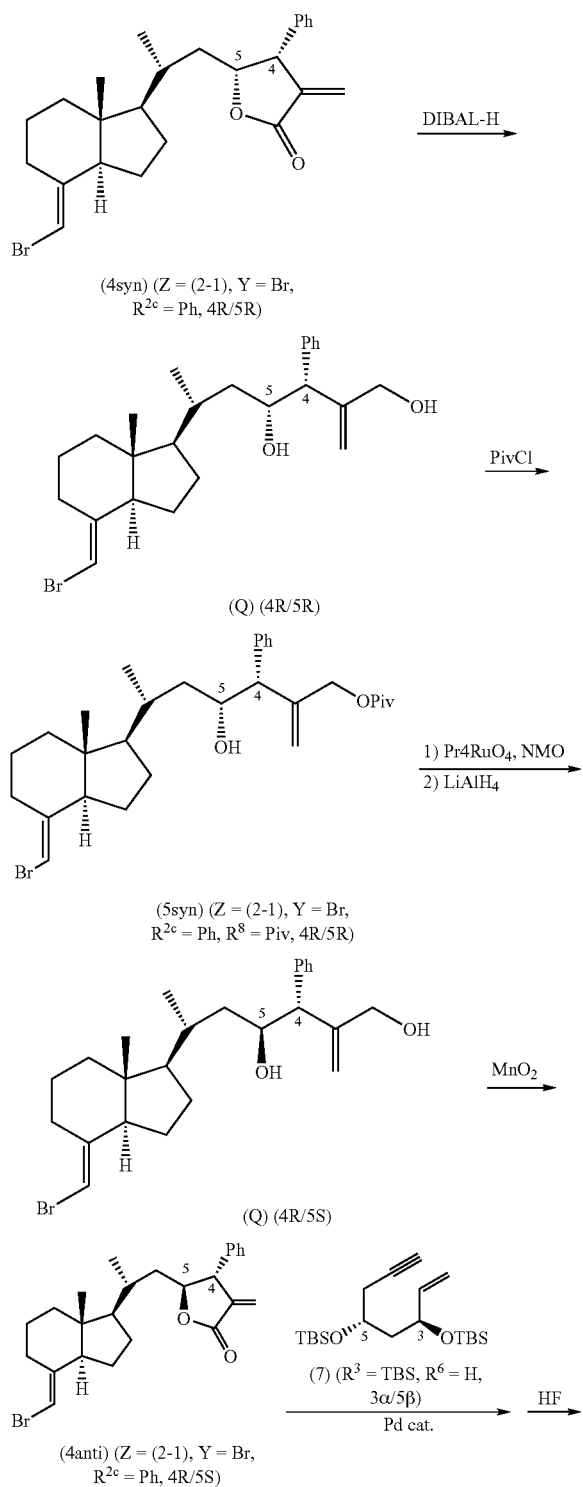

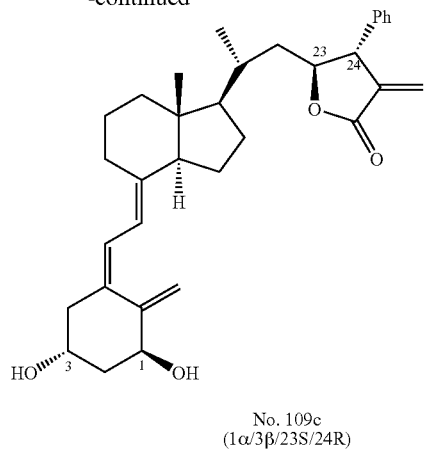

No. 109c
(1α/3β/23S/24R)

(1) Using 400 mg (0.90 mmol) of Compound (4syn) (Z=(2-1), Y=Br, $R^{2c}$=Ph, 4R/5R) obtained in Example 59(1), a reaction similar to Example 12(1) was carried out to obtain 373 mg of Compound (O) (4R/5R). Yield: 92%, a colorless solid substance.

$[\alpha]_D^{22}$+45.2 (c 1.08, CHCl$_3$)

$^1$H-NMR (CDCl$_3$) δ: 0.58 (s, 3 H), 1.02 (d, J=6.4 Hz, 3 H), 1.20-1.36 (m, 5 H), 1.41-1.75 (m, 8H), 1.86 (m, 1 H), 1.96 (ddd, J=1.7, 6.8, 12.2 Hz, 1 H), 2.03 (m, 1 H), 2.88 (m, 1 H), 3.23 (d, J=8.3 Hz, 1 H), 3.98 (s, 2 H), 4.23 (br dd, J=8.3, 8.5 Hz, 1 H), 5.16 (s, 1 H), 5.24 (s, 1 H), 5.63 (s, 1 H), 7.23-7.35 (m, 5 H).

$^{13}$C-NMR (CDCl$_3$) δ: 12.0, 18.7, 22.1, 22.6, 27.8, 31.1, 32.9, 40.0, 41.7, 45.7, 56.0, 56.42, 56.43, 65.8, 69.8, 97.4, 111.5, 127.1, 128.6 (2 C), 128.9 (2 C), 139.6, 145.0, 149.3.

LRMS m/z 446 (M$^+$), 428, 349, 331, 254

HRMS calcd for $C_{25}H_{31}O_2{}^{79}$Br 446.1820, found 446.1820

(2) Using 460 mg (1.0 mmol) of Compound (Q) (4R/5R) obtained by the above method, a reaction similar to Example 12(2) was carried out to obtain 513 mg of Compound (5syn) (Z=(2-1), Y=Br, $R^{2c}$=Ph, $R^8$=Piv, 4R/5R). Yield: 94%, a colorless oily substance.

$[\alpha]_D^{19}$+37.1 (c 1.54, CHCl$_3$)

$^1$H-NMR (CDCl$_3$) δ: 0.58 (s, 3 H), 1.02 (d, J=6.3 Hz, 3 H), 1.19 (s, 9 H), 1.23-1.38 (m, 5 H), 1.41-1.58 (m, 4 H), 1.60-1.75 (m, 3 H), 1.86 (m, 1 H), 1.96 (br dd, J=6.6, 12.2 Hz, 1 H), 2.03 (m, 1 H), 2.88 (m, 1 H), 3.20 (d, J=8.1 Hz, 1 H), 4.21 (br dd, J=8.7, 8.7 Hz, 1 H), 4.39 (s, 2H), 5.22 (s, 1 H), 5.25 (s, 1 H), 5.63 (s, 1 H), 7.24-7.35 (m, 5 H).

$^{13}$C-NMR (CDCl$_3$) δ: 12.1, 18.7, 22.2, 22.7, 27.3 (3 C), 27.8, 31.1, 32.9, 38.9, 40.0, 41.7, 45.7, 56.0, 56.2, 56.4, 66.7, 69.6, 97.4, 111.5, 127.2, 128.6 (2 C), 128.8 (2 C), 138.9, 144.5, 144.8, 177.7.

LRMS m/z 429 ((M−OPiv)$^+$), 411, 332, 255

HRMS calcd for $C_{25}H_{34}O^{79}$Br 429.1793, found 429.1797

(3) A reaction solution was prepared by adding 324 mg (0.92 mmol) of tetrapropylammonium perruthenate (Pr$_4$NRuO$_4$) and 771 mg (6.6 mmol) of N-methylmorphorine N-oxide (NMO) to a methylene chloride solution (6.6 ml) containing 700 mg (1.3 mmol) of Compound (5syn) (Z=(2-1), Y=Br, $R^{2c}$=Ph, $R^8$=Piv, 4R/5R) obtained by the above method and was stirred at room temperature for one hour. The reaction solution was filtered, and the filtrate was concentrated. The resultant crude product was dissolved in THF (10 ml). To this solution was added 82 mg (2.2 mmol) of LiAlH$_4$ at 0° C. and the resultant solution was stirred at room temperature for 3.5 hours. To this reaction solution was added water, and the resultant solution was subjected to extraction with ethyl acetate. The organic layer was washed with saturated brine and dried with anhydrous sodium sulfate. The residue obtained by distilling off the solvent was purified by silica gel column chromatography (hexane:ethyl acetate=4:1) to obtain 126 mg of Compound (O) (4R/5S). Yield: 19%, a colorless oily substance.

$[\alpha]_D^{25}$ +44.1 (c 2.31, CHCl$_3$)

$^1$H-NMR (CDCl$_3$) δ: 0.45 (s, 3 H), 0.99 (d, J=6.6 Hz, 3 H), 1.13-1.38 (m, 5 H), 1.40-1.73 (m, 8 H), 1.87-1.96 (m, 2 H), 2.25 (m, 1 H), 2.85 (m, 1 H), 3.33 (d, J=8.0 Hz, 1 H), 3.98 (d, J=13.4 Hz, 1 H), 4.04 (d, J=13.4 Hz, 1 H), 4.23 (ddd, J=4.2, 7.7, 8.0 Hz, 1 H), 5.32 (br s, 1 H), 5.33 (br s, 1 H), 5.60 (br s, 1 H), 7.20-7.32 (m, 5 H).

$^{13}$C-NMR (CDCl$_3$) δ: 11.7, 20.2, 22.1, 22.6, 27.5, 31.0, 35.2, 39.8, 41.8, 45.5, 55.7, 56.4, 57.3, 65.3, 72.4, 97.3, 113.3, 126.9, 128.3 (2 C), 128.5 (2 C), 140.5, 145.0, 148.8.

LRMS m/z 446 (M$^+$), 428, 349, 331, 254

HRMS calcd for C$_{25}$H$_{35}$O$_2^{79}$Br 446.1820, found 446.1828

(4) A solution was prepared by dissolving 136 mg (0.304 mmol) of Compound (O) (4R/5S) obtained by the above method in methylene chloride (3 ml). A reaction solution was prepared by adding 2.4 g (27.6 mmol) of MnO$_2$ to the above solution and was stirred at room temperature for 32 hours. After the reaction solution was filtered, the residue obtained by concentrating the filtrate was purified by silica gel column chromatography (hexane:ethyl acetate=19:1) to obtain 104 mg of Compound (4anti) (Z=(2-1), Y=Br, R$^c$=Ph, 4R/5S). Yield: 77%, a colorless oily substance.

$[\alpha]_D^{25}$ +59.51 (c 0.69, CHCl$_3$)

$^1$H-NMR (CDCl$_3$) δ: 0.48 (s, 3 H), 0.86 (d, J=6.6 Hz, 3 H), 1.17-1.32 (m, 3 H), 1.34-1.52 (m, 4 H), 1.57-1.72 (m, 3 H), 1.80 (ddd, J=3.5, 5.6, 14.3 Hz, 1 H), 1.87-2.00 (m, 3 H), 2.86 (m, 1H), 3.72 (ddd, J=3.2, 3, 6.8 Hz, 1 H), 4.46 (ddd, J=6.5, 6.5, 6.8 Hz, 1 H), 5.34 (d, J=3.2 Hz, 1 H), 5.63 (s, 1 H), 6.32 (d, J=3.3 Hz, 1 H), 7.19-7.21 (m, 2 H), 7.30 (m, 1 H), 7.35-7.38 (m, 2 H).

$^{13}$C-NMR (CDCl$_3$) δ: 11.9, 18.5, 22.1, 22.5, 27.6, 31.0, 33.0, 39.9, 41.3, 45.6, 53.5, 55.9, 56.0, 82.8, 97.6, 123.3, 127.8, 128.3 (2 C), 129.1 (2 C), 138.4, 140.2, 144.7, 169.6.

LRMS m/z 442 (M$^+$), 363, 227, 201, 175, 147

HRMS calcd for C$_{25}$H$_{31}$O$_2^{79}$Br 442.1507, found 442.1499

(5) Using 16 mg (36 µmol) of Compound (4anti) (Z=(2-1), Y=Br, R$^{2c}$=Ph, 4R/5S) obtained by the above method and 20 mg (54 µmol) of Compound (7) (R$^3$=TBS, R$^6$=Hydrogen atom, 3α/5β), a reaction similar to Example 14(2-a) was carried out to obtain 10 mg of Compound No. 109c. Yield: 55%.

Compound No. 109c:

$[\alpha]_D^{26}$ +7.22 (c 0.69, CHCl$_3$)

$^1$H-NMR (CDCl$_3$) δ: 0.46 (s, 3 H), 0.85 (d, J=6.6 Hz, 3 H), 1.13-1.40 (m, 3 H), 1.46-1.55 (m, 6H), 1.63-1.72 (m, 3 H), 1.81 (ddd, J=3.4, 5.6, 14.2 Hz, 1 H), 1.87-2.05 (m, 5 H), 2.31 (dd, J=6.3, 13.5 Hz, 1 H), 2.59 (dd, J=3.5, 13.5 Hz, 1 H), 2.80 (m, 1 H), 3.72 (ddd, J=3.4, 3.4, 7.0 Hz, 1 H), 4.22 (m, 1 H), 4.45 (m, 1 H), 4.50 (ddd, J=6.7, 6.7, 6.9 Hz, 1 H), 4.99 (s, 1 H), 5.32 (br s, 1 H), 5.35 (d, J=3.1 Hz, 1 H), 6.00 (d, J=11.1 Hz, 1 H), 6.33 (d, J=3.1 Hz, 1 H), 6.36 (d, J=11.1 Hz, 1 H), 7.19-7.21 (m, 2 H), 7.29-7.32 (m, 1 H), 7.35-7.39 (m, 2 H).

$^{13}$C-NMR (CDCl$_3$) δ: 11.9, 19.3, 22.3, 23.5, 27.9, 29.1, 34.1, 40.3, 41.7, 42.9, 45.3, 45.9, 53.5, 56.2, 56.5, 66.9, 70.8, 84.3, 111.7, 117.1, 123.4, 124.9, 127.7, 128.3 (2 C), 129.1 (2 C), 133.0, 139.1, 140.5, 142.7, 147.6, 169.7.

LRMS m/z 502 (M$^+$), 484, 466, 451, 278, 251, 209

HRMS calcd for C$_{33}$H$_{42}$O$_4$ 502.3083, found 502.3077

Example 61

Synthesis of 20(R)-(tetrahydro-3-methylene-2-furanone-4(S)-phenyl-5(R)-yl)methyl-9,10-secopregna-5 (Z),7(E),10(19)-triene-1α,3β-diol (Compound No. 109d)

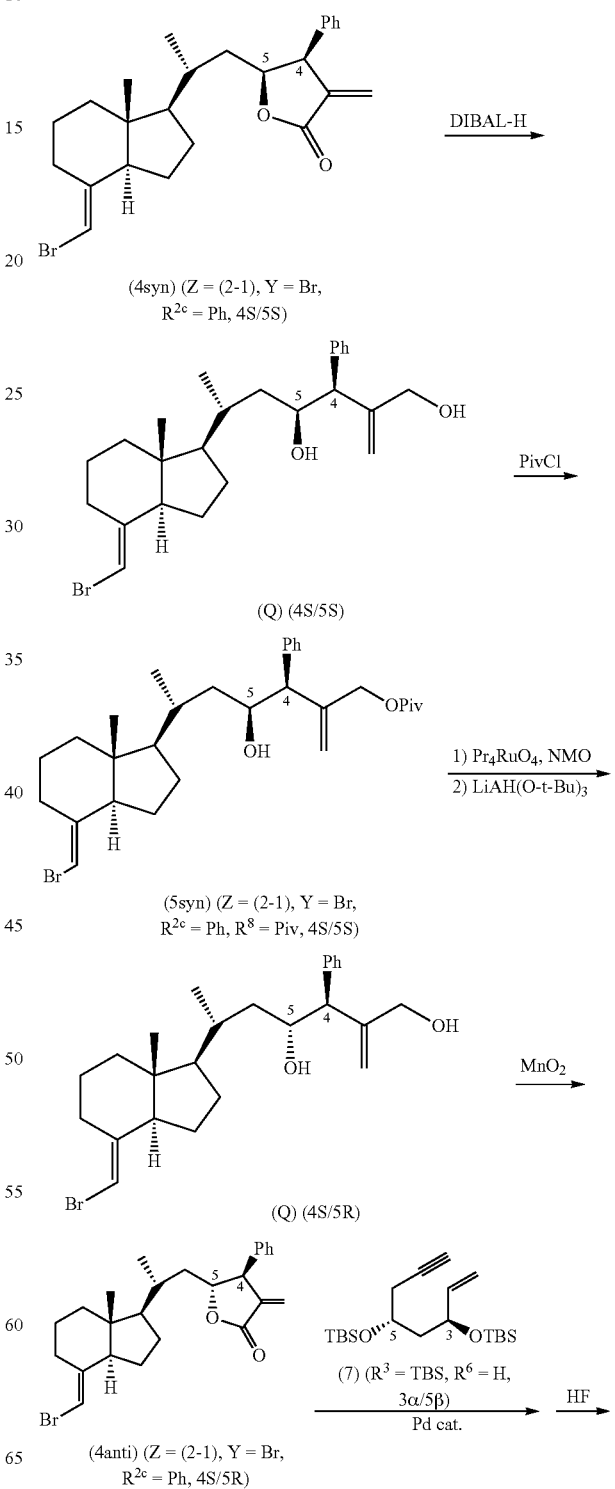

-continued

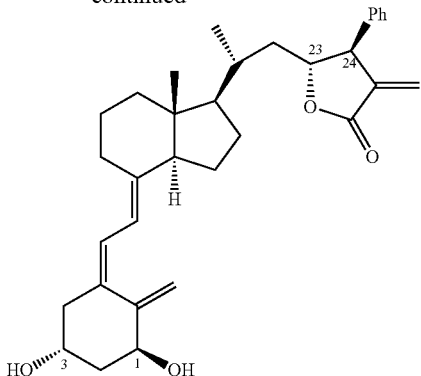

No. 109d
(1α/3β/23R/24S)

(1) Using 330 mg (0.74 mmol) of Compound (4syn) (Z=(2-1), Y=Br, $R^{2c}$=Ph, 4S/5S) obtained in Example 59(1), a reaction similar to Example 12(1) was carried out to obtain 304 mg of Compound (O) (4S/5S). Yield: 91%, a colorless solid substance.

[α]D+105.11 (c 1.08, CHCl$_3$)

$^1$H-NMR (CDCl$_3$) δ: 0.55 (s, 3 H), 1.05 (d, J=6.6 Hz, 3 H), 1.17 (ddd, J=6.8, 8.9, 14.1 Hz, 1H), 1.24-1.32 (m, 2 H), 1.38 (ddd, J=5.2, 12.0, 12.0 Hz, 1 H), 1.43-1.61 (m, 4 H), 1.65-1.83 (m, 6 H), 1.93 (dd, J=6.8, 12.5 Hz, 1 H), 2.00 (br d, J=12.7 Hz, 1 H), 2.87 (m, 1 H), 3.35 (d, J=6.0 Hz, 1 H), 4.00 (d, J=14.5 Hz, 1 H), 4.07 (d, J=14.5 Hz, 1 H), 4.23 (ddd, J=6.0, 6.1, 6.1 Hz, 1 H), 5.16 (s, 1 H), 5.27 (s, 1 H), 5.63 (s, 1 H), 7.26 (m, 1 H), 7.30-7.35 (m, 4 H).

$^{13}$C-NMR (CDCl$_3$) δ: 11.8, 19.7, 22.0, 22.5, 27.4, 31.0, 34.8, 39.8, 41.5, 45.5, 54.7, 55.8, 56.5, 65.7, 72.0, 97.4, 113.0, 127.1, 128.5 (2 C), 129.5 (2 C), 138.9, 145.0, 149.5.

LRMS m/z 428 ((M−H$_2$O)$^+$) 331, 254, 227

HRMS calcd for C$_{25}$H$_{33}$O$^{79}$Br 428.1715, found 428.1718

(2) Using 379 mg (0.85 mmol) of Compound (O) (4S/5S) obtained by the above method, a reaction similar to Example 12(2) was carried out to obtain 420 mg of Compound (5syn) (Z=(2-1), Y=Br, $R^{2c}$=Ph, $R^8$=Piv, 4S/5S). Yield: 93%, a colorless crystalline substance.

[α]$_D^{19}$+108.55 (c 0.31, CHCl$_3$)

$^1$H-NMR (CDCl$_3$) δ: 0.55 (s, 3 H), 1.05 (d, J=6.6 Hz, 3 H), 1.20 (s, 9 H), 1.24-1.34 (m, 4 H), 1.44-1.63 (m, 5 H), 1.65-1.73 (m, 3 H), 1.79 (m, 1 H), 1.94 (ddd, J=1.2, 6.8, 12.5 Hz, 1 H), 2.00 (m, 1 H), 2.87 (m, 1 H), 3.47 (d, J=5.9 Hz, 1 H), 4.22 (m, 1 H), 4.40 (d, J=13.3 Hz, 1H), 4.46 (d, J=13.3 Hz, 1 H), 5.25 (s, 1 H), 5.28 (s, 1 H), 5.63 (s, 1 H), 7.25-7.33 (m, 5 H).

$^{13}$C-NMR (CDCl$_3$) δ: 11.9, 19.8, 22.1, 22.7, 27.3, 27.6, 31.1, 35.0, 38.9, 39.9, 41.6, 45.6, 54.2, 55.8, 56.5, 66.7, 71.7, 97.4, 114.1, 127.1, 128.4 (2 C), 129.4 (2 C), 138.0, 144.78, 144.84, 177.8.

LRMS m/z 429 ((M−OPiv)$^+$) 350, 232, 175

HRMS calcd for C$_{25}$H$_{34}$O$^{79}$Br 470.1793, found 429.1792

(3) Using 405 mg (0.76 mmol) of Compound (5syn) (Z=(2-1), Y=Br, $R^{2c}$=Ph, $R^8$=Piv, 4S/5S) obtained by the above method, a reaction similar to Example 60(3) was carried out by replacing LiAlH$_4$ with LiAl(O-t-Bu)$_3$ to obtain 252 mg of Compound (O) (4S/5R). Yield: 62%, a colorless oily substance.

[α]$_D^{27}$+85.40 (c 1.00, CDCl$_3$)

$^1$H-NMR (CDCl$_3$) δ: 0.57 (s, 3 H), 0.99 (d, J=6.3 Hz, 3 H), 1.10 (m, 1 H), 1.20 (s, 9 H), 1.16-1.33 (m, 3 H), 1.38-1.49 (m, 3 H), 1.51-1.66 (m, 3 H), 1.72-1.85 (m, 2 H), 1.90 (br dd, J=7.0, 11.8 Hz, 1 H), 1.97 (br d, J=12.9 Hz, 1 H), 2.36 (br s, 1 H), 2.85 (m, 1 H), 3.26 (d, J=9.7 Hz, 1 H), 4.27 (br dd, J=9.7, 9.8 Hz, 1 H), 4.36 (d, J=13.9 Hz, 1 H), 4.53 (d, J=13.9 Hz, 1 H), 5.25 (s, 1 H), 5.34 (s, 1 H), 5.62 (s, 1 H), 7.16-7.18 (m, 2 H), 7.21-7.31 (m, 3 H).

$^{13}$C-NMR (CDCl$_3$) δ: 12.0, 18.6, 22.1, 22.6, 27.2 (3 C), 27.7, 31.1, 32.8, 38.8, 39.9, 41.1, 45.6, 56.0, 56.2, 58.4, 66.0, 68.9, 97.4, 113.7, 126.9, 128.1 (2 C), 128.6 (2 C), 139.8, 144.6, 145.0, 178.2.

LRMS m/z 512 ((M−H$_2$O)$^+$) 427, 411, 332, 255

HRMS calcd for C$_{30}$H$_{41}$O$_2^{79}$Br 512.2290, found 512.2291

(4) Using 229 mg (0.431 mmol) of Compound (Q) (4S/5R) obtained by the above method, a reaction similar to Example 60(4) was carried out to obtain 161 mg of Compound (4anti) (Z=(2-1), Y=Br, $R^{2c}$=Ph, 4S/5R). Yield: 84%, a colorless oily substance.

[α]$_D^{25}$+59.5 (c 0.69, CHCl$_3$)

IR (neat) 1765, 1456, 1234, 1140 cm$^{-1}$ $^1$H-NMR (CDCl$_3$) δ: 0.57 (s, 3 H), 0.90 (d, J=6.6 Hz, 3 H), 1.18-1.29 (m, 2 H), 1.32-1.40 (m, 2 H), 1.43-1.67 (m, 4 H), 1.78-1.87 (m, 3 H), 1.92-1.99 (m, 2 H), 2.86 (m, 1 H), 3.71 (m, 1 H), 4.46 (br dd, J=8.3, 8.3 Hz, 1 H), 5.37 (d, J=3.1 Hz, 1 H), 5.65 (s, 1 H), 6.34 (d, J=3.1 Hz, 1 H), 7.19-7.21 (m, 2 H), 7.31-7.40 (m, 3 H).

$^{13}$C-NMR (CDCl$_3$) δ: 11.9, 18.5, 22.1, 22.5, 27.6, 31.0, 33.0, 39.9, 41.3, 45.6, 53.5, 55.9, 56.0, 82.8, 97.6, 123.3, 127.8, 128.3 (2 C), 129.1 (2 C), 138.4, 140.2, 144.7, 169.6.

LRMS m/z 442 (M$^+$), 363, 227, 201, 175, 147

HRMS calcd for C$_{25}$H$_{31}$O$_2^{79}$Br 442.1507, found 442.1499

(5) Using 25 mg (56 μmol) of Compound (4anti) (Z=(2-1), Y=Br, $R^{2c}$=Ph, 4S/5R) obtained by the above method and 31 mg (84 μmol) of Compound (7) ($R^3$=TBS, $R^6$=Hydrogen atom, 3a/5β), a reaction similar to Example 14(2-a) was carried out to obtain 14 mg of Compound No. 109d. Yield: 49%. Compound No. 109d:

[α]$_D^{25}$+14.60 (c 1.00, CHCl$_3$)

$^1$H-NMR (CDCl$_3$) δ: 0.55 (s, 3 H), 0.90 (d, J=6.3 Hz, 3 H), 1.21-1.31 (m, 3 H), 1.36 (m, 1 H), 1.46-1.56 (m, 5 H), 1.64-1.69 (m, 2 H), 1.79-2.03 (m, 7 H), 2.31 (dd, J=6.2, 12.8 Hz, 1 H), 2.60 (br d, J=12.8 Hz, 1 H), 2.82 (m, 1 H), 3.71 (m, 1 H), 4.24 (m, 1 H), 4.44-4.49 (m, 2 H), 5.00 (s, 1 H), 5.33 (s, 1 H), 5.37 (d, J=2.7 Hz, 1 H), 6.00 (d, J=11.2 Hz, 1 H), 6.34-6.38 (m, 2 H), 7.19-7.21 (m, 2 H), 7.32-7.40 (m, 3 H).

$^{13}$C-NMR (CDCl$_3$) δ: 12.1, 18.5, 22.3, 23.5, 27.6, 29.1, 33.0, 40.5, 41.3, 42.9, 45.3, 46.0, 53.5, 56.3, 56.8, 66.9, 70.8, 82.9, 111.8, 117.2, 123.3, 124.8, 127.8, 128.3 (2 C), 129.1 (2 C), 133.0, 138.5, 140.3, 142.6, 147.5, 169.7.

LRMS m/z 502 (M$^+$), 484, 466, 451, 278, 251, 209

HRMS calcd for C$_{33}$H$_{42}$O$_4$ 502.3083, found 502.3081

Example 62

Synthesis of 2α-methyl-20(R)-(tetrahydro-3-methyl-ene-2-furanone-4(R))-phenyl-5(R)-yl)methyl-9,10-secopregna-5(Z),7(E),10(19)-triene-1α,3β-diol (Compound No. 209a)

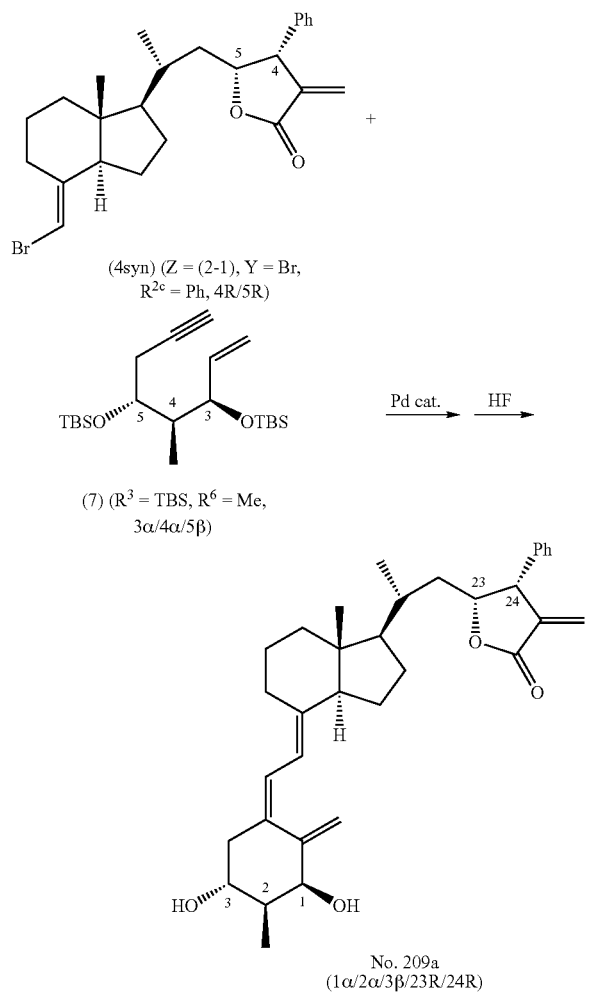

Using 16 mg (36 mmol) of Compound (4syn) (Z=(2-1), Y=Br, $R^{2c}$=Ph, 4R/5R) obtained in Example 59(1) and 21 mg (55 μmol) of Compound (7) ($R^3$=TBS, $R^6$=Me, 3α/4α/5β), a reaction similar to Example 14(2-a) was carried out to obtain 10 mg of Compound No. 209a. Yield: 54%.

[1] H-NMR (CDCl$_3$) δ: 0.51 (s, 3 H), 0.61 (ddd, J=14.5, 10.7, 2.0 Hz, 1 H), 0.91 (d, J=6.6 Hz, 3 H), 1.07 (d, J=6.8 Hz, 3 H), 1.21 (ddd, J=12.9, 12.9, 4.0 Hz, 1 H), 1.31-1.45 (m, 4 H), 1.48-1.72 (m, 9 H), 1.86-1.96 (m, 3 H), 2.22 (dd, J=13.5, 7.7 Hz, 1 H), 2.66 (dd, J=13.5, 4.2 Hz, 1 H), 2.79 (dd, J=11.9, 3.8 Hz, 1 H), 3.84 (ddd, J=12.0, 7.7, 4.2 Hz, 1 H), 4.30 (dd, J=4.0, 4.0 Hz, 1 H), 4.35 (ddd, J=7.9, 7.8, 2.7 Hz, 1 H), 4.86 (ddd, J=11.7, 7.9, 1.9 Hz, 2 H), 4.99 (d, J=2.0 Hz, 1 H), 5.27 (s, 1 H), 5.61 (d, J=2.6 Hz, 1 H), 5.97 (d, J=11.2 Hz, 1 H), 6.36 (d, J=11.2 Hz, 1 H), 6.45 (d, J=2.6 Hz, 1 H), 7.11-7.13 (m, 2 H), 7.29-7.37 (m, 3 H).

LRMS m/z 516 (M$^+$), 498, 480, 454, 265, 223

HRMS calcd for $C_{34}H_{44}O_4$ 516.3240, found 516.3243

Example 63

Synthesis of 2α-methyl-20(R)-(tetrahydro-3-methyl-ene-2-furanone-4(S))-phenyl-5(S)-yl)methyl-9,10-secopregna-5(Z),7(E),10(19)-triene-1α,3β-diol (Compound No. 209b)

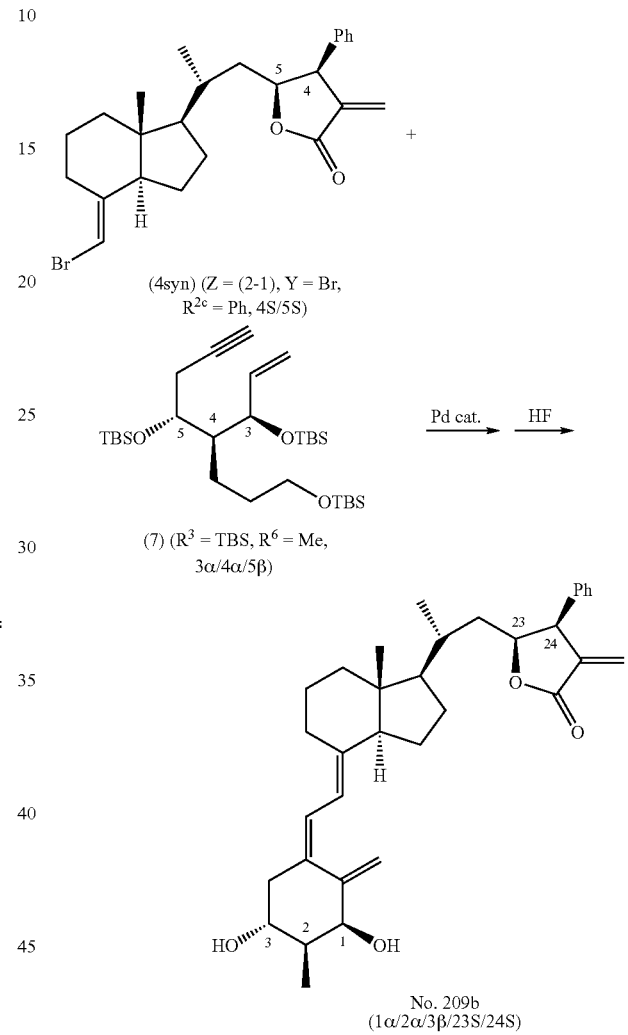

Using 26 mg (59 μmol) of Compound (4syn) (Z=(2-1), Y=Br, $R^{2c}$=Ph, 4S/5S) obtained in Example 59(1) and 34 mg (89 μmol) of Compound (7) ($R^3$=TBS, $R^6$=Me, 3α/4α/5β), a reaction similar to Example 14(2-a) was carried out to obtain 13 mg of Compound No. 209b. Yield: 43%.

[1] H-NMR (CDCl$_3$) δ: 0.35 (s, 3 H), 0.51 (m, 1 H), 0.96 (d, J=5.4 Hz, 3 H), 1.09 (d, J=6.8 Hz, 3 H), 1.17-1.32 (m, 7 H), 1.37-1.68 (m, 7 H), 1.86-1.92 (m, 3 H), 2.22 (dd, J=13.7, 8.3 Hz, 1H), 2.65 (dd, J=13.7, 3.9 Hz, 1 H), 2.78 (dd, J=12.5, 3.9 Hz, 1 H), 3.82 (m, 1 H), 4.26 (ddd, J=7.2, 2.3, 2.1 Hz, 1 H), 4.29 (br s, 1 H), 4.82 (ddd, J=7.2, 6.8, 6.8 Hz, 1 H), 4.98 (d, J=2.0 Hz, 1 H), 5.26 (s, 1 H), 5.60 (d, J=2.2 Hz, 1 H), 5.93 (d, J=11.1 Hz, 1 H), 6.36 (d, J=11.1 Hz, 1 H), 6.40 (d, J=2.2 Hz, 1 H), 7.11-7.13 (m, 2 H), 7.30-7.36 (m, 3 H).

LRMS m/z 516 (M$^+$), 498, 480, 454, 265, 223

HRMS calcd for $C_{34}H_{44}O_4$ 516.3240, found 516.3243

Example 64

Synthesis of 2α-methyl-20(R)-(tetrahydro-3-methylene-2-furanone-4(R))-phenyl-5(S)-yl)methyl-9,10-secopregna-5(Z),7(E),10(19)-triene-1α,3β-diol (Compound No. 209c)

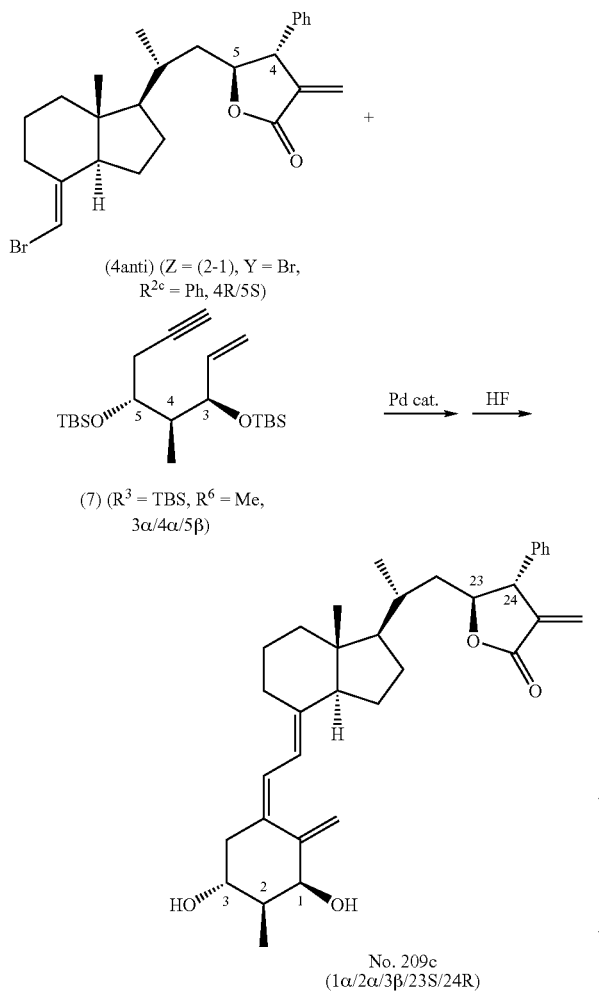

Using 17 mg (38 μmol) of Compound (4anti) (Z=(2-1), Y=Br, $R^{2c}$=Ph, 4R/5S) obtained in Example 60(4) and 22 mg (57 μmol) of Compound (7) ($R^3$=TBS, $R^6$=Me, 3α/4α/5β), a reaction similar to Example 14(2-a) was carried out to obtain 9 mg of Compound No. 209c. Yield: 45%.

$^1$H-NMR (CDCl$_3$) δ: 0.45 (s, 3 H), 0.84 (d, J=6.3 Hz, 3 H), 1.08 (d, J=6.8 Hz, 3 H), 1.12-1.32 (m, 4 H), 1.34-1.71 (m, 11 H), 1.80 (ddd, J=14.2, 6.5, 3.3 Hz, 1 H), 1.83-1.94 (m, 3 H), 1.98 (br d, J=10.4 Hz, 1 H), 2.23 (dd, J=13.4, 8.0 Hz, 1 H), 2.60 (dd, J=13.6, 4.1 Hz, 1 H), 2.80 (m, 1 H), 3.72 (ddd, J=7.0, 3.2, 3.2 Hz, 1 H), 3.84 (ddd, J=8.0, 7.6, 4.1 Hz, 1 H), 4.30 (br s, 1 H), 4.50 (ddd, J=7.0, 6.8, 6.8 Hz, 1 H), 5.00 (d, J=2.0 Hz, 1 H), 5.27 (s, 1 H), 5.35 (d, J=3.1 Hz, 1 H), 5.99 (d, J=11.4 Hz, 1 H), 6.32 (d, J=3.1 Hz, 1 H), 6.37 (d, J=11.4 Hz, 1 H), 7.18-7.21 (m, 2 H), 7.30 (m, 1 H), 7.34-7.39 (m, 2 H).

LRMS m/z 516 (M$^+$), 498, 480, 454, 265, 223

HRMS calcd for $C_{34}H_{44}O_4$ 516.3240, found 516.3245

Example 65

Synthesis of 2α-methyl-20(R)-(tetrahydro-3-methylene-2-furanone-4(S)-phenyl-5(R)-yl)methyl-9,10-secopregna-5(Z),7(E),10(19)-triene-1α,3β-diol (Compound No. 209d)

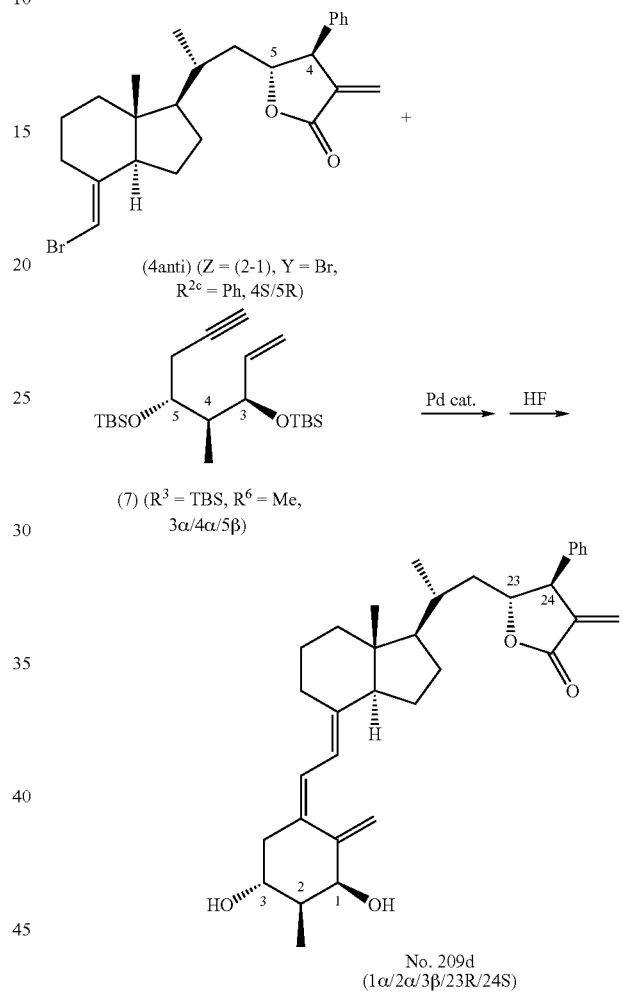

Using 27 mg (61 μmol) of Compound (4anti) (Z=(2-1), Y=Br, $R^{2c}$=Ph, 4S/5R) obtained in Example 61(4) and 28 mg (73 μmol) of Compound (7) ($R^3$=TBS, $R^6$=Me, 3α/4α/5β), a reaction similar to Example 14(2-a) was carried out to obtain 14 mg of Compound No. 209d. Yield: 45%.

$^1$H-NMR (10% CD$_3$OD in CDCl$_3$) δ: 0.54 (s, 3 H), 0.90 (d, J=6.3 Hz, 3 H), 1.08 (d, J=6.8 Hz, 3 H), 1.21-1.30 (m, 3 H), 1.33-1.41 (m, 2 H), 1.44-1.56 (m, 4 H), 1.60-1.70 (m, 2 H), 1.75-1.82 (m, 2 H), 1.84-1.99 (m, 4 H), 2.22 (dd, J=13.4, 8.3 Hz, 1 H), 2.67 (dd, J=13.4, 3.9 Hz, 1 H), 2.81 (m, 1 H), 3.71 (ddd, J=7.9, 3.2, 3.2 Hz, 1 H), 3.85 (m, 1 H), 4.31 (dd, J=4.0, 4.0 Hz, 1 H), 4.47 (ddd, J=10.3, 7.9, 2.0 Hz, 1 H), 5.00 (d, J=2.0 Hz, 1 H), 5.28 (s, 1 H), 5.37 (d, J=3.1 Hz, 1 H), 6.00 (d, J=11.2 Hz, 1 H), 6.34 (d, J=3.1 Hz, 1 H), 6.37 (d, J=11.2 Hz, 1 H), 7.19-7.21 (m, 2-H), 7.32 (m, 1 H), 7.36-7.40 (m, 2 H).

LRMS m/z 516 (M$^+$), 498, 480, 454, 265, 223

HRMS calcd for $C_{34}H_{44}O_4$ 516.3240, found 516.3242

Example 66

Synthesis of 2α-(3-hydroxypropyl)-20(R)-(tetrahydro-3-methylene-2-furanone-4(R)-phenyl-5(R)-yl)methyl-9,10-secopregna-5(Z),7(E),10(19)-triene-1α,3β-diol (Compound No. 810a)

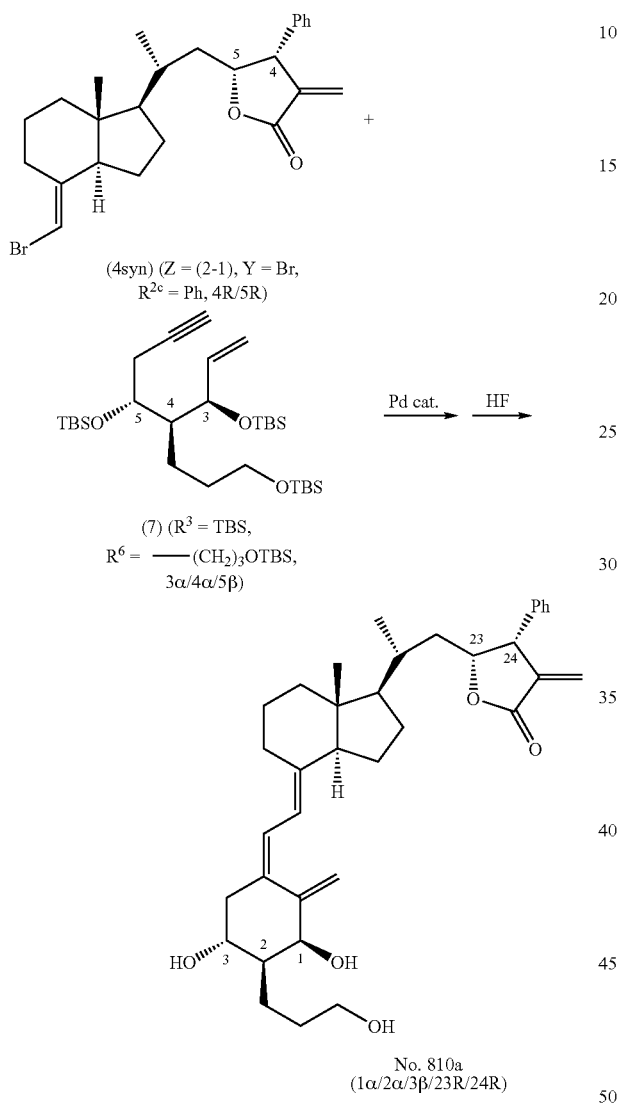

No. 810a
(1α/2α/3β/23R/24R)

Using 17 mg (38 μmol) of Compound (4syn) (Z=(2-1), Y=Br, R$^{2c}$=Ph, 4R/5R) obtained in Example 59(1) and 31 mg (57 mmol) of Compound (7) (R$^3$=TBS, R$^6$=—(CH$_2$)$_3$OTBS, 3α/4α/5β), a reaction similar to Example 14(2-a) was carried out to obtain 10 mg of Compound No. 810a. Yield: 47%.

$^1$H-NMR (CDCl$_3$) δ: 0.50 (s, 3 H), 0.61 (ddd, J=14.4, 10.7, 2.0 Hz, 1 H), 0.91 (d, J=6.6 Hz, 3 H), 1.06-1.14 (m, 2 H), 1.17-1.40 (m, 4 H), 1.45 (m, 1 H), 1.57-1.76 (m, 12 H), 1.88 (dd, J=11.1, 8.2 Hz, 1 H), 1.95 (br d, J=12.7 Hz, 1 H), 2.24 (dd, J=13.2, 8.4 Hz, 1 H), 2.65 (dd, J=13.2, 4.3 Hz, 1 H), 2.79 (br dd, J=12.1, 3.1 Hz, 1 H), 3.70 (t, J=5.7 Hz, 2 H), 3.90 (ddd, J=8.4, 8.2, 4.3 Hz, 1 H), 4.34-4.38 (m, 2 H), 4.86 (ddd, J=11.8, 7.9, 2.0 Hz, 1 H), 4.97 (d, J=1.5 Hz, 1 H), 5.27 (d, J=1.5 Hz, 1 H), 5.61 (d, J=2.6 Hz, 1 H), 5.96 (d, J=11.5 Hz, 1 H), 6.37 (d, J=11.5 Hz, 1 H), 6.45 (d, J=2.6 Hz, 1 H), 7.11-7.13 (m, 2 H), 7.28-7.37 (m, 3 H).

LRMS m/z 560 (M$^+$), 542, 524, 509, 349, 262
HRMS calcd for C$_{36}$H$_{48}$O$_5$ 560.3502, found 560.3510

Example 67

Synthesis of 2α-(3-hydroxypropyl)-20(R)-(tetrahydro-3-methylene-2-furanone-4(S)-phenyl-5(S)-yl)methyl-9,10-secopregna-5(Z),7(E),10(19)-triene-1α,3β-diol (Compound No. 810b)

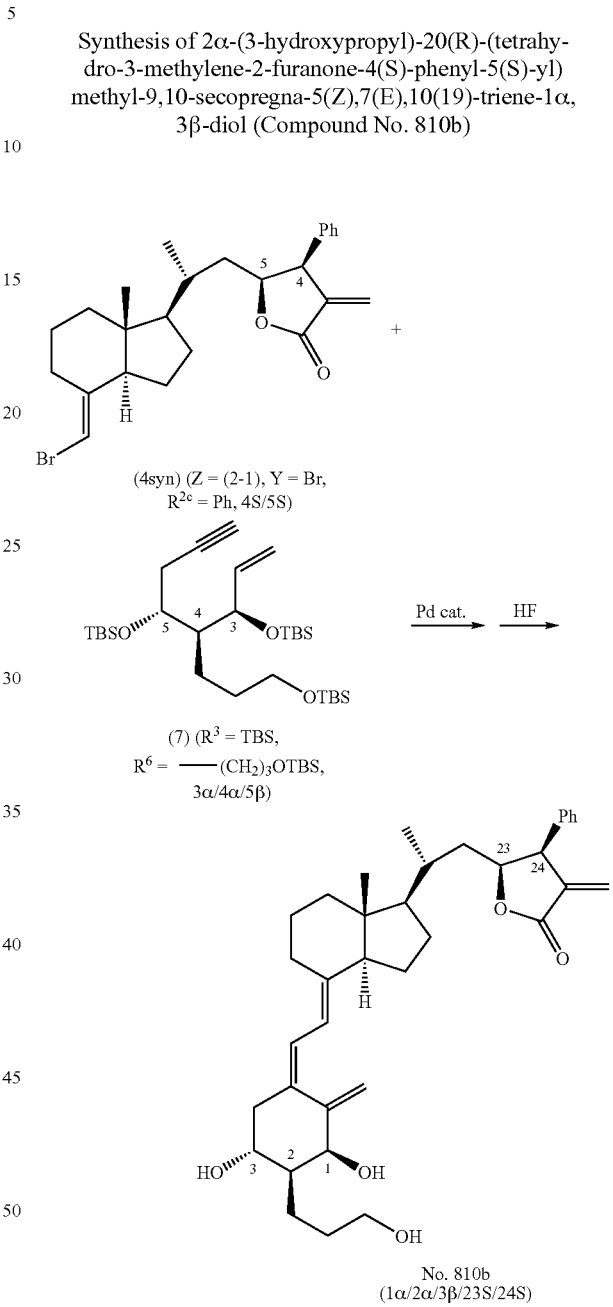

No. 810b
(1α/2α/3β/23S/24S)

Using 31 mg (70 μmol) of Compound (4syn) (Z=(2-1), Y=Br, R$^{2c}$=Ph, 4S/5S) obtained in Example 59(1) and 57 mg (105 μmol) of Compound (7) (R$^3$=TBS, R$^6$=—(CH$_2$)$_3$OTBS, 3α/4α/5β), a reaction similar to Example 14(2-a) was carried out to obtain 22 mg of Compound No. 810b. Yield: 54%.

$^1$H-NMR (CDCl$_3$) δ: 0.35 (s, 3 H), 0.51 (m, 1 H), 0.95 (d, J=5.4 Hz, 3 H), 1.14-1.37 (m, 7 H), 1.39-1.52 (m, 3 H), 1.60-1.78 (m, 9 H), 1.86-1.92 (m, 1 H), 2.24 (dd, J=13.2, 8.7 Hz, 1 H), 2.66 (dd, J=13.2, 4.3 Hz, 1 H), 2.78 (m, 1 H), 3.70 (t, J=4.9 Hz, 2 H), 3.87 (ddd, J=8.7, 7.5, 4.3 Hz, 1 H), 4.25 (ddd, J=7.3, 2.1, 2.1 Hz, 1 H), 4.82 (ddd, J=7.5, 6.8, 6.8 Hz, 1 H), 4.97 (d, J=1.7 Hz, 1 H), 5.27 (d, J=1.7 Hz, 1 H), 5.60 (d, J=2.1 Hz, 1 H), 5.92 (d, J=1.4 Hz, 1H), 6.37 (d, J=11.4 Hz, 1 H), 6.40 (d, J=2.1 Hz, 1 H), 7.11-7.13 (m, 2 H), 7.28-7.37 (m, 3H).

LRMS m/z 560 (M$^+$), 542, 524, 509, 349, 262

HRMS calcd for $C_{36}H_{48}O_5$ 560.3502, found 560.3502

Example 68

Synthesis of 2α-(3-hydroxypropyl)-20(R)-(tetrahydro-3-methylene-2-furanone-4(R)-phenyl-5(S)-yl)methyl-9,10-secopregna-5(Z),7(E),10(19)-triene-1α,3β-diol (Compound No. 810c)

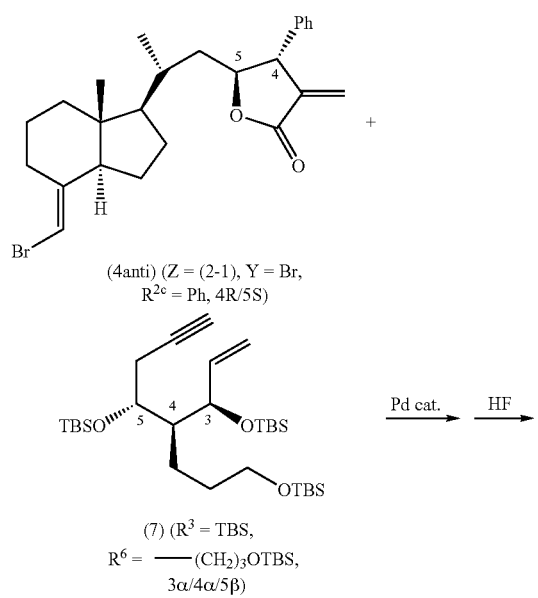

Using 19 mg (43 μmol) of Compound (4anti) (Z=(2-1), Y=Br, R$^{2c}$=Ph, 4R/5S) obtained in Example 60(4) and 35 mg (65 μmol) of Compound (7) (R$^3$=TBS, R$^6$=—(CH$_2$)$_3$OTBS, 3α/4α/5β), a reaction similar to Example 14(2-a) was carried out to obtain 10 mg of Compound No. 810c. Yield: 42%.

$^1$H-NMR (CDCl$_3$) δ: 0.45 (s, 3 H), 0.84 (d, J=6.3 Hz, 3 H), 1.13-1.39 (m, 4 H), 1.46-1.48 (m, 4 H), 1.64-2.04 (m, 14 H), 2.24 (dd, J=13.3, 8.5 Hz, 1 H), 2.65 (dd, J=13.3, 4.2 Hz, 1 H), 2.80 (br d, J=12.2 Hz, 1 H), 3.68-3.73 (m, 3 H), 3.88 (ddd, J=8.5, 8.1, 4.2 Hz, 1 H), 4.37 (s, 1 H), 4.50 (ddd, J=6.8, 6.8, 6.8 Hz, 1 H), 4.98 (s, 1 H), 5.27 (s, 1 H), 5.34 (d, J=3.2 Hz, 1H), 5.98 (d, J=11.3 Hz, 1 H), 6.32 (d, J=3.2 Hz, 1 H), 6.38 (d, J=11.3 Hz, 1 H), 7.18-7.20 (m, 2 H), 7.28-7.38 (m, 3 H).

LRMS m/z 560 (M$^+$), 542, 524, 509, 349, 262

HRMS calcd for $C_{36}H_{48}O_5$ 560.3502, found 560.3495

Example 69

Synthesis of 2α-(3-hydroxypropyl)-20(R)-(tetrahydro-3-methylene-2-furanone-4(S)-phenyl-5(R)-yl)methyl-9,10-secopregna-5(Z),7(E),10(19)-triene-1α,3β-diol (Compound No. 810d)

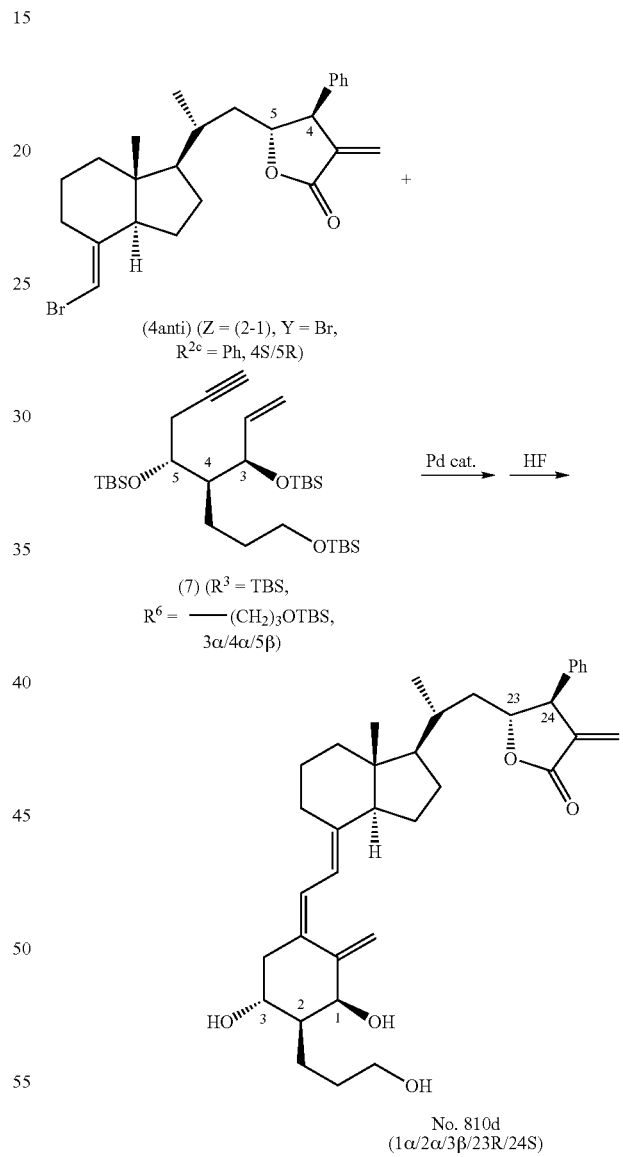

Using 21 mg (47 μmol) of Compound (4anti) (Z=(2-1), Y=Br, R$^{2c}$=Ph, 4S/5R) obtained in Example 61(4) and 38 mg (70 μmol) of Compound (7) (R$^3$=TBS, R$^6$=—(CH$_2$)$_3$OTBS, 3α/4α/5β), a reaction similar to Example 14(2-a) was carried out to obtain 12 mg of Compound No. 810d. Yield: 45%.

$^1$H-NMR (10% CD$_3$OD in CDCl$_3$) δ: 0.54 (s, 3 H), 0.89 (d, J=6.6 Hz, 3 H), 1.20-1.29 (m, 4H), 1.36 (m, 1 H), 1.43-1.53 (m, 3 H), 1.63-1.98 (m, 14 H), 2.24 (dd, J=13.4, 8.9 Hz, 1 H), 2.66 (dd, J=13.4, 4.2 Hz, 1 H), 2.81 (br d, J=13.7 Hz, 1 H), 3.68-3.73 (m, 3 H), 3.90 (ddd, J=8.3, 8.3, 4.4 Hz, 1 H), 4.37 (d, J=2.9 Hz, 1 H), 4.46 (m, 1 H), 4.98 (d, J=1.7 Hz, 1 H), 5.27 (d, J=1.7 Hz, 1 H), 5.37 (d, J=3.2 Hz, 1 H), 6.00 (d, J=11.2 Hz, 1 H), 6.34 (d, J=3.2 Hz, 1 H), 6.38 (d, J=11.2 Hz, 1 H), 7.19-7.21 (m, 2 H), 7.32 (m, 1 H), 7.36-7.40 (m, 2 H).
LRMS m/z 560 (M$^+$), 542, 524, 509, 349, 262
HRMS calcd for $C_{36}H_{48}O_5$ 560.3502, found 560.3502

Example 70

Synthesis of 2α-(3-hydroxypropoxy)-20(R)-(tetrahydro-3-methylene-2-furanone-4(R)-phenyl-5(R)-yl)methyl-9,10-secoprejna-5(Z),7(E),10(19)-triene-1α,3β-diol (Compound No. 1110a)

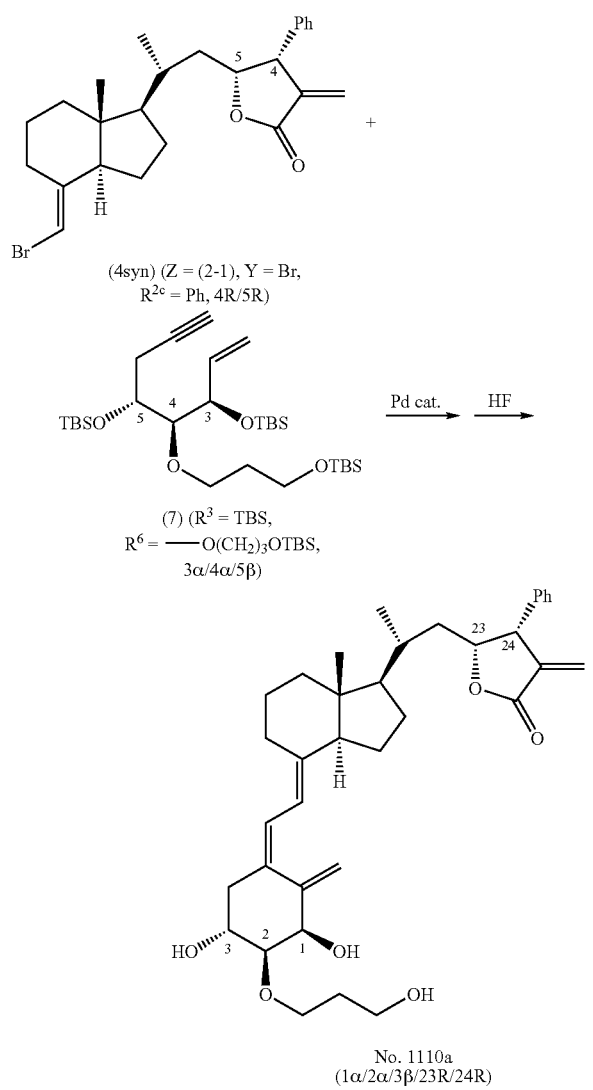

No. 1110a
(1α/2α/3β/23R/24R)

Using 18 mg (41 μmol) of Compound (4syn) (Z (2-1), Y=Br, $R^{2c}$=Ph, 4R/5R) obtained in Example 59(1) and 34 mg (61 μmol) of Compound (7) ($R^3$=TBS, $R^6$=—O(CH$_2$)$_3$OTBS, 3α/4α/5β), a reaction similar to Example 14(2-a) was carried out to obtain 12 mg of Compound No. 110a. Yield: 51%.

$^1$H-NMR (CDCl$_3$) δ: 0.51 (s, 3 H), 0.61 (ddd, J=14.4, 10.6, 1.8 Hz, 1 H), 0.91 (d, J=6.3 Hz, 3 H), 1.06-1.14 (m, 2 H), 1.21 (ddd, J=12.8, 12.8, 3.7 Hz, 1 H), 1.31-1.39 (m, 2 H), 1.42-1.71 (m, 6 H), 1.86-1.90 (m, 3 H), 1.95 (br d, J=12.7 Hz, 1 H), 2.19 (br s, 1 H), 2.22 (dd, J=13.2, 9.0 Hz, 1 H), 2.39 (br s, 1 H), 2.52 (br s, 1 H), 2.67 (dd, J=13.3, 4.4 Hz, 1 H), 2.79 (br d, J=12.2 Hz, 1 H), 3.38 (dd, J=7.3, 3.2 Hz, 1 H), 3.74-3.90 (m, 4 H), 4.06 (m, 1 H), 4.35 (ddd, J=7.8, 2.4, 2.4 Hz, 1 H), 4.43 (br s, 1 H), 4.86 (ddd, J=11.6, 7.9, 1.8 Hz, 1 H), 5.07 (d, J=1.5 Hz, 1 H), 5.38 (s, 1 H), 5.61 (d, J=2.6 Hz, 1 H), 5.97 (d, J=11.2 Hz, 1 H), 6.39 (d, J=11.2 Hz, 1 H), 6.45 (d, J=2.6 Hz, 1 H), 7.11-7.13 (m, 2 H), 7.29-7.37 (m, 3 H).
LRMS m/z 576 (M$^+$), 558, 540, 482, 428, 351, 309, 267
HRMS calcd for $C_{36}H_{48}O_6$ 576.3451, found 576.3447

Example 71

Synthesis of 2α-(3-hydroxypropoxy)-20(R)-(tetrahydro-3-methylene-2-furanone-4(S)-phenyl-5(S)-yl)methyl-9,10-secopregna-5(Z),7(E),10(19)-triene-1α,3β-diol (Compound No. 1110b)

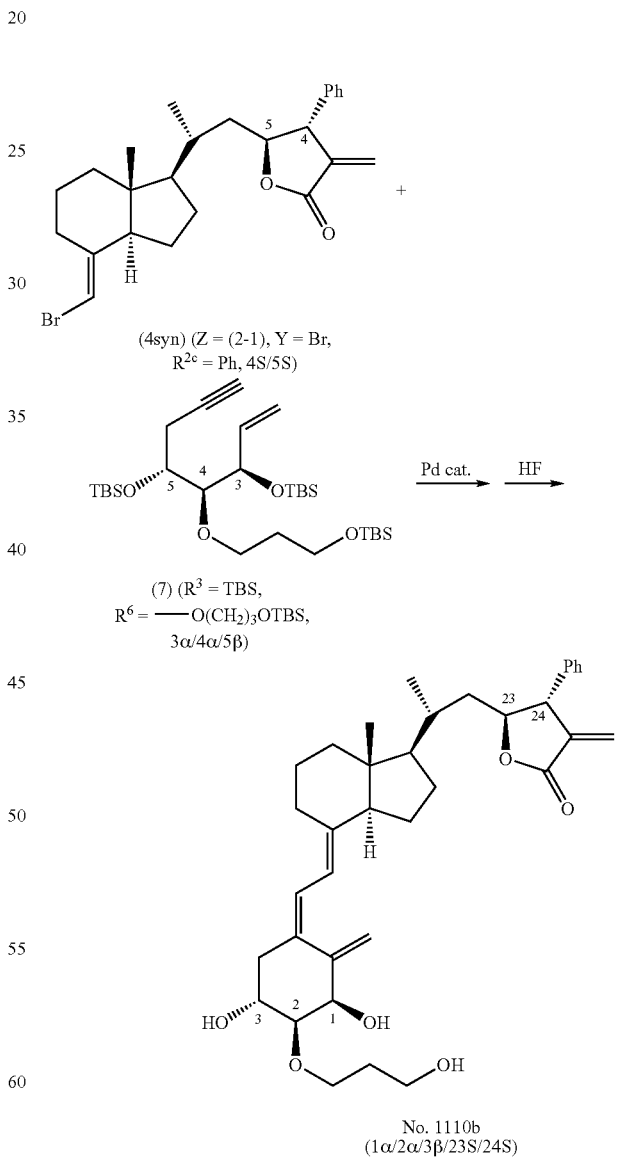

No. 1110b
(1α/2α/3β/23S/24S)

Using 40 mg (90 μmol) of Compound (4syn) (Z=(2-1), Y=Br, $R^{2c}$=Ph, 4S/5S) obtained in Example 59(1) and 75 mg (135 μmol) of Compound (7) ($R^3$=TBS, $R^6$=—O(CH$_2$)$_3$ OTBS, 3α/4α/5β), a reaction similar to Example 14(2-a) was carried out to obtain 24 mg of Compound No. 1110b. Yield: 46%.

¹H-NMR (CDCl₃) δ: 0.35 (s, 3 H), 0.43 (m, 1 H), 0.95 (d, J=5.1 Hz, 3 H), 1.15-1.31 (m, 6 H), 1.40-1.52 (m, 3 H), 1.59-1.63 (m, 2 H), 1.87-1.91 (m, 4 H), 2.20-2.25 (m, 2 H), 2.47 (br s, 1 H), 2.53 (br s, 1 H), 2.66 (dd, J=13.5, 4.5 Hz, 1 H), 2.77 (br d, J=11.5 Hz, 1 H), 3.36 (m, 1H), 3.75-3.92 (m, 4 H), 4.04 (m, 1 H), 4.25 (m, 1 H), 4.44 (s, 1 H), 4.82 (m, 1 H), 5.07 (s, 1H), 5.38 (s, 1 H), 5.60 (s, 1 H), 5.93 (d, J=10.7 Hz, 1 H), 6.37-6.40 (m, 2 H), 7.11-7.12 (m, 2H), 7.30-7.35 (m, 3 H).

LRMS m/z 576 (M⁺), 558, 540, 482, 428, 351, 309, 267

HRMS calcd for $C_{36}H_{48}O_6$ 576.3451, found 576.3453

Example 72

Synthesis of 2α-(3-hydroxypropoxy)-20(R)-(tetrahydro-3-methylene-2-furanone-4(R)-phenyl-5(S)-yl)methyl-9,10-secopregna-5(Z),7(E),10(19)-triene-1α,3β-diol (Compound No. 1110c)

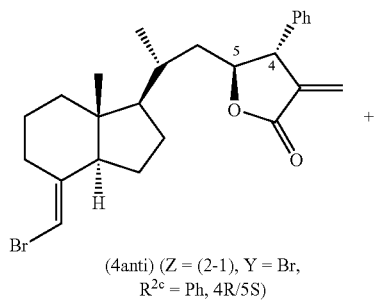

(4anti) (Z = (2-1), Y = Br, R²ᶜ = Ph, 4R/5S)

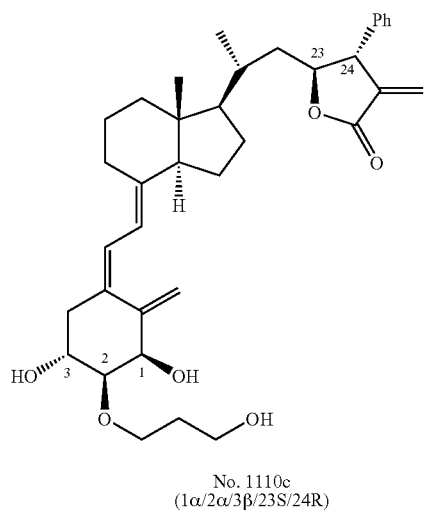

No. 1110c
(1α/2α/3β/23S/24R)

Using 21 mg (47 μmol) of Compound (4anti) (Z=(2-1), Y=Br, R²ᶜ=Ph, 4R/5S) obtained in Example 60(4) and 40 mg (72 μmol) of Compound (7) (R³=TBS, R⁶=—O(CH₂)₃OTBS, 3α/4α/5β), a reaction similar to Example 14(2-a) was carried out to obtain 10 mg of Compound No. 1110c. Yield: 37%.

¹H-NMR (CDCl₃) δ: 0.45 (s, 3 H), 0.83 (d, J=6.6 Hz, 3 H), 1.13-1.38 (m, 3 H), 1.46-1.54 (m, 4 H), 1.64-1.71 (m, 3 H), 1.77-2.00 (m, 6 H), 2.23 (dd, J=13.4, 8.6 Hz, 1 H), 2.53 (m, 3 H), 2.67 (dd, J=13.4, 4.5 Hz, 1 H), 2.80 (br d, J=12.9 Hz, 1 H), 3.37 (dd, J=7.3, 3.2 Hz, 1 H), 3.72 (m, 1 H), 3.74-3.91 (m, 3 H), 4.05 (ddd, J=8.6, 7.5, 4.5 Hz, 1 H), 4.44 (s, 1 H), 4.56 (ddd, J=7.5, 6.8, 6.8 Hz, 1 H), 5.08 (d, J=2.7 Hz, 1 H), 5.34 (d, J=3.1 Hz, 1 H), 5.38 (br s, 1 H), 5.99 (d, J=11.1 Hz, 1 H), 6.32 (d, J=3.1 Hz, 1 H), 6.40 (d, J=11.1 Hz, 1 H), 7.18-7.20 (m, 2 H), 7.30 (m, 1 H), 7.34-7.38 (m, 2 H).

LRMS m/z 576 (M⁺), 558, 540, 482, 428, 351, 309, 267

HRMS calcd for $C_{36}H_{48}O_6$ 576.3451, found 576.3452

Example 73

Synthesis of 2α-(3-hydroxypropoxy)-20(R)-(tetrahydro-3-methylene-2-furanone-4(S)-phenyl-5(R)-yl)methyl-9,10-secopregna-5(Z),7(E),10(19)-triene-1α,3β-diol (Compound No. 1110d)

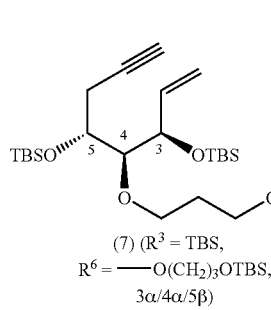

(7) (R³ = TBS, R⁶ = —O(CH₂)₃OTBS, 3α/4α/5β)

Pd cat. → HF →

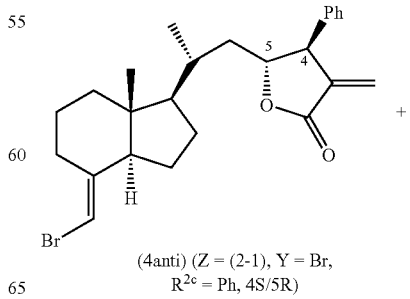

(4anti) (Z = (2-1), Y = Br, R²ᶜ = Ph, 4S/5R)

-continued

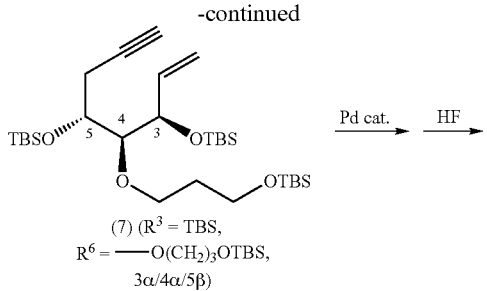

(7) (R³ = TBS, R⁶ = —O(CH₂)₃OTBS, 3α/4α/5β)

Pd cat. HF →

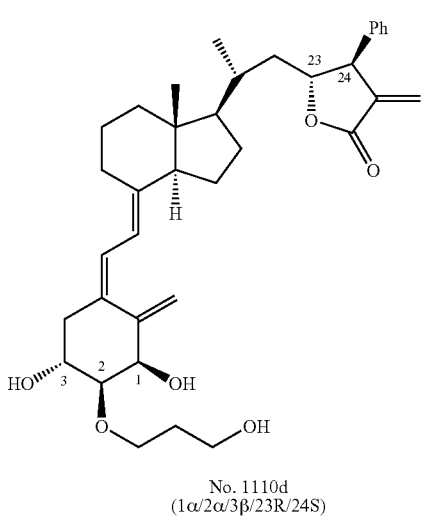

No. 1110d
(1α/2α/3β/23R/24S)

Using 17 mg (38 μmol) of Compound (4anti) (Z=(2-1), Y=Br, $R^{2c}$=Ph, 4S/5R) obtained in Example 61(4) and 32 mg (57 μmol) of Compound (7) ($R^3$=TBS, $R^6$=—O(CH₂)₃OTBS, 3α/4α/5β), a reaction similar to Example 14(2-a) was carried out to obtain 9 mg of Compound No. 1110d. Yield: 41%.

$^1$H-NMR (CDCl₃) δ: 0.54 (s, 3 H), 0.89 (d, J=6.6 Hz, 3 H), 1.18-1.30 (m, 4 H), 1.36 (m, 1 H), 1.45-1.56 (m, 3 H), 1.60-1.68 (m, 2 H), 1.75-1.82 (m, 2 H), 1.84-1.89 (m, 2 H), 1.92-1.99 (m, 2 H), 2.15 (br s, 1 H), 2.23 (dd, J=13.7, 8.6 Hz, 1 H), 2.40 (br s, 1 H), 2.50 (br s, 1 H), 2.68 (dd, J=13.7, 4.3 Hz, 1 H), 2.81 (br d, J=12.5 Hz, 1 H), 3.38 (dd, J=7.2, 3.3 Hz, 1 H), 3.71 (ddd, J=7.7, 3.2, 3.2 Hz, 1 H), 3.75-3.91 (m, 4 H), 4.06 (ddd, J=8.6, 8.1, 4.3 Hz, 1 H), 4.44-4.84 (m, 2 H), 5.08 (d, J=2.0 Hz, 1 H), 5.37 (d, J=3.2 Hz, 1 H), 5.39 (br s, 1 H), 6.00 (d, J=11.5 Hz, 1 H), 6.35 (d, J=3.2 Hz, 1 H), 6.40 (d, J=11.5 Hz, 1 H), 7.19-7.21 (m, 2 H), 7.32 (m, 1 H), 7.36-7.40 (m, 2 H).

LRMS m/z 576 (M⁺), 558, 540, 482, 428, 351, 309, 267
HRMS calcd for $C_{36}H_{48}O_6$ 576.3451, found 576.3466

Example 74

Synthesis of 20(R)-(tetrahydro-3-methylene-2-furanone-4,4-dimethyl-5(R)-yl)methyl-9,10-secopregna-5(Z),7(E),10(19)-triene-1α,3β-diol (Compound No. 111a) and 20(R)-(tetrahydro-3-methylene-2-furanone-4,4-dimethyl-5(S)-yl)methyl-9,10-secopregna-5(Z),7(E),10(19)-triene-1α,3β-diol (Compound No. 111b)

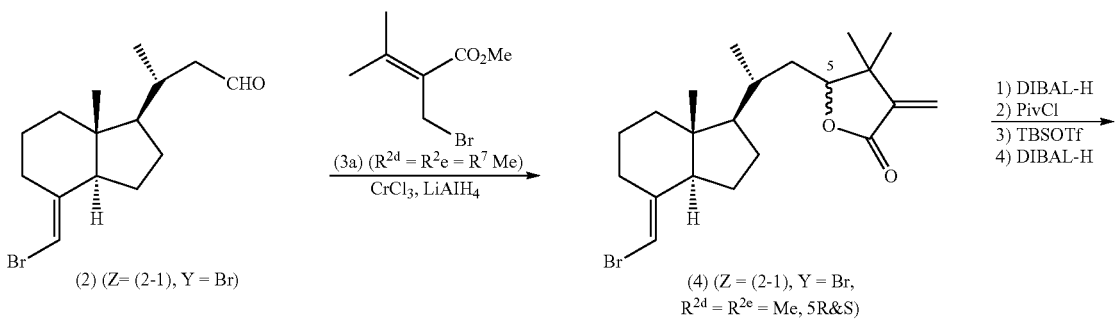

-continued

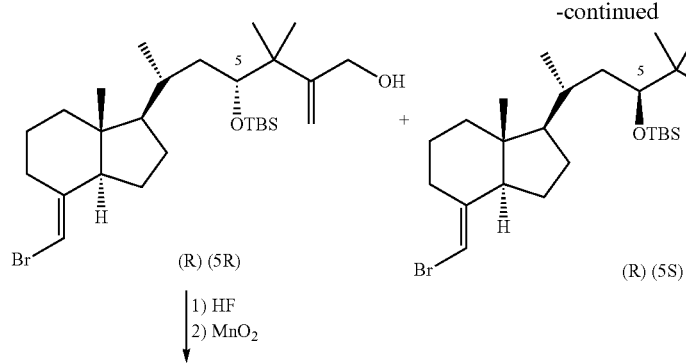

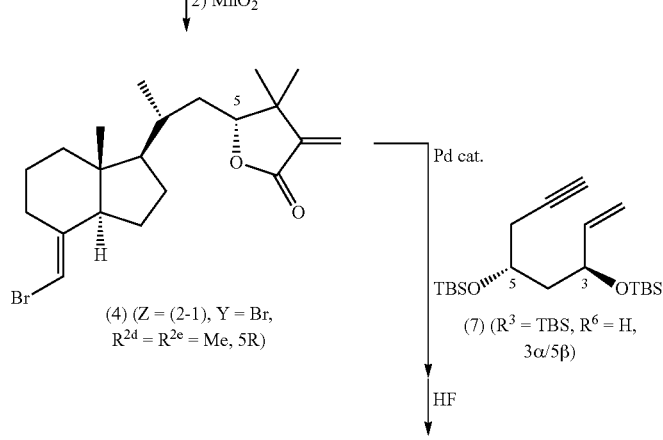

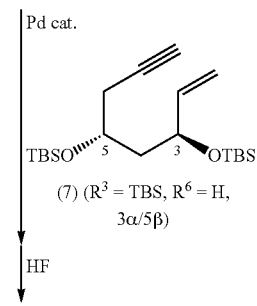

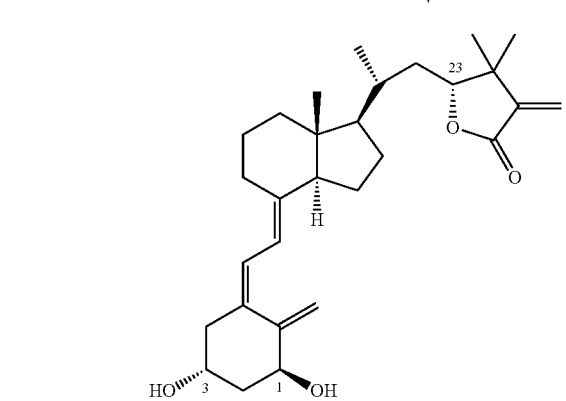

(1) A solution was prepared by adding 94 mg (2.3 mmol) of LiAlH$_4$ to a THF (23 ml) suspension containing 739 mg (4.7 mmol) of chromium chloride (III) at 0° C. and was stirred at room temperature for 30 minutes. A reaction solution was prepared by adding a THF (8 ml) solution containing 486 mg (2.34 mmol) of Compound (3a) ($R^{2d}=R^{2e}=R^7=Me$) obtained in Reference Example 11 and a THF (8 ml) solution containing 350 mg (1.17 mmol) of Compound (2) (Z=(2-1), Y=Br) obtained by a method known in the literature (for example, the specification of International Publication WO 95/33716) (原原の誤り) to this solution and was stirred at the same temperature for one hour. Water was added to the reaction solution, and the aqueous layer was extracted with diethyl ether. The combined organic layer was washed with saturated brine, and dried with anhydrous sodium sulfate. The residue obtained by distilling off the solvent under reduced pressure was purified by silica gel column chromatography (hexane: ethyl acetate=10:1) to obtain 390 mg (yield: 80%, isomer ratio: 2:1) of a mixture of Compound (4) (Z=(2-1), Y=Br, $R^{2d}=R^{2e}$=Me, 5R) and Compound (4) (Z=(2-1), Y=Br, $R^{2d}=R^{2e}$=Me, 5S). These compounds each were obtained as a single material by carrying out the conversion shown in (2), (3-a) and (3-b) processes described below.

(2) A reaction solution was prepared by adding 5 ml (1.04 M, 5.0 mmol) of a toluene solution of DIBAL-H to a toluene solution (3.3 ml) containing 390 mg (1.0 mmol) of a mixture of Compound (4) (Z=(2-1), Y=Br, $R^{2d}=R^{2e}$=Me, 5R) and Compound (4) (Z=(2-1), Y=Br, $R^{2d}=R^{2e}$=Me, 5S) obtained by the above method at 0° C. and was stirred at room temperature for 14 hours. Methanol and a 10% aqueous solution of sodium potassium tartrate were added to the reaction solution, and the resultant solution was stirred at room temperature for 5 minutes. Then the aqueous layer was subjected to extraction with ether. The organic layer was washed with saturated brine and dried with anhydrous sodium sulfate. The residue obtained by distilling off the solvent under reduced pressure was dissolved in 2.8 ml (0.3 mol) of pyridine and then 0.16 ml (1.3 mmol) of pivaroyl chloride was added to the solution at 0° C. The resultant solution was stirred at room temperature for one hour. After water was added to the reaction solution at 0° C., the aqueous layer was subjected to extraction with diethyl ether. The organic layer was washed with saturated brine and dried with anhydrous sodium sulfate. The residue obtained by distilling off the solvent under reduced pressure was dissolved in 2.8 ml of methylene chloride, and then 0.5 ml (2.1 mmol) of TBSOTf and 0.5 ml (4.2 mmol) of 2,6-lutidine were added to the solution at 0° C. The resultant solution was stirred at room temperature for 5 hours. After water was added to the reaction solution at 0° C., the aqueous layer was subjected to extraction with diethyl ether. The organic layer was washed with saturated brine and dried with anhydrous sodium sulfate. The residue obtained by distilling off the solvent under reduced pressure was dissolved in a toluene solution (3.0 ml), and 5 ml (1.04 M, 5.0 mmol) of a toluene solution of DIBAL-H was added to the solution at 0° C. The resultant solution was stirred at room temperature for 14 hours. Methanol and a 10% aqueous solution of sodium potassium tartrate were added to the reaction solution. After the resultant solution was stirred at room temperature for 5 minutes, the aqueous layer was subjected to extraction with ether. The organic layer was washed with saturated brine and dried with anhydrous sodium sulfate. The residue obtained by distilling off the solvent under reduced pressure was purified by silica gel column chromatography (hexane:ethyl acetate=5:1) to obtain 231 mg (yield: 54%) of Compound (R) (5R) and 69 mg (yield: 18%) of Compound (R) (5S).

Compound (R) (5R):

$^1$H-NMR (CDCl$_3$) δ: 0.09 (s, 3 H), 0.12 (s, 3 H), 0.56 (s, 3 H), 0.89 (d, J=6.7 Hz, 3 H), 0.93 (s, 9 H), 1.07 (s, 3 H), 1.10 (s, 3 H), 1.15-1.32 (m, 3 H), 1.37-1.70 (m, 8 H), 1.88-2.02 (m, 3H), 2.84-2.88 (m, 2 H), 3.55 (d, J=9.3 Hz, 1 H), 3.97 (dd, J=8.1, 13.4 Hz, 1 H), 4.25 (dd, J=2.2, 13.4 Hz, 1 H), 4.94 (d, J=1.1 Hz, 1 H), 5.16 (d, J=1.1 Hz, 1. H) 5.64 (s, 1 H).

LRMS m/z 495 ((M-OH)$^+$), 455, 416, 364

HRMS calcd for C$_{27}$ H$_{48}$O$^{79}$BrSi 495.2658, found 495.2643

Compound (R) (5S)

$^1$H-NMR (CDCl$_3$), δ: 0.13 (s, 6 H), 0.54 (s, 3 H), 0.92 (s, 9 H), 1.00 (d, J=11.2 Hz, 3 H), 1.05 (m, 1 H), 1.11 (s, 3 H), 1.11 (s, 3 H), 1.14-1.33 (m, 5 H), 1.38-1.68 (m, 4 H), 1.87-2.04 (m, 4H), 2.86 (m, 1 H), 3.08 (dd, J=3.9, 8.7 Hz, 1 H), 3.60 (dd, J=3.9, 7.3 Hz, 1 H), 3.97 (dd, J=8.4, 13.0 Hz, 1 H), 4.26 (dd, J=3.2, 13.0 Hz, 1 H), 5.00 (d, J=1.1 Hz, 1 H), 5.22 (d, J=1.1 Hz, 1 H), 5.64 (s, 1 H).

LRMS m/z 495 ((M-OH)$^+$), 455, 416, 364

HRMS calcd for C$_{27}$ H$_{48}$O$^{79}$BrSi 495.2658, found 495.2683

(3-a) A reaction solution was prepared by dissolving 200 mg (0.39 mmol) of Compound (R) (5R) obtained by the above method in acetonitrile and adding hydrofluoric acid/acetonitrile (1:9, 2 ml), and was stirred at room temperature for one hour. To the reaction solution was added a saturated aqueous solution of sodium hydrogen carbonate, and the aqueous layer was subjected to extraction with ethyl acetate. The organic layer was washed with saturated brine and dried with anhydrous sodium sulfate. The residue obtained by distilling off the solvent under reduced pressure was dissolved in methylene chloride (3.9 ml) and 729 mg (8.4 mmol) of MnO$_2$ was added to the solution. The resultant solution was stirred at room temperature for 24 hours. After the reaction solution was filtered, the residue obtained by concentrating the filtrate was purified by silica gel column chromatography (hexane:ethyl acetate=10:1) to obtain 140 mg of Compound (4) (Z=(2-1), Y=Br, R$^{2d}$=R$^{2e}$=Me, 5R). Yield: 91%, a colorless solid substance.

[α]$_D^{24}$+141.2 (c 0.38, CHCl$_3$)

$^1$H-NMR (CDCl$_3$) δ: 0.59 (s, 3 H), 1.00 (d, J=6.3 Hz, 3 H), 1.05 (s, 3 H), 1.11 (dd, J=11.2, 13.4 Hz, 1 H), 1.21 (s, 3 H), 1.25-1.36 (m, 3 H), 1.44-1.66 (m, 7 H), 1.89 (m, 1 H), 1.96-2.04 (m, 2 H), 2.89 (dd, J=6.8, 15.6 Hz, 1 H), 4.14 (d, J=10.5 Hz, 1 H), 5.47 (s, 1 H), 5.65 (s, 1H), 6.15 (s, 1 H).

$^{13}$C-NMR (CDCl$_3$) δ: 11.9, 18.6, 22.1, 22.5, 22.8, 25.1, 27.6, 31.0, 32.9, 35.9, 39.9, 41.9, 45.6, 55.9, 56.2, 84.2, 97.6, 119.1, 144.7, 146.1, 170.3.

LRMS m/z 394 (M$^+$), 315, 256, 227

HRMS calcd for C$_{21}$ H$_{31}$O$_2$$^{79}$Br 394.1507, found 394.1508

(3-b) Using 87 mg (0.17 mmol) of Compound (R) (5S) obtained by the above method, a reaction similar to Example 74(3-a) was carried out to obtain 55 mg of Compound (4) (Z=(2-1), Y=Br, R$^{2d}$=R$^{2e}$=Me, 5S). Yield: 82%, a colorless solid substance.

[α]$_D^{24}$+31.4 (c 0.85, CHCl$_3$)

$^1$H-NMR (CDCl$_3$) δ: 0.58 (s, 3 H), 1.05 (s, 3 H), 1.08 (d, J=6.6 Hz, 3 H), 1.21 (s, 3 H), 1.25-1.70 (m, 11 H), 1.95-2.04 (m, 3 H), 2.88 (dd, J=3.9, 15.9 Hz, 1 H), 4.10 (dd, J=2.9, 9.0 Hz, 1 H), 5.46 (s, 1 H), 5.65 (s, 1 H), 6.14 (s, 1 H).

$^{13}$C-NMR (CDCl$_3$) δ: 11.8, 19.7, 22.1, 22.5, 23.0, 24.3, 27.8, 31.0, 35.3, 35.5, 39.8, 42.6, 45.6, 55.7, 55.9, 86.1, 97.5, 118.9, 144.8, 146.1, 170.5.

LRMS m/z 394 (M$^+$), 315, 256, 227

HRMS calcd for C$_{21}$ H$_{31}$O$_2$$^{79}$Br 394.1507, found 394.1508

(4-a) Using 30 mg (76 μmol) of Compound (4) (Z=(2-1), Y=Br, R$^{2d=R2e}$=Me, 5R) obtained by the above method and 42 mg (0.114 μmol) of Compound (7) (R$^3$=TBS, R$^6$=Hydrogen atom, 3α/5β), a reaction similar to Example 14(2-a) wa's carried out to obtain 27 mg of Compound No. 111a. Yield: 78%.

Compound No. 111a:

[α]$_D^{24}$+56.160 (c 1.15, CHCl$_3$)

$^1$H-NMR (CDCl$_3$) δ: 0.57 (s, 3 H), 0.99 (d, J=6.6 Hz, 3 H), 1.05 (s, 3 H), 1.11 (dd, J=1.47, 10.5 Hz, 1 H), 1.21 (s, 3 H), 1.26 (m, 3 H), 1.45-1.76 (m, 9 H), 1.83-2.04 (m, 5 H), 2.31 (dd, J=6.5, 13.3 Hz, 1 H), 2.60 (dd, J=3.4, 13.4 Hz, 1 H), 2.83 (dd, J=3.9, 12.0 Hz, 1 H), 4.14 (dd, J=1.6, 11.6 Hz, 1 H), 4.24 (s, 1 H), 4.43 (s, 1 H), 5.00 (s, 1 H), 5.33 (s, 1 H), 5.47 (s, 1H), 6.12 (d, J=11.4 Hz, 1 H), 6.15 (s, 1 H), 6.37 (d, J=11.4 Hz, 1 H).

$^{13}$C-NMR (CDCl$_3$) δ: 12.1, 18.6, 22.3, 22.8, 23.6, 25.1, 27.6, 29.1, 32.9, 35.9, 40.5, 42.0, 42.9, 45.3, 46.0, 56.4, 57.0, 66.8, 70.8, 84.3, 111.7, 117.2, 119.1, 124.7, 133.1, 142.6, 146.2, 147.5, 170.4.

LRMS m/z 454 (M$^+$), 418, 403

HRMS calcd for C$_{29}$H$_{42}$O$_4$ 454.3083, found 454.3083

(4-b) Using 31 mg (78 μmol) of Compound (4) (Z=(2-1), Y=Br, R$^{2d}$=R$^{2e}$=Me, 5S) obtained by the above method and 43 mg (0.117 mmol) (原原の誤り) of Compound (7) (R$^3$=TBS, R$^6$=hydrogen atom, 3α/5β), a reaction similar to Example 14(2-a) was carried out to obtain 22 mg of Compound No. 111b. Yield: 62%.

Compound No. 111b:

[α]$_D^{24}$-21.8 (c 0.85, CHCl$_3$)

$^1$H-NMR (CDCl$_3$) δ: 0.56 (s, 3 H), 1.05 (s, 3 H), 1.07 (d, J=6.6 Hz, 3 H), 1.21 (s, 3 H), 1.25-1.72 (m, 13 H), 1.88-2.06 (m, 5 H), 2.32 (dd, J=6.3, 13.4 Hz, 1 H), 2.60 (dd, J=3.5, 13.3 Hz, 1 H), 2.83 (dd, J=3.8, 11.8 Hz, 1 H), 4.10 (dd, J=3.4, 9.0 Hz, 1 H), 4.23 (s, 1 H), 4.43 (s, 1 H), 5.00 (dd, J=1.5, 1.6 Hz,

1 H), 5.33 (dd, J=1.6, 1.7 Hz, 1 H), 5.45 (s, 1 H), 6.02 (d, J=11.2 Hz, 1 H), 6.13 (s, 1 H), 6.38 (d, J=11.2 Hz, 1 H).

$^{13}$C-NMR (CDCl$_3$) δ: 12.0, 19.7, 22.3, 23.0, 23.6, 24.4, 27.9, 29.1, 35.4, 35.6, 40.4, 42.6, 42.9, 45.3, 46.0, 56.2, 56.7, 66.8, 70.8, 86.3, 111.6, 117.1, 118.8, 124.8, 133.0, 142.8, 146.2, 147.6, 170.5.

LRMS m/z 454 (M$^+$), 418, 403

HRMS calcd for C$_{29}$H$_{42}$O$_4$ 454.3083, found 454.3083

Example 75

Synthesis of 2α-methyl-20(R)-(tetrahydro-3-methylene-2-furanone-4,4-dimethyl-5(R)-yl)methyl-9,10-secopregna-5(Z),7(E),10(19)-triene-1α,3β-diol (Compound No. 211a)

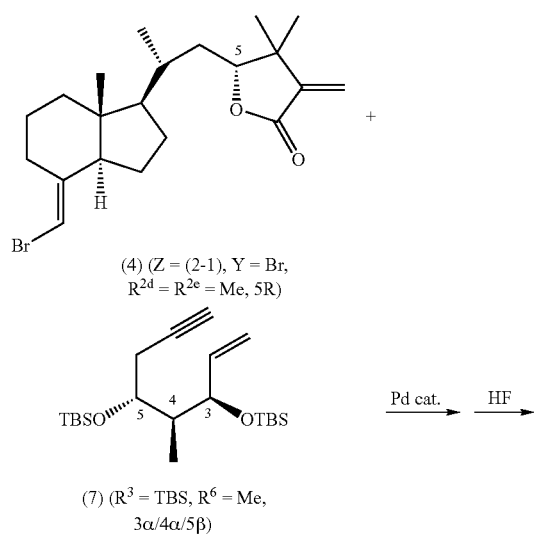

Using 26 mg (66 μmol) of Compound (4) (Z=(2-1), Y=Br, R$^{2d}$=R$^{2e}$=Me, 5R) obtained in Example 74(3-a) and 40 mg (105 μmol) of Compound (7) (R$^3$=TBS, R$^6$=Me, 3α/4α/5β), a reaction similar to Example 14(2-a) was carried out to obtain 18 mg of Compound No. 211a. Yield: 58%.

$^1$H-NMR (CDCl$_3$) δ: 0.56 (s, 3 H), 1.00 (d, J=6.7 Hz, 3 H), 1.06 (s, 3 H), 1.08 (d, J=6.7 Hz, 3 H), 1.12 (m, 1 H), 1.21 (s, 3 H), 1.26-1.34 (m, 3 H), 1.46-1.72 (m, 10 H), 1.90-2.04 (m, 3 H), 2.23 (dd, J=7.9, 13.3 Hz, 1 H), 2.67 (dd, J=4.0, 13.5 Hz, 1 H), 2.83 (dd, J=3.8, 11.9 Hz, 1H), 3.85 (ddd, J=4.2, 7.5, 7.5 Hz, 1 H), 4.15 (dd, J=1.3, 11.6 Hz, 1 H), 4.31 (br, 1 H), 5.01 (d, J=2.0 Hz, 1 H), 5.28 (s, 1 H), 5.47 (s, 1 H), 6.01 (d, J=11.2 Hz, 1 H), 6.15 (s, 1 H), 6.38 (s, J=11.2 Hz, 1 H).

LRMS m/z 468 (M$^+$), 451, 434, 419, 404

HRMS calcd for C$_{30}$H$_{44}$O$_4$ 468.3240, found 468.3264

Example 76

Synthesis of 2α-methyl-20(R)-(tetrahydro-3-methylene-2-furanone-4,4-dimethyl-5(S)-yl)methyl-9,10-secopregna-5(Z),7(E),10(19)-triene-1α,3β-diol (Compound No. 211b)

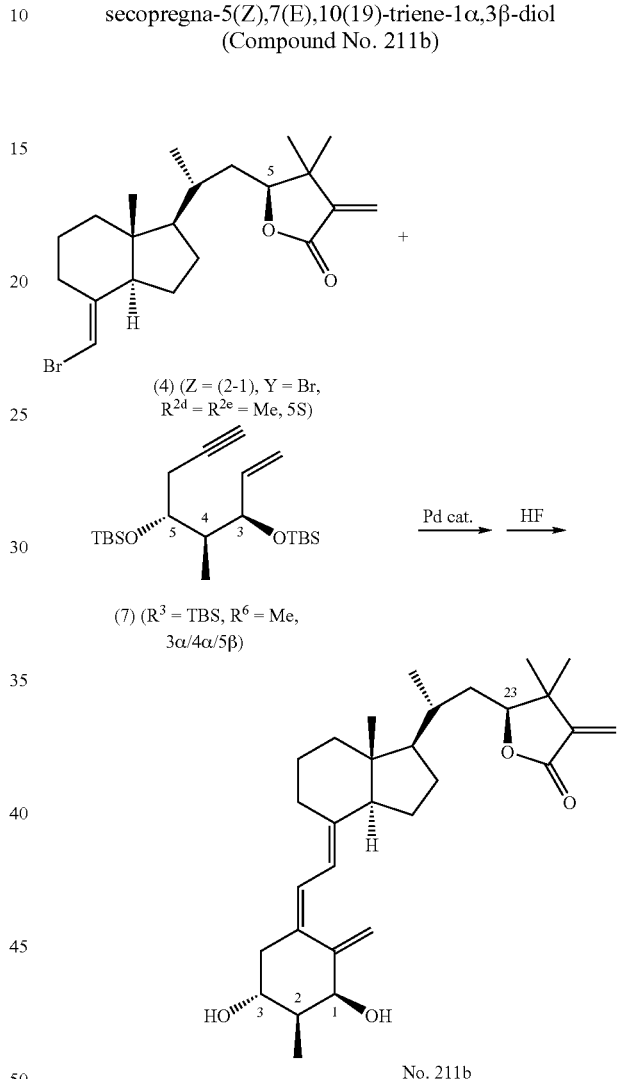

Using 25 mg (63 μmol) of Compound (4) (Z=(2-1), Y=Br, R$^{2d}$=R$^{2e}$=Me, 5S) obtained in Example 74(3-b) and 41 mg (107 μmol) of Compound (7) (R$^3$=TBS, R$^6$=Me, 3α/4α/5β), a reaction similar to Example 14(2-a) was carried out to obtain 14 mg of Compound No. 211b. Yield: 47%.

$^1$H-NMR (CDCl$_3$) δ: 0.55 (s, 3 H), 1.04 (s, 3 H), 1.06 (d, J=6.7 Hz, 3 H), 1.07 (d, J=6.7 Hz, 3 H), 1.21 (s, 3 H), 1.25-1.70 (m, 13 H), 1.88-2.04 (m, 4 H), 2.23 (dd, J=8.1, 13.7 Hz, 1 H), 2.66 (dd, J=4.0, 13.8 Hz, 1 H), 2.82 (dd, J=3.7, 12.2 Hz, 1 H), 3.84 (ddd, J=4.2, 7.6, 7.6 Hz, 1H), 4.10 (dd, J=3.4, 8.8 Hz), 4.31 (d, J=3.2 Hz, 1 H), 5.00 (d, J=1.7 Hz, 1 H), 5.27 (dd, J=1.0, 2.0 Hz, 1 H), 5.45 (s, 1 H), 6.01 (d, J=11.2 Hz, 1 H), 6.13 (s, 1 H), 6.38 (d, J=11.2 Hz, 1 H).

LRMS m/z 468 (M$^+$), 451, 434, 419

HRMS calcd for C$_{30}$H$_{44}$O$_4$ 468.3240, found 468.3248

Example 77

Synthesis of 2α-(3-hydroxypropyl)-20(R)-(tetrahydro-3-methylene-2-furanone-4,4-dimethyl-5(R)-yl)methyl-9,10-secopregna-5(Z),7(E),10(19)-triene-1α,3β-diol (Compound No. 812a)

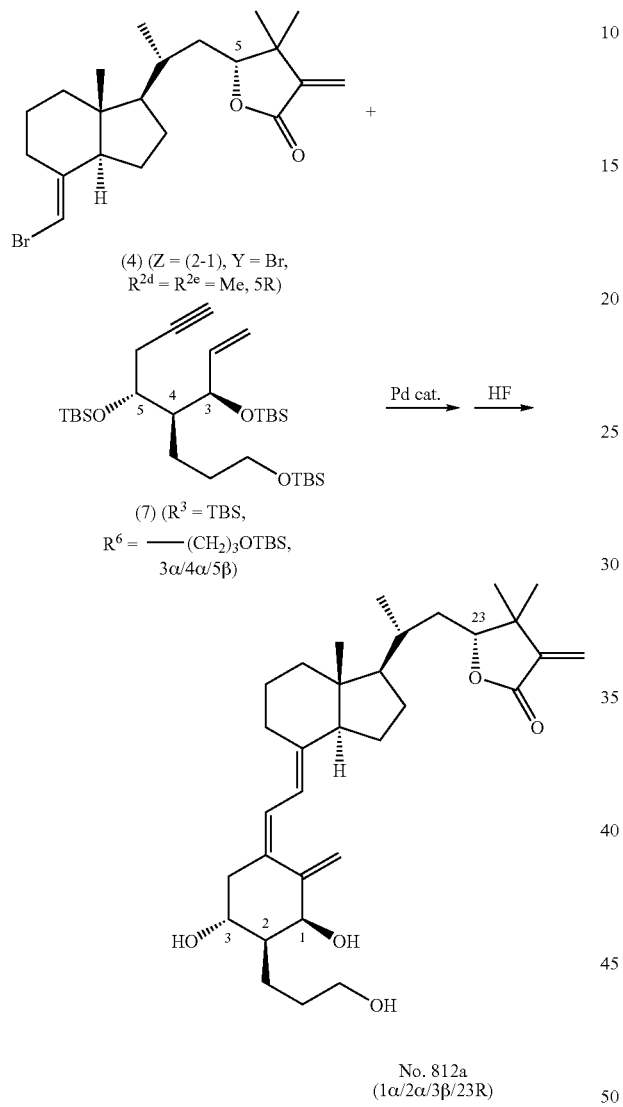

No. 812a
(1α/2α/3β/23R)

Using 39 mg (76 μmol) of Compound (4) (Z=(2-1), Y=Br, $R^{2d}=R^{2e}$=Me, 5R) obtained in Example 74(3-a) and 68 mg (126 μmol) of Compound (7) ($R^3$=TBS, $R^6$=—(CH$_2$)$_3$OTBS, 3α/4α/5β), a reaction similar to Example 14(2-a) was carried out to obtain 18 mg of Compound No. 812a. Yield: 46%.

$^1$H-NMR (CDCl$_3$) δ: 0.56 (s, 3 H), 0.99 (d, J=6.3 Hz, 3 H), 1.06 (s, 3 H), 1.11 (m, 1 H), 1.21 (s, 3 H), 1.26-1.35 (m, 5 H), 1.48-1.86 (m, 11 H), 1.97-2.05 (m, 3 H), 2.25 (dd, J=8.7, 13.1 Hz, 2 H), 2.28 (br, 1 H), 2.66 (dd, J=4.2, 13.4 Hz, 1 H), 2.83 (m, 1 H), 3.69-3.70 (m, 2 H), 3.90 (ddd, J=4.3, 8.2, 8.2 Hz, 1 H), 4.15 (dd, J=1.1, 11.4 Hz, 1 H), 4.38 (d, J=2.9 Hz, 1 H), 4.99 (d, J=1.7 Hz, 1 H), 5.28 (d, J=1.7 Hz, 1 H), 5.47 (s, 1 H), 6.00 (d, J=11.2 Hz, 1 H), 6.15 (s, 1 H), 6.39 (d, J=11.2 Hz, 1 H).

LRMS m/z 512 (M$^+$), 495, 478, 461
HRMS calcd for C$_{32}$H$_{48}$O$_5$ 512.3502, found 512.3502

Example 78

Synthesis of 2α-(3-hydroxypropyl)-20(R)-(tetrahydro-3-methylene-2-furanone-4,4-dimethyl-5(S)-yl)methyl-9,10-secopregna-5(Z),7(E),10(19)-triene-1α,3β-diol (Compound No. 812b)

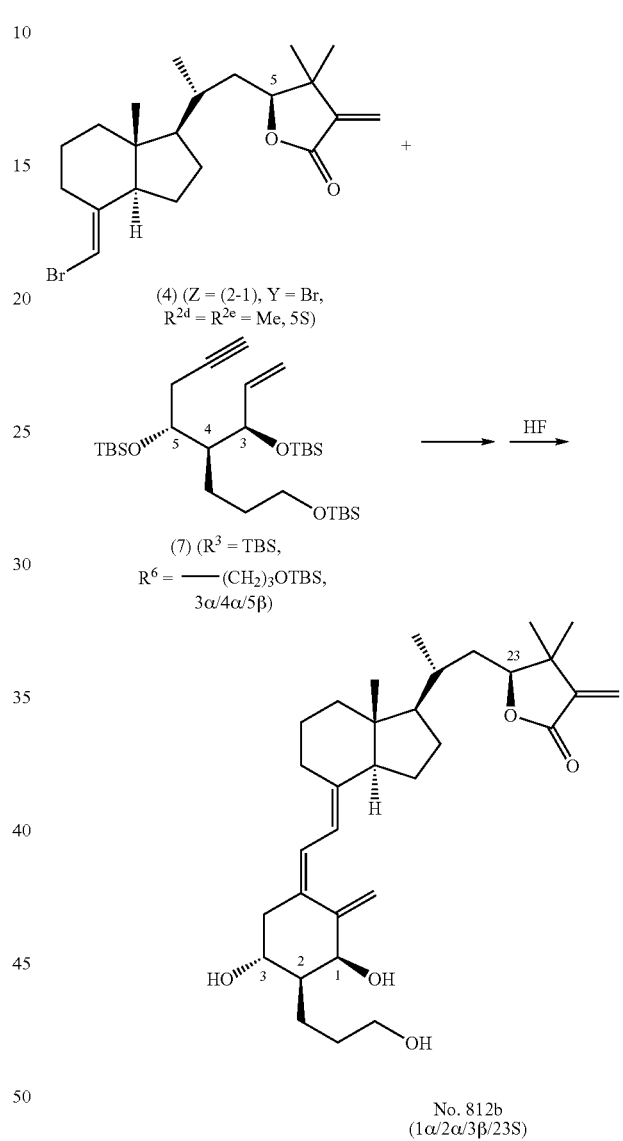

No. 812b
(1α/2α/3β/23S)

Using 18 mg (46 μmol) of Compound (4) (Z=(2-1), Y=Br, $R^{2d}=R^{2e}$=Me, 5S) obtained in Example 74(3-b) and 37 mg (68 μmol) of Compound (7) ($R^3$=TBS, $R^6$=—(CH$_2$)$_3$OTBS, 3α/4α/5β), a reaction similar to Example 14(2-a) was carried out to obtain 9 mg of Compound No. 812b. Yield: 39%.

$^1$H-NMR (CDCl$_3$) δ: 0.55 (s, 3 H), 1.05 (s, 3 H), 1.07 (d, J=6.6 Hz, 3 H), 1.21 (s, 3 H), 1.24-1.54 (m, 10 H), 1.58-1.77 (m, 7 H), 1.92-2.02 (m, 5 H), 2.25 (dd, J=13.5, 8.9 Hz, 1 H), 2.66 (dd, J=4.3, 13.5 Hz, 1 H), 2.83 (m, 1 H), 3.70 (m, 2 H), 3.89 (ddd, J=4.4, 8.3, 8.3 Hz, 1H), 4.11 (dd, J=3.2, 9.0 Hz, 1 H), 4.38 (d, J=2.9 Hz, 1 H), 5.00 (d, J=1.6 Hz, 1 H), 5.28 (d, J=1.6 Hz, 1 H), 5.46 (s, 1 H), 6.00 (d, J=11.4 Hz, 1 H), 6.14 (s, 1 H), 6.40 (d, J=11.4 Hz, 1H).

LRMS m/z 512 (M+), 495, 478, 461
HRMS calcd for $C_{32}H_{48}O_5$ 512.3502, found 512.3490

Example 79

Synthesis of 2α-(3-hydroxypropoxy)-20(R)-(tetrahydro-3-methylene-2-furanone-4,4-dimethyl-5(R)-yl)methyl-9,10-secopregna-5(Z),7(E),10(19)-triene-1α,3β-diol (Compound No. 1112a)

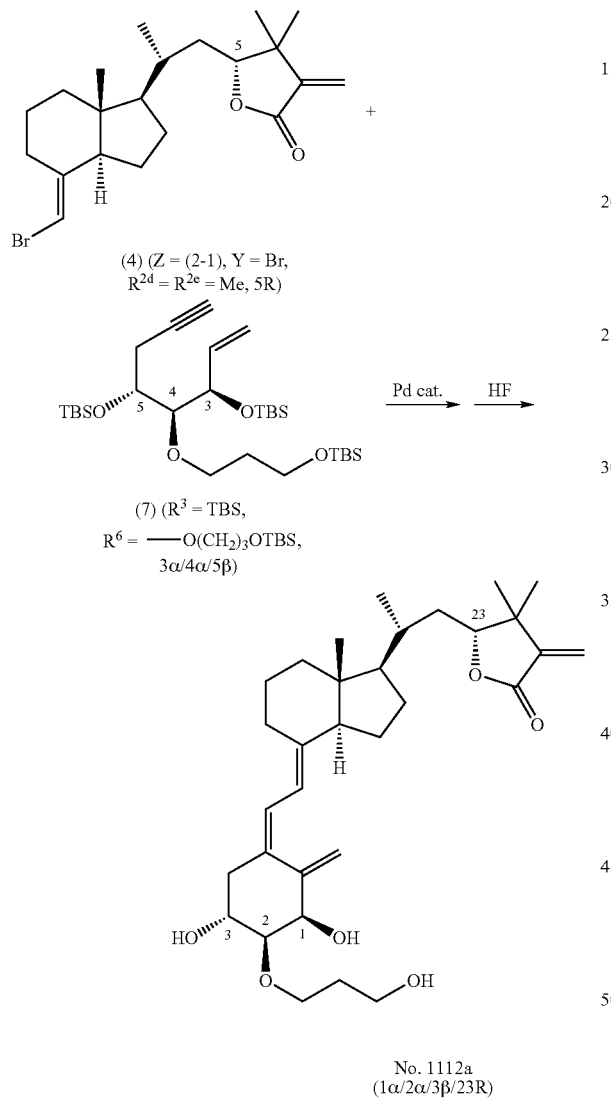

Using 30 mg (76 μmol) of Compound (4) (Z=(2-1), Y=Br, $R^{2d}=R^{2e}$=Me, 5R) obtained in Example 74(3-a) and 71 mg (128 μmol) of Compound (7) ($R^3$=TBS, $R^6$=—O(CH$_2$)$_3$OTBS, 3α/4α/5β), a reaction similar to Example 14(2-a) was carried out to obtain 23 mg of Compound No. 1112a. Yield: 57%.

$^1$H-NMR (CDCl$_3$) δ: 0.56 (s, 3 H), 0.99 (d, J=6.6 Hz, 3 H), 1.05 (s, 3 H), 1.11 (m, 1 H), 1.21 (s, 3 H), 1.23-1.35 (m, 4 H), 1.47-1.56 (m, 3 H), 1.66-1.88 (m, 6 H), 1.96-2.05 (m, 2 H), 2.24 (dd, J=8.8, 1.34 Hz, 1 H), 2.68 (dd, J=4.4, 13.7 Hz, 1 H), 2.73 (br, 3 H), 2.83 (m, 1 H), 3.37 (dd, J=3.2, 7.6 Hz, 1 H), 3.74-3.91 (m, 4 H), 4.06 (ddd, J=4.4, 8.2, 8.2 Hz, 1 H), 4.15 (dd, J=1.2, 11.5 Hz, 1 H), 4.45 (d, J=2.9 Hz, 1 H), 5.09 (d, J=1.7 Hz, 1 H), 5.39 (s, 1 H), 5.47 (s, 1 H), 6.12 (d, J=11.2 Hz, 1 H), 6.15 (s, 1 H), 6.41 (d, J=11.2 Hz, 1 H).

LRMS m/z 528 (M+), 511, 494, 477, 435
HRMS calcd for $C_{32}H_{48}O_6$ 528.3451, found 528.3449

Example 80

Synthesis of 2α-(3-hydroxypropoxy)-20(R)-(tetrahydro-3-methylene-2-furanone-4,4-dimethyl-5(S)-yl)methyl-9,10-secopregna-5(Z),7(E),10(19)-triene-1α,3β-diol (Compound No. 1112b)

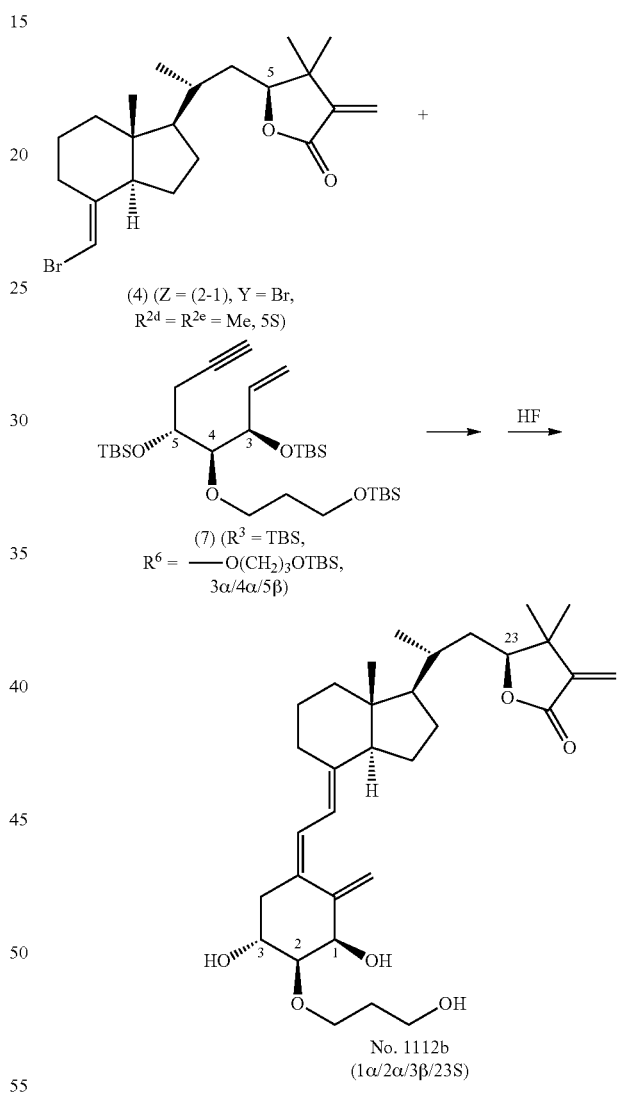

Using 14 mg (35 μmol) of Compound (4) (Z=(2-1), Y=Br, $R^{2d}=R^{2e}$=Me, 5S) obtained in Example 74(3-b) and 35 mg (63 μmol) of Compound (7) ($R^3$=TBS, $R^6$=—O(CH$_2$)$_3$OTBS, 3α/4α/5β), a reaction similar to Example 14(2-a) was carried out to obtain 13 mg of Compound No. 1112b. Yield: 69%.

$^1$H-NMR (CDCl$_3$) δ: 0.70 (s, 3 H), 1.05 (s, 3 H), 1.06 (d, J=6.6 Hz, 3 H), 1.21 (s, 3 H), 1.23-1.72 (m, 11 H), 1.84-2.04 (m, 5 H), 2.24 (dd, J=9.2, 13.5 Hz, 1 H), 2.53 (br, 3 H), 2.68 (dd, J=4.6, 13.7 Hz, 1 H), 2.82 (m, 1 H), 3.38 (dd, J=3.3, 7.4 Hz, 1 H), 3.83 (m, 4 H), 4.05 (m, 1 H), 4.10 (dd, J=3.3, 8.9 Hz,

1 H), 4.45 (d, J=2.9 Hz, 1 H), 5.10 (d, J=1.5 Hz, 1 H), 5.39 (d, J=1.5 Hz, 1 H), 5.46 (s, 1 H), 6.02 (d, J=11.2 Hz, 1 H), 6.13 (s, 1 H), 6.42 (d, J=11.2 Hz, 1 H).

LRMS m/z 528 (M+), 511, 494, 477, 435

HRMS calcd for $C_{32}H_{48}O_6$ 528.3451, found 528.3451

Example 81

The Binding Affinity to the 1α,25-dihydroxyvitamine $D_3$ Receptor (VDR) in Chicken Small Intestinal Mucosal Cells The example was carried out according to the method described in Ishizuka et al., Steroids, Vol. 37, 33-43, 1982. That is, a solution was prepared by adding a 10 μl ethanol solution of [26,27-methyl-$^3$H]1α,25-dihydroxyvitamine $D_3$ (180 Ci/mmol) with 15,000 dpm and a 40 μl ethanol solution of the compound of the present invention to a polypropylene tube with 12×75 mm. To this solution was added a solution which was prepared by dissolving 0.2 mg of the 1α,25-dihydroxyvitamine $D_3$ receptor protein in chicken small intestinal mucosal cells and 1 mg of gelatin in 1 ml of phosphate buffer solution (pH: 7.4) and the resultant solution was reacted at 25° C. for one hour. A 1 ml aliquot of 40% polyethylene glycol 6000 solution was added to the tube and the resultant mixture was stirred vigorously. The mixture was subjected to centrifugation at 4° C. for 60 minutes at 2260×g for separation. The precipitated portion of the tube was cut off with a cutter knife to put in a vial for a liquid scintillator, and 10 ml of dioxane scintillator was added to the vial. Then the radioactivity was measured by a liquid scintillation counter. From the measured data, the concentration at which 50% of the binding of the [26,27-methyl-$^3$H]1α,25-dihydroxyvitamine $D_3$ to the receptor was inhibited was determined for the compound of the present invention, and the concentration was expressed as a relative intensity ratio with respect to the 50% inhibitory concentration of 1α,25-dihydroxyvitamine $D_3$ defined as 1. The results are shown in the following table.

The Binding Affinity of the Compound of the Present Invention to the 1α,25-dihydroxyvitamine $D_3$ Receptor in Chicken Small Intestinal Mucosal Cells

| VDR Affinity* | Compound No. |
|---|---|
| 1-1/5 | 101c, 101d, 102d, 103d, 105d, 106d, 107d, 109b, 110d, 111b, 201a, 201b, 201c, 201d, 202b, 202c, 205b, 205c, 206b, 209b, 211a, 211b, 801a, 802a, 802b, 802c, 802d, 810a, 810b, 810c, 812a, 812b, 1101a, 1102b, 1102c, 1102d, 1110a, 1110b, 1110c, 1110d, 1112a, 1112b |
| 1/5-1/10 | 101a, 102c, 105c, 109a, 109c, 111a, 202a, 202d, 205a, 205d, 206a, 209a, 209c, 209d, 801b, 810d, 1101b, 1102a |
| 1/10-1/30 | 101b, 102a, 102b, 103a, 103b, 103c, 105a, 105b, 107a, 107b, 107c, 109d, 110a, 110b, 110c, 114a, 114b, 206c, 206d |

*1α,25-dihydroxyvitamine $D_3$ = 1

These results have demonstrated that, the compounds of the present invention bind to VDR with extremely high affinity. Consequently, in view of the antagonist action of the compounds of the present invention described below, it has been demonstrated that these compounds are expected to have a high Vitamin D antagonist action and are effective as a therapeutic agent to Paget's disease of bone and hypercalcemia induced by an increased action of active form of vitamin $D_3$.

Example 82

The Vitamin $D_3$ Antagonist Action Determined by Using the Induction of HL-60 Cell Differentiation by 1α,25-dihydroxyvitamine $D_3$ as an Indicator (1) HL-60 cells that were purchased from a cell bank (Japanese Cancer Research Resources Bank, Cell No. JCRB0085) were used. The cells were maintained as a frozen preservation stock to prevent changes in cellular characteristics by subculture. The stock was thawed before starting the experiment, and the cells which subsequently initiated subculture were used. The cells with subcultivation approximately over one month to a half year were used for the experiment. The subcultivation was performed by first centrifuging and collecting cells in suspension culture, and then diluting the collected cells by approximately a factor of 100 to a concentration of $1×10^4$ to $2×10^4$ cells/ml in a fresh culture medium. An RPMI-1640 medium with 10% fetal bovine serum was used as the culture medium.

(2) The cells that had been subcultured in (1) were collected by centrifugation and dispersed to a concentration of $2×10$ cells/ml in the culture medium, and the dispersed cells were subsequently seeded with 1 ml/well in a 24-well culture dish. To this system was added an ethanol solution, which was prepared with $1×10^{-5}$ M of 1α,25-dihydroxyvitamine $D_3$ and $1×10^{-8}$ M to $10^{-4}$ M of the compound of the present invention, at 1 μl per well (the final concentration: $1×10^{-8}$ M of 1α,25-dihydroxyvitamine $D_3$ and $1×10^{-11}$ M to $10^{-7}$ M of the compound of the present invention). As a control, ethanol was added at 1 μl per well. The cells were incubated under 5% $CO_2$ at 37° C. for 4 days, and the culture medium was subjected to centrifugation to collect the cells.

(3) The induction of nitroblue tetrazolium (hereinafter referred to as NBT) reducing activity was used as an indicator of the induction of HL-60 cell differentiation. The NBT reducing activity was measured according to the procedures described below. That is, after the centrifuged and collected cells were suspended in a fresh culture medium, NBT and 12-O-tetradecanoylphorbol-13-acetate were added to the medium to make their concentrations 0.1% and 100 ng/ml, respectively, and then the medium was incubated at 37° C. for 25 minutes to create a Cytospin sample. After air drying the resultant sample, Kernechtrot staining was performed to determine the ratio of NBT reducing activity-positive cells under an optical microscope. A percent ratio of the positive cell ratio obtained by the concomitant treatment with $1×10^{-8}$ M of 1α,25-dihydroxyvitamine $D_3$ and $1×10^{-11}$ M to $1×10^{-7}$ M of the compound of the present invention to the positive cell ratio obtained by the treatment of $1×10^{-8}$ M of 1α,25-dihydroxyvitamine $D_3$ alone was plotted as a function of the treatment concentration of the compound of the present invention. The plotted results were used to calculate the treatment concentration of the compound of the present invention corresponding to the percent ratio of 50%, which was designated as the $IC_{50}$ value (nM). The results are shown in the following table.

The Effect on the Induction of NBT Reducing Activity in HL-60 Cells (The Inhibitory Effect of the Compound of the Present Invention on the Cell Differentiation Induction by 1α,25-dihydroxyyitamine $D_3$)

| $IC_{50}$ (nM) | Compound No. |
|---|---|
| <10 | 101c, 101d, 102d, 103c, 103d, 105d, 106d, 107d, 110d, 111b, 114a, 201a, 201b, 201c, 201d, 202a, 202b, 202c, 205a, 205b, 205c, 206b, 206c, 209a, 209b, 211a, 211b, 801a, 801b, 802b, 802c, 810a, 810b, 810c, 812a, 812b, 1101b, 1102b, 1102c, 1110a, 1110b, 1110c, 1112b |
| 10-100 | 101b, 102b, 102c, 103a, 103b, 104b, 105b, 105c, 106c, 107a, 107c, 108a, 108b, 108c, 108d, 109a, 109b, 109c, 110a, 110b, |

| IC$_{50}$ (nM) | Compound No. |
|---|---|
| | 110c, 111a, 114b, 114c, 202d, 206a, 209c, 802a, 802d, 810d, 1101a, 1102a, 1102d, 1110d, 1112a |
| 100-300 | 101a, 102a, 104a, 105a, 106a, 106b, 109d, 206d, 209d |

The results have demonstrated that the compound of the present invention suppressed the cell differentiation induction induced by 1α,25-dihydroxyvitamine D$_3$. That is, the compound of the present invention has been demonstrated to act as an antagonist against 1α,25-dihydroxyvitamine D$_3$. Consequently, the compound of the present invention has been shown to be effective as a therapeutic agent to Paget's disease of bone and hypercalcemia induced by increased action of active form of vitamin D$_3$.

Industrial Applicability

The compound of the present invention can be used as an active ingredient of a pharmaceutical product. A pharmaceutical composition comprising the compound of the present invention as an active ingredient is used as a therapeutic agent to Paget's disease of bone and hypercalcemia.

What is claimed is:

1. A compound represented by the following Formula (1):

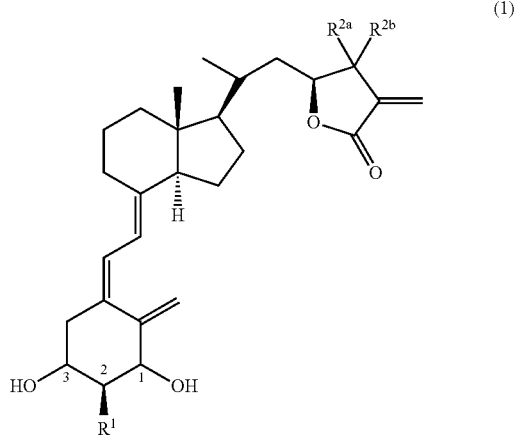

(1)

wherein R$^1$ is a methyl group, a 3-hydroxypropyl group, or a 3-hydroxypropoxy group and a combination of R$^{2a}$ and R$^{2b}$ is hydrogen atom and methyl group, hydrogen atom and ethyl group, hydrogen atom and propyl group, hydrogen atom and butyl group, hydrogen atom and isobutyl group, both hydrogen atoms or both methyl groups, or alternatively R$^{2a}$ and R$^{2b}$ may be combined together to form a cyclopropane ring together with the carbon atom to which they are bonded; with the proviso that a compound in which R$^1$ is methyl group and R$^{2a}$ and R$^{2b}$ are hydrogen atoms is excluded, and wherein the steric configuration of the 1-position of the above Formula (1) is α configuration and that of the 3-position is β configuration.

2. The compound according to claim 1, wherein in the above Formula (1), R$^1$ is methyl group and a combination of R$^{2a}$ and R$^{2b}$ is hydrogen atom and methyl group; R$^1$ is methyl group and a combination of R$^{2a}$ and R$^{2b}$ is hydrogen atom and ethyl group; R$^1$ is methyl group and a combination of R$^{2a}$ and R$^{2b}$ is hydrogen atom and butyl group; R$^1$ is methyl group and a combination of R$^{2a}$ and R$^{2b}$ is hydrogen atom and isobutyl group; or R$^1$ is methyl group and both R$^{2a}$ and R$^{2b}$ are methyl groups.

3. The compound according to claim 1, wherein in the above Formula (1), R$^1$ is 3-hydroxypropyl group and both R$^{2a}$ and R$^{2b}$ are hydrogen atoms; R$^1$ is 3-hydroxypropyl group and a combination of R$^{2a}$ and R$^{2b}$ is hydrogen atom and methyl group; R$^1$ is 3-hydroxypropyl group and a combination of R$^{2a}$ and R$^{2b}$ is hydrogen atom and ethyl group; R$^1$ is 3-hydroxypropyl group and a combination of R$^{2a}$ and R$^{2b}$ is hydrogen atom and butyl group; R$^1$ is 3-hydroxypropyl group and a combination of R$^{2a}$ and R$^{2b}$ is hydrogen atom and isobutyl group; or R$^1$ is 3-hydroxypropyl group and both R$^{2a}$ and R$^{2b}$ are methyl groups.

4. The compound to claim 1, wherein in the above Formula (1), R$^1$ is 3-hydroxypropoxy group and both R$^{2a}$ and R$^{2b}$ are hydrogen atoms; R$^1$ is 3-hydroxypropoxy group and a combination of R$^{2a}$ and R$^{2b}$ is hydrogen atom and methyl group; R$^1$ is 3-hydroxypropoxy group and a combination of R$^{2a}$ and R$^{2b}$ is hydrogen atom and ethyl group; R$^1$ is 3-hydroxypropoxy group and a combination of R$^{2a}$ and R$^{2b}$ is hydrogen atom and butyl group; R$^1$ is 3-hydroxypropoxy group and a combination of R$^{2a}$ and R$^{2b}$ is hydrogen atom and isobutyl group; or R$^1$ is 3-hydroxypropoxy group and both R$^{2a}$ and R$^{2b}$ are methyl groups.

5. A therapeutic agent for Paget's disease of bone comprising the compound or the pharmaceutically acceptable solvate thereof according to claim 1 as an active ingredient.

6. A therapeutic agent for hypercalcemia comprising the compound or the pharmaceutically acceptable solvate thereof according to claim 1 as an active ingredient.

7. A pharmaceutical composition comprising the compound according to claim 1 and a pharmaceutically acceptable carrier.

8. A process for synthesizing a compound represented by the following Formula (4syn-a), wherein the relative configuration of carbon a and carbon b is syn,

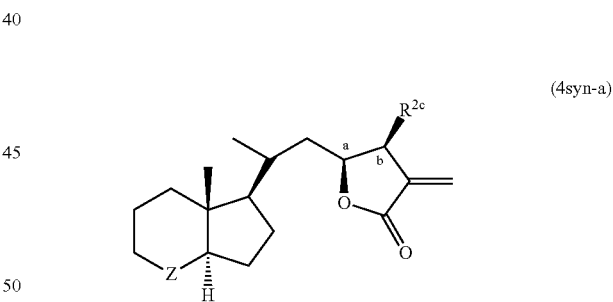

(4syn-a)

comprising reacting, in the presence of divalent chromium, an aldehyde compound represented by the following Formula (2):

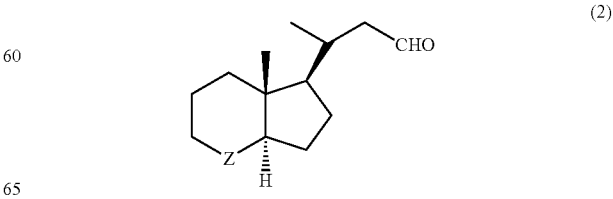

(2)

wherein Z refers to any one of Formulas (2-1), (2-2), (2-3), (2-4) and (2-5):

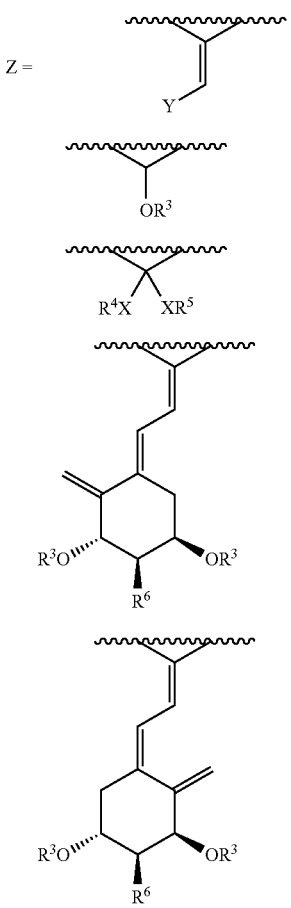

wherein Y refers to bromine atom or iodine atom; $R^3$ refers to trimethylsilyl group, triethylsilyl group, triisopropylsilyl group, t-butyldimethylsilyl group, t-butyldiphenylsilyl group, acetyl group, benzoyl group, methoxymethyl group or tetrahydro-4H-pyran-2-yl group; $R^4$ or $R^5$ independently refers to methyl group, ethyl group, propyl group, trichloroethyl group, or $R^4$ and $R^5$ are combined to refer to ethylene group or propylene group, X refers to oxygen atom or sulfur atom; $R^6$ refers to hydrogen atom, $C_1$-$C_6$ alkyl group optionally substituted with a hydroxyl group protected by a group defined by $R^3$, or $C_1$-$C_6$ alkoxy group optionally substituted by a hydroxyl group protected by a group defined by $R^3$, with an acrylic acid derivative represented by the following Formula (3),

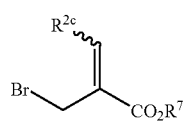

wherein $R^{2c}$ refers to $C_1$-$C_{10}$ alkyl group optionally substituted with hydroxyl group protected by a group defined by $R^3$ of the above Formula (2), $C_6$-$C_{10}$ aryl group optionally substituted with hydroxyl group protected by a group defined by $R^3$ of the above Formula (2), or $C_7$-$C_{12}$ aralkyl group optionally substituted with hydroxyl group protected by a group defined by $R^3$ of the above Formula (2), and $R^7$ refers to $C_1$-$C_6$ alkyl group, wherein $R^{2c}$ in the above Formula (4syn-a) has the same definition as in the above Formula (3), and Z in the above Formula (4syn-a) has the same definition as in the above Formula (2).

9. A process which comprises, in the following order, the steps of: reducing a lactone ring of a lactone compound represented by the following Formula (4syn-b),

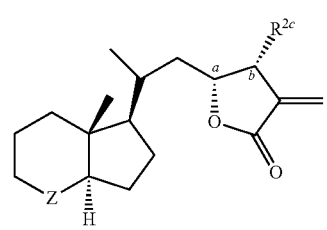

wherein $R^{2c}$ has the same definition as in the above Formula (3), Z has the same definition as in the above Formula (2), and the relative configuration of carbon a and carbon b is syn; protecting the resultant primary hydroxyl group to obtain an alcohol compound represented by the following Formula (5 syn),

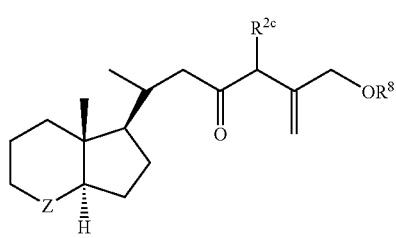

wherein $R^{2c}$ has the same definition as in the above Formula (3), Z has the same definition as in the above Formula (2), $R^8$ refers to acetyl group, 4-oxopentanoyl group, pivaroyl group, benzoyl group, triisopropylsilyl group, t-butyldimethylsilyl group or t-butyldiphenylsilyl group and the relative configuration of carbon a and carbon b is syn; oxidizing the secondary hydroxyl group of the alcohol compound to obtain a ketonic compound represented by the following Formula (6), (6)

wherein $R^{2c}$ has the same definition as in the above Formula (3), Z has the same definition as in the above Formula (2), and $R^8$ has the same definition as in the above Formula (5syn); reducing the ketone group of the ketonic compound to obtain an alcohol compound represented by the following Formula (5anti),

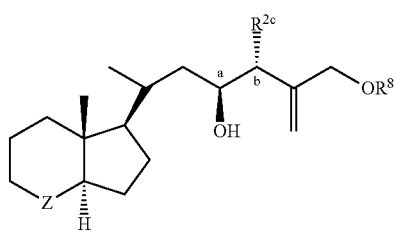
(5anti)

wherein $R^{2c}$ has the same definition as in the above Formula (3), Z has the same definition as in the above Formula (2), $R^8$ has the same definition as in the above Formula (5syn), and the relative configuration of carbon a and carbon b is anti; and deprotecting $R^8$ of the alcohol compound and then oxidizing the resultant primary hydroxyl group to form a lactone ring, for synthesizing a lactone compound represented by the following Formula (4anti),

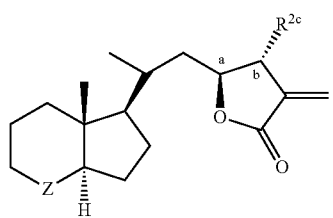
(4anti)

wherein, $R^{2c}$ has the same definition as in the above Formula (3), Z has the same definition as in the above Formula (2), and the relative configuration of carbon a and carbon b is anti.

* * * * *